United States Patent
Francois et al.

(10) Patent No.: US 11,069,430 B2
(45) Date of Patent: Jul. 20, 2021

(54) PATIENT STATE REPRESENTATION ARCHITECTURES AND USES THEREOF

(71) Applicant: Revon Systems, Inc., Crestwood, KY (US)

(72) Inventors: Cedric Francois, Prospect, KY (US); Gaurav Bazaz, Edgewater, NJ (US); Patrick White, Leesburg, VA (US)

(73) Assignee: Zyus Life Sciences US Ltd., Saskatoon (CA)

( * ) Notice: Subject to any disclaimer, the term of this patent is extended or adjusted under 35 U.S.C. 154(b) by 1123 days.

(21) Appl. No.: 15/202,223

(22) Filed: Jul. 5, 2016

(65) Prior Publication Data

US 2017/0039324 A1  Feb. 9, 2017

Related U.S. Application Data

(60) Provisional application No. 62/188,297, filed on Jul. 2, 2015.

(51) Int. Cl.
*G16H 10/60* (2018.01)
*G16H 50/30* (2018.01)
*G16H 50/20* (2018.01)

(52) U.S. Cl.
CPC ............. *G16H 10/60* (2018.01); *G16H 50/20* (2018.01); *G16H 50/30* (2018.01)

(58) Field of Classification Search
CPC ........ G16H 10/60; G16H 50/30; G16H 50/20; G06F 19/324
See application file for complete search history.

(56) References Cited

U.S. PATENT DOCUMENTS

2005/0144042 A1  6/2005  Joffe et al.
2008/0040151 A1*  2/2008  Moore ................. G06F 19/324
705/2

(Continued)

FOREIGN PATENT DOCUMENTS

WO  WO 2014/105752 A1  7/2014

OTHER PUBLICATIONS

International Search Report and Written Opinion dated Mar. 30, 2016 for International Application No. PCT/US2015/060737, 14 pages.

(Continued)

*Primary Examiner* — Michael Tomaszewski
*Assistant Examiner* — Mohmad Muqueeth
(74) *Attorney, Agent, or Firm* — Frost Brown Todd LLC

(57) ABSTRACT

Using a centralized system, it is possible to allow multiple disparate health care providers to gain a complete view of data regarding a patient's health and health care. Data accessible through such a central system can also be made available for researchers after being de-identified. Data in such a central system can not only include data culled from traditional physical and electronic medical records, but can also include data from distributed diagnostic devices, such as fitness trackers and consumer diagnostic equipment. Such a central system could potentially be accessed through applications made available to patients and health care providers and, in implementations where they are present, such applications could also be used for other purposes, such as performing interactive health evaluations and making recommendations of actions to take to maintain or restore a user's health.

13 Claims, 146 Drawing Sheets

(56) References Cited

U.S. PATENT DOCUMENTS

2011/0246224 A1* 10/2011 Green, III ............. G06Q 50/24
705/2
2012/0253207 A1   10/2012 Sarkar et al.
2014/0006039 A1    1/2014 Khan et al.
2017/0293700 A1   10/2017 Bazaz et al.

OTHER PUBLICATIONS

U.S. Election Restriction dated Apr. 3, 2020, for U.S. Appl. No. 15/584,249, 7 pages.
U.S. Non-Final Office Action dated Aug. 5, 2020, for U.S. Appl. No. 15/584,249, 12 pages.

* cited by examiner

FIG. 116

PATIENT STATE REPRESENTATION ARCHITECTURES AND USES THEREOF

FIELD

The disclosed technology can be used for purposes such as facilitating the provision of health care and/or collecting, maintaining and using information about health and health care.

BACKGROUND

Interactions between patients and physicians have traditionally been episodic. Patients typically seek treatment from a physician for newly arising medical conditions and may return to the same physician for follow-up or be referred to a different physician who may then assume responsibility for treating the patient for that condition. Patients may visit more than one physician for the same complaint or consult different specialists for different complaints. Many patients suffer from several chronic diseases, require multiple medications, and are under the care of multiple physicians, who may practice at different health care institutions and may not even be aware that they each care for a particular patient. Additionally, many patients may use health maintenance technology, such as fitness trackers or consumer diagnostic equipment, which could collect data relevant to health care provided by their physicians, but which their physicians may not know exists. As a result of this, health data pertaining to a particular patient or patients is often dispersed among diverse systems, is often organized in diverse manners, may be stored in or reflect information in a variety of different formats, and may not be readily accessible to physicians who are responsible for providing care or to others who could make patients aware of opportunities to improve their health (e.g., people or organizations who could inform a patient that his or her health information indicated that he or she was eligible to participate in a trial of a promising new treatment).

Accordingly, there is a need for technology which can address one or more of the issues associated with the fragmentary and often inaccessible nature of existing health data. Additionally, there is a further need for technology which can assist patients and/or doctors with using information in, and adding information to, medical records for the purpose of improving health care and maintenance. There is a further need for technology which can be used for assembling information in medical records and processing it as appropriate (e.g., de-identifying it) so that it is usable for purposes such as research, as well as for supporting such research and other activities which rely on medical data.

SUMMARY

In some aspects, the disclosed technology can be used to implement systems and methods addressing one or more of the problems or shortcomings associated with existing technology.

In some aspects, a system for analyzing, facilitating access to, and performing actions based on health information is provided. Such a system could comprise a plurality of patient state objects. Each such patient state object could correspond to, and provide a holistic and continuously upgradeable view of, a different patient from a plurality of patients registered with the system. Additionally, each of the patient state objects in such a system could be data structures adapted to store, for the patient to whom it corresponds, data comprising physiological data regarding that patient, behavioral data regarding that patient, and demographic data regarding that patient. Such patient state objects could store all health data used by the system for performing actions for the patients to which they correspond.

In some aspects, each patient state object may be a multidimensional vector accessible using an identifier for the corresponding patient as an argument to a patient state object retrieval function.

In some aspects, in a system which comprises patient state objects storing demographic data for corresponding patients, each the patient state object might store demographic data comprising: age of the corresponding patient; gender of the corresponding patient; income level of the corresponding patient; education level of the corresponding patient; environment of the corresponding patient; and location of the corresponding patient. In some aspects, patient state objects might also store behavioral data for corresponding patients, in which case each patient state object might store the following behavioral data: compliance by the corresponding patient with requests for survey data; compliance by the corresponding patient with using medications as directed; a compliance level score for the corresponding patient; a recent compliance level score for the corresponding patient; a compliance score trend for the corresponding patient; a compliance score volatility for the corresponding patient; and for each of a plurality of body monitors, a compliance score for providing measurements from that body monitor. In some aspects, patient state objects might also store physiological data, in which case each patient state object might store the following physiological data: an overall health score for the corresponding patient; a heath score trend for the corresponding patient; a health score volatility for the corresponding patient; a general hospitalization risk for the corresponding patient; an overall exacerbation risk for the corresponding patient; allergies of the corresponding patient; and medications taken by the corresponding patient. Additionally, in some aspects such physiological data might include, for each of a plurality of conditions, a risk level for the corresponding patient for that condition, and a condition exacerbation risk for the corresponding patient for that condition. Additionally, in some aspects, such physiological data might include, for each of a plurality of body monitors, an urgency score for the corresponding patient for that body monitor, and a risk level for the corresponding patient for that body monitor.

In some aspects, a system comprising a plurality of patient state objects might also comprise a state controller engine ("SCE") having a plurality of rules for updating patient state objects. In some aspects, for each patient state object, such a system may be adapted to cause the SCE to evaluate rules for updating patient state objects based on one or more of: receipt of new data regarding the patient corresponding to that patient state object; and a periodically scheduled trigger for determining updates to that patient state object based on historical data regarding that patient state object. In some aspects, such a system may have only a single SCE, and all updates to all patient state objects may be performed using that SCE. In some aspects, the system may be configured to use the SCE to continuously update the plurality of patient state objects as new data becomes available.

In some aspects, a system comprising a plurality of patient state objects may comprise an action controller engine ("ACE") having a plurality of rules for determining actions to perform based on data from patient state objects. In some aspects, for each patient state object, such a system may be adapted to cause the ACE to evaluate rules for taking action based on data from patient state objects based on one or more of: receipt of a message indicating an update to that patient state object; and a time based trigger for running rules in a batch process. In some aspects, an ACE in such a system may have rules adapted to, based on evaluation of rules with data from a patient state object corresponding to a specific patient, cause the system to perform actions comprising: communicating with the specific patient by sending a message to a computer of the specific patient; communicating with a healthcare provider of the specific patient by sending a message to a computer of the healthcare provider of the specific patient; communicating with a caregiver of the specific patient by sending a message to a computer of the caregiver of the specific patient; requesting health data from the specific patient; requesting an update to a body monitor measurement for the specific patient; recommending that the specific patient take a medication; sending a reminder message to the specific patient; and adjusting a timing or frequency for collecting data from the specific patient. In some aspects, such rules may also comprise rules adapted to cause the system to recommend the specific patient seek medical attention by performing an action selected from a group consisting of calling 911 and calling a physician.

In some aspects, a system comprising an ACE having a plurality of rules may have the plurality of rules organized into a plurality of nodes. In some aspects such a plurality of nodes may comprise a plurality of macro nodes, wherein each macro node is dedicated to a specific rule type and comprises a set of micro nodes. In some aspects, each micro node may comprise one or more rules which, when that micro node is run for a patient, are evaluated with data from the patient state object corresponding to the patient for which that micro node is run; have a single output instruction it could potentially issue upon being run; and have a local priority establishing an order in which it is run in the macro node it is comprised by.

In some aspects, a system comprising an ACE organized into a plurality of macro nodes comprising a plurality of micro nodes may have an ACE configured to perform a smart symptom tracker ("SST") session for a patient by performing a set of acts comprising: running each macro node from the plurality of macro nodes in a predetermined sequence, wherein, for each macro node, running that macro node comprises running the micro nodes comprised by that macro node for the patient for which the SST session is being performed in descending order of the local priorities of those micro nodes; adding all output instructions issued by the micro nodes comprised by the macro nodes while running the macro nodes in the SST session for the patient to a stack; and holding the output instructions issued by the micro nodes comprised by the macro nodes while running the macro nodes in the SST session for the patient in the stack until the SST session for the patient is concluded. Further, in some aspects, such a system may be adapted to after the SST session for the patient is concluded, provide the patient for whom the SST session was performed with information specified by the output instructions added to the stack during the SST session for the patient via an interface on a computing device associated with the patient for whom the SST session was performed.

In some aspects, the SST session may be a virtual SST session. In some aspects, in a system where the SST session is a virtual SST session, the ACE is adapted to evaluate, at initiation of the virtual SST session, a rule for modifying the patient state object corresponding to the patient for whom the virtual SST session is performed to indicate that the virtual SST session is in progress for that patient. Similarly, in some aspects, such a system may be configured to during performance of the virtual SST session for the patient, implement any modifications to the patient state object corresponding to the patient for which the virtual SST sessions is performed triggered by evaluation of rules during the virtual SST session. Also, in some aspects, in such a system the ACE may be adapted to conclude the virtual SST session for the patient by evaluating a rule for modifying the patient state object corresponding to the patient for whom the virtual SST session is performed to indicate that no virtual SST session is in progress for that patient. In some aspects, such a system may comprise an output instructions data structure comprising all output instructions which could potentially be issued by the micro nodes comprised by the macro nodes while running the macro nodes in the SST session for the patient. In some aspects, adding all output instructions issued by the micro nodes comprised by the macro nodes while running the macro nodes in the SST session for the patient to the stack comprises, for each issued output instruction, modifying information in the output instructions data structure for that output instruction to indicate that that instruction should be issued to the patient for whom the virtual SST session is performed. Similarly, in some aspects, providing the patient form whom the virtual SST session was performed with information specified by the output instructions added to the stack during the SST session for the patient may comprise: analyzing the output instructions which information in the output instructions data structure indicates should be issued to the patient for whom the virtual SST session was performed for conflicts; modifying information in the output instructions data structure for any conflicting output instructions to indicate that the conflicting instructions should not be issued to the patient for whom the virtual SST session was performed; and providing the patient for whom the virtual SST session was performed with information specified by the output instructions which information in the output instructions data structure indicates should be issued to the patient for whom the virtual SST session was performed. In some aspects, the output instructions data structure may be an array.

In some aspects, a system comprising an ACE organized into a plurality of macro nodes comprising a plurality of micro nodes may have the plurality of macro nodes comprise a macro node dedicated to triage instruction rules and first in a predetermined sequence. In some aspects, such a macro node may comprise a micro node comprising one or more rules which, when evaluated, could potentially issue an instruction to call 911, wherein the local priority of this micro node is greater than the local priority of all other micro nodes within the macro node dedicated to triage instructions; a micro node comprising one or more rules which, when evaluated, could potentially issue an instruction to call a physician, wherein the local priority of this micro node is greater than the local priority of all other micro nodes within the macro node dedicated to triage instructions, with the exception of the micro node comprising one or more rules which, when evaluated, could potentially issue an instruction to call 911; a micro node comprising one or more rules which, when evaluated, could potentially issue an instruction to take action if there is no improvement after 24 hours, wherein the local priority of this micro node is less than the priority of the micro node comprising one or more rules which, when evaluated, could potentially issue an instruction to call a physician but greater than the local priority of all other micro nodes within the macro node dedicated to triage instructions; and a micro node comprising one or more rules which, when evaluated, could potentially issue an instruction that no triage action should be taken, wherein the local priority of this micro node is less than the priority of all other micro nodes within the macro node dedicated to triage instructions.

Further, in some aspects, in such a system the plurality of macro nodes may further comprise a macro node dedicated to medication instruction rules and be second in the predetermined sequence. In some aspects, such a macro node may comprise: a micro node comprising one or more rules which, when evaluated, could potentially issue an instruction to use a medical device, wherein the local priority of this micro node is greater than the local priority of all other micro nodes within the macro node dedicated to medication instructions; and a micro node comprising one or more rules which, when evaluated, could potentially issue an instruction to take a medication, wherein the local priority of this micro node is greater than the local priority of all other micro nodes within the macro node dedicated to medication instructions, with the exception of the micro node comprising one or more rules which, when evaluated, could potentially issue an instruction to use a medical device. Additionally, in some aspects, the plurality of macro nodes could comprise a macro node dedicated to future instruction rules, wherein at least one micro node comprised by the macro node dedicated to future instruction rules comprises one or more rules which, when evaluated, could potentially trigger a future SST session after conclusion of the SST session being performed for the patient. In some aspects, in such a case the medical device may be a nebulizer, and the medication may be a steroid.

In some aspects, a system comprising an ACE comprising a plurality of rules might organize such a plurality of rules into a plurality of nodes wherein each node in the plurality of nodes: comprises one or more rules; has sequencing data indicating, when data is to be evaluated by rules from multiple nodes, an order of activation for the nodes comprising the rules by which the data is to be evaluated. In some aspects, such a system may be adapted to maintain node type data indicating, for each node from the plurality of nodes, types of data to be evaluated by rules from that node which, in some aspects, might be an index comprised by the ACE. Additionally, when a data item in a patient state object is updated, some systems comprising ACEs with rules organized in this manner may be configured to evaluate that data item with only the nodes indicated by the node type data as comprising rules for evaluating the data type of the data item updated in the patient state object. In some aspects, node type data may indicate a node as comprising rules for evaluating a particular data type by indicating either the node comprises rules which are specific to the particular data type, or the node comprises rules which are general rules applying to multiple data types.

In some aspects, a system comprising an ACE configured to perform an SST session may be adapted to, during the SST session, provide one or more prompts requesting information to the patient for whom the SST session is performed. In some aspects, a system comprising an ACE may be configured to use the ACE to flexibly react to patient data in a real time manner.

In some aspects, the disclosed technology could be used to provide a machine comprising: a means for creating, updating and maintaining a patient interface data set, wherein the means for creating, updating, and maintaining a patient interface data set is configured to receive data from a doctor; a means for responding to a patient event, wherein the means for responding to a patient event is configured to receive data from the patient interface data set and communicate with a patient; a means for controlling data, wherein the means for controlling data is configured to receive data from the patient interface data set and write data to a patient data set; a means for maintaining a patient state data set, wherein the means for maintaining a patient state data set is configured to receive data from the patient interface data set and write data to a patient status data set; a means for consolidating a set of relevant rules, wherein the means for consolidating a set of relevant rules is configured to receive data from the patient status data set and provide data to the means for responding to a patient event; and a means for delivering messages to patients, wherein the means for delivering messages to patients is configured to communicate with the means for responding to a patient event.

In some aspects, the disclosed technology could be used to provide a machine comprising: a means for gathering health information for, and providing trial and health information to, a patient; a means for providing patient information to, allowing patient information to be updated by, and plan creation and assignment by, a physician; a means for enabling enrollment of patients in trials and providing details on trial and trial volunteer status; and a means for automatically identifying patients as potential participants in trials.

In some aspects, the disclosed technology could be used to provide a system for presenting and allowing modification of health data regarding patients, the system comprising instructions stored on a non-transitory computer readable medium and operable to configure a computer to, when instructed, cause an outcomes chart for a selected patient to be presented to a user, wherein the outcomes chart displays outcomes data for the selected patient and events which have occurred for the selected patient based on data for the selected patient available to the system. In such a system, the events which the outcomes chart would display for a selected patient could comprise one or more of the following types of events: hospitalization events; SST session performance events; and physician intervention events. In some aspects, events displayed in the outcomes chart may be displayed as vertical lines with pictorial event type indications at their tops or bottoms. In some aspects, the outcomes chart may be operable by the user to interactively provide additional event information. In some aspects, it may be operable in this manner by, when the user selects a pictorial event type indication for a SST session performance event, providing the user with: questions asked during the SST session; answers given during the SST session; and final recommendations provided for the SST session. Additionally or alternatively, in some aspects, it may be operable in this manner by, when the user selects a pictorial event type indication for a hospitalization event, providing the user with: an identification of the hospital where the selected patient was admitted; and a date the selected patient was admitted to the hospital. Additionally or alternatively, in some aspects, it may be operable in this manner by, when the user selects a pictorial event type indication for a physician intervention event, providing the user with: the name of the physician who performed the physician intervention; the date on which the physician intervention was performed; and actions by the physician who performed the physician intervention.

In some aspects, an outcomes chart may be presented with a timescale operable by the user to specify time periods which should be used as limits for the outcomes data and events displayed on the outcomes chart. In some aspects, a system may be adapted to associate outcomes data with conditions, and an outcomes chart may be presented with a legend operable by the user to specify display parameters comprising: conditions for which outcomes data should be displayed; and types of outcomes data which should be displayed. In some aspects, in such a system, the legend may identify a plurality of conditions for which outcomes data could potentially be displayed in the outcomes chart, each condition identified in the legend may be associated with a different color, and for each condition identified in the legend, information regarding each type of outcomes data associated with that condition is displayed on the outcomes chart in a different shade of the color associated with that condition. Similarly, in some aspects, for each type of outcomes data displayed in the outcomes chart for the selected patient, the outcomes chart displays a corresponding axis indicating a scale at which information for that type of outcomes data is displayed, wherein the corresponding axis is displayed in the same color and shade as the information regarding the type of outcomes data to which it corresponds. Further, in some aspects, the system may be adapted to maintain information indicating whether a particular item of outcomes data was provided by a patient or a physician, the outcomes chart may be adapted to allow the user to view physician entered outcomes data separately from patient entered outcomes data, and axes corresponding to physician entered outcomes data may be displayed on the opposite side of the outcomes chart from axes corresponding to patient entered outcomes data.

In some aspects where an outcomes chart displays outcomes data for a selected patient, this display may be done by, for one or more types of outcomes data provided by the selected patient, using continuous lines displayed on the outcomes chart for those types of outcome data. Similarly, in some aspects where an outcomes chart displays outcomes data for a selected patient, this display may be done by, for one or more types of outcomes data comprising measurements indicating outcomes on a predetermined scale, displaying those types of outcomes data as a horizontal bar for each measurement with an indication on the bar reflecting the measurement's location on the predetermined scale. Additionally, in some aspects, an outcomes chart may be operable by the user to interactively provide additional outcomes data information by displaying a popup when the user: mouses over a continuous line used to display a type of outcomes data within a predetermined distance of a coordinate corresponding to a measurement of the type of outcomes data displayed using that continuous line; or mouses over an indication on a horizontal bar of the location on a predetermined scale of the measurement corresponding to that horizontal bar. In some aspects, an outcomes chart may be continuously updated with new outcomes data and events so that it provides a real time reflection of the latest data for the selected patient.

In some aspects, an outcomes chart may be displayed as part of a patient profile for a selected patient. In such a case, the patient profile for the selected patient is presented as part of a portal for a research coordinator for a pharmaceutical research trial, and the patient profile may comprise, in addition to the outcomes chart, a status indicator indicating the progress of the selected patient in enrollment for the pharmaceutical research trial. Similarly, in some aspects, an outcomes chart displayed as part of a patient profile may be presented as part of a portal for a physician providing health care for the selected patient as a health care provider, and the patient profile may be operable by that physician to submit health information for the selected patient to be stored and made accessible by the system.

BRIEF DESCRIPTION OF THE DRAWINGS

The drawings and detailed description which follow are intended to be illustrative and are not intended to imply limitations on the scope of embodiments or potential implementations of the disclosure set forth herein.

FIG. 8A is placed directly above FIG. 8B the two figures together form a complete image, illustrate at a high level certain logic nodes which could be included in some embodiments which implement a state controller engine.

FIG. 14 illustrates global instruction data structures and certain interactions they could be involved in.

FIG. 116 illustrates an interface which could be used for physician outcome entry.

DETAILED DESCRIPTION

Figure 1:
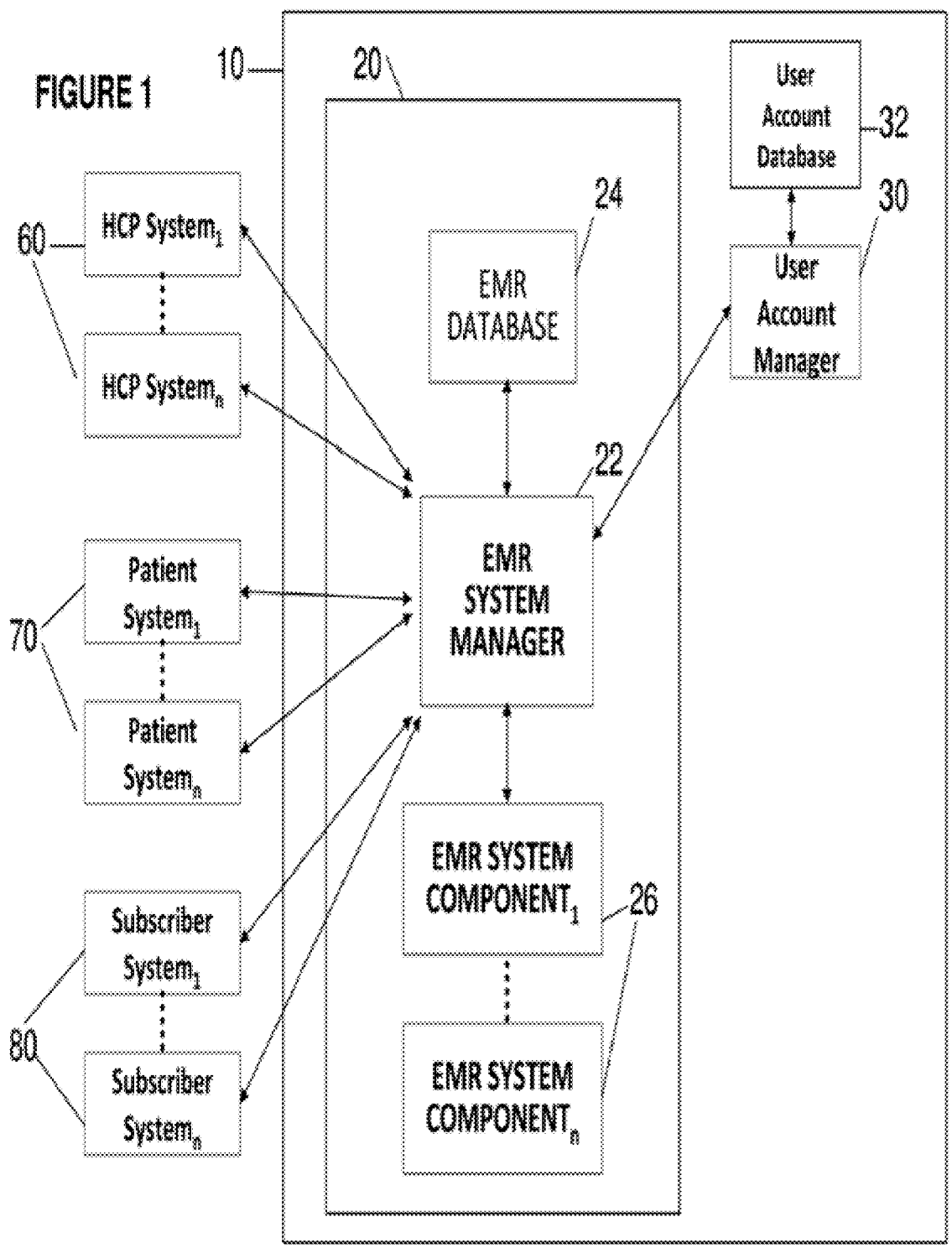
FIG. 1 presents an exemplary high level architecture in which a centralized EMR system serves as a focal point for interactions between a variety of different entities.
Figure 2:
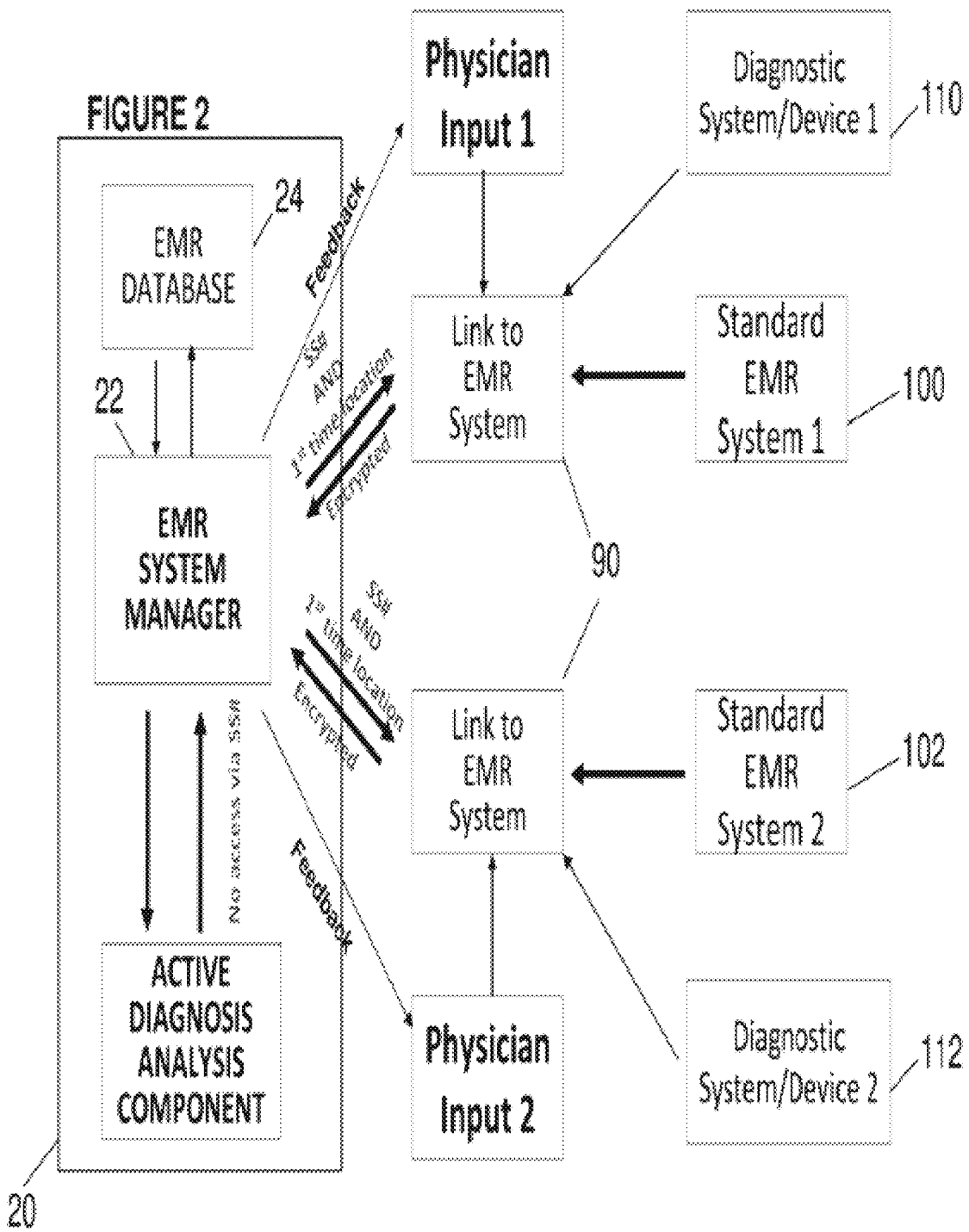
FIG. 2 provides an exemplary high level architecture in which information from external systems such as standard EMR systems can be provided to, and feedback can be received from, a centralized EMR system.
Figure 3:
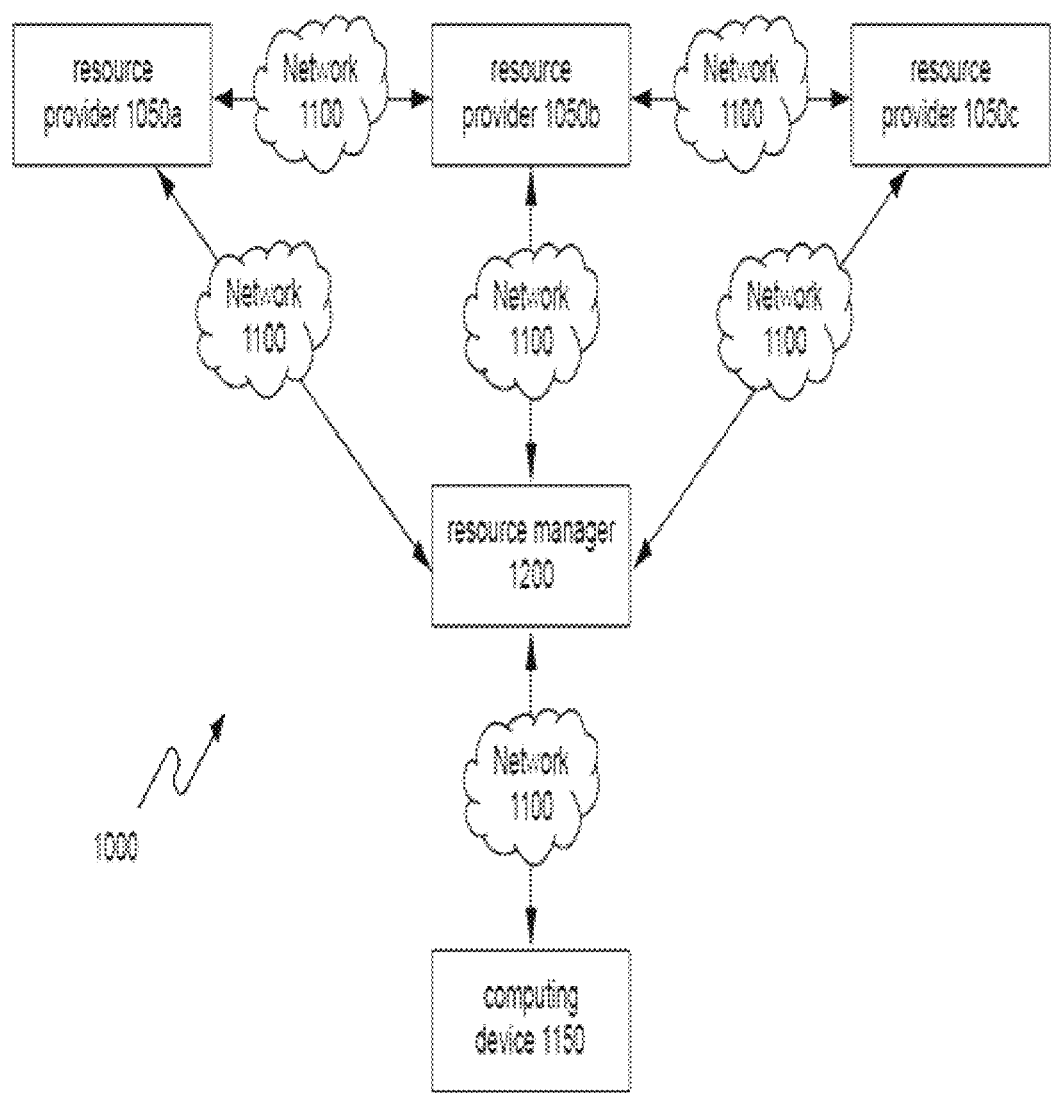
FIG. 3 provides an exemplary high level architecture of a cloud computing environment which could be used in implementing aspects of the disclosed technology.

As will be immediately apparent to those of ordinary skill in the art in light of this disclosure, the technology described in this document can be implemented in a variety of different manners, and using a variety of different architectures. FIGS. 1-3 illustrate architectures which could be used in such implementations. However, it should be understood that other architectures could potentially be used without undue experimentation by those of ordinary skill in the art when implementing aspects of the disclosed technology. Accordingly the architectures of FIGS. 1-3 should be understood as being illustrative only, and should not be treated as implying limitations on the protection accorded by this, or any related, document. It should also be understood that aspects of the disclosed technology may be implemented as an apparatus, machine, computer program product, or combination of any one or more of the foregoing. For example, and without limitation, aspects of the disclosed technology could be implemented at least in part in the form of a computer readable medium having computer-executable instructions stored thereon. It would be understood that a computer readable medium could be non-volatile (retains the stored information even if it is not constantly supplied with electric power) or volatile (requires power to maintain the stored information). Examples of computer readable media that could be used include, but are not limited to, random access memory (e.g., dynamic random access memory, static random access memory), read only memory, non-volatile random access memory, flash memory, hard disk, optical disk, USB flash drive, memory card, and magnetic tape. A computer readable medium could be the main memory of a computer or could be a secondary memory. It would also be understood that health data collected or used by a system implementing the disclosed technology could be stored on a computer readable medium, e.g., in a database.

Turning now to the figures, FIG. 1 presents an exemplary high level architecture in which a centralized electronic medical record ("EMR") system 20, serves as focal point for interactions with a variety of different entities. In an architecture such as shown in FIG. 1, the EMR system 20 can be a system which handles (e.g., receives, analyzes, stores and/or transmits) health information (which term is used interchangeably herein with the term "health data"). The entities (e.g., individuals) which would interact with such a system could include health care providers ("HCPs") and patients and could further include subscribers (e.g., researchers or others who have purchased a subscription to be able to use de-identified health data from the EMR system 20). As shown in FIG. 1, these entities can interact with a centralized EMR system 20 using their own local systems. For example, a physician or other HCP could access the centralized EMR system 20 using a HCP system 60 in the form of a desktop computer which could access a web interface made available via an EMR system manager 22 (discussed infra). Similarly, a patient could access the centralized EMR system 20 via an application on a patient system 70 taking the form of a smartphone, tablet computer or similar device on which the application had been installed. Likewise, a subscriber could access the centralized EMR system 20 through use of a subscriber system 80, which could, for example, be a desktop computer or take the form of a dedicated research terminal. It should be understood that some implementations may not include subscriber systems. While not depicted on FIG. 1, caregivers (who might be family or friends of a patient or might be individuals for whom caregiving is an occupation) could also interact with system 20. Such interaction might be via an application on a patient system or via an application on a caregiver system, which might take the form of a smartphone, tablet computer or similar device on which the application had been installed.

Implementations of the disclosed technology which follow the architecture of FIG. 1 will often have the capability of supporting an arbitrary (within reason) number of interactions with patients, HCPs, and subscribers. This is shown in FIG. 1 through the use of the subscripts 1-n on the HCP Systems 60, Patient Systems 70, and Subscriber Systems 80. Additionally, the disclosed technology may be implemented in such a manner that the use of specific types of HCP Systems 60, Patient Systems 70 and Subscriber Systems 80 will not be required for interactions with a centralized EMR system 20. For example, while the preceding portion of the disclosure listed particular types of computers (i.e., desktop computers, tablet computers, smartphones, dedicated terminals) for use by different entities in interacting with an EMR system 20, an implementation following FIG. 1 may in some embodiments allow any type of computer to support any type of user interaction (e.g., a patient could interact with the EMR system 20 using a dedicated terminal, a physician could interact with the EMR system 20 using a smartphone to which an appropriate application had been downloaded, etc). Accordingly, the discussion of the various types of entities which could interact with a centralized EMR system 20 in an implementation following the architecture of FIG. 1, as well as the examples of systems which could support those interactions, should be understood as being illustrative only, and should not be treated as limiting. It should also be understood that the principles described herein regarding the various types of entities which could interact with a centralized EMR system 20 also apply in the case of other systems that could be implemented using aspects of the disclosed technology. It should also be understood that a system implementing one or more aspects of the disclosed technology could provide suitable applications and/or user interfaces through which the various users could interact with the system. Different applications and/or user interfaces may be provided that are suitable for use by different types of users (e.g., to support the features and functionality provided to such users). For example, a system could provide an application suitable for use by HCPs (sometimes referred to herein as an "HCP application") and an application suitable for use by patients (sometimes referred to herein as a "patient application"). A system could provide an application suitable for use by other types of users such as caregivers and/or subscribers. Of course it should be understood that an HCP application could in some instances be used by non-HCPs as well as by HCPs. For example, such an application could be used by authorized individuals who work under the direction of an HCP. Likewise, a patient application could in some instances be used by a patient's caregiver or other individual on behalf of the patient. Different applications and/or user interfaces may be provided for different types of computer and/or for computers with different operating systems. It should also be understood that aspects of the disclosed technology could take the form of one or more web applications that could be used on any computer running a compatible browser. The disclosed technology could be used by HCPs of various types, such as physicians, nurse practitioners, physician assistants, nurses, physical therapists, nutritionists, psychologists, and dentists. Where the present disclosure refers to use of the disclosed technology by a physician it should be understood that such description could apply to use of the disclosed technology by HCPs of any type.

As shown in FIG. 1, an EMR system 20 can be made up of multiple components, such as an EMR system manager 22, an EMR database 24, and one or more additional EMR components 26 labeled in FIG. 1 as EMR component$_1$— EMR component$_n$. In an EMR system 20 of the type shown in FIG. 1, the EMR system manager 22 could be used for managing communications and/or interactions. These communications and/or interactions could be either internal to the EMR system 20 (i.e., communications and/or interactions between various components of the EMR system 20 itself), external to the EMR system 20 (i.e., communication and/or interactions between the EMR system 20 and users or external systems), or both. For example, an EMR manager 22 may receive health information from an HCP, transfer the health information to an EMR component 26 for analysis, receive a response from the EMR component 26, and/or transmit the response to a user. An EMR manager 22 might also (or alternatively) include or interface with a database management system ("DBMS") for an EMR database 24. For example, an EMR manager 22 might (via a DMBS) extract information from an EMR database 24 in response to a request from a user, or might add data to the EMR database 24, either in response to a request from a user or in other circumstances (e.g., after the data has been analyzed and approved by a EMR component 26).

Moving on from the discussion of the EMR manager 22, as shown in FIG. 1, an EMR system 20 can also include additional EMR components 26. In some embodiments, these will include an analysis component that analyzes health information received by the EMR system 20. Such analysis may include, for example, determining whether information submitted by an HCP is adequate to meet some predefined set of criteria (e.g., by verifying that a form submitted by an HCP includes all expected information, verifying that a diagnosis submitted by an HCP is accompanied by sufficient diagnostic information for the diagnosis to be reliable, etc). Such an analysis component may provide feedback based on its analysis, which feedback could in turn be transmitted to the user. This feedback could take a variety of forms including, for example, a message to an HCP requesting submission of additional information to validate a diagnosis, or an alert to a patient indicating that information he or she had provided indicates a condition which the patient should take some action to address.

EMR components 26 may also include (either as part of an analysis component or as a separate component) a query component that analyzes and/or processes queries from users (e.g., HCPs, patients, subscribers). For example, such a query component may convert a raw query (e.g., a natural language query) into a format acceptable to a DBMS. EMR components 26 may also (or alternatively) include a clinical decision support system component (CDSS) or an interface thereto, a computerized physician order entry component or an interface thereto, a billing component or an interface thereto, and/or a scheduling component or an interface thereto, etc. EMR components 26 may include one or more components that interface with an application running on a portable electronic device, either directly, or through an EMR manager 22 as described above.

As shown in FIG. 1, an EMR system 20 can be included as part of a larger system 10 which could also include various ancillary components, such as a user account manager 30. A user account manager 30 could also or alternately be an integral component of EMR system 20. In implementations where it is present, such a user account manager 30 may perform any of a variety of functions connected with the administration of user accounts, such as the establishment, maintenance, and/or updating of those accounts. For example, a user account manager 30 may perform functions such as receiving registration information from users, assigning user IDs or passwords, checking login information received from users, etc. User account manager 30 may maintain and/or interface with a user account database 32, which stores user account data. User account manager 30 may be responsible for storing information in, and extracting information from, such a user account database 32, and may also perform similar functions such as analyzing that information or transmitting it to other system components. User account manager 30 may also (or alternatively) have at least partial responsibility for comparing login credentials supplied by users against information stored in user account database 30 and instructing EMR manager 22 to provide, limit, or deny access to the EMR system 20 or portions thereof based at least in part on that comparison. User account manager 30 may also perform other types of tasks related to user accounts or the subscriptions of the associated users (e.g., billing subscribers, transmitting renewal reminders to subscribers, monitoring and controlling use of the EMR system 20 by subscribers, etc.).

Turning now to FIG. 2, that figure provides an exemplary high level architecture in which information from external systems such as standard EMR systems 100 102 can be provided to, and feedback can be received from, a centralized EMR system 20. As shown in FIG. 2, a centralized EMR system 20 may interact with various external systems via links 90 with one or more networks. These external systems may each include one or more computers that may or may not be in communication with one another, though preferably each such system in an implementation following the architecture of FIG. 2 will include at least one device that is capable of communicating with the centralized EMR system 20. Examples of these external systems include (but are not limited to) a computer located in a physician's office (or elsewhere in a health care facility), a computer located in a facility that performs clinical chemistry tests (or any other type of medical tests), a computer that interfaces with or is part of a medical imaging system (or any system used to perform medical tests), a standard EMR system (e.g., a commercially available computer program product for the creation or maintenance of EMRs, such as those listed on the website of the Certification Commission for Health Information Technology or other similar certification body) or a system in which a standard EMR (i.e., an EMR created using a standard EMR system) is stored, a pharmacy system, an electronic prescription system, a practice management system, an appointment scheduling system, a medical billing/ claims system (which term refers to a system that performs one or more functions relating to payment for health care (such as generating, submitting, transmitting, processing, or analyzing medical bills or claims for reimbursement for health care services), etc. In some embodiments communication between EMR system 20 and one or more external systems may take place over the Internet.

In an implementation following the architecture of FIG. 1 or FIG. 2, information provided to an EMR system 20 could include a variety of types of information, such as administrative information and health information. For example, in some implementations, in order to establish or access an EMR for a patient, the HCP may be required to enter the patient's social security number ("SS #") (or other identifier), which could then be transmitted to the EMR system 20 in encrypted form. Similarly, an HCP could send various types of health information to the EMR system 20, such as by entering it into the EMR system through a form or similar tool, by having it sent directly from one or more external EMR systems 100 102 via an interface provided by the EMR system 20. In response, the EMR system 20 could provide various types of feedback to the HCP. For example, in response to an HCP providing a SS # (or other information which could identify a particular patient, such as an alternative identifier assigned to the patient for use instead of a SS #) the EMR system 20 could provide feedback in the form of a message indicating whether there was already information for that patient available from or through the EMR system 20. Similarly, in response to an HCP providing information on a recommended treatment for a patient, the EMR system 20 could provide feedback in the form of an alert which could make the HCP aware of a possible interaction between the recommended treatment and a medication which the patient had previously been prescribed. In some embodiments EMR system 20 could additionally or alternately receive information from external systems (e.g., external EMR systems) without requiring action on the part of an HCP. Information entered into an external system may, for example, be automatically transferred to EMR system 20. Such transfer may, for example, occur on a predetermined basis (e.g., daily or weekly) or may be triggered as a consequence of health data being entered into the external system. Additionally or alternatively, EMR system 20 may periodically send requests for updates to external systems.

Thus in many implementations EMR system 20 would not be limited to only receiving data which was entered directly by an HCP or which was already present in some standard EMR system 100 102. For example, as shown in FIG. 2, health information might also be provided to an EMR system 20 by one or more systems or devices (exemplified as diagnostic systems or devices 110 112 in FIG. 2). Such systems or devices could include any of a wide variety of monitoring devices, e.g., personal monitoring devices (e.g., activity tracking devices, diagnostic devices), environmental monitoring devices (e.g., in a patient's indoor environment), etc. For example, software running on a patient mobile device (e.g., a patient's smartphone) could communicate (e.g., via Bluetooth) with a fitness tracker or consumer diagnostic device (e.g., a home glucose monitor) and upload information retrieved from that fitness tracker or consumer diagnostic device to a record for that patient maintained in the EMR database 24 of the EMR system 20. It should be understood that a patient's computer (e.g., smartphone or other portable computing device) or its case may itself serve as a monitoring device. Suitable sensors may be incorporated into the housing of a patient's computer (e.g., smartphone or other portable computing device) or its case. In some embodiments, health information might be uploaded to a server associated with a monitoring device and then provided to an EMR system 20. Various types of health information entry (e.g., via a physical or virtual keyboard, through use of a mouse or other computer pointing device, orally (such as by dictation) through speech recognition software, etc.) could be supported and will be immediately apparent to those of ordinary skill in the art in light of this disclosure. Accordingly, the examples shown in FIG. 2 and provided in the accompanying discussion should be understood as being illustrative only, and should not be treated as limiting. It should also be understood that the examples of external systems and devices shown in FIG. 2 and provided in the accompanying discussion, as well as the types of data that could be obtained from and/or provided to such systems and devices, are illustrative only and should not treated as limiting. Additional or alternative systems, devices, and/or sources of health data could be utilized, and the protection provided by this or any related document should not be limited in this respect. Examples include a practice management system, an appointment scheduling system, a medical billing/claims system (which term refers to a system that performs one or more functions relating to payment for health care (such as generating, submitting, transmitting, processing, or analyzing medical bills or claims for reimbursement for health care services)). In some aspects, the disclosed technology can be used for purposes such as collecting, maintaining and using information relating to payments for health care. For example, bills or claims for reimbursement for health care services could serve as a source of data indicating, for example, that such health services had been provided to a patient. Other sources from which health data may be obtained could include, for example, government or non-government entities that collect environmental data (such as outdoor temperature, levels of pollen or pollutants), population-based data, or epidemiologic data (such as data about the incidence or prevalence of infectious diseases).

Data collected by or provided by a system implementing the disclosed technology could include one or more time stamps. A time stamp could indicate when a particular measurement was made or when a particular input was entered or received.

Turning now to FIG. 3, that figure provides an exemplary high level architecture of a cloud computing environment 1000 which could be used in implementing aspects of the disclosed technology. For example, in an implementation using an architecture such as shown in FIG. 3, an EMR system 20 could be implemented, e.g., in a redundant manner, using various physical components (e.g., databases, servers, etc) managed by one or more resource providers 1050a 1050b 1050c (collectively, 1050). Such resource providers 1050 could provide various hardware and/or software resources used to process data (such hardware and/or software resources being referred to as "computing resources") and could be connected to each other in the cloud computing environment 1000, or could (additionally or alternatively) be connected with one or more computing devices 1150 over a computer network 1100.

To facilitate interaction with the various resource providers, the cloud computing environment of FIG. 3 also includes a resource manager 1200. Such a resource manager 1200 could have a role in the cloud computing environment 1000 similar to that of the EMR manager 22 in the EMR system 20. For example, in operation, a resource manager 1200 might receive a request for a computing resource from a computing device 1150 (e.g., a mobile computing device operated by a patient). It might then respond to this request by identifying one or more resource providers 1050 capable of providing the requested resource (e.g., if the patient requested stored information regarding his or her health, this identification might include determining which resource provider provided storage for health information which could be linked with particular patients) and establishing a connection between one of the capable resource providers 1050 and the computing device 1150 from which the request had been received. In this way, despite the possibility that numerous physical devices might be involved in providing different functionality, the implementation complexity can be hidden from, and therefore be irrelevant to, the various types of end users (e.g., HCPs, patients, etc).

While the discussion of the architectures of FIGS. 1-3 focused on the collection and accessing of health information in the form of EMRs, in some embodiments the disclosed technology could include functionality in addition to (or as an alternative to, as a component of, or independently of) the EMR centralization and retrieval technology which was the focus of the discussion of FIGS. 1-3. As an example of such functionality, consider the possibility of providing condition specific health tracking and management plans. In this document, these plans are referred to variously as T-Plans (treatment plans) or D-plans (data plans), with the terms T-Plan and D-plan being understood as being alternative terms for the same thing. These plans will preferably be assigned by an HCP to a patient and will be stored in a database, e.g., a database similar to that discussed previously with respect to EMRs, thereby providing a convenient way to make it possible for some or all of a patient's HCPs to be able to determine what plans had been assigned to him or her. After being assigned, D-Plans could be used for purposes such as facilitating the collection of data, helping ensure the patient's compliance with a treatment or maintenance program provided by the HCP, and/or facilitating care coordination among multiple HCPs of a patient, to name a few, though, as set forth below, the specific functionality of a D-Plan and the uses to which it could be put will be determined at least in part by the D-Plan's modules, and may vary from case to case.

A system that provides D-Plans, which may be referred to as a "D-Plan system" could have an architecture analogous to the architecture depicted in FIG. 1 wherein a system 20 communicates with multiple HCP systems and multiple patient systems (which could comprise any of the types of computers described above) or an architecture analogous to the architecture depicted in FIG. 2 wherein system 20 also communicates with one or more additional systems that could obtain or store health data of various types or otherwise serve as sources of health data. Such systems or devices could include any of a wide variety of monitoring devices, e.g., personal monitoring devices (e.g., activity tracking devices, consumer diagnostic devices), environmental monitoring devices (e.g., in a patient's indoor environment), etc., as described above in regard to FIGS. 1 and 2. In certain implementations, patients would interact with a D-Plan system using a mobile computing device or desktop computer and HCPs would interact with a D-Plan system using a desktop computer. Alternately or additionally, HCPs may interact with a D-Plan system using a mobile computing device. A D-Plan system could be implemented using a cloud computing environment such as that shown in FIG. 3. A D-Plan system could be implemented independently of an EMR system. In some embodiments such a D-Plan system may communicate with one or more EMR systems, e.g., an EMR system such as EMR system 20. A D-Plan system could obtain data from an EMR system, provide data to an EMR system, or both. A HCP might interact with a D-Plan system using the same computer that he or she uses to interact with an EMR system. Alternatively or additionally, a D-Plan system could be implemented as part of an EMR system, e.g., as part of an EMR system such as EMR system 20.

A D-Plan system could perform any of a wide variety of functions relating to D-Plans. A D-Plan system may, for example, provide functions that permits HCPs to use predetermined templates ("D-Plan templates") to generate D-Plans for patients and to assign such D-Plans to their patients (prescribe D-Plans). For example, a physician who has a patient with a particular condition might assign a D-Plan for that condition to the patient. A D-Plan system may additionally provide other functions such as permitting HCPs to enter data describing patient characteristics (e.g., conditions that the patient has, risk factors for various conditions (such as smoking), etc.), create a patient profile with such characteristics, customize D-Plans for individual patients, create and save new D-Plan templates, etc.

While the disclosed technology will preferably be implemented in a manner which is flexible with respect to the types of modules which would be included in a D-Plan, it is expected that most implementations will have certain types of modules which are present in some (if not all) of their D-Plans. These types of modules can include data collection modules which specify one or more particular type(s) of data to collect (e.g., physiological data such as "weight" or "blood oxygen saturation", health care event data (e.g., data relating to predefined health events, such as results of medical tests) and might also specify a timing (e.g., a frequency) for collecting data of a particular type and modules which provide recommendations (sometimes referred to herein as directions or instructions or advice) to a patient in response to particular health data input by a patient or obtained from monitoring devices. For example, if health data indicate that a clinically significant health change has occurred, the system could recommend to the patient to seek medical attention and/or to take appropriate medication(s). D-Plan modules may further include educational modules which specify educational material to provide to a patient. D-Plan modules may alternatively or additionally include health care event modules which specify particular health care events that have been recommended or prescribed to a patient by a physician. Health care events might include, for example, patient events and/or physician events (as further described below). D-Plan modules might include data collection modules that collect data confirming the occurrence of such health care events and/or collect data arising from such health care events (e.g., results of medical tests). D-Plan modules may also include modules with instructions which could be used in supporting the functions to be provided by those modules for the D-Plan. For example, a data collection module for "blood oxygen saturation" could include data which would cause a computer (e.g., a smartphone running an application which configures it to present questions for a patient) to provide a prompt such as "what is the reading on your pulse oximeter," or to search for and (if found) establish a connection with a patient's pulse oximeter so that the patient's blood oxygen saturation could be obtained directly from that device.

A D-Plan system may configure a D-Plan for a particular condition using a D-Plan template for that condition. Contents of the D-Plan (e.g., the particular modules included in it, particular details of the modules, or both) may be selected based on the condition and, in some embodiments, on patient characteristics. For example, a patient with a particular condition could be assigned a D-Plan for that condition, comprising one or more modules for collection of health data relevant to the condition. A data collection module might, for example, specify collection of physiological data, behavioral data, symptom data, and/or environmental data relevant to the condition. It might specify collection of data elements of a single data element type or multiple different data element types. A D-Plan could also or alternatively include one or more modules for collection of health data, e.g., physiological data, symptom data, behavioral data and/or environmental data pertaining to a patient characteristic relevant to the condition. A D-Plan could also or alternatively include one or more education modules containing educational material relating to the condition or to a patient characteristic that is relevant to the condition. Patient characteristics may be entered by a HCP or otherwise available to the system (e.g., through entry by a patient or from an external system). The D-Plan system may provide a predetermined list of patient characteristics relevant to a particular condition from which a HCP could select those that apply to a particular patient to whom a D-Plan for that condition is assigned. The D-Plan could then be automatically configured to collect health data relating to such characteristics and could take such characteristics into account in the recommendations provided by it.

Data collected according to a D-Plan could be obtained from a patient (or the patient's environment) while the patient is not hospitalized, between the patient's encounters with his or her HCP, and made available to the HCP by the system, thus providing a way for the HCP to gain insight into the patient's health and behavior during the patient's daily life. The system could provide data at least in part in the form of graphics such as plots, charts, etc. Data could also be made available to the patient by the D-Plan system. In some embodiments at least some of the content of a D-Plan assigned to a patient by a patient's HCP, data collected according to a D-Plan, or both, can be viewed by one or more other HCPs who provide care to the patient. For example, the system may provide such HCPs with ability to view a list or description of the D-Plan's modules, data collected by one or more of the D-Plan's data collection modules, or both. Such functionality could be used by HCPs with whom a patient has an existing ongoing relationship, HCPs who may not be familiar with the patient's history (e.g., HCPs who may be seeing the patient for the first time such as HCPs to whom a patient has been newly referred, HCPs in urgent care clinics or emergency rooms, HCPs providing care when a patient's regular HCP is not available, etc.). A D-Plan system might be used by emergency response personnel or other individuals who may need or want to rapidly obtain information regarding the patient's health status or health data.

To illustrate how D-Plans might be assigned and used in patient health care, consider a hypothetical 78 year old patient who has been diagnosed with chronic obstructive pulmonary disease (COPD) and diabetes and who smokes cigarettes. Such a patient could be assigned a D-Plan for COPD by a HCP, perhaps by a specialist in pulmonary medicine. The D-Plan could include one or more modules for collection of health data relevant to COPD, e.g., physiological data such as blood oxygen saturation, behavioral data such as number of cigarettes smoked per day. The D-Plan could also include one or more educational modules containing educational material about COPD. The D-Plan could include an educational module containing educational material relevant to smoking, such as educational material about health risks of smoking or about smoking cessation.

Of course, it should be understood that the separation of D-Plan modules into separate types which perform functions such as collecting data and specifying recommendations to patients in response to health changes is intended to be illustrative only, and that a wide variety of organizations of D-Plan modules is possible. For example, some implementations may include a module (referred to as Smart Symptom Tracker, or "SST"), which could include instructions for collecting data, analyzing that data, and making recommendations or taking actions based on the results of that analysis. In some implementations where they are provided, these SSTs would be condition specific, so that they could easily be added to a D-Plan for a patient based on an HCP's evaluation of the patient's health (e.g., based on a condition that the patient has been diagnosed as having). The data that could be collected by an SST would typically, though not necessarily, include symptom data. Additionally or alternatively, data collected by an SST could comprise other types of health data such as physiological data, behavioral data, environmental data, or other types of data that could be useful in evaluating a patient's health status and determining recommendations. Thus, while the discussion herein of SSTs refers primarily to symptom data, it should be understood that the discussion applies equally to other types of health data. The SST could encode medical knowledge regarding a particular condition, e.g., regarding the significance of particular symptoms, signs, and other types of health data in the context of providing appropriate recommendations to a patient for managing that condition. Such knowledge could be obtained, for example, from health care providers with appropriate training and/or expertise, e.g., HCPs who practice in the specialty that would typically care for patients having the particular condition. In some implementations, recommendations provided by a system could be categorized as "triage" recommendations and "medication" recommendations. A triage recommendation would generally recommend a particular action with regard to seeking medical attention (e.g., seek immediate medical attention, call 911, call your physician, call your physician if your condition does not improve within X hours (for example)). Of course if the system determined that the patient is not in need or potentially in near-term need of medical attention, the system could inform the patient accordingly. A medication recommendation would specify one or more medications that a patient could use (or other patient self-management actions that a patient could take). A patient would typically receive a single triage recommendation at a particular time (though in some instances multiple triage recommendations could be provided if appropriate). A patient could additionally or alternately receive one or more medication recommendations.

To illustrate the role a condition specific SST might have in the management of a patient's health, consider the case of a patient with chronic obstructive pulmonary disease ("COPD"). Such a patient could be assigned a SST designed at least in part to detect a COPD exacerbation, or detect a deterioration that may develop into a COPD exacerbation. This SST (referred to as a "COPD exacerbation SST," though other names could be used as well), could provide instructions which would cause a mobile device used by the patient to perform an interactive health evaluation (e.g., asking questions such as "are you more short of breath than normal", asking the patient to enter physiological data (e.g., measurements of physiological variables) or obtaining such measurements from a personal monitoring device, or both), and then use the results of that evaluation to recommend courses of action to the patient. Such recommendations could include, for example, "I would like you to take one dose of medication X, and call your physician for an appointment" or "you should see a doctor immediately, as the information you have provided may indicate an exacerbation requiring immediate attention." In this way, by assigning a single condition specific SST, an HCP could ensure that the patient's D-Plan included gathering, evaluating and taking actions on, data relevant to the patient's condition. Of course it should be understood that a D-Plan for a particular condition could automatically be configured to include one or more SSTs designed to detect clinically significant health changes relevant to that condition.

Of course, while the above description focused on SSTs which are used (e.g., would be included in D-Plans) for particular conditions, it is possible that some implementations of the disclosed technology could include SSTs which could be used for multiple conditions, or even by multiple health care providers in multiple disciplines. For example, in some implementations, there could be an SST for arrhythmias, which, because arrhythmias are clinically significant for a variety of cardiac disorders, could be included in D-Plans for multiple cardiac conditions. By contrast, a COPD exacerbation SST such as described above would more likely be used in D-Plans for COPD, though their use is not limited to such D-Plans. (For example, a COPD SST might be used in a D-Plan for a different condition, where it might be important to distinguish a COPD exacerbation from an exacerbation of the different condition.) Other relationships, such as where multiple SSTs might be included in a D-Plan for a single condition (e.g., where a particular condition renders a patient prone to multiple distinct types of clinically significant occurrence, in which case a D-Plan for that condition could include a SST for each of those types of occurrence) are also possible and will be immediately apparent to those of ordinary skill in the art. Thus, the discussion above of potential implementations and organizations for SSTs (or other types of modules) within D-Plans should be understood as being illustrative only, and should not be treated as limiting.

It should also be understood that the functions (e.g., collecting data, analyzing that data, and making recommendations or taking actions based on the results of that analysis) of two or more SSTs designed to detect different types of health changes that might occur in patients with a given condition or that might occur in patients with different conditions or in a patient with two or more conditions could be included in a single SST. Such an SST could be designed so as to take into account the potential for overlap between symptoms and signs associated with certain health changes that could occur in the same or different conditions or to distinguish between different health changes that could occur in a single condition. For example, a patient with multiple different conditions could potentially have symptoms that could indicate an exacerbation of either or both of two (or more) conditions. A single SST could be designed to be able to detect an exacerbation of either type.

It should also be understood that in some instances an SST included in a particular D-Plan might analyze and make recommendations based on analysis of data collected by one or more other modules of that D-Plan or data collected by module(s) of one or more other D-Plans assigned to the patient in combination with or instead of data collected by that SST. Such an instance might occur, for example, if other module(s) had already collected some or all of the data required or desirable for the SST to analyze for purposes of making a recommendation (and such data was collected sufficiently recently to remain valid for such purpose). In some instances, execution of an SST might be triggered by the detection of an abnormal value for an element of health data. For example, entry of an abnormally low value for blood oxygen saturation (which could be a sign that a patient is experiencing an exacerbation of a condition that affects breathing such as COPD or asthma) might trigger an SST that collects additional data that could be used to determine whether the patient is having such an exacerbation, analyze the data, and provides a recommendation to the patient based on the analysis. In some instances, a system could provide the patient with the option of executing an SST at any time. A patient might, for example, choose to execute an SST if the patient was concerned about particular symptoms or other health data (e.g., physiological data).

Recommendations to be provided to a patient by a D-Plan system (e.g., by an SST) could have been approved for that patient by the patient's HCP as part of the process of assigning the D-Plan to the patient, which process could include selecting particular medications that the patient would be recommended to use.

As described above, D-Plans can be specialized through the inclusion of appropriate modules for a D-Plan's condition. However, other types of specialization are also possible, and could be supported by a system implemented using the disclosed technology. For example, in some implementations, a base set of D-Plans and/or associated modules might be provided, and HCPs might be given the option of either using the base D-Plans/modules or customizing them for their own use or use by others. These customizations could include adding or removing particular modules or portions thereof, selecting a specific medication from a group of medications, modifications to prompts and/or recommendations which could be provided in performance of a D-Plan (e.g., in execution of an SST) to include the name of the specific patient to whom the D-Plan is assigned, the name of the HCP assigning the D-Plan, or different wording which the HCP believes would be better received or understood by his or her patient population (or any particular patient).

Similarly, in some implementations, the manner for actions to be taken in performing a D-Plan might also be customizable. To illustrate this potential feature, consider the case of an SST which encodes specialized knowledge relevant to a particular condition in the form of weights for symptoms represented by information the SST would collect. In such a case, the SST could use the weights of the symptoms indicated by a patient to determine the urgency of the patient's condition and the recommendations which should be given to him or her (e.g., if the combined weights of the patient's symptoms exceed a threshold for a high priority situation, the patient could be given a message to seek immediate medical attention (e.g., advised to call 911); if the combined weights exceeded a medium priority threshold but did not reach the high priority threshold, the patient could be advised to make an appointment with his or her health care provider, etc.). A doctor might customize the SST by modifying the weight values for particular symptoms, or by changing how those weight values would determine what instructions should be provided (e.g., changing thresholds for determining whether the patient was in a high priority situation). Assigning weights or modifying weights could be performed automatically by the system, e.g., based on physician input. For example, a physician might specify particular health data or combinations thereof that would cause the physician to recommend a particular course of action to a patient. The system might use such input to assign or modify weights. It should be understood that assigning weights to symptoms or other health data and using such weights to determine instructions is but one approach that could be used in implementing an SST.

Of course, other types of customizations are also possible, and could be implemented without undue experimentation by, one of ordinary skill in the art in light of this disclosure. For example, in a case where an SST reflects specialized knowledge relevant to a condition in the form of a decision tree tying specific statements to particular information a user might provide, customization of the SST could be supported through allowing HCPs to modify the structure of the decision tree or the particular types of information which would cause the SST to traverse its particular branches. Accordingly, the discussion of customization through modification of weights assigned to symptoms or statements which could be provided to a patient should be understood as being illustrative only, and should not be treated as limiting.

While the above discussion of D-Plans focused on how the disclosed technology can provide functionality which would interact directly with a patient to help support his or her health care and/or maintenance, it is possible that the disclosed technology could be used to implement a system which would support similar or additional functionality, which might in some instances be useful for other types of user, as well (or as an alternative to the D-Plans described previously). To illustrate, consider a data structure, referred to as an active diagnosis module ("ADM"), which could be used both to aggregate a patient's health data relevant to a particular condition, and provide one or more schedules comprising condition-relevant events and the times at which such events could take place. Such schedules could include, in addition to, or as alternatives to, actions or behaviors a HCP recommends to a patient as part of patient self-management (referred to herein as "patient events"), actions to be performed by the physician or other HCP or which would otherwise take place in a health care setting (referred to herein as "physician events"). Patient events could include, for example, taking medications, making or attending appointments for follow-up visits with an HCP, making or attending appointments for medical tests such as imaging studies or clinical chemistry tests (e.g., for purposes of monitoring a condition), etc. Physician events could include, for example, follow-up visits, medical tests or other procedures, any other types of health care events that involve interaction with health care In implementations in which they are present, these ADMs and the associated ADM schedules could provide condition-relevant event integration and could function as a centralized store of both health information and treatment plans, while at the same time providing views of relevant events and responsibilities which are customized for particular users and/or user roles. It should be noted that ADMs and/or ADM schedules or one or more features thereof, could be provided as module(s) of a D-Plan.

Figure 4A:
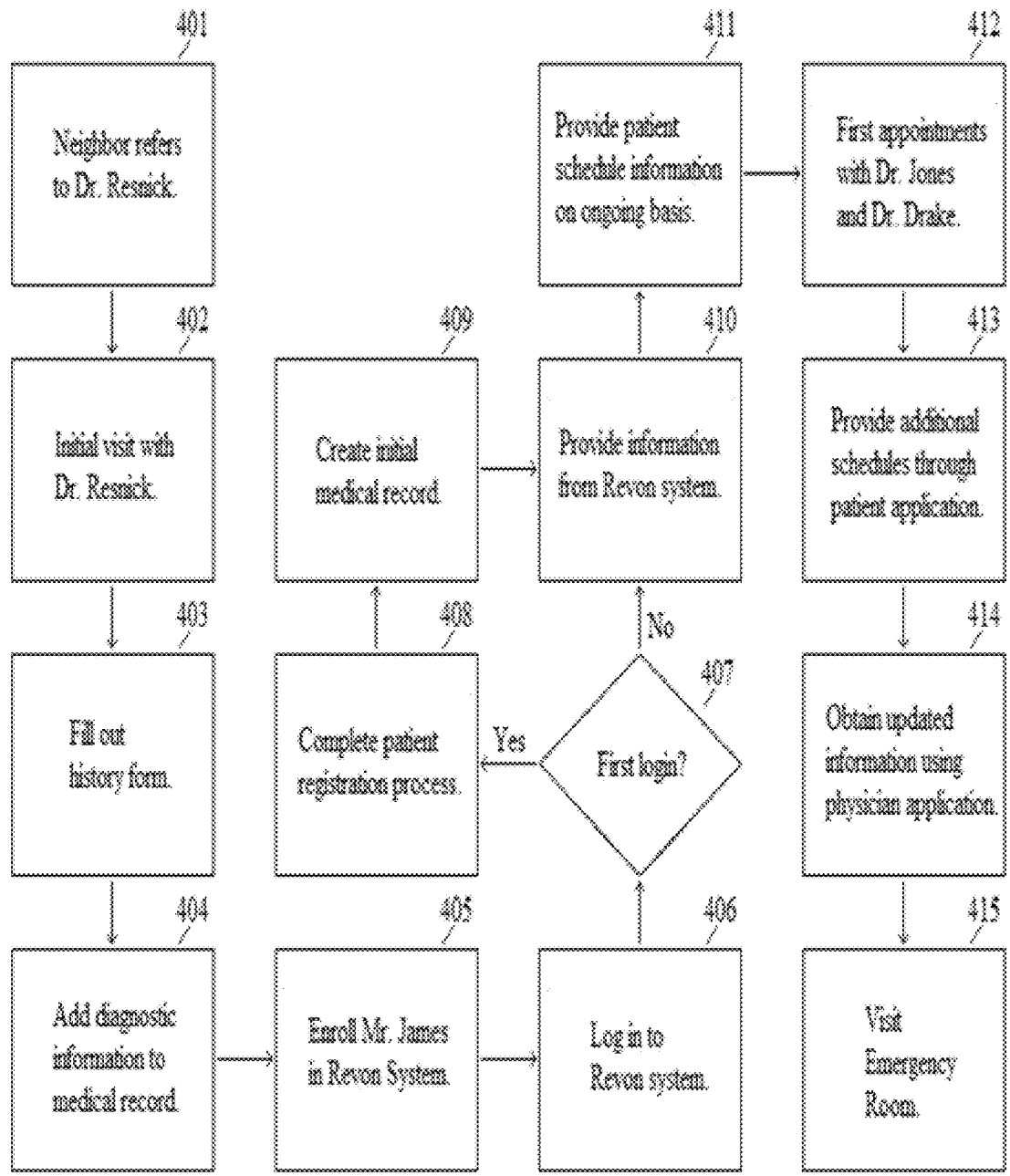
FIGS. 4A-4B provide an exemplary use case in which an implementation of the disclosed technology is used to facilitate health care for a hypothetical 75 year old man with a history of type II diabetes, macular degeneration, and COPD.
Figure 4B:
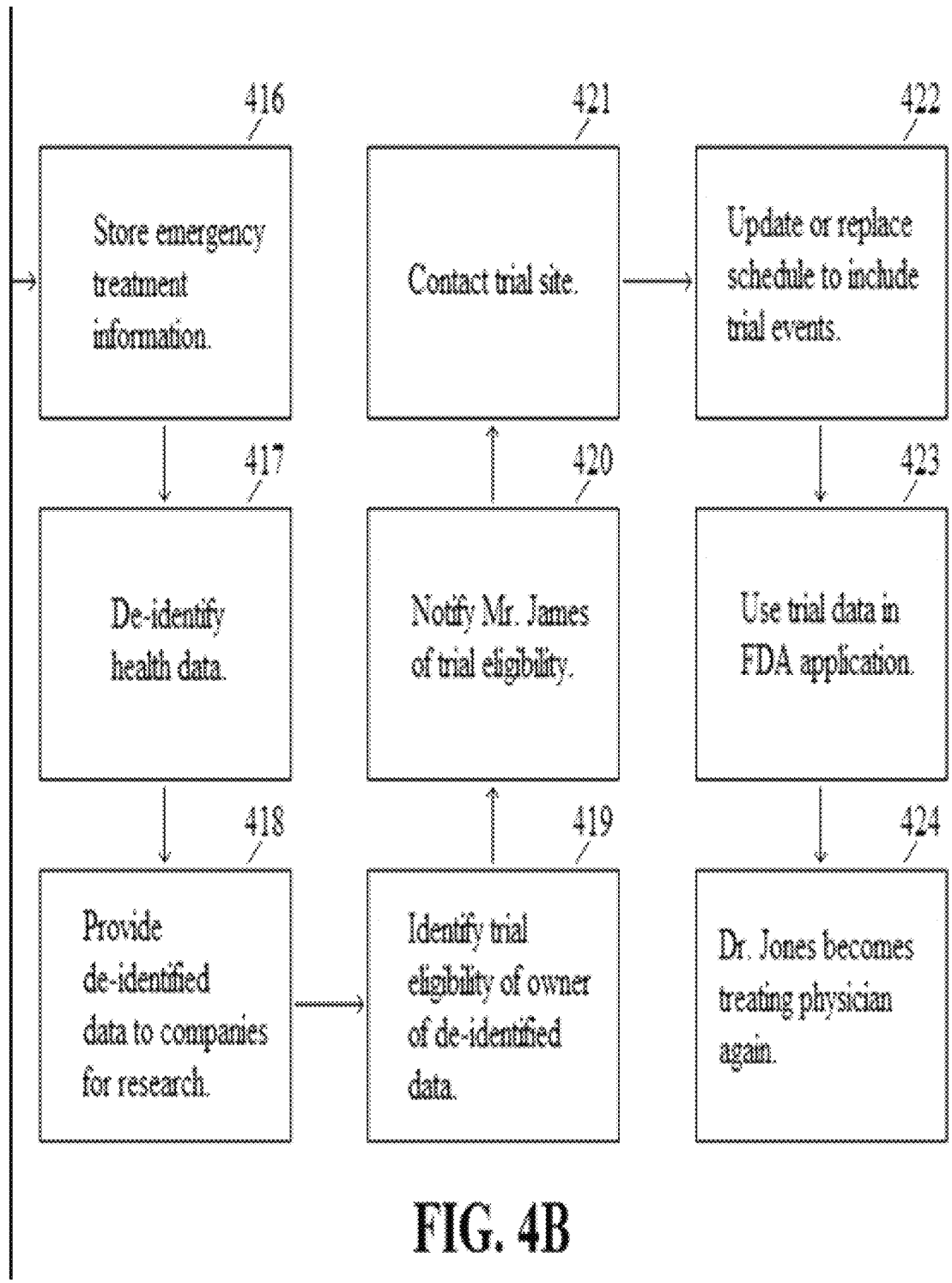

A system implementing or implemented using one or more aspects of the disclosed technology may be referred to as a Revon system (and, correspondingly, the entity maintaining that system may be referred to as "Revon"). A Revon system may, for example, be a D-Plan system, an ADM system, or a D-Plan system that incorporates or makes use of one or more features of an ADM system. To further illustrate how a system implementing one or more aspects of the disclosed technology could be used, consider the following the exemplary use case of FIGS. 4A-4B (which can be combined into a single flow chart by placing FIG. 4B to the right of FIG. 4A), in which an implementation of the disclosed technology is used to facilitate health care for Mr. John James, a hypothetical 75 year old man with a history of type II diabetes, macular degeneration, and COPD. In the use case of FIGS. 4A-4B, Mr. James has recently moved to Louisville, Ky., and needs to find a primary care physician. Therefore, he talks to his neighbor who, in the use case of FIGS. 4A-4B, is already a Revon patient (i.e., a patient who has created or otherwise acquired an account that allows him or her to use a system implemented using the disclosed technology), and his neighbor refers him 401 to Dr. Randall Resnick, a Revon physician (i.e., a physician who has created or otherwise acquired an account that allows him or her to use a system implemented using the disclosed technology). Based on this referral, Mr. James then makes an appointment and visits 402 Dr. Resnick's office for an initial appointment.

While waiting for his appointment with Dr. Resnick, Mr. James fills out 403 a standard medical history form. Dr. Resnick could review the form, and confirm that Mr. James has type II diabetes and convey this diagnosis to an administrator working in his practice who could add the diagnosis, along with information about Mr. James' COPD, to a medical record 404. Dr. Resnick also could also refer Mr. James to a retinal specialist, Dr. Melissa Jones (also a Revon physician), to check for complications of diabetes that can affect the eye and for management of his macular degeneration, and to a pulmonologist, Dr. Frances Drake (also a Revon physician), for management of his COPD. Additionally, in the use case of FIGS. 4A-4B, at the conclusion of the appointment with Dr. Resnick, Mr. James meets with the administrator, who enrolls him in the Revon system 405, and explains features of the Revon patient registration process and the Revon patient application (i.e., an application which Mr. Jones could execute on a mobile device to see his ADM schedule or perform similar activities).

After being enrolled in the Revon system 405, Mr. James could be sent an email with a download for the Revon patient application. Once the application has been downloaded, when Mr. James could use it to log in 406 to the Revon system (e.g., by entering login credentials provided set up by the administrator when enrolling him in the Revon system 405). The application can then check 407 (e.g., by issuing a database call to a central EMR system) if this was the first time Mr. James had logged in. Then, if this was the first time Mr. James had logged in, could perform a patient registration process 408 in which Mr. James would enter information about his medical history, and might also be prompted to provide other information which could be relevant to the care and maintenance of his health (e.g., the names and location of HCPs who had provided care to Mr. James in the past). The Revon system could then use the medical history information provided during performance of the registration process 408, potentially combined with health information obtaining by requesting records from HCPs who had treated Mr. James (e.g., Dr. Resnick) in the past to create 409 an initial medical record for Mr. James.

Once the patient registration process was complete, Mr. James could be provided 410 with information from the Revon system relevant to his health and health care. Such information could include, for example, a type II diabetes ADM Schedule which might have been prescribed by Dr. Resnick during Mr. James' initial visit, and which could include various events that are part of Dr. Resnick's preferred treatment plan for type II diabetes (e.g., medication, monitoring blood glucose level, diet, exercise, and follow-up appointments). In addition to Dr. Resnick's preferred treatment plan, the ADM schedule might also include other customizations, such as if Dr. Resnick had customized his standard type II diabetes ADM schedule for Mr. James's needs by adjusting one or more medication dosages referenced in the schedule. The type II diabetes ADM Schedule could also include other relevant information, such as that Mr. James should return for an initial follow-up appointment with Dr. Resnick in 6 weeks and then every 6 months, and that he should have an annual eye exam.

After Mr. James had been provided 410 with information relevant to his health by the Revon system, the use case of FIGS. 4A-4B continues with the patient application providing 411 Mr. James with patient schedule information on an ongoing basis. This ongoing provision 411 of patient schedule information could take place in a variety of manners. For example, schedule information could be provided using a reactive model, such as if the patient application configured the device used to execute it to allow Mr. James to view his type II diabetes ADM schedule whenever he liked. Alternatively, schedule information could be provided on a proactive basis, such as by providing reminders to Mr. James of events in his schedule (or schedules, such as might be the case if Mr. James had been prescribed a first ADM schedule for type II diabetes, and a second ADM schedule for COPD). Of course combined approaches (e.g., where the patient application could both provide reminders and allow Mr. James to view his schedule) are also possible, and so the description of proactive and reactive models for providing 411 patient schedule information on an ongoing basis should be understood as being illustrative only, and should not be treated as limiting.

Of course, it should be understood that, while FIGS. 4A-4B illustrate the ongoing operation of the patient application in terms of providing patient schedule information, it is also possible that a patient application could be used to provide other kinds of information, or to perform other types of acts, either in addition to, or as alternatives to the ongoing provision 411 of schedule information illustrated in FIGS. 4A-4B. For example, a patient application could be configured to confirm that various acts associated with patient events (e.g., taking medications, monitoring blood glucose level, exercising, and keeping to the diet recommended by Dr. Resnick) had taken place, and could send data indicating that confirmation to the Revon system for storage in a record associated with Mr. James. Similarly, a Revon patient application could also provide Mr. Jones with feedback informing him of his achievements in terms of adhering to Dr. Resnick's treatment program, and might even provide a channel through which Mr. Jones could communicate with other patients who also have type II diabetes. A patient application could also provide certain social functionality, for example, by allowing Mr. James to communicate with networks of people having the conditions (e.g., type II diabetes and/or COPD) he has been diagnosed with. Accordingly, just as the discussion of providing patient schedule information on an ongoing basis should not be treated as implying limitations on providing that information in a reactive or proactive manner, that discussion should also not be treated as implying that ongoing operation of a Revon patient application such as could be used in the use case of FIGS. 4A-4B would be limited to providing information to a patient about his or her schedule(s).

Continuing with the use case of FIGS. 4A-4B, in that use case, a week after the initial visit 402 with Dr. Resnick, Mr. James has his first appointments 412 with Dr. Jones, the retinal specialist, and Dr. Drake, the pulmonologist. Since Dr. Jones and Dr. Drake are Revon physicians, they will have physician applications which can be used to access the Revon system to obtain data about their patients. Accordingly, they will be able to view Mr. James' medical history information, and so Mr. James will not need to complete a paper medical history form for his appointments with either of those doctors and those doctors will already know about Mr. James' existing conditions and treatments (e.g., that he has type II diabetes and has been prescribed Dr. Resnick's type II diabetes ADM schedule). They will also be able to customize and prescribe additional ADM schedules for Mr. James as they see appropriate. For example, Dr. Jones could prescribe an ADM schedule which includes events that are part of her treatment plan for macular degeneration, and Dr. Drake could prescribe an ADM schedule which includes events which are part of his treatment plan for COPD. These schedules could then automatically be provided 413 by the Revon system to Mr. James through his patient application which, from that point on, could display the condition-specific schedules so that Mr. James can see the events for each condition and an integrated schedule that displays events for the three conditions in a consolidated manner.

Just as a Revon physician application could be used by Drs. Jones and Drake to obtain information in preparation for their initial appointments with Mr. James, that application could also be used by Dr. Resnick to obtain 414 updated information on Mr. James' health and health care for use during Mr. James' follow up visits. Thus, in the use case of FIGS. 4A-4B, on the day of Mr. James's next appointment, Dr. Resnick can use the Revon physician application to review Mr. James's self-reported adherence to his recommendations pertaining to medications, monitoring blood glucose level, diet, and exercise. During the appointment, Dr. Resnick can use this information as the basis of a discussion with Mr. James regarding how he could improve his self-management of his condition. The Revon physician application could also inform Dr. Resnick of events which took place during the appointments with Drs. Drake and Jones (e.g., confirming that an eye exam scheduled as a physician event by Dr. Resnick had taken place during Mr. James' appointment with Dr. Jones), and that Mr. Jones now has a macular degeneration ADM Schedule and a COPD ADM Schedule. In this way, the disclosed technology can be used to assure an enrolled HCP that a patient is receiving treatment for his or her diagnosed conditions, and that the various events needed to address those conditions have taken place.

Subsequently (e.g., later that year), the use case of FIGS. 4A-4B continues with Mr. James, while visiting his son in Denver, Colo., suddenly starting to feel short of breath and visiting 415 an emergency room. In this case, the emergency room physician is a Revon physician and is able to access Mr. James's Patient Medical History in the Revon system, thereby learning immediately that Mr. James has a history of COPD and which medications he is taking. In the emergency room, a chest X-ray is taken and Mr. James is given oxygen, and each of these emergency room treatment events could be stored 416 by the Revon system in its records for Mr. James. Then, during Mr. James' next appointment with Dr. Drake, Dr. Drake could see that Mr. James visited the emergency room and that a chest X-ray was taken, and could ask Mr. James about the event in order to determine whether he has had further episodes that may require adjustment of the treatment plan.

Meanwhile, in addition to being used as described, in the use case of FIGS. 4A-4B, the data from Mr. James' three ADM schedules (as well as other data from the Revon system) is de-identified 417 and provided 418 to subscribing pharmaceutical companies for use in developing new medications. The use case continues with one of these companies which is looking for subjects for a clinical trial of an experimental therapy for macular degeneration, identifying 419 Mr. James's de-identified ADM as an ADM of an individual who is eligible for the trial. The system could then notify 420 Mr. James (e.g., with an alert which could be provided to Mr. James next time he opens the patient application) of his eligibility. This notification could not only inform Mr. James of his eligibility, but could also provide him with certain additional information, such as the therapy which is the subject of the trial, the dates on which the trial takes place, and the contact information for the site where the trial will be conducted.

After this notification, the use case of FIGS. 4A-4B continues with Mr. James contacting 421 the site and making an appointment to be screened. Mr. James then enrolls in the trial and the ADM schedule for macular degeneration is updated or replaced 422 by one that includes the various events required by the clinical trial protocol. Additionally, the records for Mr. James maintained by the Revon system can be updated to indicate that, during the trial, the principal investigator on the trial is the treating physician for the macular degeneration ADM, and the ADM schedule containing the clinical trial events could be used instead of the macular degeneration ADM schedule from Dr. Jones. Such a clinical trial ADM schedule could, among other things, remind Mr. James of the medical appointments related to his participation in the clinical trial. It could also be used to collect patient-reported outcomes of treatment. Finally, once the trial is complete, the pharmaceutical company that sponsored the clinical trial would use 423 the data in its application to the Food and Drug Administration for approval of the new therapy, and Mr. James could return to being treated by Dr. Jones, who would become 424 the treating physician for his macular degeneration ADM once again.

Of course, it should be understood that, while the above discussion of the use case of FIGS. 4A and 4B was intended to illustrate how data structures such as ADMs and ADM schedules could be integrated into a system implementing the disclosed technology, variations on the approaches described in that discussion are possible, and so that discussion should not be treated as limiting on the scope of protection provided by this or any related document. For example, while the discussion of FIGS. 4A and 4B included separate steps for a patient to be enrolled 405 by an administrator and to register 408 when he or she first logs into the patient application, the disclosed technology could be implemented in such a manner as to make such separate enrollment 405 and registration 408 unnecessary (e.g., the creation 409 of the initial medical record for the patient could happen during enrollment 405 rather than the initial medical record only being created later at registration 408). Similarly, while the discussion of FIGS. 4A and 4B focused on implementations of the disclosed technology which used ADMs and ADM schedules, similar processes could take place in implementations where those particular data structures were absent (e.g., the functionality described for the patient application in the context of ADMs, such as providing reminders of upcoming events, could alternatively be provided by other types of data structures, such as SSTs).

Variations are also possible in terms of how various components such as described in the context of FIGS. 1-3 could operate to provide functionality such as described in the context of FIGS. 4A-4B. For example, consider the execution of instructions for making recommendations or taking actions based on the analysis of health data which was discussed in the context of SSTs. In some implementations, these instructions would be executed on a mobile device running a patient application which had been suitably configured using an SST, ADM, or other similar data structure. However it is also possible that the disclosed technology could be implemented to execute those instructions on a central system which a user would interact with using a browser or some other type of general purpose interface application. Accordingly, it should be understood that particular approaches described for distributing processing and other responsibilities among devices used to implement the disclosed technology are intended to be illustrative only, and should not be treated as limiting.

A number of variations and modifications might be adopted by those of ordinary skill in the art when implementing one or more aspects of the disclosed technology. For example, aspects of the disclosed technology could be implemented in a patient centric manner. An illustration of this is provided in FIG. 5, which depicts a high level architecture which could be used to manage data and trigger actions on a virtual representation of a patient, illustrated in FIG. 5 as a "Patient State Object" (PSO) 501. As described in more detail below, an architecture such as illustrated in FIG. 5 can be implemented to use a virtual representation of a patient as a centralized location for patient information, with components such as a state controller engine 502 (which could use a first set of rules to determine how to update a patient's virtual representation upon receipt of new data) being used to make sure a patient's virtual representation is up to date, and an action controller engine 503 (which could use a second set of rules to determine what actions should be taken after being triggered by an update in the patient's virtual representation) to determine what types of actions the system should take.

Figure 5:
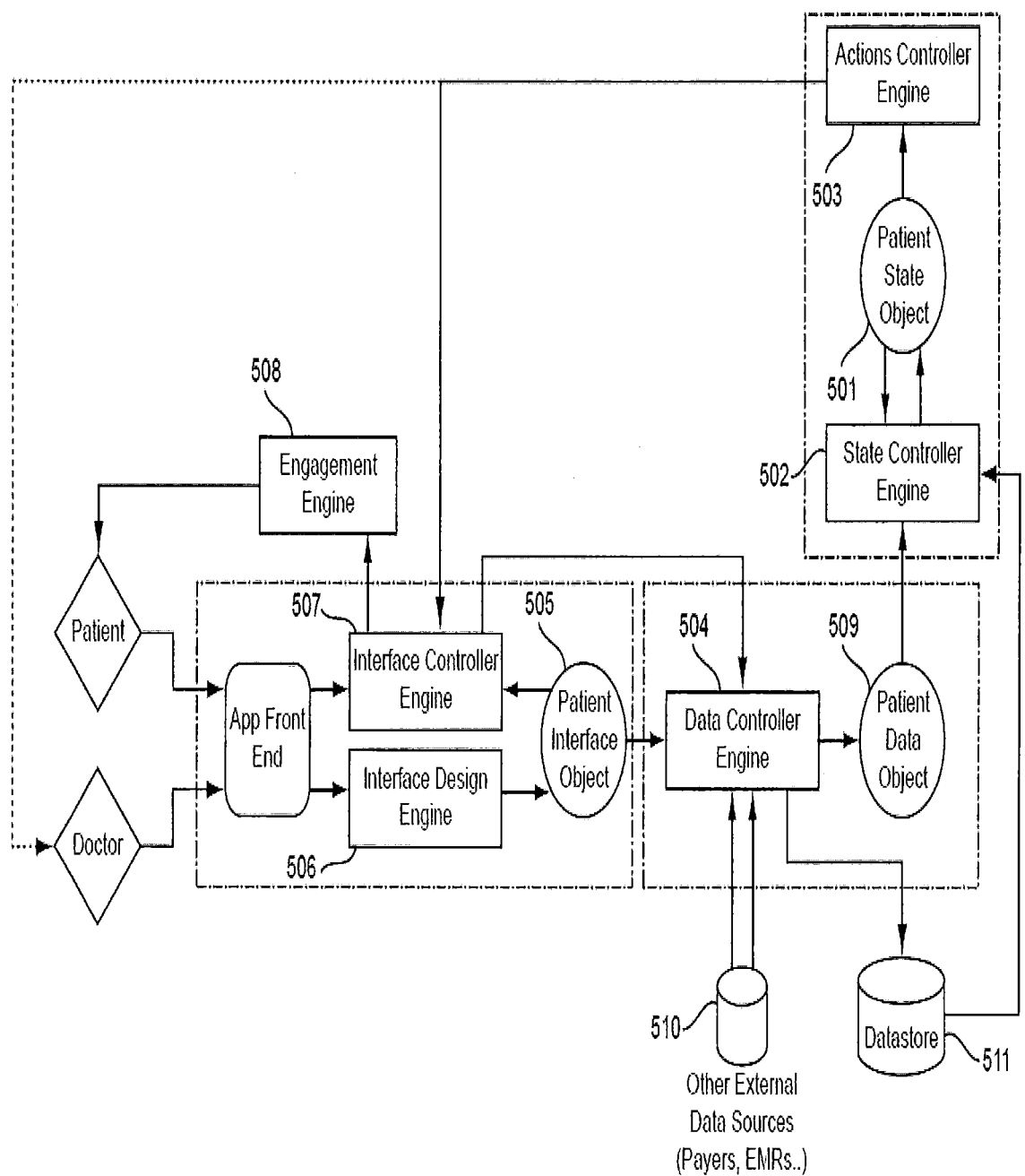
FIG. 5 depicts a high level architecture which could be used to manage data and trigger actions on a virtual representation of a patient.

Turning now to a more detailed discussion of the individual items illustrated in FIG. 5, a patient state object 501 might include any of a wide variety of types of information that are relevant or related in some way to the patient's health. Such information could comprise individual data elements such as recently gathered physiological data, behavioral data, environmental data, and the like, e.g., data element types that could indicate that a particular action should be triggered. Information in a PSO 501 would often include demographic information (e.g., age, gender, income level, education level, and the like). At least some implementations of a PSO 501 could include one or more risk levels. Such risk levels might be derived based on, e.g., a patient's: medical history (e.g., past health care events such as past hospitalizations), past and/or current conditions (e.g., their identity, severity, etc.), family history, genotype, environment, compliance (e.g. with requests from the system for entry of data, with using medications as directed, or the performance of any other health-related actions that could be tracked by the system (e.g., through a mobile device)), demographic factors, social factors, volatility in health data measurements. A PSO 501 could include general risk levels that are not specific to a particular condition (e.g., they are relevant to the patient's overall health or to at least a substantial proportion of the conditions that the patient has), condition-specific risk levels, or both. Condition-specific risk levels could be a function of severity of the condition, relevant comorbidities, medical history with respect to that condition, among others. Elements in a patient state representation might be derived from multiple different data elements or data element types. For example a risk level could be derived from multiple data elements for that patient.

To store this information, a patient state object 501 could be implemented as a multi-dimensional vector reflecting the current understanding of the patient's health state. An example of a multidimensional vector patient state object 501 is provided below in table 1.

TABLE 1

Exemplary vector representation of a patient state object

PSO(patient_k) = {
    [overall_health_score, health_trend, health_score_volatility, gen_hospitalization_risk, ..],
    [compliance_level, recent_compliance_level, compliance_trend, compliance_volatility, BM1_compliance, BM2_compliance..],
    [disease_x_risk_level, disease_y_risk_level, comorb_x_risk_level, ..],
    [BM_overall_risk_level, BM_1_risk_level, BM_2_risk_level,..],
    [BM_1_urgency, BM_2_urgency, ..]
    [overall_exacerbation_risk, disease_x_exacerbation_risk, disease_y_exacerbation_risk, ...]
  }

Such a vector could be seen as a multi-dimensional health score for a patient, and, as will be apparent in light of this disclosure, could reflect all relevant aspects of patient health.

The following description of an exemplary indicative operation of a patient state object 501 and related items further illustrates the role that a patient state object 501 could play in a system following the architecture of FIG. 5. Initially, when a patient creates an account with the entity operating the system, a patient state object 501 will be created for that patient and start at a default state (e.g., a null state). As the patient completes a profile, his or her patient state object 501 will be updated based on the profile data the patient provides. This could comprise:

Updates based on medical data (allergies, medications, any medical history they provide)
    Updates based on demographic data—age, location/neighborhood, income level, education level etc.

Further updates, reflecting disease and comorbidities, can take place once the patient gets his or her first D-plan. Subsequently, updates can take place based on BM data, edu interactions, SST interactions. Such updates may comprise:

Using raw measurement data (BP, pulse, SpO2, weight) as it comes in from BMs to update the PSO 501
    Using interaction data, as it comes in, to update the PSO 501 (% requests completed, time to respond, etc.)
    When SST runs: data gathered by an SST, will feed back into patient state, and update it in near real time Actions to be executed based on the available data about the patient may be executed by the Actions Controller Engine 503 (discussed in more detail infra). This module may run when the PSO 501 is updated and may have a set of rules for determining if any action should to be taken based on current patient state. In some embodiments, an ACE 503 may be configured to look across lot of parameters very easily to make decisions. For example, in some embodiments, to trigger an SST it can look at certain BM values, recent patient compliance level, exacerbation risk for related disease, and then decide. Actions may include one or more of:

Request another BM or update to a BM
    Request an SST to be run
    Issue instruction to patient (call doctor's office, call 911 . . . )
    Send reminder to patient
    Send edu material to patient
    Send notification to physician
    Send notification to caregiver (relative, friend) . . .

There may be one or more sets of rules, which may be same as rules for SSTs and BMs for triggering instructions and actions. These sets of rules may include rules for the SCE 502 (discussed in more detail infra), which determines how the PSO 501 is updated based on the incoming raw data about the patient. They may also include rules for the ACE 503, which could control what actions are triggered by the ACE 503 based on the PSO 501. Embodiments using the architecture described herein may allow ACE 503 rules may be able to leverage all the data about a patient, rather than being limited to one measurement or SST (which might be the case for some other embodiments), creating a split between the interpretation of the raw data from the actions executed based on the data. Additionally, in some embodiments, SSTs may ask questions and gather data, but will not issue instructions themselves. Their data will update the PSO 501, and the ACE 503 will issue instructions based on the updates to the PSO 501. In such embodiments, the actions will preferably reflect the available data about the patient (captured in PSO 501) and not just what this SST run captured.

The patient state representation could be designed to closely reflect the actual state of the patient's health, such that, for example, when the patient state representation of a particular patient shows a certain risk of hospitalization in percentage form, approximately that percentage of patients (e.g., ±5%), with the profile of the particular patient, would in fact be admitted to the hospital over a period of time. In some aspects, an implementation that utilizes a patient state representation could provide flexibility and enhanced functionality in any of a variety of ways. For example, it could allow a system to incorporate a wide variety of relevant information in determining recommendations (which information could include both individual data elements as well as longer term metrics such as trends, risk levels), allow for flexibility in the system's behavior (e.g., providing for follow-up in instances in which the system has recommended that the patient take particular actions or in which the system has detected a concerning trend in the patient's health status), etc. Of course these are but a few examples illustrative of capabilities that a system implementing a patient state representation could have. It should also be understood that an implementation of a patient state representation could be used for a variety of other purposes in addition to, as part of, or instead of in providing or facilitating provision of health care to a patient or implementing a patient health tracking and management system. For example, a system implementing a PSO 501 could be used to predict the future health or health care utilization of a patient or population of patients, simulate the effect of particular health care interventions on a particular patient or population of patients, identify patients who would benefit from particular health interventions, etc. Such uses could be implemented as part of a system that provides or facilitates provision of health care to a patient (such as a patient health tracking and management system) or could be implemented as an independent system.

Figure 6A:
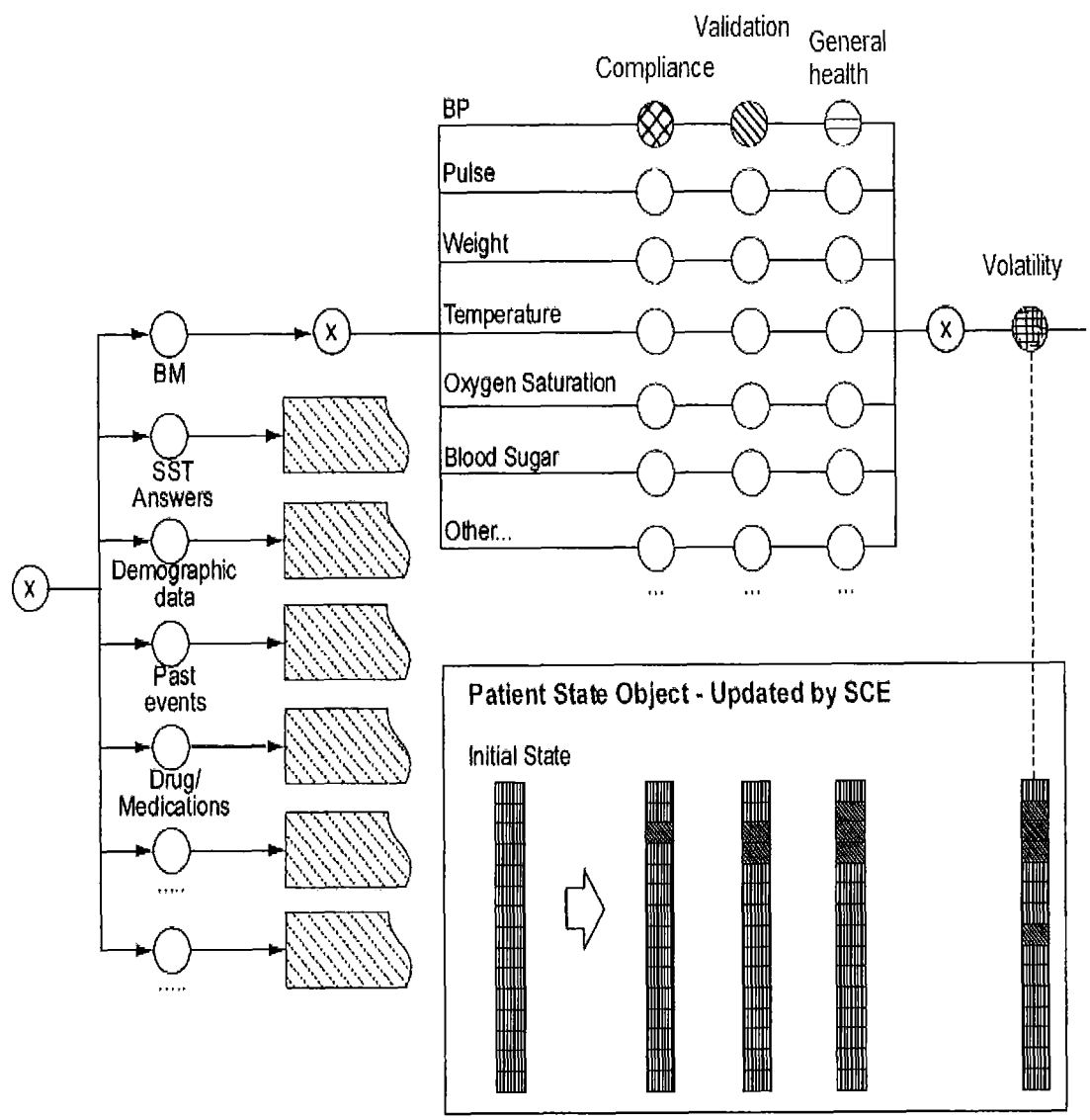
FIGS. 6A-6B illustrate how a state controller engine could update a patient state object.
Figure 6B:
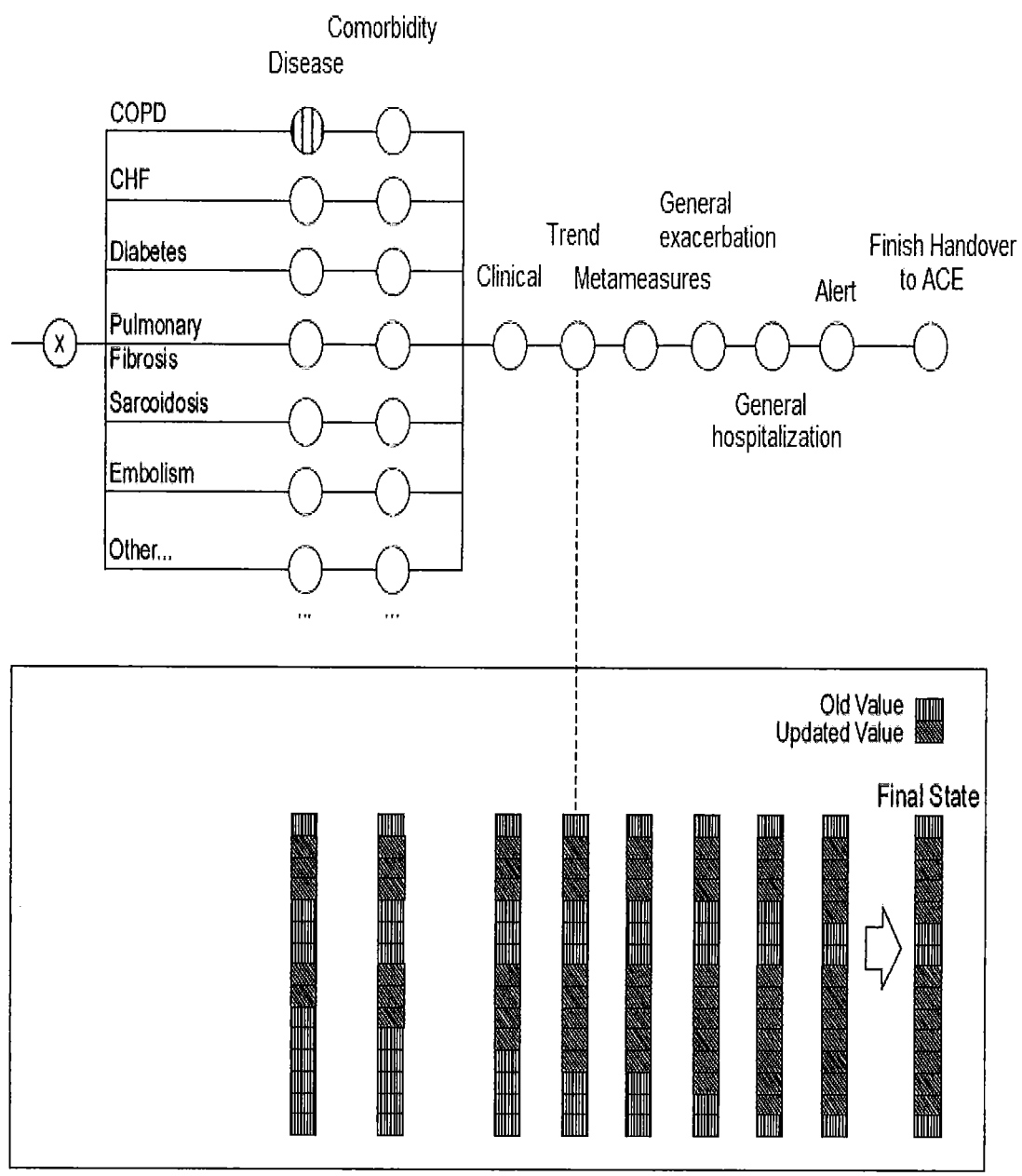
Figure 7:
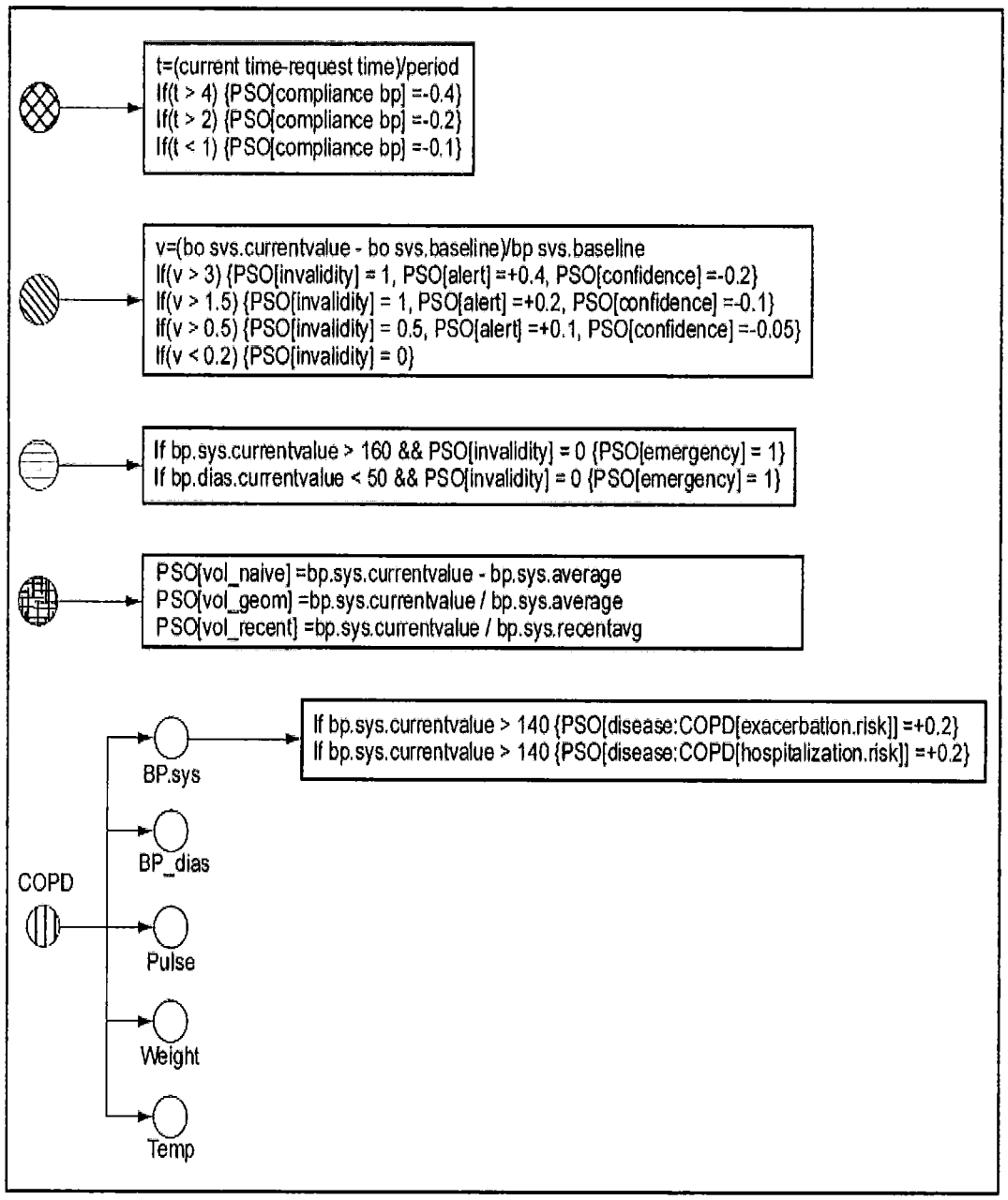
FIG. 7 illustrates logic which could be used by a state controller engine to make changes to a patient state object.
Figure 8A:
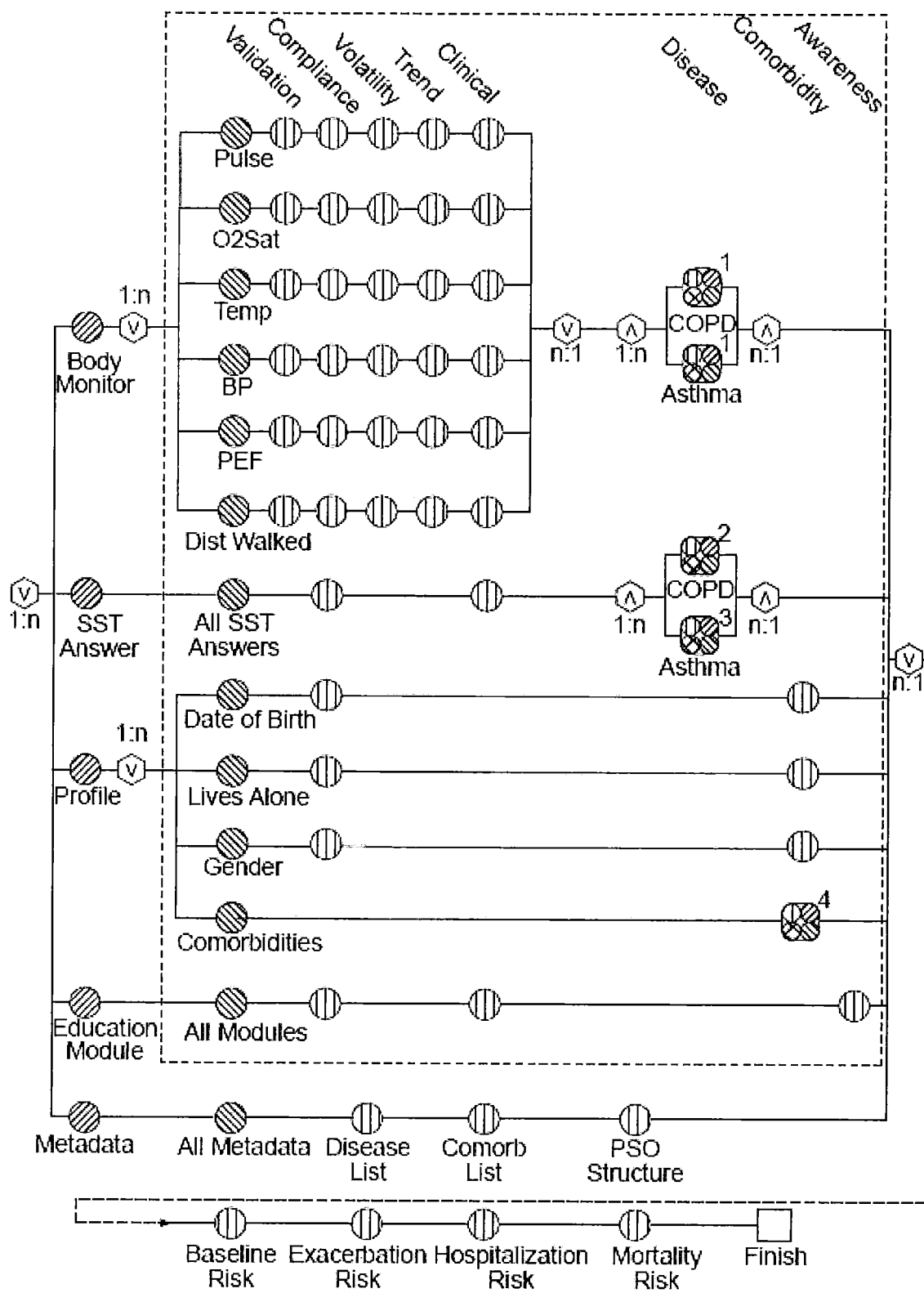
FIGS. 8A-8B, in which when
Figure 8B:
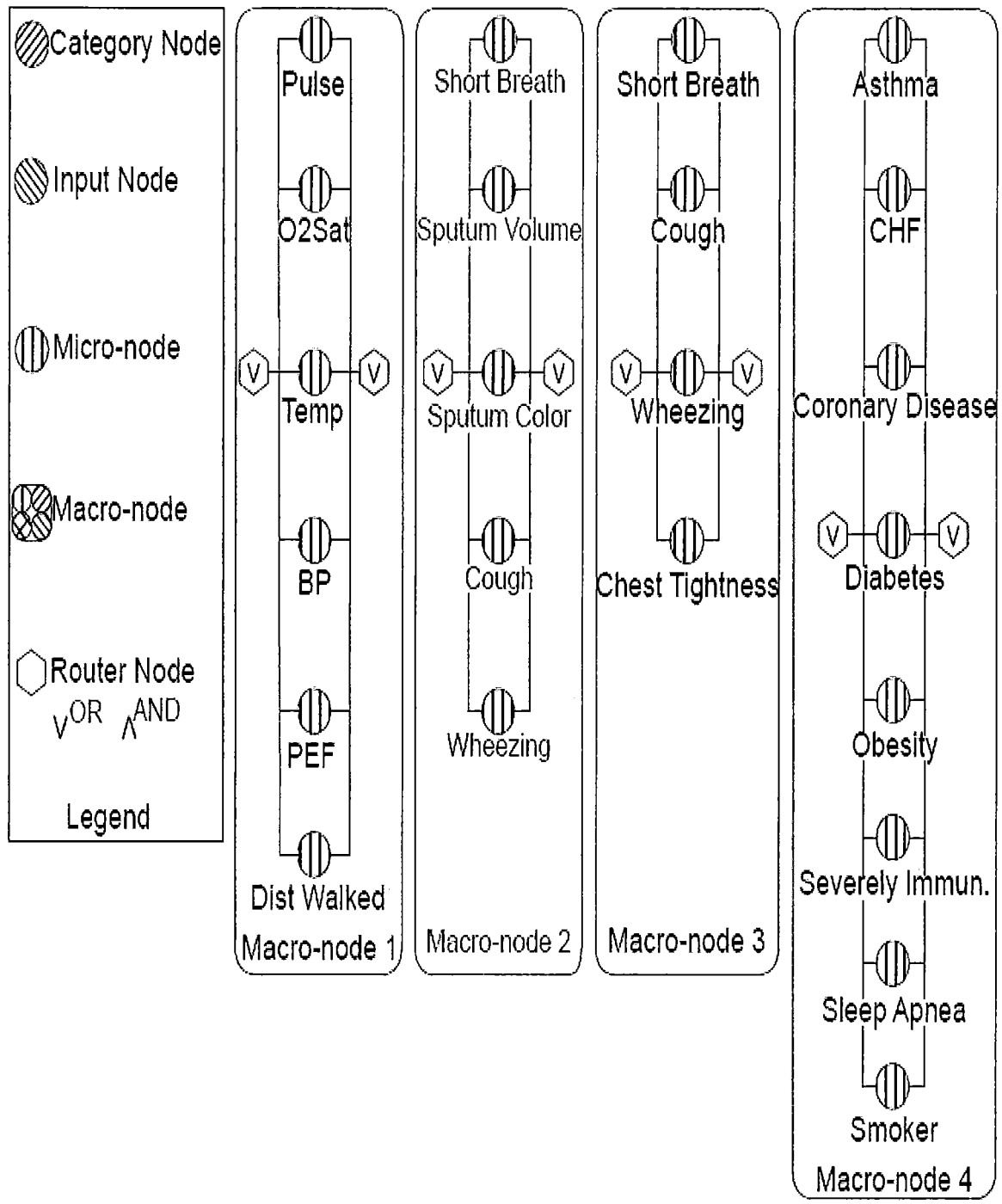

Turning now to FIG. 5's state controller engine (SCE) 502, that element could be implemented as a module containing a set of rules which would be invoked when a data item about a patient is captured to determine whether and how the PSO 501 should be updated. In a system implemented using the architecture of FIG. 5, there could potentially be only a single state controller engine 502 which would be used for controlling updates to patient state objects 501 for all patients. Such a SCE 502 could be implemented by starting with a few basic rules, and continuing to add new rules over time to make the SCE 502 more intelligent. An SCE 502 will preferably have access to all raw data for a patient, as well as access to the current PSO 501 and all past states of the PSO 501. In practice, a SCE 502 will likely to implemented to generally look at only the latest piece of data about a patient and use it when updating a PSO 501. However, it is possible that an SCE 502 may also choose to look at some other patient when formulating an update. Such an update could be triggered in a variety of ways, and there could be multiple ways of triggering an update implemented even within a single embodiment. For example, it is possible that a single implementation may include an SCE 502 which would be fired in one of two ways: either when data is updated for a patient a message could be passed (e.g., by a DCE 504, discussed infra) to the SCE 502 causing it to fire, or the SCE 502 could collect historical data on a regular schedule and update a patient state object 501 accordingly. FIGS. 6A and 6B (in which FIGS. 6A and 6B form a single drawing when the right side of FIG. 6B is placed adjacent to the left side of FIG. 6A) illustrate how a SCE 502 could update a PSO 501. FIG. 7 illustrates logic which could be used by a SCE 502 to make changes to a PSO 501 at various points shown in FIGS. 6A and 6B. FIGS. 8A-8B illustrate at a high level certain logic nodes which could be included in some embodiments which implement an SCE 502 such as illustrated in FIG. 5.

Turning now to FIG. 5's action controller engine (ACE) 503, in an embodiment following FIG. 5, the action controller engine 503 may be called when a PSO 501 is updated by a SCE 502. The ACE 503 may then evaluate rules using data from the PSO 501 to determine what (if any) action(s) should be taken as a result of the update and may also take appropriate action, including in cooperation with other components of the system, to implement a multi-user synchronous push of information added to or updated in a patient state object. {{It may be worth mentioning that the multi-user synchronous push of information aspect could be used in implementations of the Revon system that do not involve the patient state representation architecture.}} In some implementations, when a PSO 501 is updated, the ACE 503 might access a list of entities who have authorization to view information for the patient represented by the updated PSO 501 (such a list could be stored in the PSO 501 itself, but could also be maintained elsewhere in the system, such as in a globally accessible data structure which would be accessible to the ACE 503 as well as other components shown in FIG. 5) and send messages to those entities informing them of the update to the PSO 501. For example, the ACE 503 could send a message to the interface controller engine 507 (discussed infra), informing it that the relevant entities should be informed of the update to the PSO 501. Then, if any of those entities was currently accessing information on the patient whose PSO 501 had been updated, the ICE 507 could update the information presented to the entity or entities to reflect the current state of the PSO 501, and could potentially combine such updates with alerts notifying them that the change had been made so that it would not be inadvertently overlooked. The ICE 507 could also potentially send messages to individuals who were not currently accessing information on the patient corresponding to the updated PSO 501, such as by sending a real time update notification to the entities who were connected to the system but not viewing information for the patient, and/or by storing a message in an internal queue to send to entities who were not currently connected to the system which would inform those entities of the change next time they connected. In this way, a multi-user synchronous push (which could also be implemented in embodiments of the disclosed technology which do not follow the architecture of FIG. 5, such as by adding data structures of the type described above for the ACE and ICE into those other embodiments as appropriate given their particular architectures) could address the internet centric challenge of making sure that all individuals who should be made aware of health related, and potentially time sensitive information would be provided with that information regardless of whether they were actually accessing an interface which would normally provide that information at the time it becomes available.

Additionally, in some implementations, an ACE 503 might also perform functionality which was not tied to PSO 501 updates. For example, in some cases an ACE 503 may also include rules which are run on batch processes triggered by a clock based on time, rather than being triggered by an update to a PSO 501. Actions which could be triggered by an ACE 503 could include any actions the individual or entity operating the system in which that ACE 503 is present chooses. For example, such actions could involve communication with a patient, HCP, or caregiver computer. Such actions might include, for example, requesting health data from the patient, requesting an update to a body monitor measurement, providing recommendations to the patient (e.g., recommending that the patient seek medical attention, recommending that the patient take particular medications, etc.), providing notifications to one or more of the patient's HCPs or caregivers (e.g., notifying a HCP or caregiver of the patient's state or of a change in the patient's state), triggering an SST, sending a reminder to the patient, or issuing an instruction to a patient (e.g., call 911, call a doctor), to name a few. Actions triggered by an update in the PSO 501 could include altering the frequency or timing with which particular health data is collected and/or causing the collection of additional or different health data from the patient.

In some embodiments, the rules that an ACE 503 could use to trigger actions could read the patient state representation and, based on the risk and state scores, determine whether or that certain actions should be triggered automatically. Actions that could be triggered by rules based on a patient state representation could include, e.g., providing recommendations and/or notifications to a patient, health care provider, or caregiver. Additionally, actions that could be triggered include those affecting the system, e.g., causing changes in behaviors of the system. Behaviors of the system could include, e.g., interactions with users, e.g., patients and/or HCPs. For example, actions could include altering the frequency at which the system requests data from a patient or from a monitoring device. One or more rules could be invoked upon an update in the patient state representation. A given rule might trigger one or more additional rules.

Alternatively or additionally, an action controller engine 503 might have one or more rules that specify situations in which an SST should be executed, rules that specify which among multiple different SSTs to execute under specified circumstances, or both. For example, an action controller engine 503 might have rule(s) that cause an SST to be executed upon receipt of an abnormal value of a physiological variable, rules that specify which SST to execute given a normal value of a physiological variable, or both. An action controller engine 503 might have rules that assemble an SST by, for example, selecting appropriate (as determined by the rules) data requests from a set of data requests. Such an SST may be referred to as a "virtual" SST. The content of such an SST (e.g., data requests included in it, instructions issued by it) could be determined based on the patient's state at the time. The content of a virtual SST could vary depending on, e.g., individual patient characteristics (e.g., risk level, comorbidities), which could be included among the data in the patient state object for that patient or could be stored in a patient record in the database and used by the SST. When asking questions from a virtual SST, the answer to each question in the virtual SST session could be treated as if it were completely independent of every other question, and the answers to the questions could be run through the SCE 502, which would make updates to the PSO 501. Control would then be handed back to the ACE 503, which could read the PSO 501 to determine which questions/instructions should be provided to the patient.

In embodiments where the virtual SST concept is implemented, a virtual SST session could be triggered by body monitor readings. For example, if a body monitor reading is in a certain range, a node in the SCE 502 could trigger a VSST session by setting a VSST session in the PSO 501. The node in the SCE 502 could also turn on the questions in a global questions array (discussed infra) for the patient for whom the VS ST session would take place. Once the VSST session has been triggered, control could be handed over to the ACE 503, and a dedicated "super rule" in the ACE 503 dedicated to running a VSST session could be fired. This node in the ACE 503 could read the PSO 501 and see that the VSST flag is set to ON. In response, it could go to the global questions array, find the questions for that patient, check which questions are on, and send the first question which is ON for that patient to him or her by adding it to the ICE 507 schedule (discussed infra) with an immediate timestamp. After a question has been asked, it can be marked as asked for that patient, and switched off of a pending questions list. When the answers to the questions come back, they can be run through the SCE 502 nodes dedicated to the given SST questions. The logic in these nodes can update PSO 501 scores. They can also trigger new questions to be switched on in the Global Questions Array for the patient. They can also switch on medication instructions in the Global Instructions array. An instructions issuing node in the ACE 503, may prevent any instructions from the Global Instructions Array from being sent to the patient, until the VSST session is over (flag in PSO 501 is set to OFF). Once the session is over, the instructions issuing node can review the instructions switched ON in the global instructions array, and check if there are conflicts. If there are conflicts, it removes them, and then sends the ON instructions out to the patient.

Of course, it should be noted that, in some embodiments, an instructions issuing node in an ACE 503 could also be utilized outside of the context of a VSST session. If there is no VSST session on, but a new datapoint comes in (body monitor answer), that may also trigger instructions in the Global Instructions List to be turned ON. In this case, when control passes to the Instructions Issuing Node in the ACE 503, it will simply push the instructions out. Similarly, just as an instructions issuing node could potentially be used both inside and outside of the context of a VSST session, it is also possible that, in some embodiments, data other than that collected in a VSST session could be used in determining recommendations determining when to trigger an SST, and/or determining the content of an SST. For example, other data that could be contained in the patient's PSO 501, e.g., data such as the patient's age, overall health status, other conditions, risk levels, etc., could be used for such purposes. Further, SSTs could be specialized for particular purposes. For example, certain SSTs could be designed for following up with a patient after the system provided a recommendation or detected a trend of concern. Follow-up provided by a system (whether through SSTs or otherwise) could be designed to collect data allowing the system to determine whether the patient had followed the recommendation, had improved or worsened, whether additional recommendations are warranted, etc., and could include the provision of additional recommendations based on analysis of the data collected during the follow-up and, in some instances, data collected previously by the system.

Figure 9:
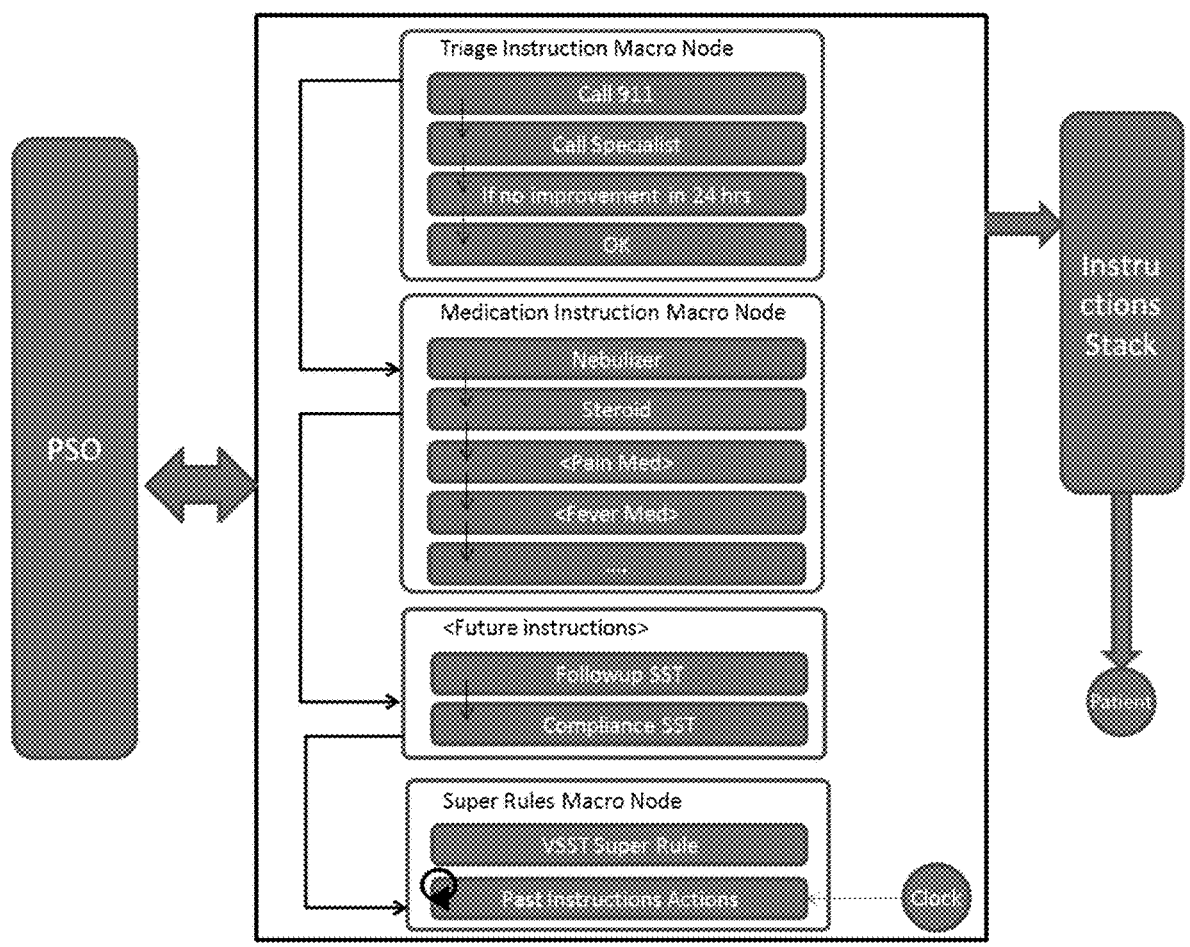
FIG. 9 illustrates an architecture which could be used to implement an action controller engine.
Figure 10:
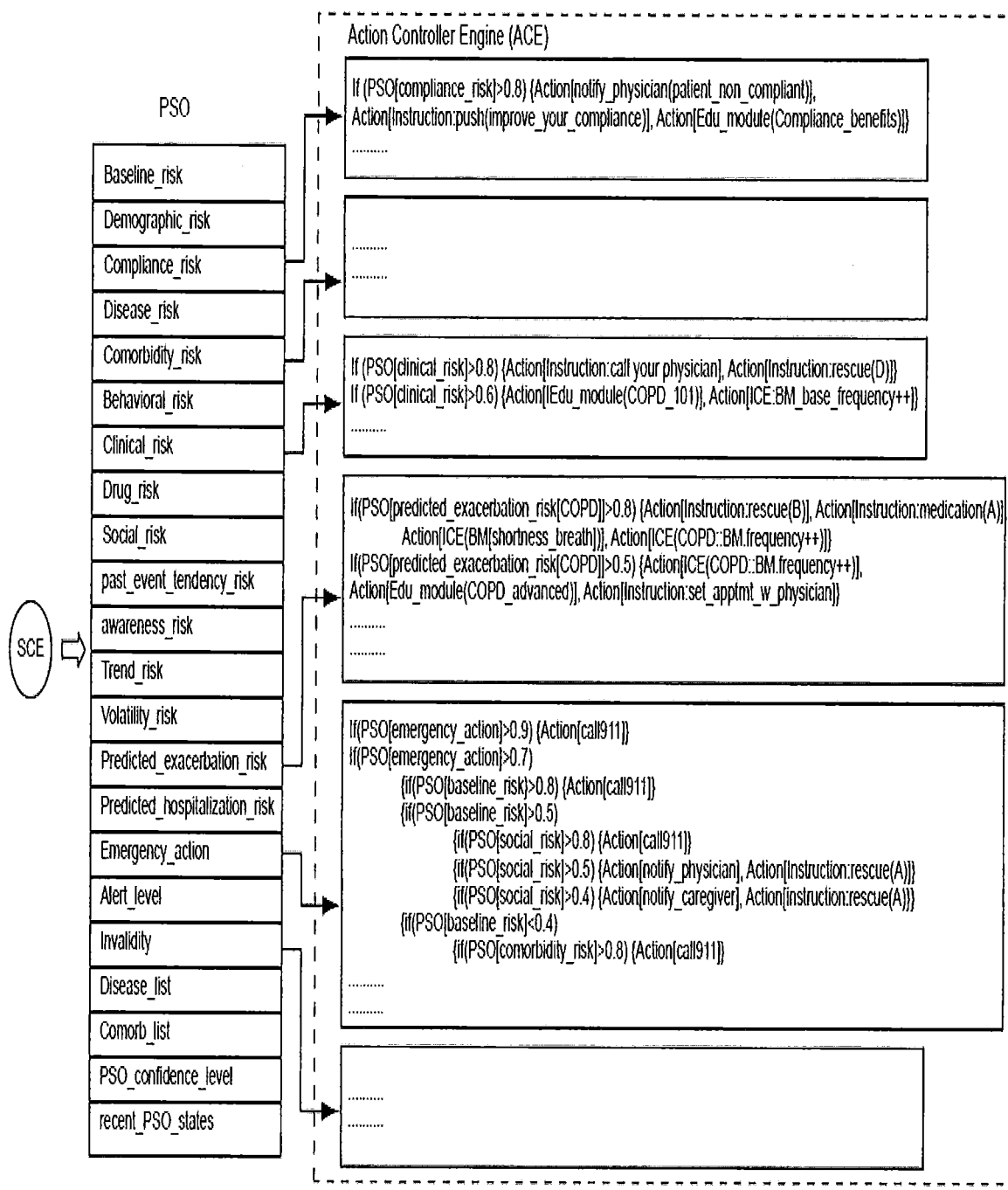
FIG. 10 provides certain details regarding particular types of evaluations which could be performed by an action controller engine.

A diagram of an architecture which could be used to implement an ACE 503 is provided in FIG. 9, with FIG. 10 providing more details of particular types of evaluations which could be made by such an ACE 503. In an ACE 503 implemented as shown in FIG. 9, each macro node could be dedicated to a certain type of rules, and each micro node could have one possible output instruction. Within a macro node, the micro nodes could be run in an order set based on their priority, and once each micro node in a macro node has been run, execution could move to the next macro node so that the micro nodes in that macro node could be run as well. As shown in FIG. 9, each node could potentially create an instruction, which could be placed on a stack, though in some embodiments instructions may not be sent out till ACE 503 completes its processing. In such embodiments, once ACE 503 completes its processing, instructions from the stack are sent to patient. This may be done directly, or, in some embodiments, another check might be performed before the instructions are sent out.

Of course, it should be understood that other architectures than a macro node/micro node architecture such as shown in FIG. 9 could also be used when implementing an ACE 503. For example, in some cases, rather than organizing rules into macro and micro nodes as described, rules could be organized into a single type of nodes, such as nodes based on subject matter (e.g., nodes with rules used for processing temperature data). In such a case, when an ACE 503 was triggered to process information from a PSO 501, the ACE 503 could take the information to be processed (e.g., information updated by an SCE 502) and provide it to the relevant nodes (e.g., if the information to be processed is temperature information, it could use a data structure such as an index to identify the temperature specific nodes and nodes with rules for generic body monitors, and then provide the information to those nodes) so that they could evaluate it and generate whatever instructions (e.g., output instructions, modifying the PSO 501, triggering other rules or nodes, etc) their rules indicated were appropriate. In such a case, node sequencing could be controlled by an execution order parameter specified as part of the definitions of the relevant nodes, and separate sequencing and organization on macro and micro node levels could be omitted. Accordingly, the discussion of the macro/micro node architecture from FIG. 9 should be understood as being illustrative only, and should not be treated as limiting on the protection provided by this or any related document.

Taken together, a PSO 501, an SCE 502 and an ACE 503 can be conceptualized as a three level architecture for converting input data about a person into a holistic representation of a patient's health state which can be used as basis for further action. The first level (SCE 502) converts raw data (e.g., values of physiological variables, patient responses to questions about symptoms) to a patient state representation (the PSO 501). The second level is the patient state representation (PSO 501) which can be represented in the form of a numerical score assignment to various aspects of (or related to) a patient's health. The third level (ACE 503) is the reading of the patient state representation to trigger health actions which can be used in managing a patient's health, e.g., for purposes of improving/maintaining patient health and/or improving health outcomes. The three levels could run without human intervention based on rules embedded in the system. Input data could be a combination of any one or more of the following: answers to questions about physiological variables (e.g., requests to the patient to enter and measure such variables), answers to symptom questions, data from monitoring devices, patient profile data (e.g., patient characteristics such as risk factors or behavior patterns that can affect health), patient disease data (e.g., which conditions a patient has, their severity, or other relevant information), patient demographic data, patient social data, and other possible data sources such as those discussed herein. Input data about a person, as used herein, could include data about such person's environment (physical, social). A patient state representation can be created by converting raw medical data into a scoring model, where raw data is used to calculate or refine a risk or state score for the patient. The mapping of raw data to risk data could be done by a variety of approaches. For example, a combination of medical research interpretation (e.g., analysis of studies reported in the medical literature) and learning models which take historical patient raw data and final outcomes data to derive appropriate scoring regimes could be used. A system implementing the disclosed technology could evolve over time from one that utilizes primarily scoring models derived from analysis of the medical literature to one that utilizes scoring models derived from the raw data and outcome data gathered by the system. An example of medical research that could be used in deriving a scoring model would be studies that have examined factors associated with mortality, hospitalization, hospital readmission, or health care utilization of or by patients with particular conditions.

Advantages, some or all of which could be provided by various embodiments implemented using an architecture such as shown in FIG. 5 with a PSO 501, SCE 502 and ACE 503 as described herein include the following:

1) A patient state object 501 may provide a complete holistic view of patient at all times.

2) Data feeds ramifications into one place—which can facilitate making decisions and taking actions based on complete information about patient health 3) Very sophisticated decision logic can be implemented for actions. E.g.: When asking patient to call 911, it is possible to look at answers to subjective question, recent BM measurements, volatility in BM measurements, recent trends in BM measurements, prior patient risk level of exacerbation for given disease, patient general risk level which is influenced by comorbidities and so on. For example, a patient who has low risk based on subjective questions but high general risk level due to comorbidities, will get 911 much faster than someone who has very low general risk level due to lack of comorbidities. This could provide for more powerful analysis than would be generally be available by focusing on SST questions alone.

4) The concept of a virtual software model of the patient is powerful and allows for high level of extensibility.

5) This model largely separates data capture, data interpretation and decision logic, which allows maximum modularity.

6) Any decisions made regarding a patient (trigger SST, ask for BM, issue action/instruction, notify physician etc.) can be done from this a single object. Decision logic can be localized in one place, allowing easy updating, easy adding of new rules, logic and actions 7) It could be possible to add any new rule into an existing system, since it will be part of the SCE 502 or ACE 503. SSTs, BMs etc may not require modification to add such new rules, but instead might be treated as naked sensors, with no intelligence of their own.

8) It could be possible to evolve ACE 503 and SCE 502 over time and AI technologies can be applied here, in a very clean and elegant way 9) Every feature added in the future that may understand patient state may not be required to query any object other than the PSO 501. This could avoid the necessity of having to go to n different data points to make a decision. Accordingly, a decision can be made simply from looking at some component of PSO 501.

10) The architecture allows for separation of interaction modules (BM, SST etc) from knowledge modules (rules from medical team) from learning modules (how to update patient state object based on incoming data, to best reflect TRUE patient state). Each can be developed and modified independently.

Moving beyond the PSO 501, SCE 502, and ACE 503, FIG. 5 also depicts a patient interface object (PIO) 505, which can be implemented as a data structure which reflects the merged and optimized specifications of interaction modules that interact with the patient. Such a PIO 505 could define information for a patient such as what SSTs will run, which body monitors (BMs) will run, what educational modules are relevant for a given patient, what sensors the patient interacts with, at what frequencies data is captured, what channels data is captured from etc, and may also include data for controlling the frequencies and expiration of these elements. Preferably, each patient for whom information is managed by a system following the architecture of FIG. 5 will have his or her own patient interface object 505, allowing the patient's specific PIO 505 to be updated as necessary as new data sources are added for him or her.

To illustrate the type of information which could be maintained by a PIO 505, in some embodiments, a PIO 505 could include:

Which DCM's (i.e., Data Capture Modules, a phrase used in this document to refer to Revon application modules which get data about a patient, from the patient or elsewhere) to run for this patient;

When to run each DCM;

What is the D-plan parentage of each DCM, which can be relevant when a D-Plan is changed or removed.

Such a PIO 505 can be implemented as a graph data structure or a simple multidimensional vector, an example of which is presented below in table 2.

TABLE 2

Exemplary Patient Interface Object

PIO(patient_k) = {
   [tplan1[(SST: SST_copd(24), SST_asthma(72))(BM: bp_BM(48), pulse_BM(48), weight_BM(96))(Edu: copd_101, asthma_101,smoking_cess)]]
   [tplan2[(SST: SST_asthma(48), SST_diabetes(96))(BM: bp_BM(24), pulse_BM( )48), sugar_BM(24))(Edu: asthma_101, smoking_cess, diabetes_101)]]
   [merged_DCM[(SST: SST_copd(24), SST_asthma(48), SST_diabetes(96))(BM: bp_BM(24), pulse_BM(48), weight_BM(96), sugar_BM(24))(Edu: copd_101, asthma_101, smoking_cess, diabetes_101)]]
}

Figure 13:
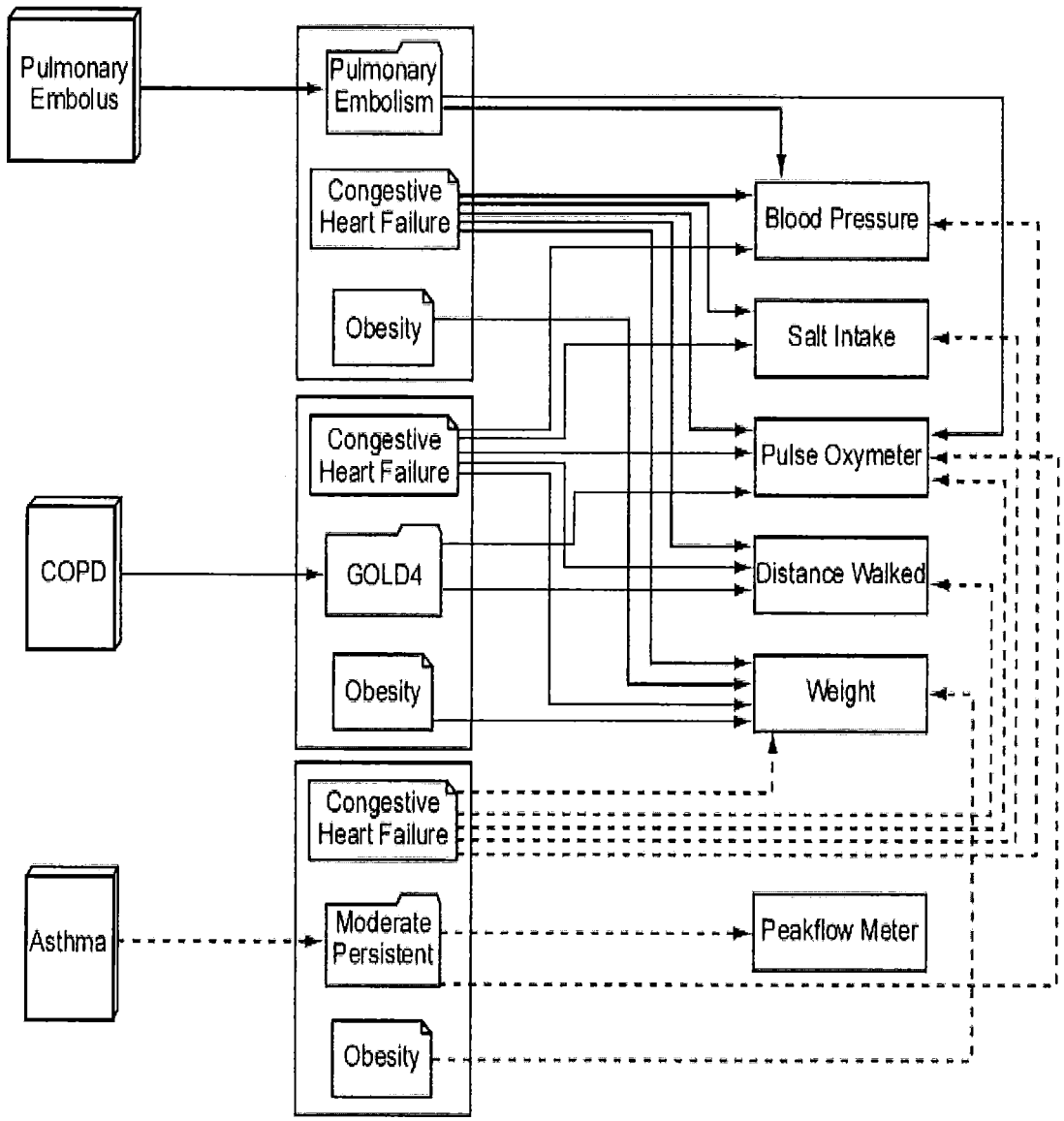
FIG. 13 illustrates a patient interface object organized into a three level graph.

An illustration of a PIO 505 organized into a three level graph (with the levels corresponding to a D-plan family, a D-plan, and body monitor modules) is provided in FIG. 13. In that figure, as D-plans are added to a patient profile, the IDE 506 adds vertices to the PIO graph. In an organization as shown in that figure, the body monitor modules (which can also be referred to as data capture modules), can be contained in a data capture sensor pool. If a module has multiple parents (such as weight, as shown in FIG. 13), the frequency which could be defined in that module by the PIO 505 could be the smallest frequency defined by any of the parents. When doctors turn on/off modules in a D-plan, the IDE 506 responds by adding or removing edges or vertices from the graph.

Moving on from the PIO 505, FIG. 5 also illustrates an interface design engine (IDE) 506, which can perform actions such as taking D-plan specifications from the physician and determining which SSTs, which BMs and which Edu modules (potentially including medications, procedures, etc) to run for the patient. In some implementations, an IDE 506 could also determine how to merge and de-merge SSTs, BMs and Edu modules, and create the Data Capture Sensor Pool (DCSP) for the patient, which reflects the final merged and optimized set of SSTs, BMs and other data capture components. Preferably, as D-Plans are updated by physicians, new ones added, old ones removed, comorbidities changed and so on, the IDE 506 will update the patient's PIO 505 to reflect the current active set of Data Capture Modules. A system implemented according to the architecture of FIG. 5 could include only a single IDE 506, which would update all PIOs 505, with each patient having his or her own PIO 505. The IDE 506 will take as input the physician specifications of D-plans for a given patient. With this input, it will create the PIO 505 data structure. When physicians update (or add, delete) D-plans, the IDE 506 will update the patient's PIO 505 accordingly. An IDE 506 takes as inputs the D-Plans assigned to the patient by the physicians. It translates the D-Plans into a set of DCMs, such as SST's, Body Monitors and Education Modules that interact with the patient. This can be useful because multiple D-Plans can have an overlap in the data capture modules they contain. They can also have a conflict, where the same DCM prescribed has some differing characteristic such as frequency. However, as far as the patient is concerned, there can be only one unique manifestation of each DCM. The IDE 506 is therefore tasked with merging and demerging different D-Plans and having the D-Plan changes reflect in the PIO 505. The IDE's 506 output is writing and editing the PIO for a given patient.

Preferably, in operation, an IDE will execute the following rules:

1) If a new D-plan is added, it checks what BM, SST and Edu modules this D-Plan adds. It then checks if any of the BM, SST or Edu modules are already active for the patient from an earlier D-plan.

2) If, for a given DCM such as a BM, there is no existing requirement, the IDE 506 will add that BM by writing it into the patient's PIO 505.

3) If a given DCM, such as a BM or SST, is already in the patient's PIO 505, it checks if the new D-plan's specifications for the given DCM are different from the existing specification (e.g., the DCM's frequencies and alert level).

4) If the specifications are the same, it does nothing, as the DCM is already active for the patient. If the specifications are different, it selects the higher 'strength' specifications and rewrites the PIO 505 to change the DCM specifications to the stronger (e.g., higher alert level and/or higher frequency) specifications from the new D-plan.

5) When a D-plan is removed, the IDE 506 checks which all DCMs this D-plan imported into the patient's PIO 505. For each DCM imported into the PIO 505 by this D-plan, it checks if that DCM is also applicable to any other active D-plan. If not, the DCM is switched off. If the DCM is applicable to another D-plan, the IDE 506 checks if this D-plan's specifications for the DCM are stronger or weaker. If weaker, it makes no change. If stronger, it checks other D-plans, and downgrades the DCM's specifications to the next strongest specifications.

For the purpose of implementing these rules, it should be understood that when a DCM is added, whether Body Monitor or SST, each will preferably come with 3 frequency levels—High, Medium, Low. Based on the alert level set for the DCM, one of the frequencies will be used. The frequency will be set by default in the D-plan, but the physician can reset the frequency up/down by changing the alert level. It should also be understood that there could be a separate patient alert level, which would be specified in the PIO 505. In some embodiments, such a patient alert level could be limited to two states—High and Normal. In such an embodiment, if the patient alert level is Normal, the system would simply use the individual alert levels for each DCM to select the frequency. Alternatively, if the patient alert level is set to high, the system would use the highest alert level for each DCM. A list of exemplary interactions a doctor could have with an app front end in some embodiments which could cause a message to be posted to an IDE 506 and the IDE 506 to update a PIO 505 to track the modified D-plan are set forth below in table 3.

TABLE 3

Exemplary actions which could trigger a message to an IDE.

Add a D-plan
Add comorbidities (these may actually be imported from the patient profile, which the doctor may modify)
Turn SSTs on/off
Turn monitors on/off
Turn education modules on/off
Change the frequency of any of the above 3
Remove a D-plan
Remove comorbidities from the patient profile In addition to the IDE 506, the architecture of FIG. 5 also includes an interface controller engine (ICE) 507. The Interface Controller Engine 507 reads the PIO 505 to understand what actions should be taken with respect to the patient (e.g., app initiated requests for data). Accordingly, it is possible to conceive of the PIO 505 as functioning as an instruction sheet for the ICE 507 to follow. Based on the PIO 505, the ICE 507 will know which SST, BM or other modules to run and when, for any given patient. The ICE 507 reads the PIO 505 of a patient and figures out what actions to schedule, and could potentially maintain a local database of patient requests for data so that it can autonomously schedule and post such requests. It converts data from the PIO 505 into a queue of actions with appropriate times for the actions (e.g., figuring out which BM requests to send and/or which SST requests (if any) to send). In some embodiments, an ICE 507 could also be implemented to track when a request is not filled, and if to run a follow up to get the data from the patient. When the patient responds (e.g. by entering data into an app), the ICE 507 gets the data back and passes it (either directly or after performing some level of validation on it) to the DCE 504 to store and process. To facilitate this, the ICE 507 could be configured with an inventory of actions (e.g., notifications) available to it. Using the PIO 505, it selects from this inventory of actions, and puts them on a queue for delivery to the patient, with ideal delivery times. The messages may then go to the Engagement Engine (EE) 508 (discussed infra) or could be sent directly to the patient via an application front end or to other appropriate endpoint (e.g., a BM), depending on the embodiment and the context in which it is deployed.

Conceptually, some embodiments of an ICE 507 can be seen as responding to four types of events. Those types events, as well as actions which could be performed on incoming user data, are described below:

Administrative:
  Responds to "new patient" message from PIO. Updates local database of schedule requests
  Responds to "change patient alert state" from ACE. Updates local database, based on PIO
App-initiated, Scheduled:
  Maintains local database of all some or all requests to make to patients
  posts requests to EE as scheduled, based on database
  once a request is posted, the database is updated and request scheduled for next time, based on frequency
  when patient responds to request, ICE asynchronously sends response to DCE App-initiated, Unscheduled:
  receives request from ACE for information
  request immediately appears on app front end as a dialog box, page, etc
  patient response collected by ICE and sent to DCE
User-initiated:
  User may volunteer to enter data at any time
  ICE receives any new data and posts to DCE
All user data:
  May be filtered by ICE for basic out-of-range. If so, user is immediately asked for new data. (there could be a handshake protocol between app front end and ICE for this)
  Results in an update to the ICE scheduling database. ICE searches for the next scheduled collection point of received data and changes the next scheduled time, based on prescribed frequency Another way of conceptualizing the role an ICE may play in interactions with patients in some embodiments is as performing the following four functions:
1) The ICE 507 schedules and sends to the patient the following types of data
  Questions to ask the patient from an SST session, now
  Instructions to issue the patient, now
  Scheduled notifications to send, based on T-plan frequencies, at a future time
  Follow-up questions from body monitors
2) The ICE 507 processes and sends to the DCE 504 the following patient input
  Answers to immediate questions
  Answers to scheduled notifications
  Unprompted data input
3) The ICE 507 is responsible for maintaining metadata on patient input
  Where the input comes from (SST, unprompted, prompted, etc.)
  Timestamp
  Type of input (monitor, symptom, profile, etc.)
  Was the data on time, or expired (if prompted?)
4) The ICE 507 maintains, at all times, a schedule of upcoming notifications to send including, time to send, time of expiry and scheduled frequency, for each notification.

It should be noted that, while the above discussion focused on scheduled actions based on information from a PIO 505, in some embodiments, an ICE 507 could handle unscheduled actions and/or actions based on information from other components of the system. For example, in some embodiments, an ICE 507 could handle direct requests from an ACE 503, such as to send data requests to a patient. These interactions could be scheduled interactions (which would likely be the case in an embodiment in which an ACE was configured to handle unscheduled interactions through another component, such as directly through an EE 508), or could be unscheduled interactions as well. For example, in some embodiments, an ACE 503 could send an ICE 507 instructions to trigger actions such as sending a BM question or SST question out of schedule. An exemplary output packet for communicating data from an ACE 503 to an ICE 507 is provided below in table 4.

TABLE 4

Exemplary data packet from ACE to ICE packetID
patientID
Timestamp
Type - instruction, question, scheduled notification TABLE 4-continued Exemplary data packet from ACE to ICE Content - text of message, etc.
ScheduledDeliveryTime - either NOW or future date
Duration - time until expiration
Frequency - how long until resend (not always used)

Figure 11:
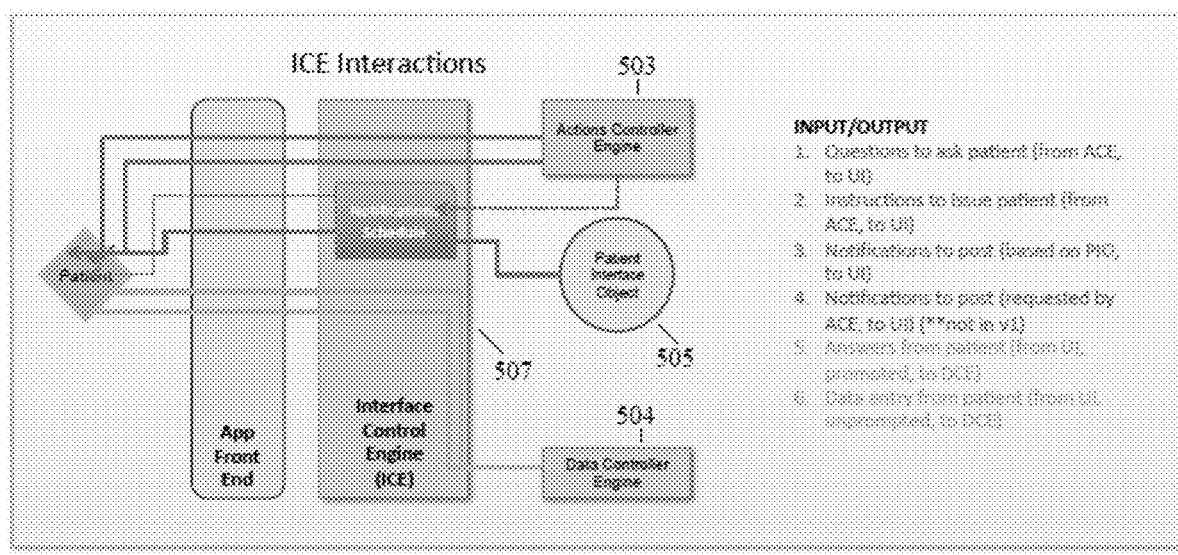
FIG. 11 provides a high level chart of data flows which could take place in some implementations of the disclosed technology.
Figure 12:
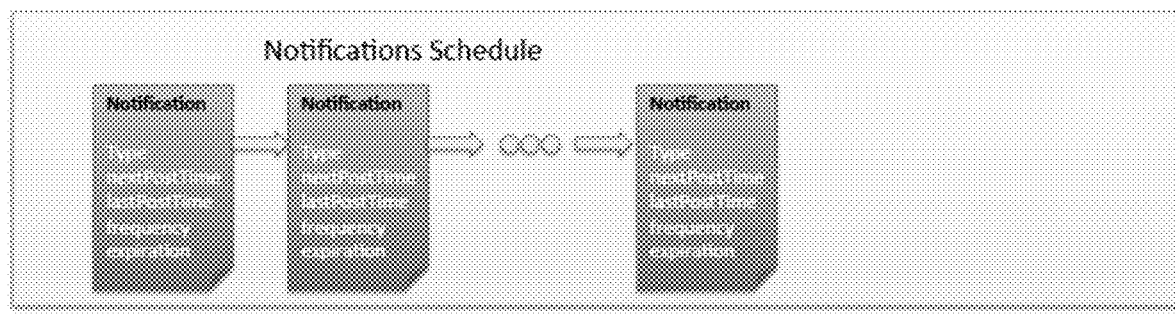
FIG. 12 illustrates how a notifications schedule from an interface controller engine could be represented.

FIG. 11 provides a high level chart of data flows which could be involved in this process, as well as data flows from the PIO 505 through an ICE 507 to a patient and from the patient through the ICE 507 to a DCE 504. FIG. 12 illustrates how a notifications schedule from an ICE 507 such as shown in FIG. 11 could be represented.

The final element illustrated in FIG. 5 for interacting with a patient is the engagement engine 508. As set forth above, an engagement engine 508 may deliver messages provided to it from an ICE 507. Such delivery could take place at a time requested by an ICE 507, or could be at another time if the EE 508 feels the need to modify it. While the architecture of FIG. 5 may be implemented without an engagement engine 508 separate from the ICE 507, in embodiments where it is present, the EE 508 will control delivery of messages to users, mainly patients. This can take place with the EE 508 being called by the ICE 507, and receiving a current scheduled list of notifications, to send the patient, reorders the list as necessary by rescheduling events, and sends the list back to the ICE 507. In embodiments where this takes place, there could be a parallel process for questions/instructions to be asked/executed "now", which the ICE 507 could filter out before sending a list of notification to the EE 508 and processing directly itself. Similarly, it is possible that an EE 508 could read an array/list of output packet objects (e.g., objects including data such as shown in table 4) maintained by the ICE 507, and reschedule them by updating a ScheduledDeliveryTime element in the header of a packet, effectively resetting the scheduling of the corresponding notification. In some embodiments it may not generate messages (which function could be performed by ACE 503), but it controls when and how the messages get delivered, to maximize the engagement of the user and optimize the user experience. In some embodiments, there may be only one engagement engine 508 across the application.

The final group of item illustrated in FIG. 5, the data controller engine (DCE) 504 and patient data object (PDO) 509 may be used to control the data available to an entity operating a system implemented according to the architecture of FIG. 5 (e.g., by controlling where data captured by an ICE 507 is stored). These modules may also provide a simple intelligent interface for other modules to request raw patient data. The PDO 509+DCE 504 can control storage and access to raw patient data, while the PSO 501 uses this raw data to provide a summary view of the current patient state, calculating various measures based on this raw data. Each of the data controller engine 504 and patient data object 509 is discussed in more detail below.

Turning first to the patient data object 509, in some embodiments, that item could be implemented as a simple data structure which represents a map of data items collected about a patient and where they are stored (e.g., an XML file that describes what data is collected for a patient and maintains metadata about this data). Each patient will preferably have his own PDO 509, which reflects the list of sources of data used for that patient. In effect, the PDO 509 says what data we are collecting for a given patient. In some cases, such as where the only source of data for a patient is what is specified in D-plans, the PDO 509 and PIO 505 for a patient will likely hold substantially the same information about a patient. However, if there are additional sources of data (e.g., non-D-plan sources of data), then these will preferably be reflected in the PDO, but not included in the PIO 505 as well.

Preferably, the PDO 509 will not store raw data, but instead will only keep a map of what data is collected and, in some cases, where it is stored. The State Controller Engine (SCE) 502 will read the PDO 509 to figure out what data is being collected for a patient, and collect that data from the relevant datastore itself for any scheduled updates to the PSO 501. In some embodiments, other services may also use the PDO 509 to figure out what data is available for a given patient. An illustrative example of a data structure which could be used to implement a PDO 509 is provided below in table 5.

TABLE 5

Exemplary patient data object data structure

```
<PDO>
    <PatientID>192863</PatientID>
    <DateCreated>201404101110</DateCreated>
    <DCM>
        <BM>
            {Blood_Pressure, Internal,  Float_regular, S3, PHI, {SCE},
            201406201238, None}
        </BM>
        <BM>
            {Temperature, Internal, Float_regular, S3, PHI, {SCE}, 201406201238,
            None}
        </BM>
        <BM>
            {Weight, Internal, Float_regular, S3, PHI, {SCE}, 201406201238, None}
        </BM>
        <BM>
            {Distance_walked,  Internal,  Float_regular, S3, PHI,  {SCE},
            201406201238, None}
        </BM>
        <SST>
            {Shortness_breath, Internal, Int_regular, S3, PHI, {SCE}, 201406201238,
            None}
        </SST>
```

TABLE 5-continued

Exemplary patient data object data structure

```
    <SST>
        {Wheezing, Internal, Int_regular, S3, PHI, {SCE}, 201406201238, None}
    </SST>
    <SST>
        {sputum-color, Internal, Int_regular, S3, PHI, {SCE}, 201406201238,
        None}
    </SST>
    <SST>
        {sputum-volume, Internal, Int_regular, S3, PHI, {SCE}, 201406201238,
        None}
    </SST>
    <SST>
        {chest-pain, Internal, Int_regular, S3, PHI, {SCE}, 201406201238, None}
    </SST>
    <Payer_records>
            <Provider_name>BCBSKY-Horizon</Provider_name>
            <Provider_ID>1234</Provider_ID>
            <Provider_data_elements>
            {Policy-Info, External, JSON, S3, PHI, {SCE}, 201404101045,
            None}
            {Events, External, JSON, S3, PHI, {SCE}, 201404101045, None}
        </Provider_data_elements>
    </Payer_records>
    </DCM>
</PDO>
```

As stated previously, the PDO 509 will preferably not store raw data. Instead, raw data coming from an ICE 507 or other data source 510 will be taken and stored in a datastore 511 by DCE 504. The DCE 504 which may then update the PDO 509 if necessary to reflect where and how the data is being collected for a given patient (e.g., in a datastore 511 implemented as columnar SQL databases, NoSQL datastores, flat files, JSON documents and/or other possible data stores, as appropriate for given raw data type). The DCE 504 can also send a message to the SCE 502 letting it know that data has been updated for a patient and what new data items have been added so that the SCE 502 can pick up that data and use it to update the patient's PSO 501. In this manner, any BM measurement, any profile data edit, any SST answer, and any D-plan changes by a physician can update the PSO 501, allowing the PSO 501 to function as a single version of all truth about a patient. The PSO 501 can be seen as a virtual representation of the actual patient (i.e., a representation of the patient person). In addition to being responsible for updating a PDO 509 as changes are made to a PIO 505 or available external sources 510 (including addition of new data sources), a DCE 504 could also be responsible for creating a new (generally empty) PDO 509 upon enrollment of a new patient. This can be achieved by implementing a DCE 504 as a set of rules which are updated when new data sources are added to the system. Preferably there will only be one such set of rules/DCE 504 per system implemented according to the architecture of FIG. 5, and that single set of rules/DCE 504 will be used to update, create and maintain the PDOs 509 for all enrolled patients.

In general, a DCE 504 will be configured to write/update data in a PDO 509 in the following circumstances:
1) when a new patient is added to the system
2) when a D-plan is associated with a patient, in which case the IDE 506 hands control to the DCE 504, and the DCE 504 has access to the PIO 505. The DCE 504 reads the PIO 505 to understand what all data capture modules (DCMs) have been assigned to the patient by the physician. This tells the DCE 504 what all data is being collected for the patient from the D-plans. The DCE 504 uses the PIO 505 information to write into the PDO 509 the list of all data items being collected for the patient, which could initially result in this list simply being the list of BM, SST and Edu modules active for the patient.
3) When a new D-plan is added or any changes are made to existing D-plans, the DCE 504 gets the message from the IDE 506. The DCE 504 then reads the updated PIO 505 and checks if any changes are required to the PDO 509 and makes them if required.
4) If new external data sources are added for a patient, such as Payer Data, EMR data, Pharmacy Data—the DCE 504 is instructed that a new data source has been added for the patient. Part of this instruction will preferably include:
a. PatientID
b. Data Source Name
c. Data description elements described above
The DCE 504 then uses this information to update the patient PDO 509 by writing into the PDO 509 details about the new data source.

Preferably, in a system following the architecture of FIG. 5, when other components send a message to a DCE 504, the message will:
1) Identify patientID to access patient's PDO 509
2) Tell DCE one of following:
 a. New datasource being added
 b. New raw data for patient
3) If new a datasource is being added, provide:
 a. Data source name
 b. Internal or external
 c. Data format
 d. Data storage location
 e. Data privacy type: PHI or non-PHI
 f. Data access permissions: which modules can access the data (usually only SCE 502)
 g. Date source added
 h. Source expiration: usually none
4) If new raw data coming, provide the raw data type (e.g, BM, SST, Edu, external (payer, EMR, etc)). The DCE 504 will check the PDO 509 for where this data type needs to be stored, store the data in the required location and, once confirmation on data storage has been received from the relevant data store, hand over control to the SCE 502.

In addition to the items and data structures illustrated in FIG. 5, a system implemented using that architecture could also include certain shared data structures, such as lists of questions and instructions which could be read and write accessible by both an SCE 502 and ACE 503. Such lists could also be linked to individual patients, with each patient having different state flags indicating the state of the questions/instructions for him or her. Where it is present, a list of questions could be implemented as an array, e.g., an array identified as AllQuestions[ ]. Where such an array is present, it may be accessed indirectly, so AllQuestions[cough] would a question, even though 'cough' may not be the direct index value of the array. The array would preferably be susceptible to re-ordering without impacting the interface, and be associated with two Boolean flags for individual patients which could be accessed indirectly (e.g., via references to AllQuestions[q]. Ask and AllQuestions[q]. Asked (for any question q)). There may also be a function to initialize all Boolean fields for the questions to 'false.' Instructions could potentially be represented similarly (i.e., in an indirectly accessed array). Additionally, it is possible that instructions and/or questions could be organized into multiple arrays, which each might have their own flags. For example, instructions could be organized into AllTriageInstructions[ ] and MedicationInstructions[ ] arrays, where each element in the AllTriageInstructions[ ] array has a single flag (e.g., AllTriageInstructions[x]. On), while medication instructions would not only have that flag but could also be organized as a two dimensional array with medications grouped by both type and specific medicine (e.g., MedicationInstructions [antibiotic]. On=true could be executed as a general instruction, or MedicationInstructions[antibiotic][amoxicillin]. On=true could be implemented as a specific instruction). In such a case, an SCE 502 could turn on MedicationInstructions[ ] as a result of questions being asked, and the ACE 503 would turn on TriageInstructions[ ] by looking at a SSTscore field in a PSO 501 and read the "On" instructions to determine what to tell the patient.

Figure 14:
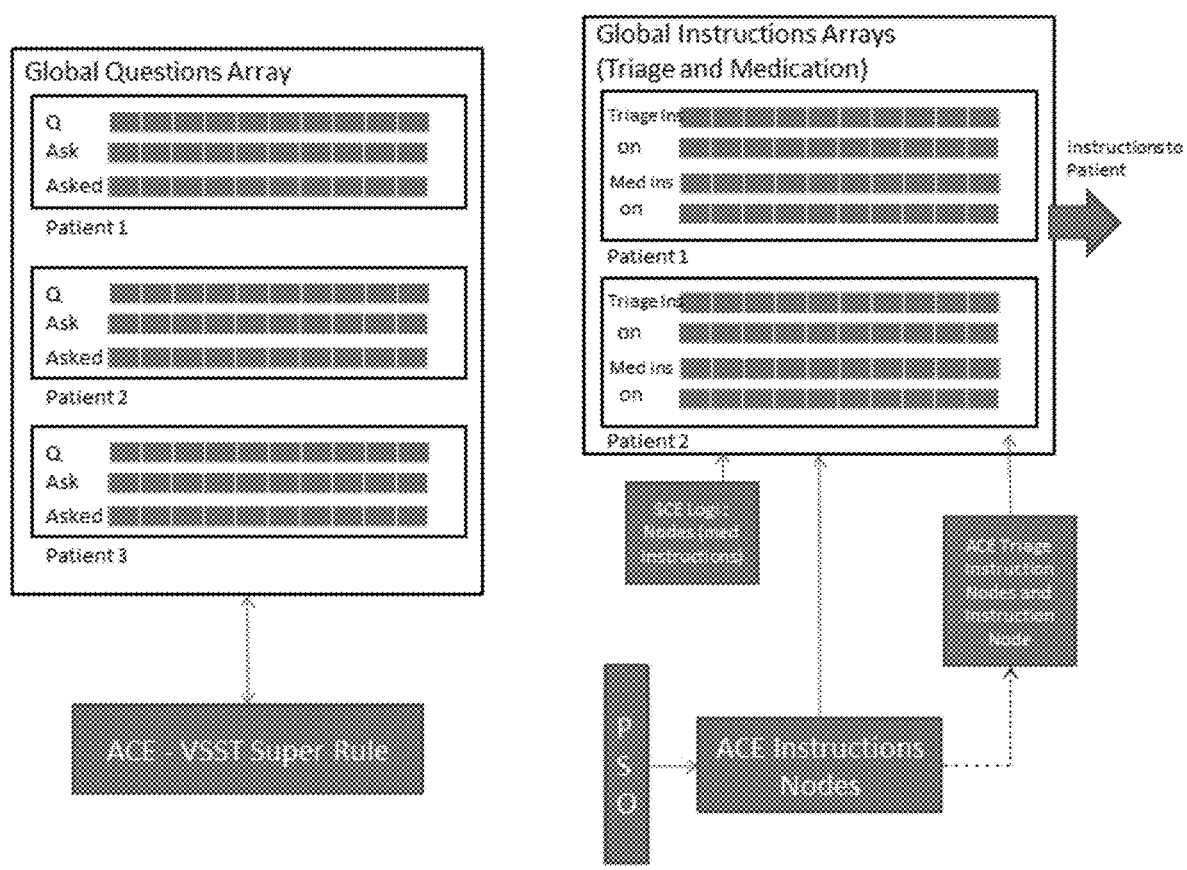
Figure 15:
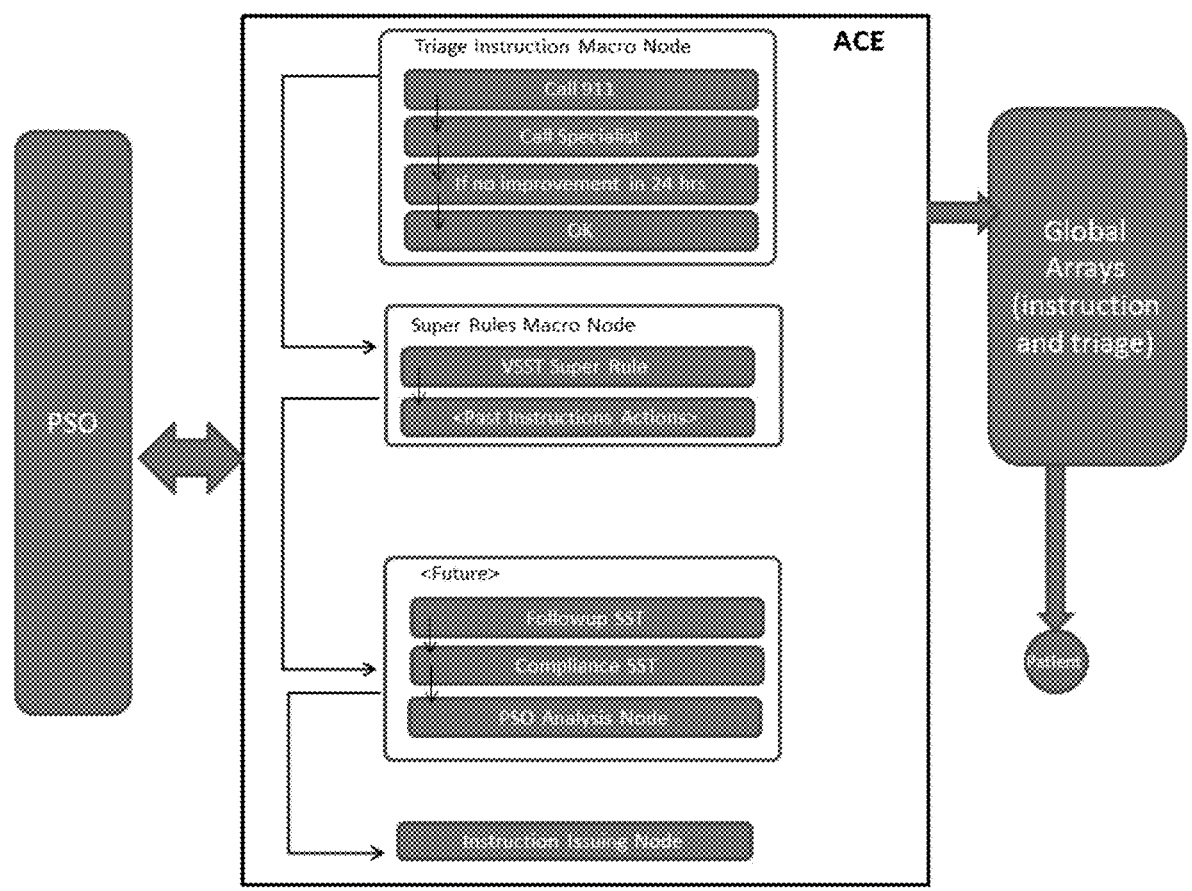
FIG. 15 illustrates a sequence of events as nodes are executed by an action controller engine.
Figure 16:
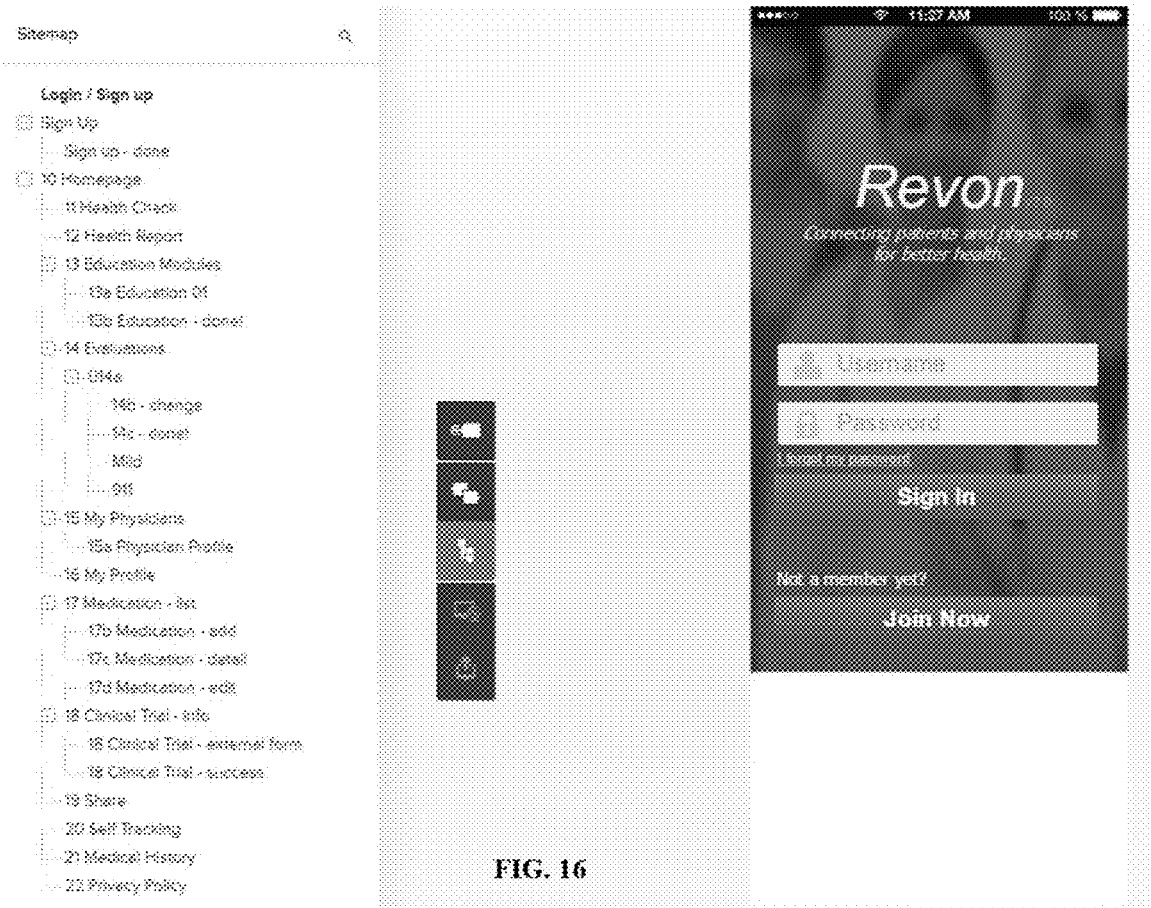
FIGS. 16-43 illustrate interfaces which could be presented by an application based patient portal, along with an application map in the leftmost portion of the illustrations illustrating how the various interfaces relate to each other.
Figure 17:
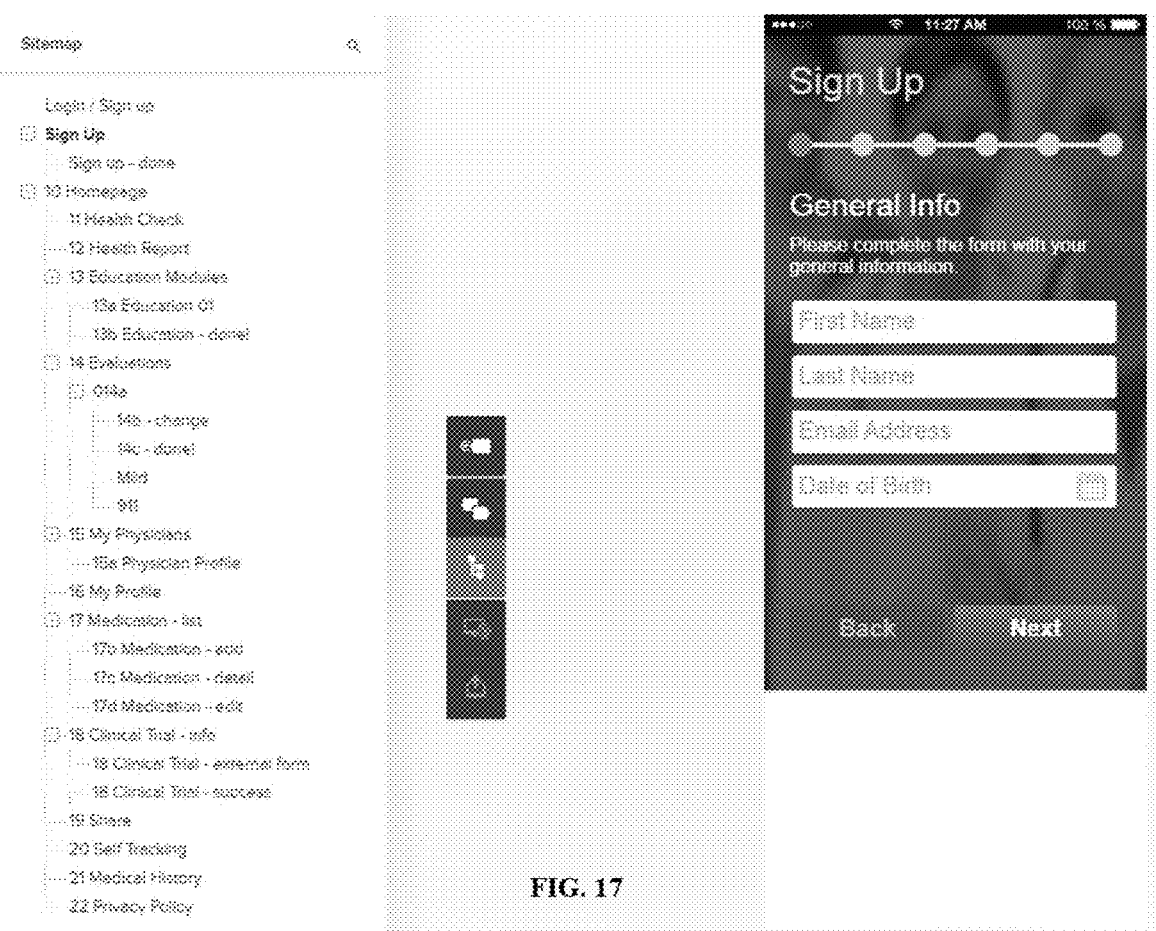
Figure 18:
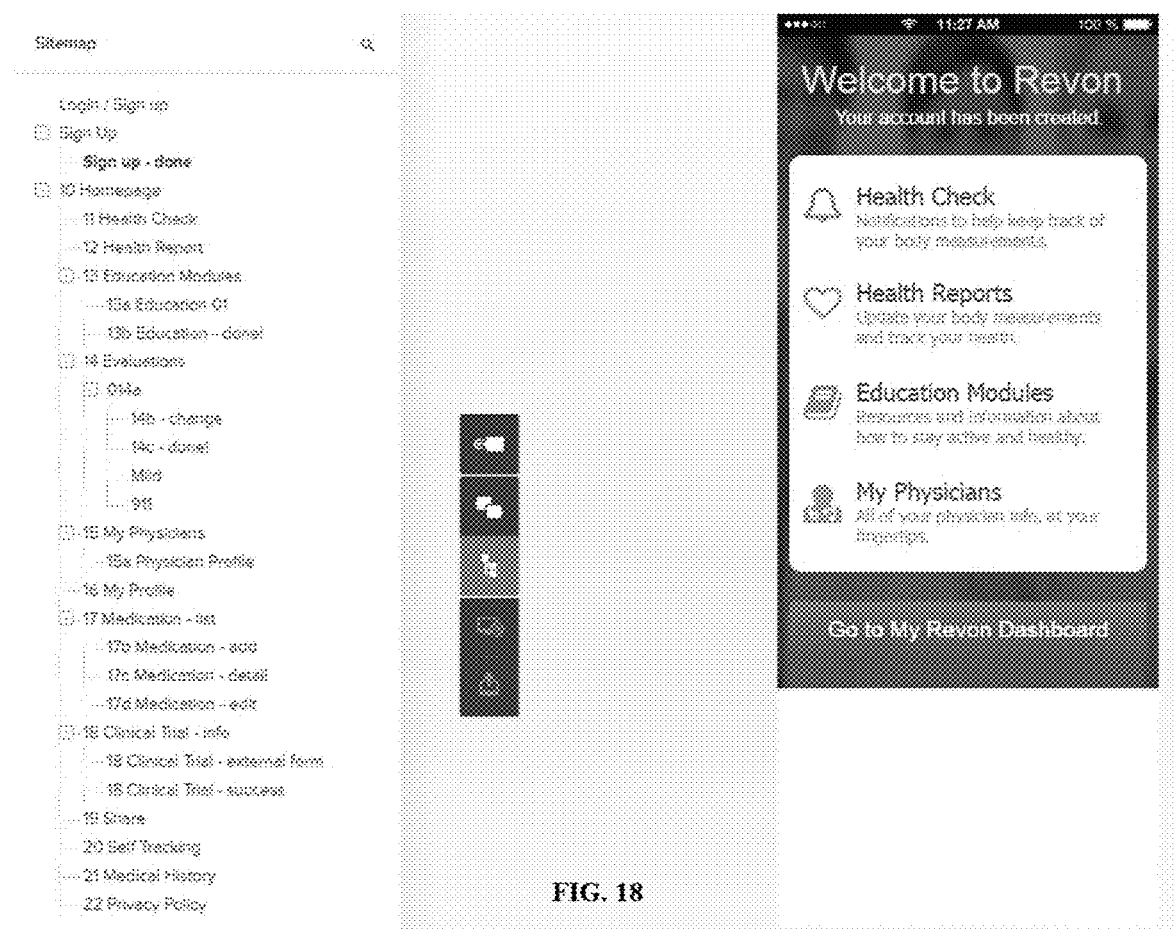
Figure 19:
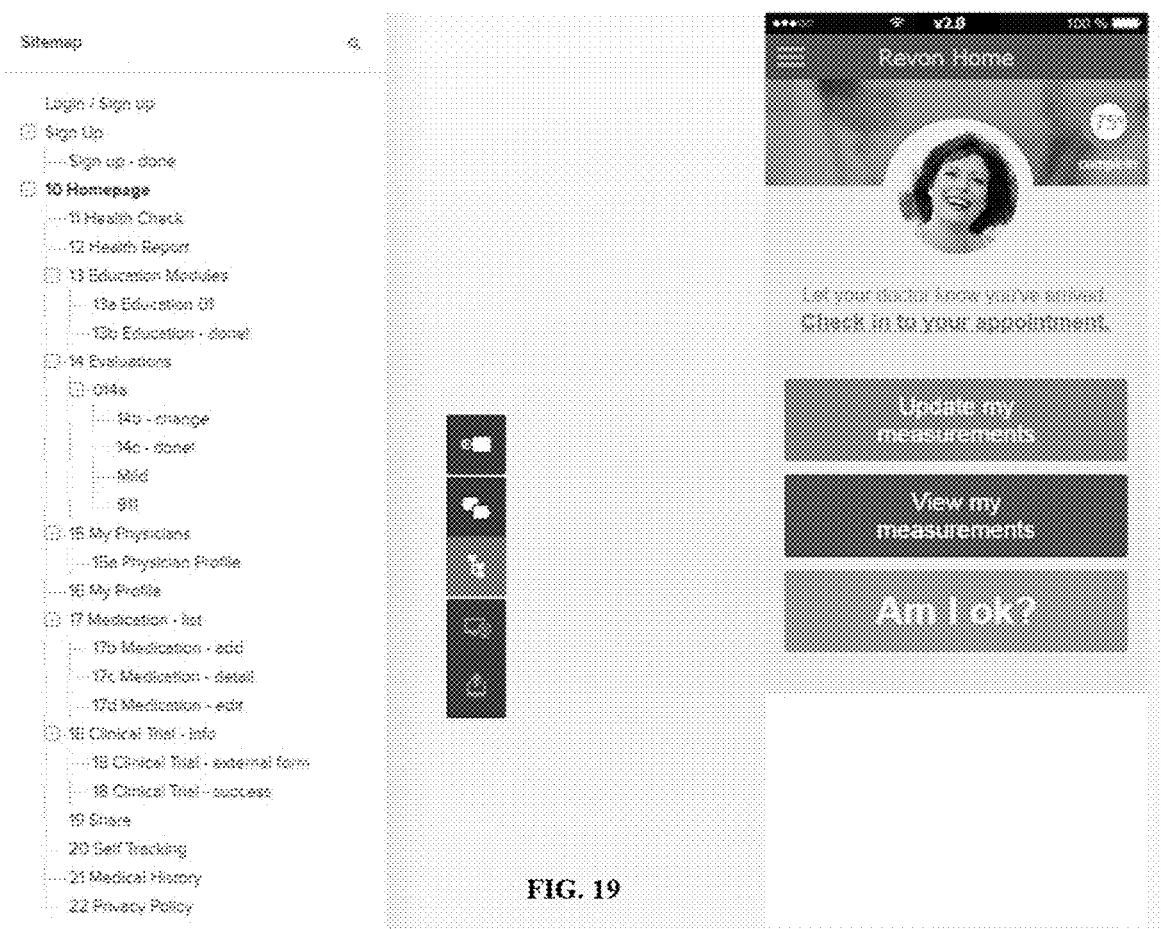
Figure 20:
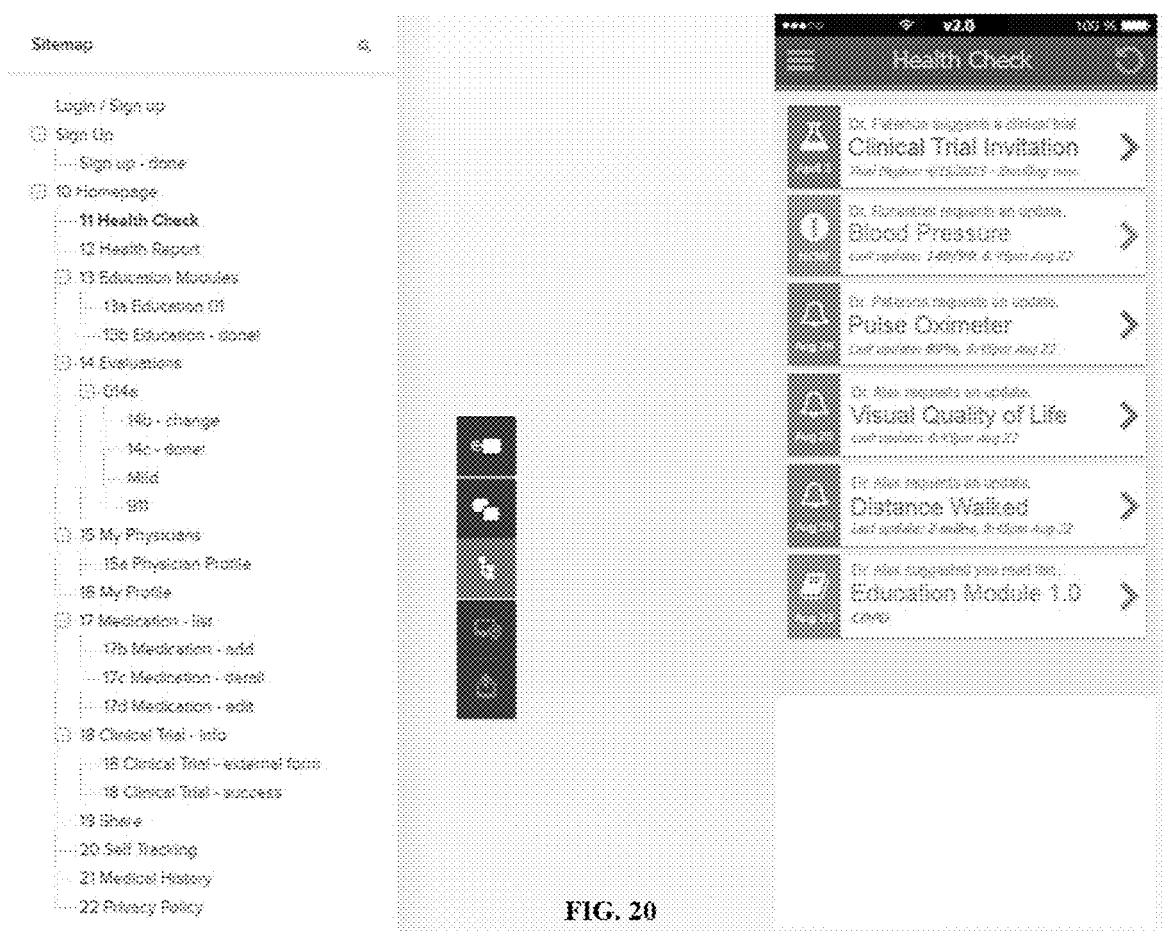
Figure 21:
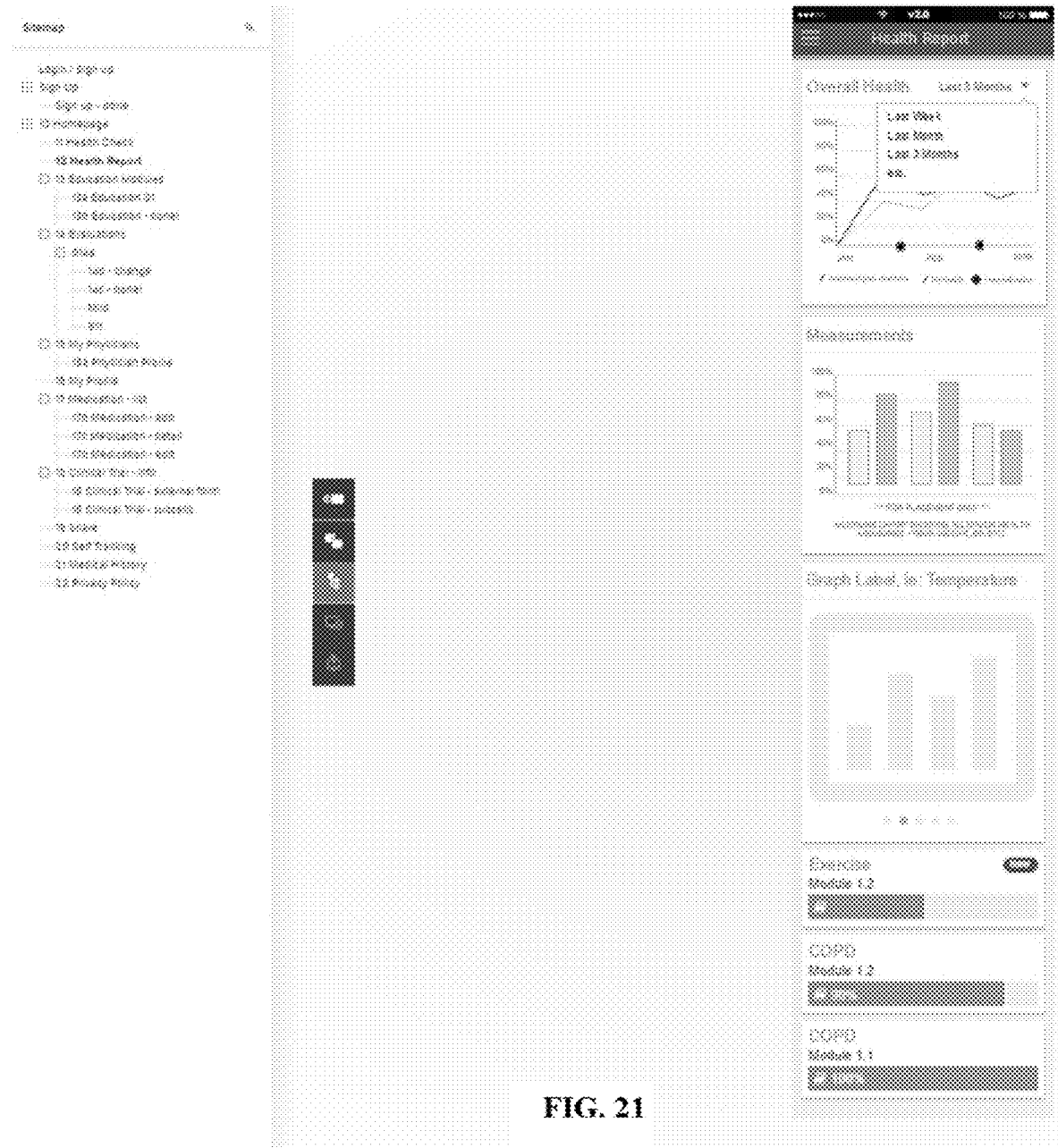
Figure 22:
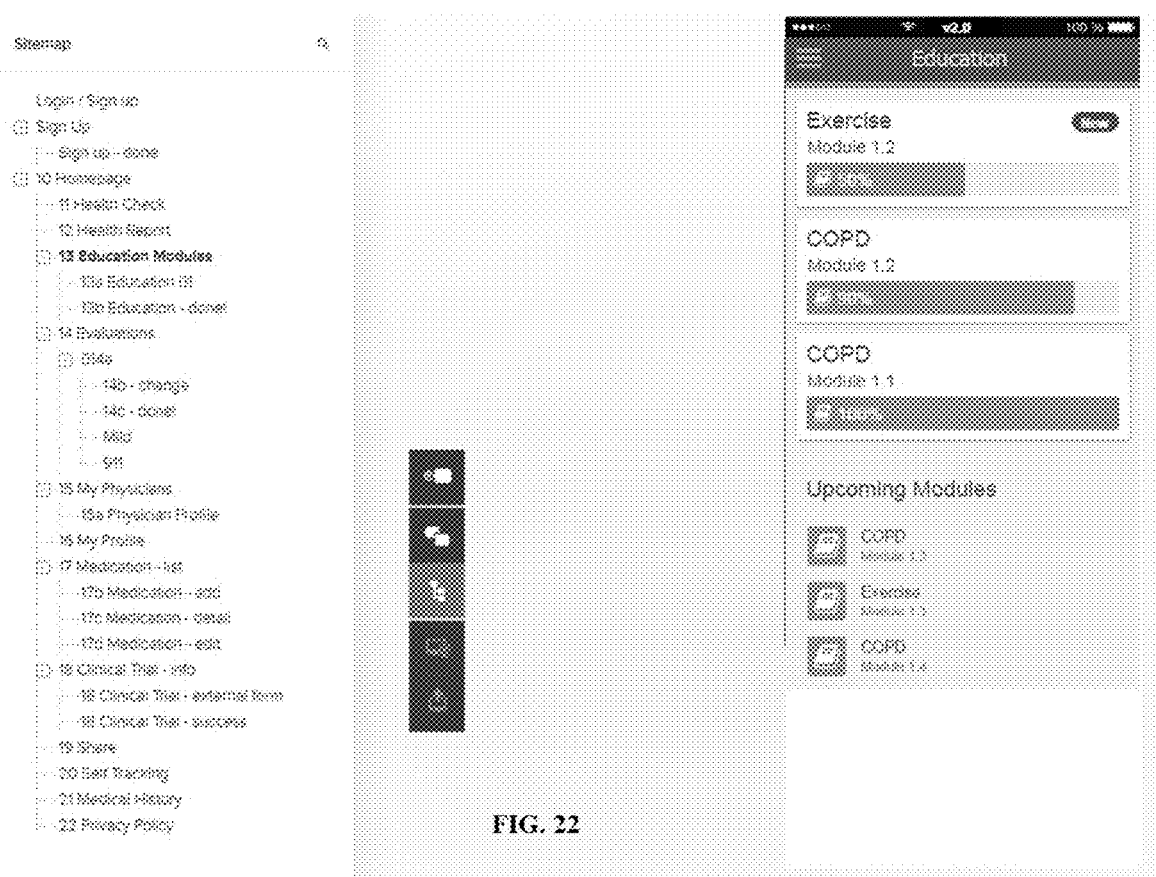
Figure 23:
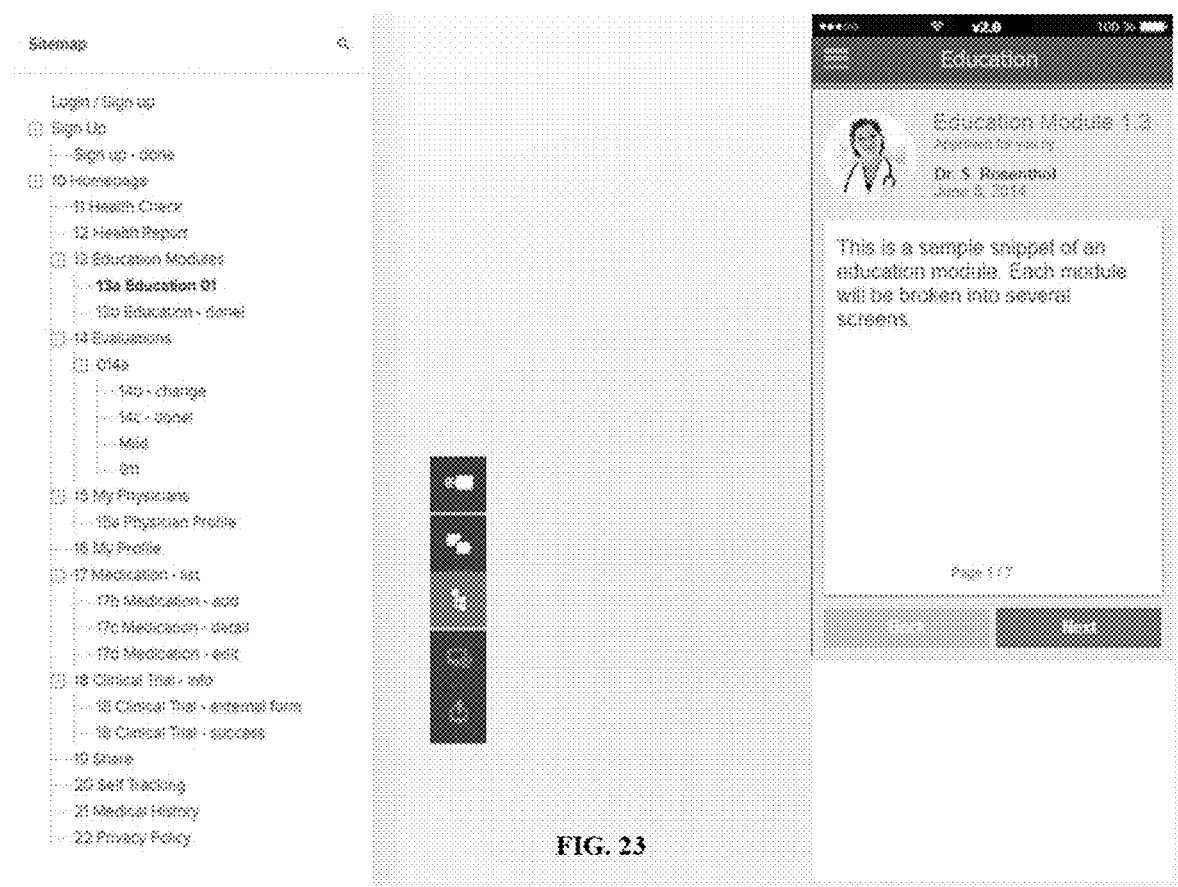
Figure 24:
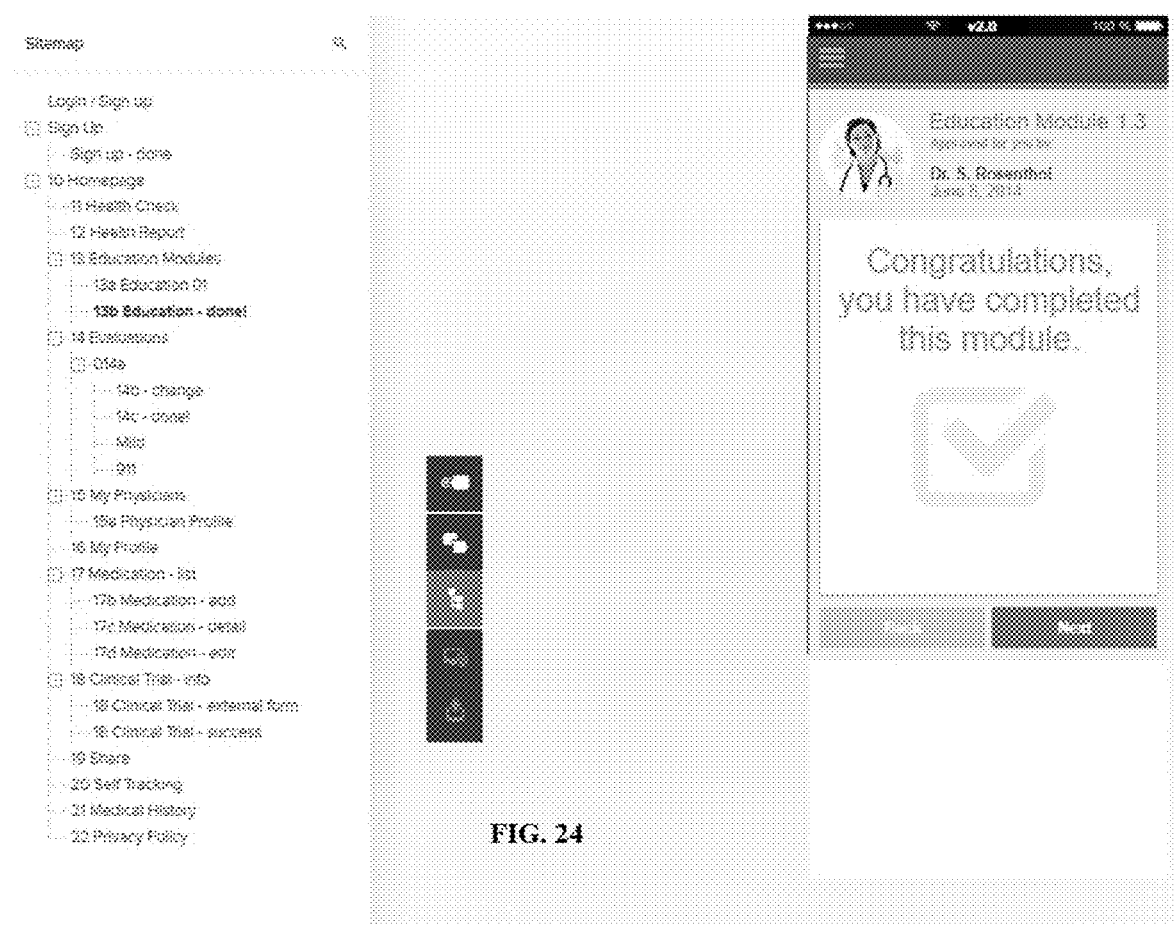
Figure 25:
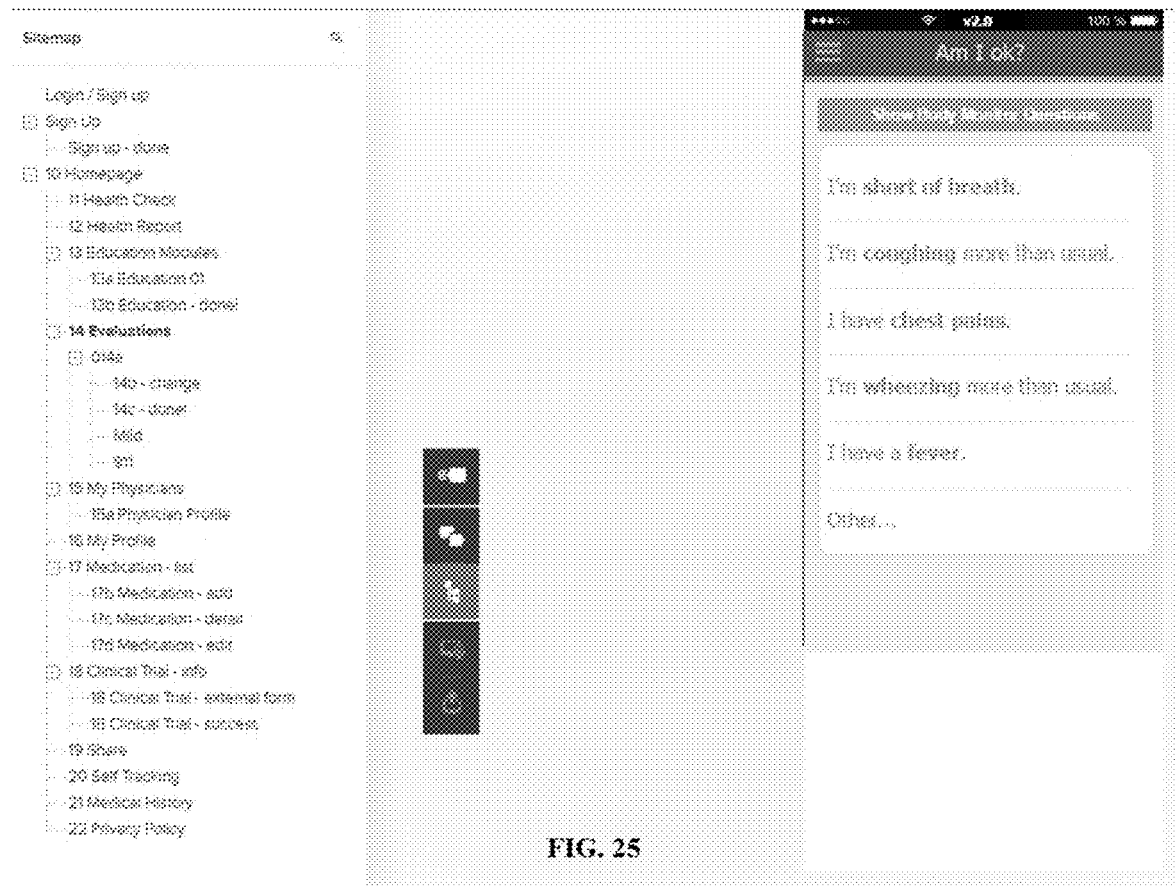
Figure 26:
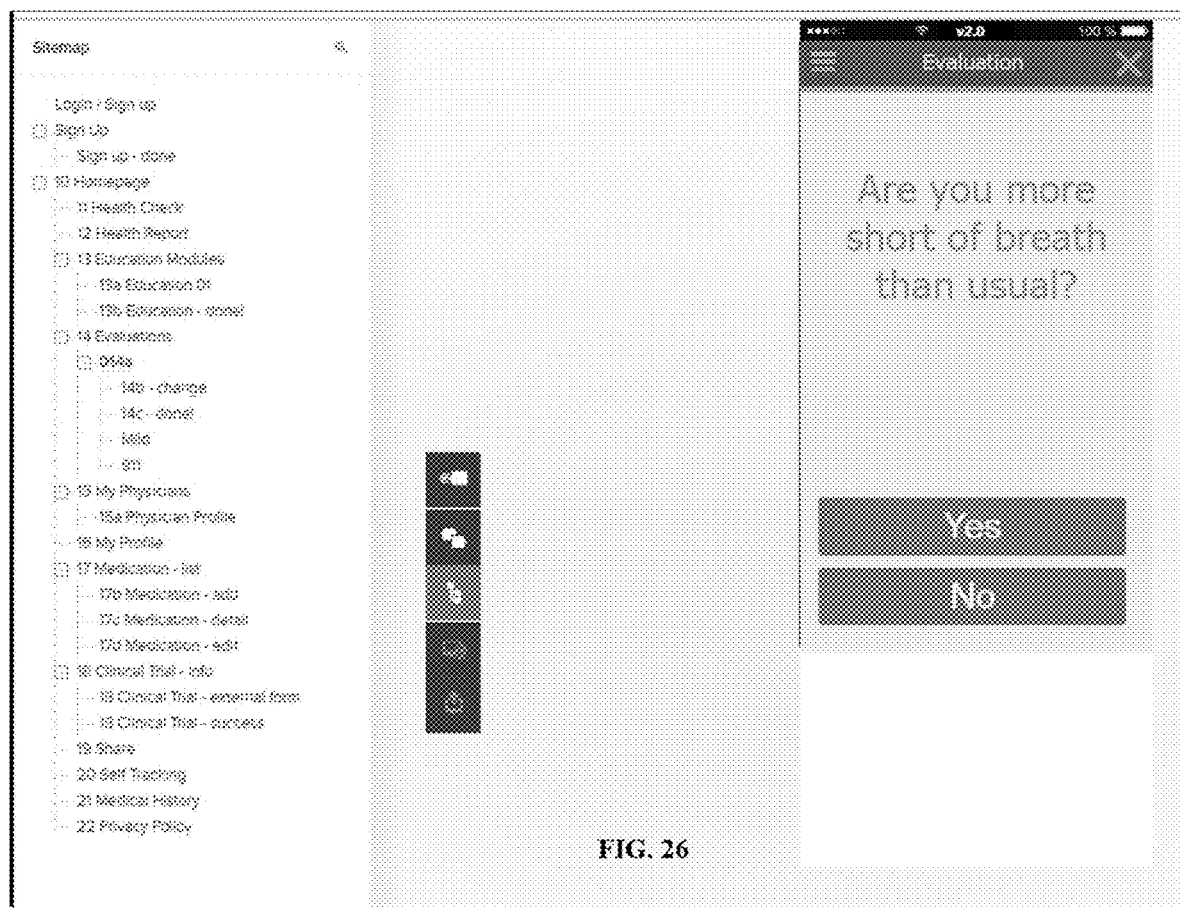
Figure 27:
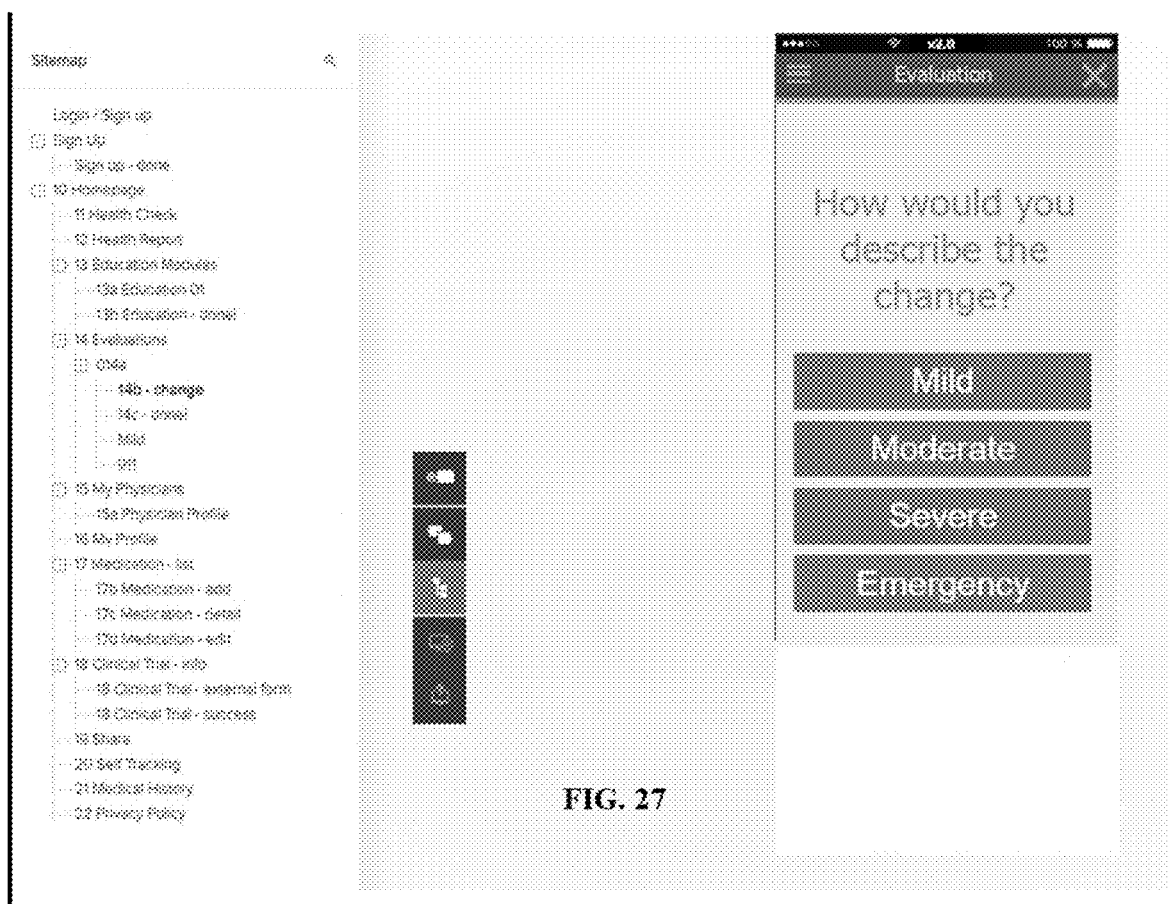
Figure 28:
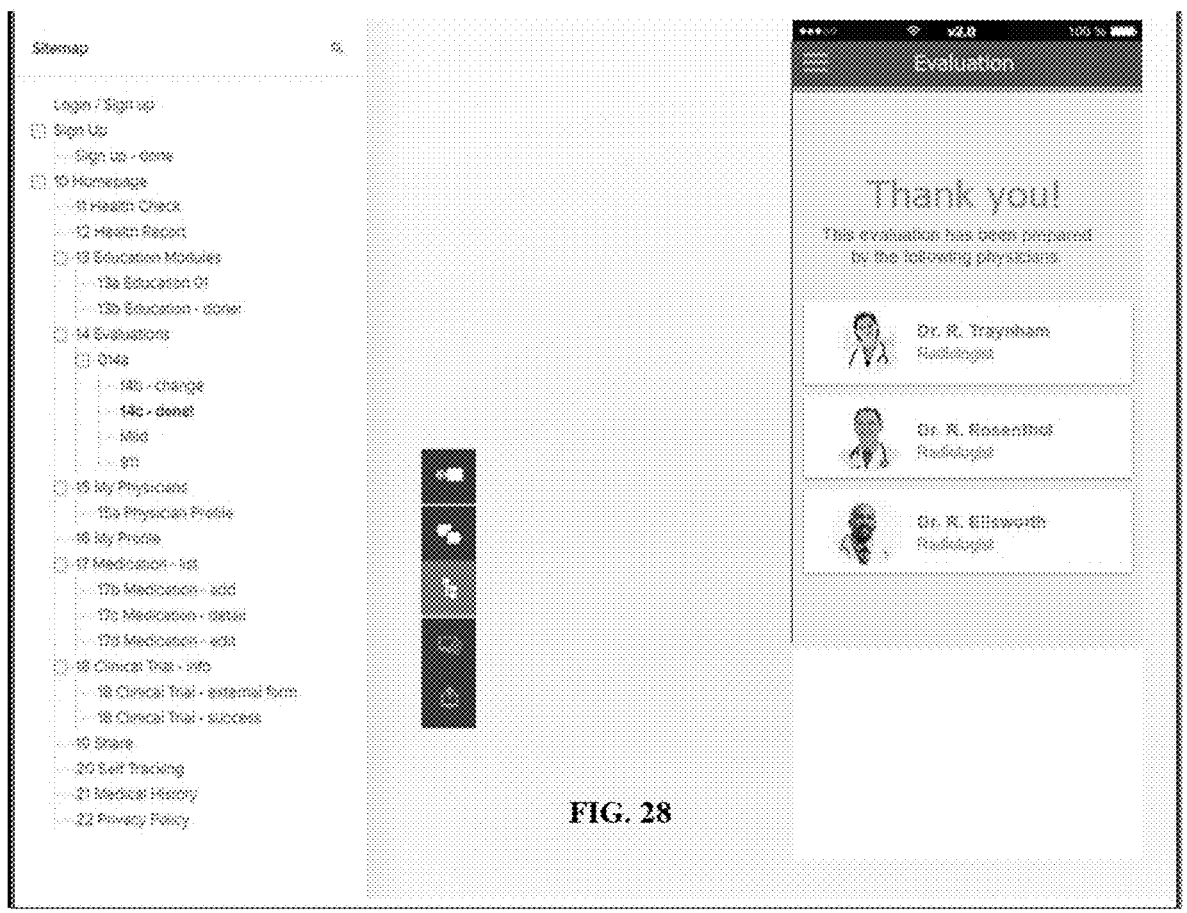
Figure 29:
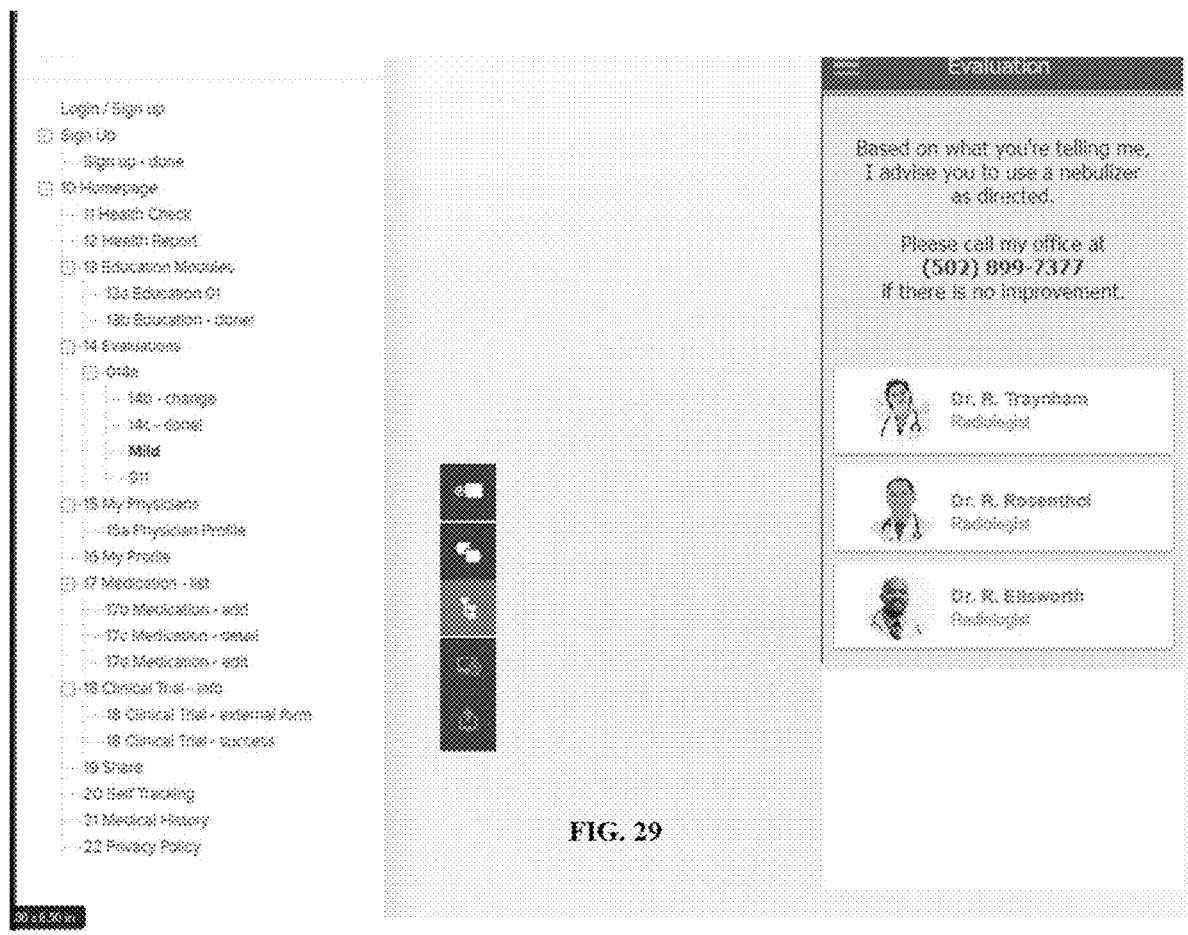
Figure 30:
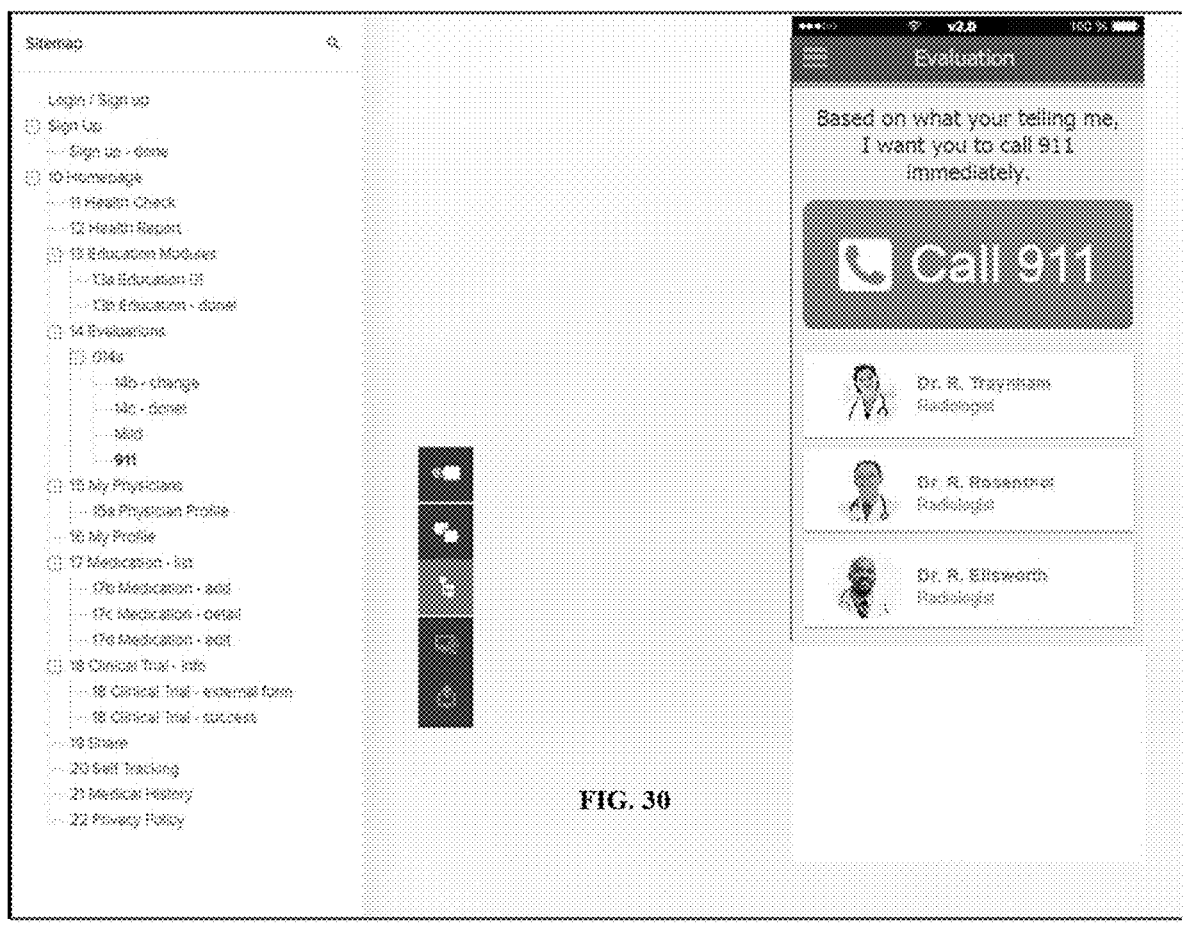
Figure 31:
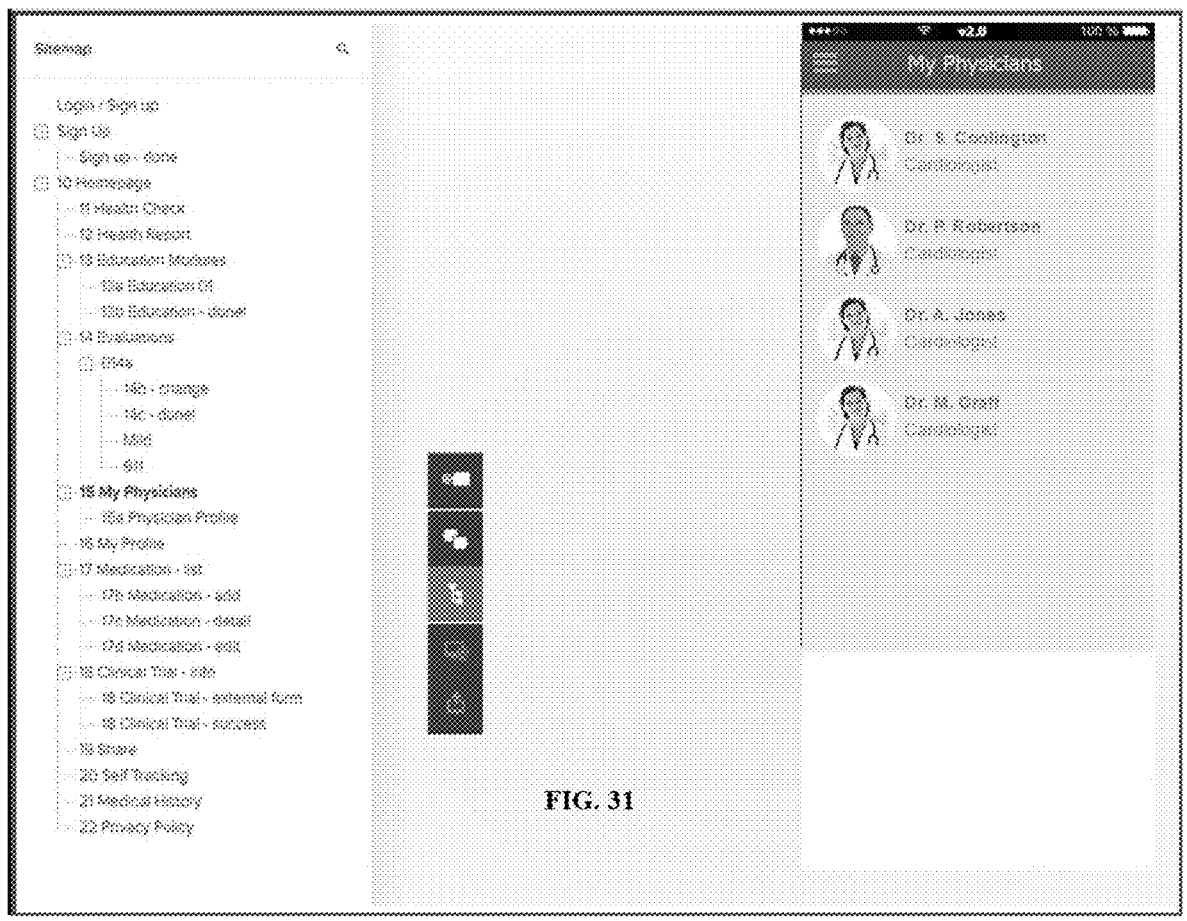
Figure 32:
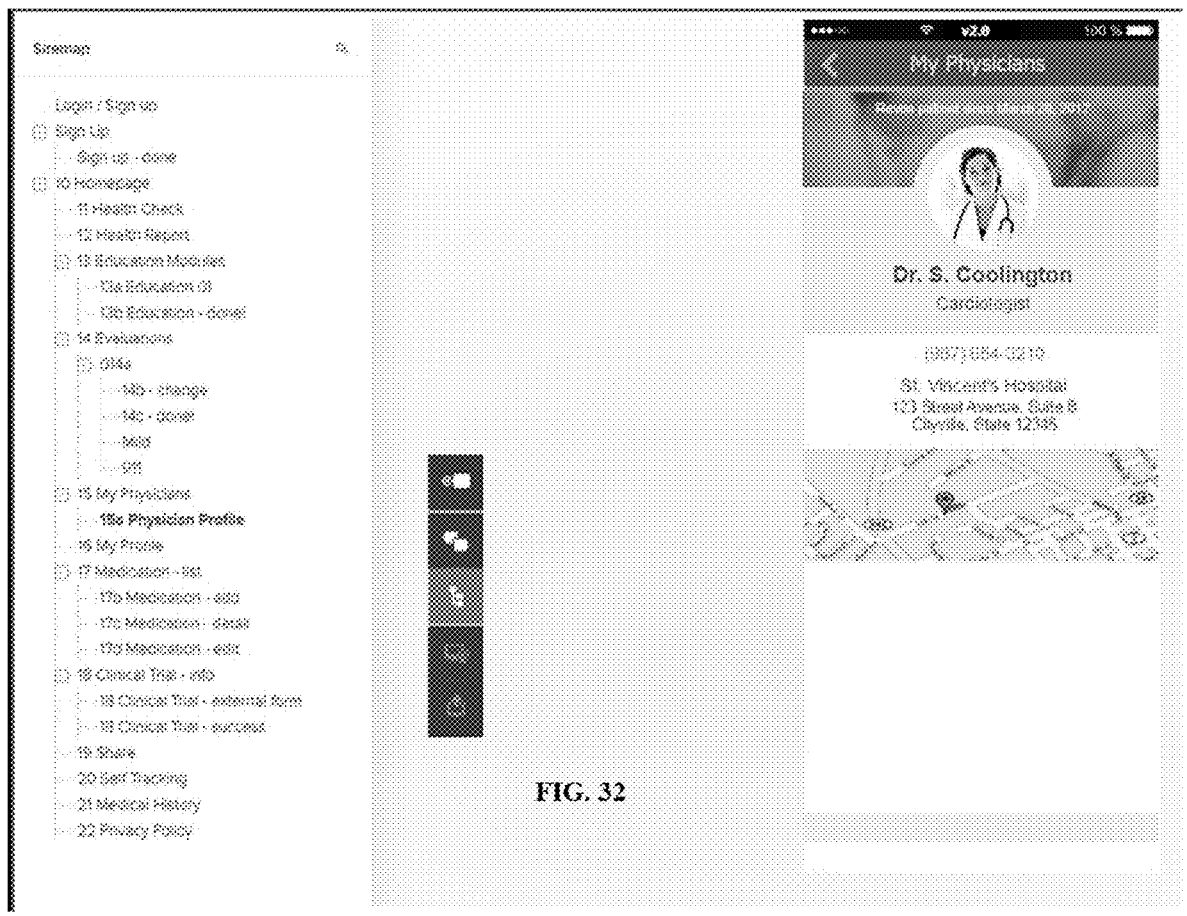
Figure 33:
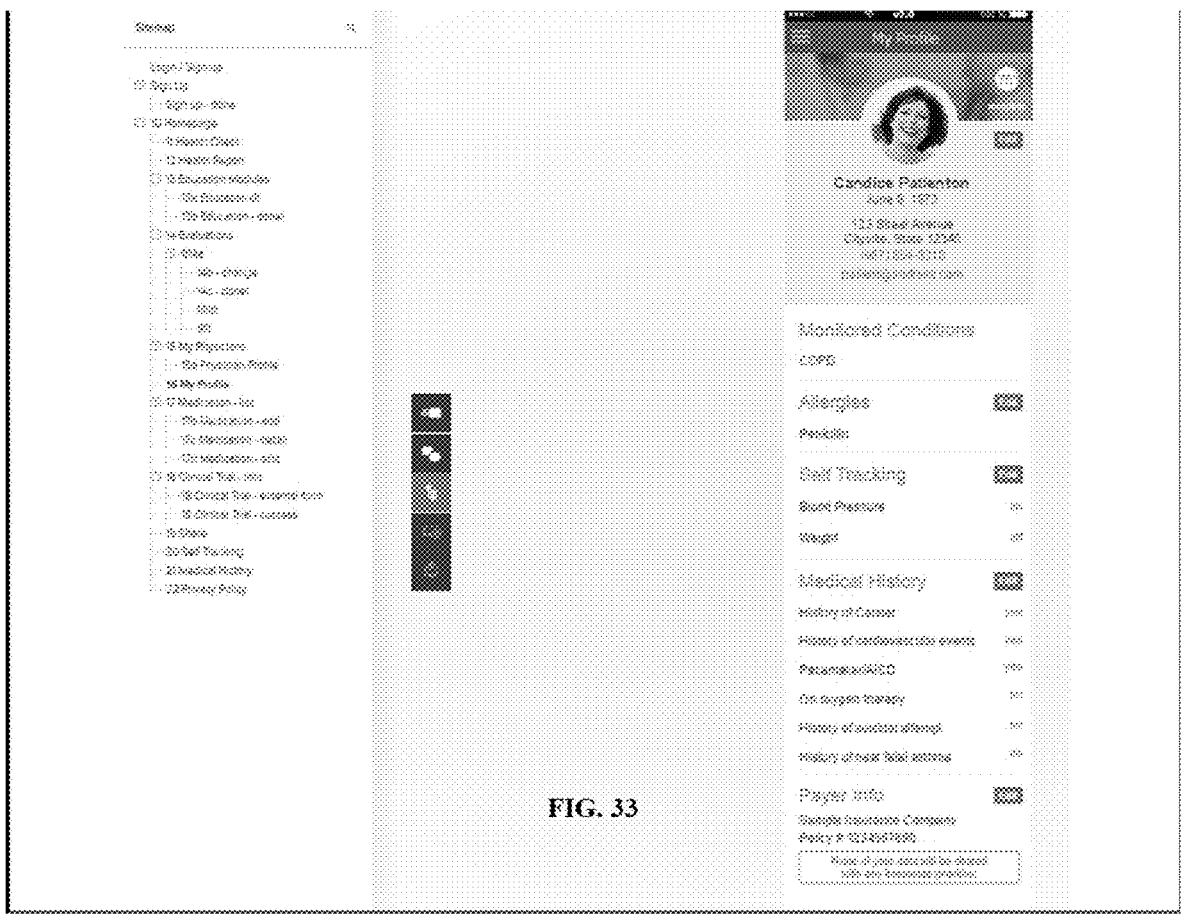
Figure 34:
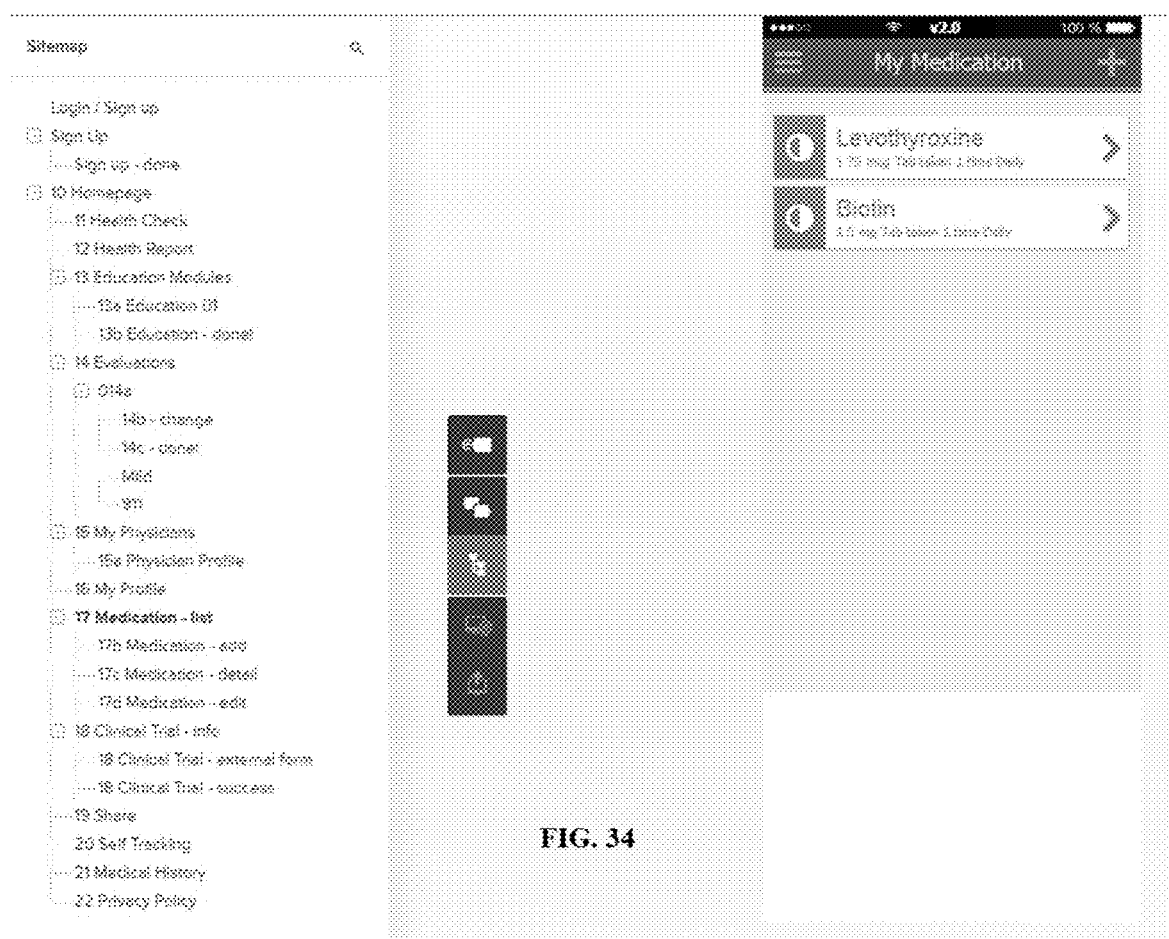
Figure 35:
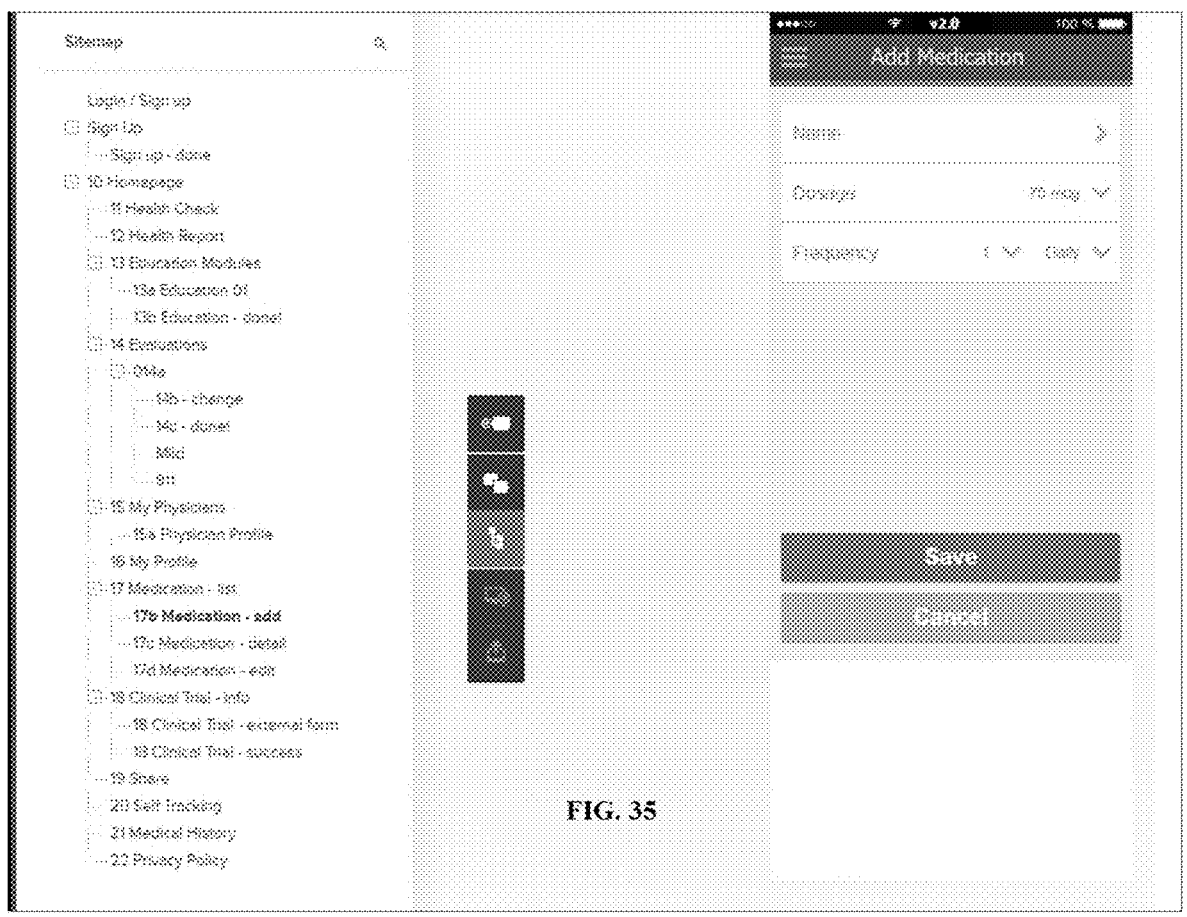
Figure 36:
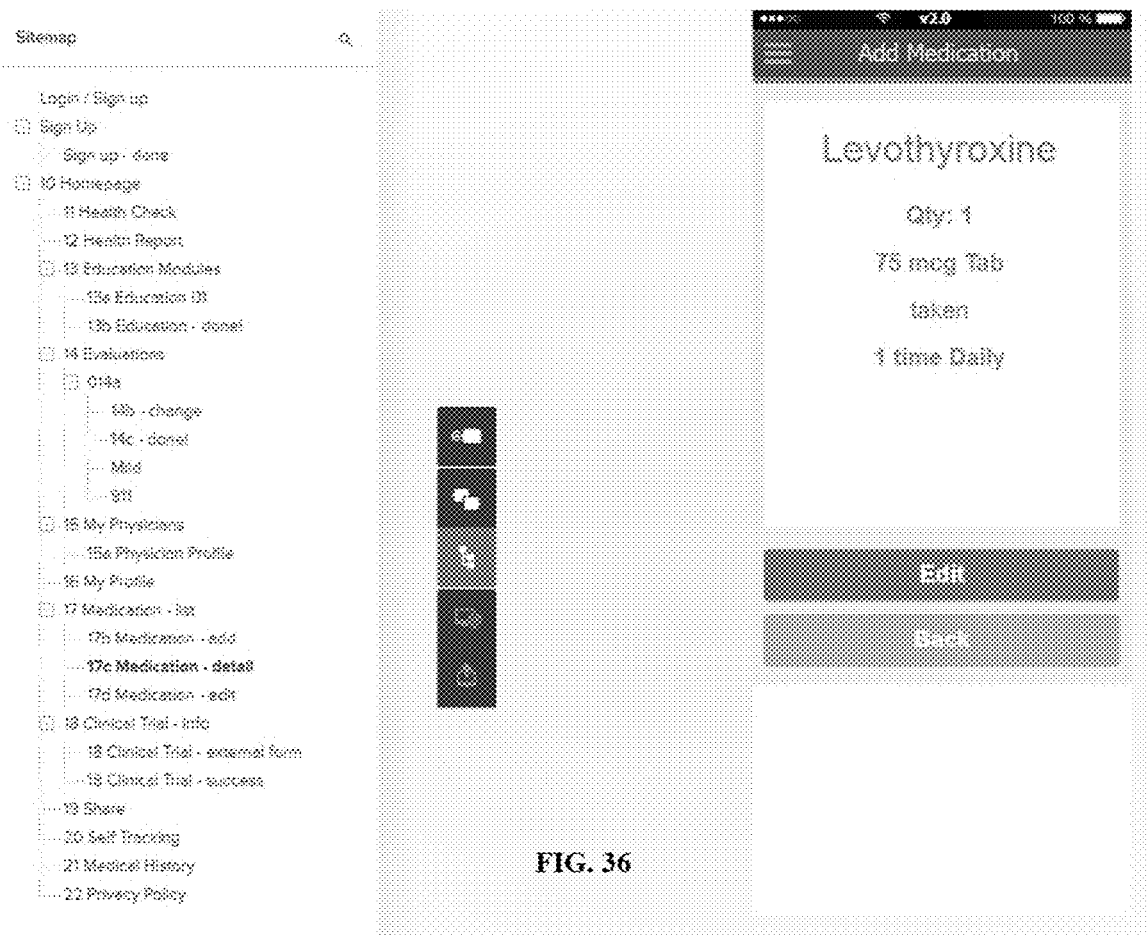
Figure 37:
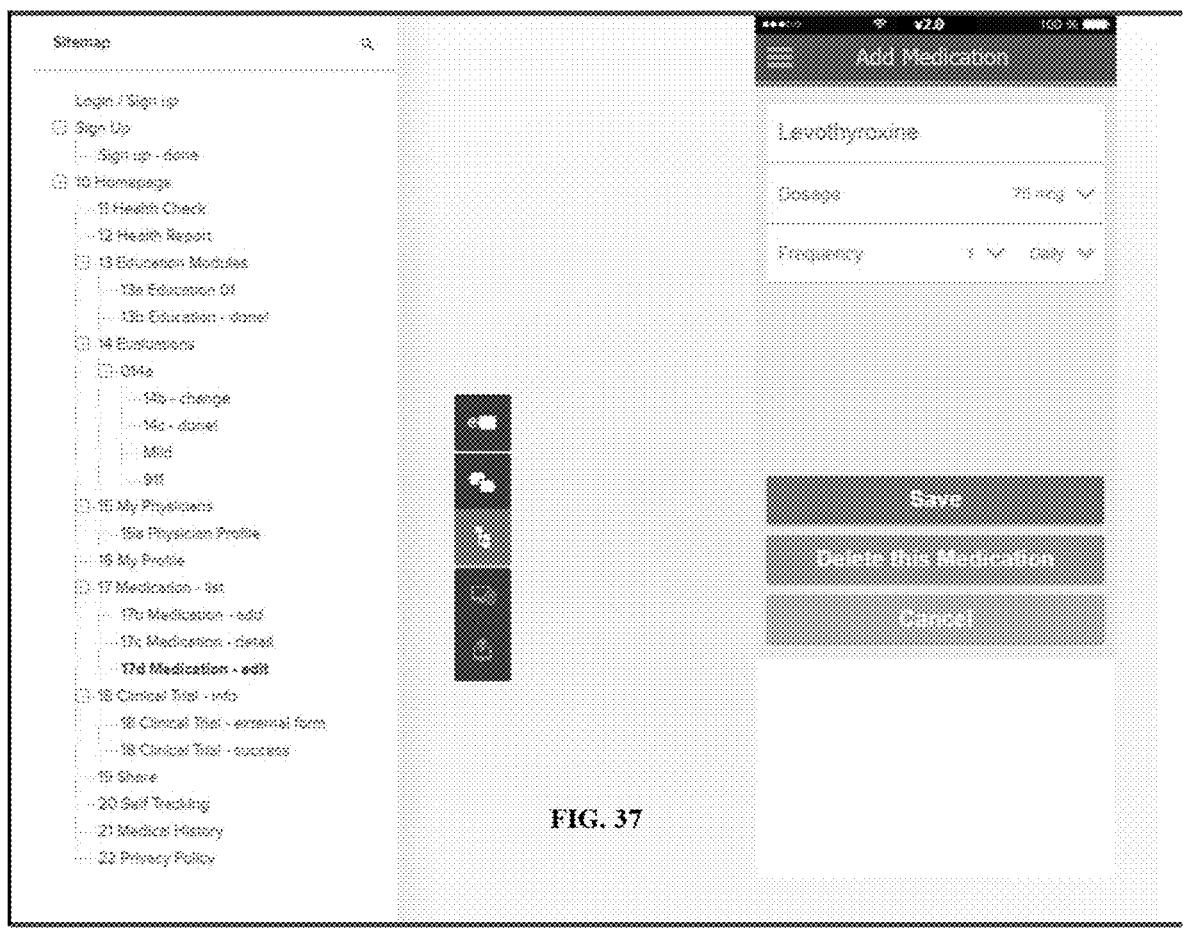
Figure 38:
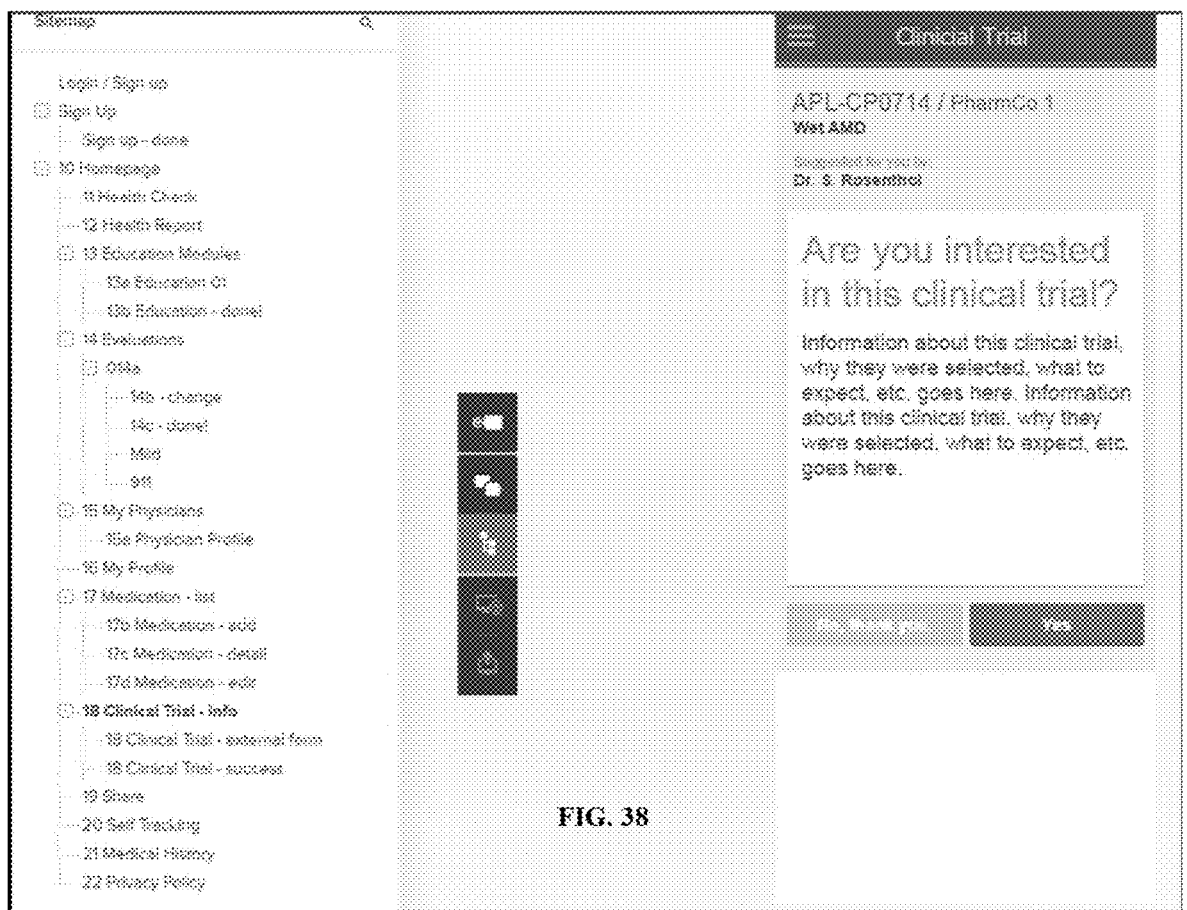
Figure 39:
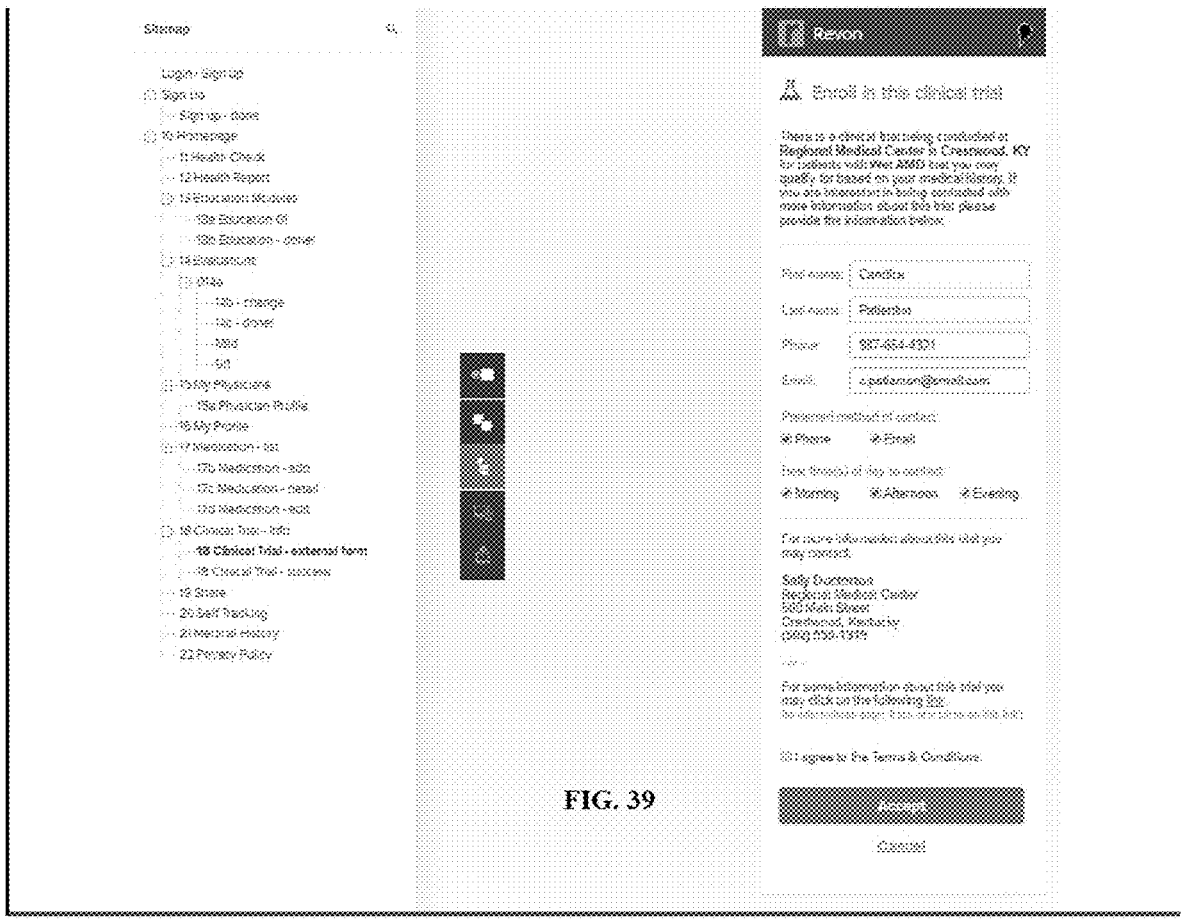
Figure 40:
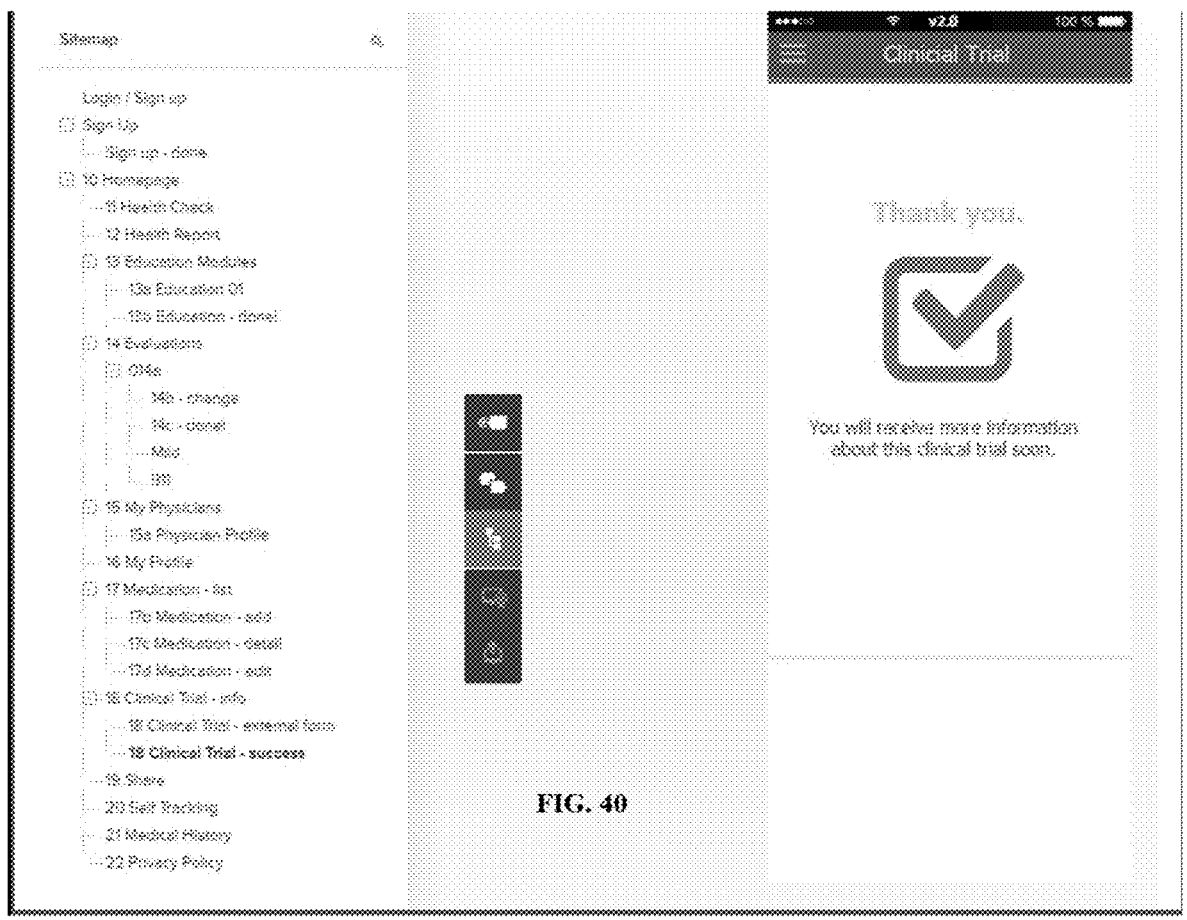
Figure 41:
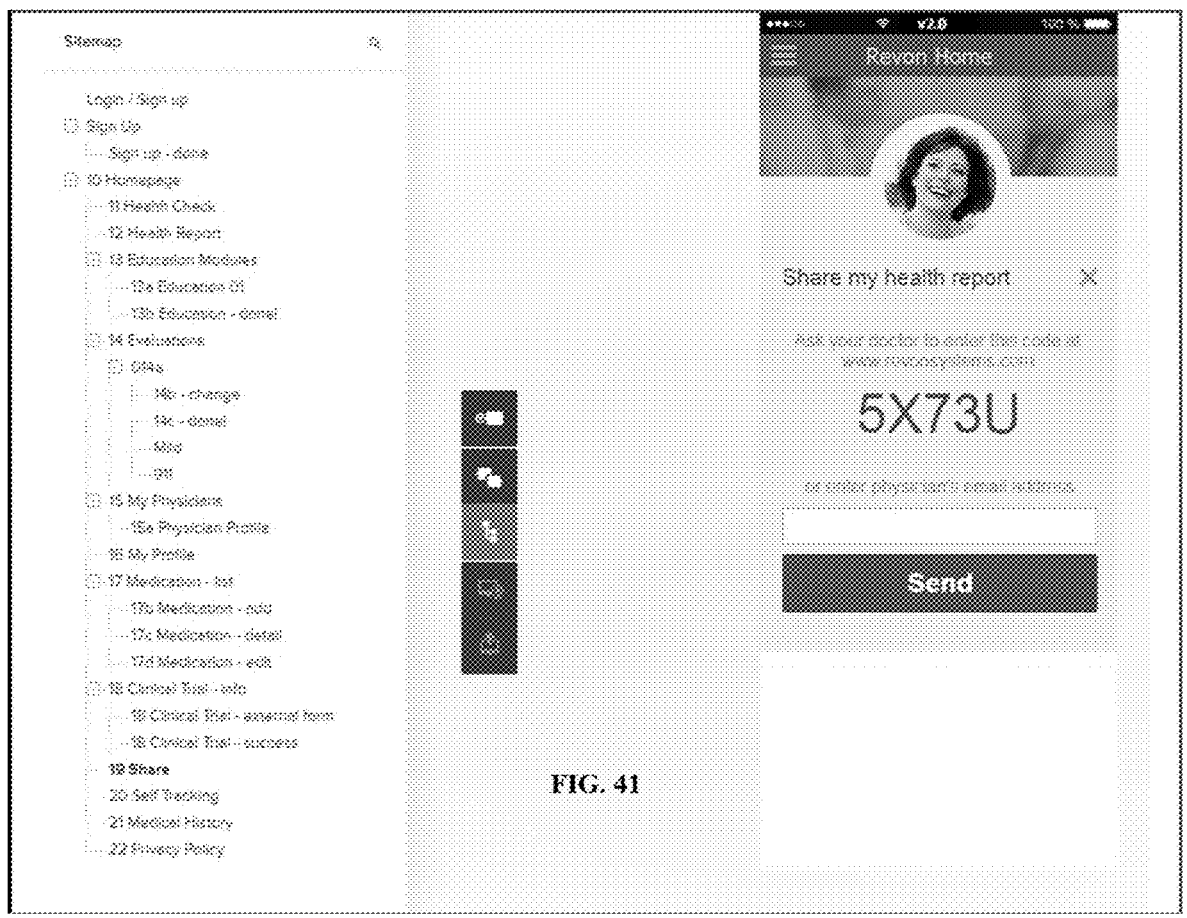
Figure 42:
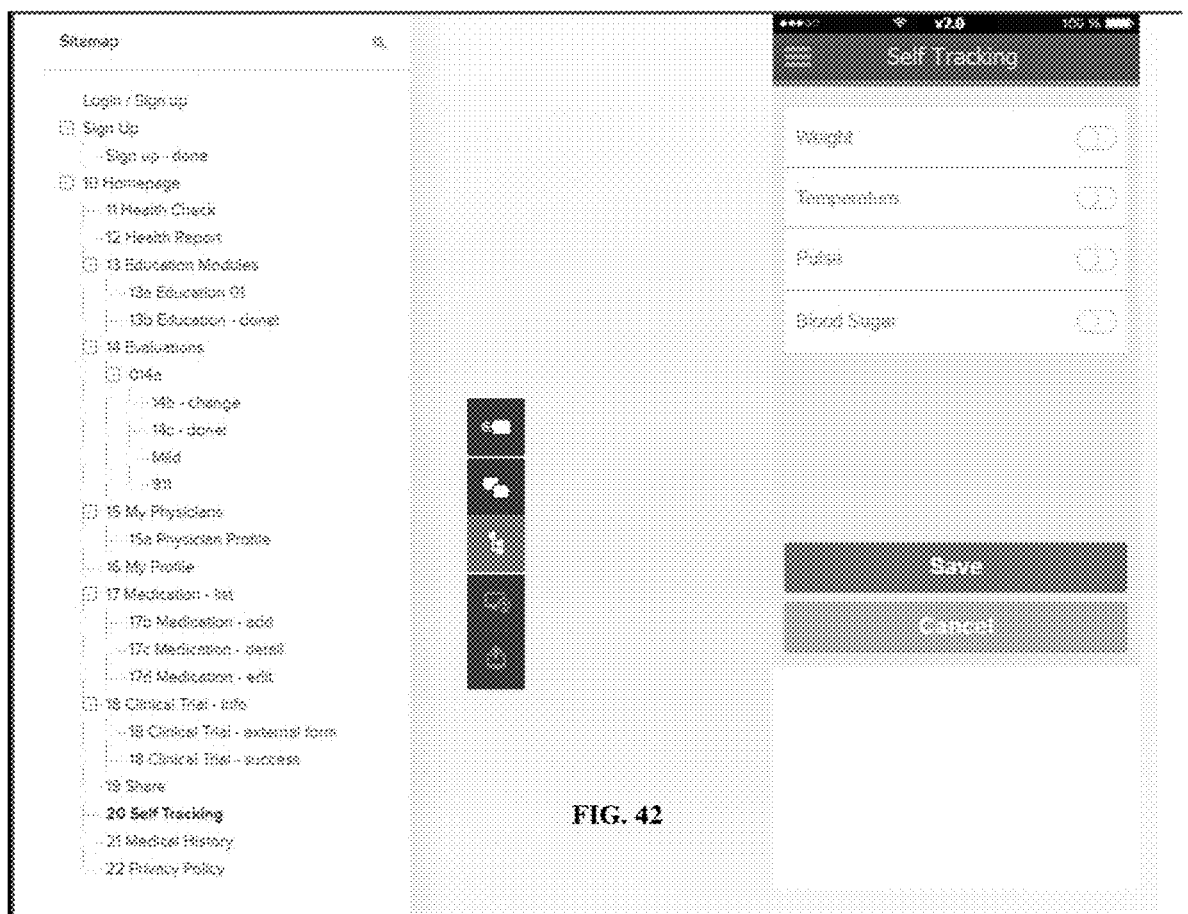
Figure 43:
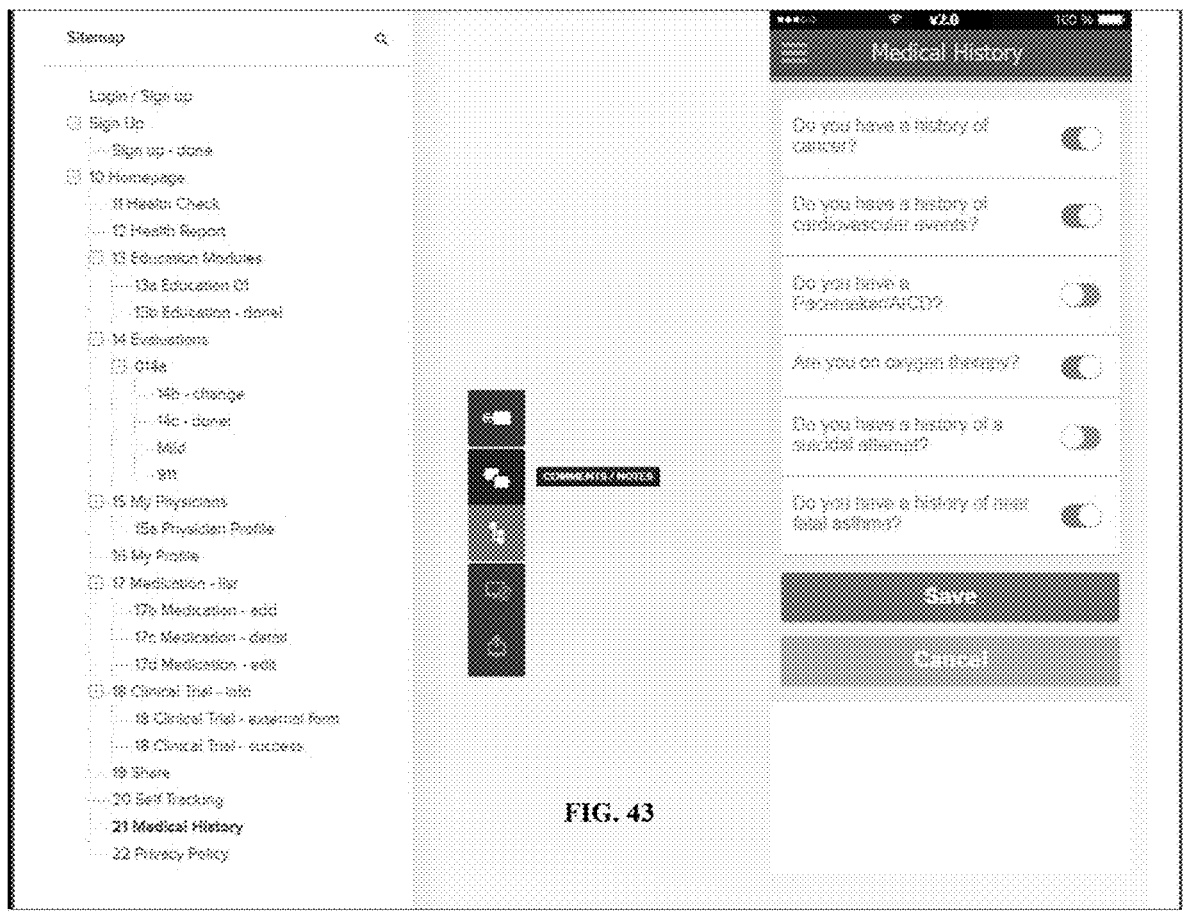
Figure 44:
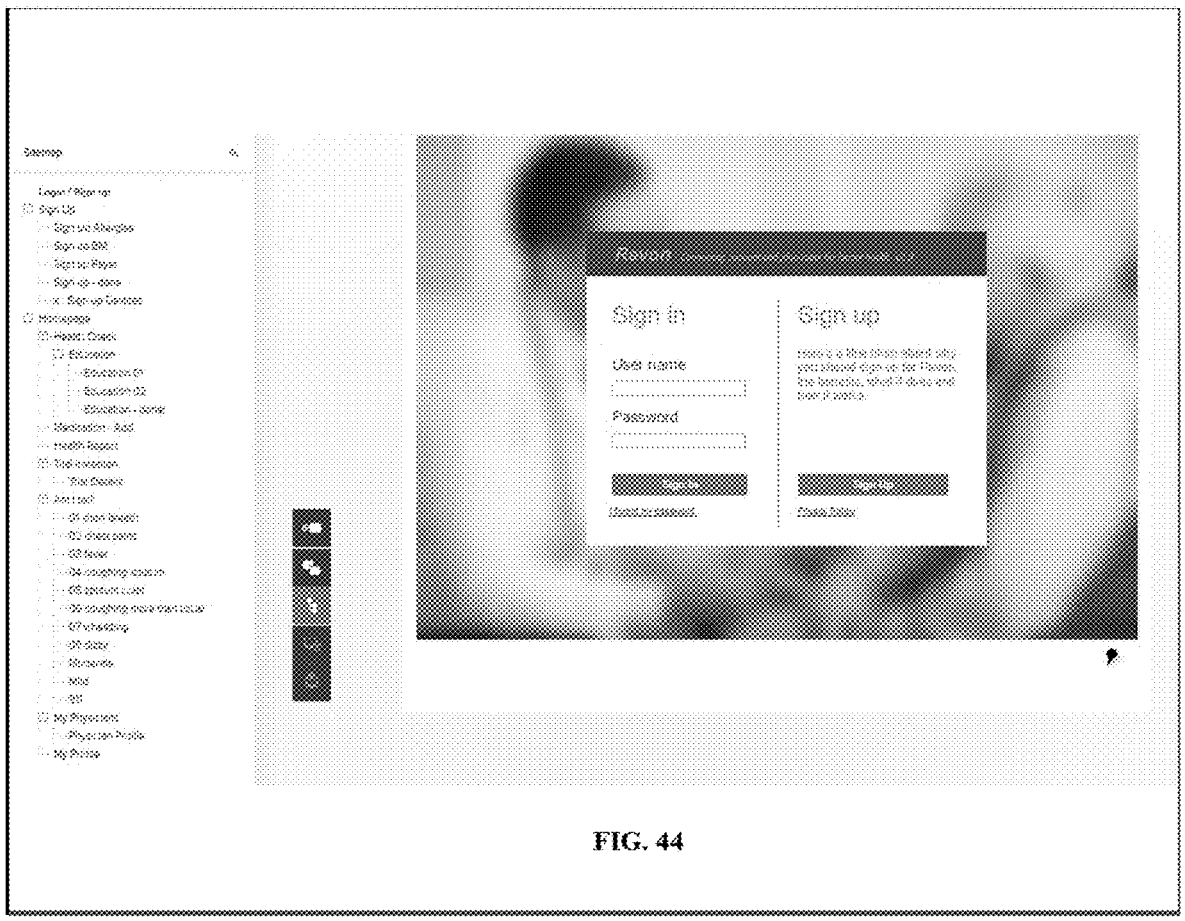
FIGS. 44-75 illustrate interfaces which could be presented by a web based patient portal, along with a site map in the leftmost portion of the illustrations illustrating how the various interfaces relate to each other.
Figure 45:
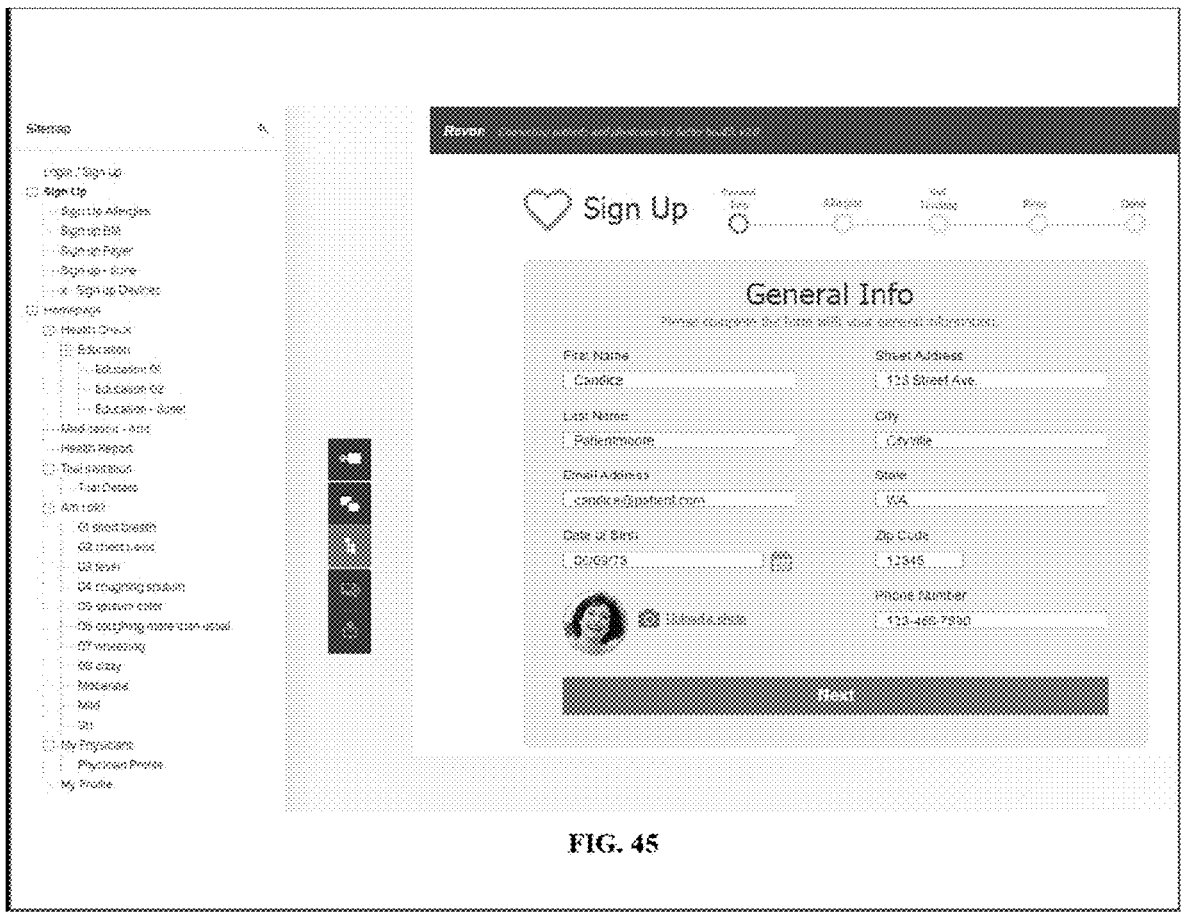
Figure 46:
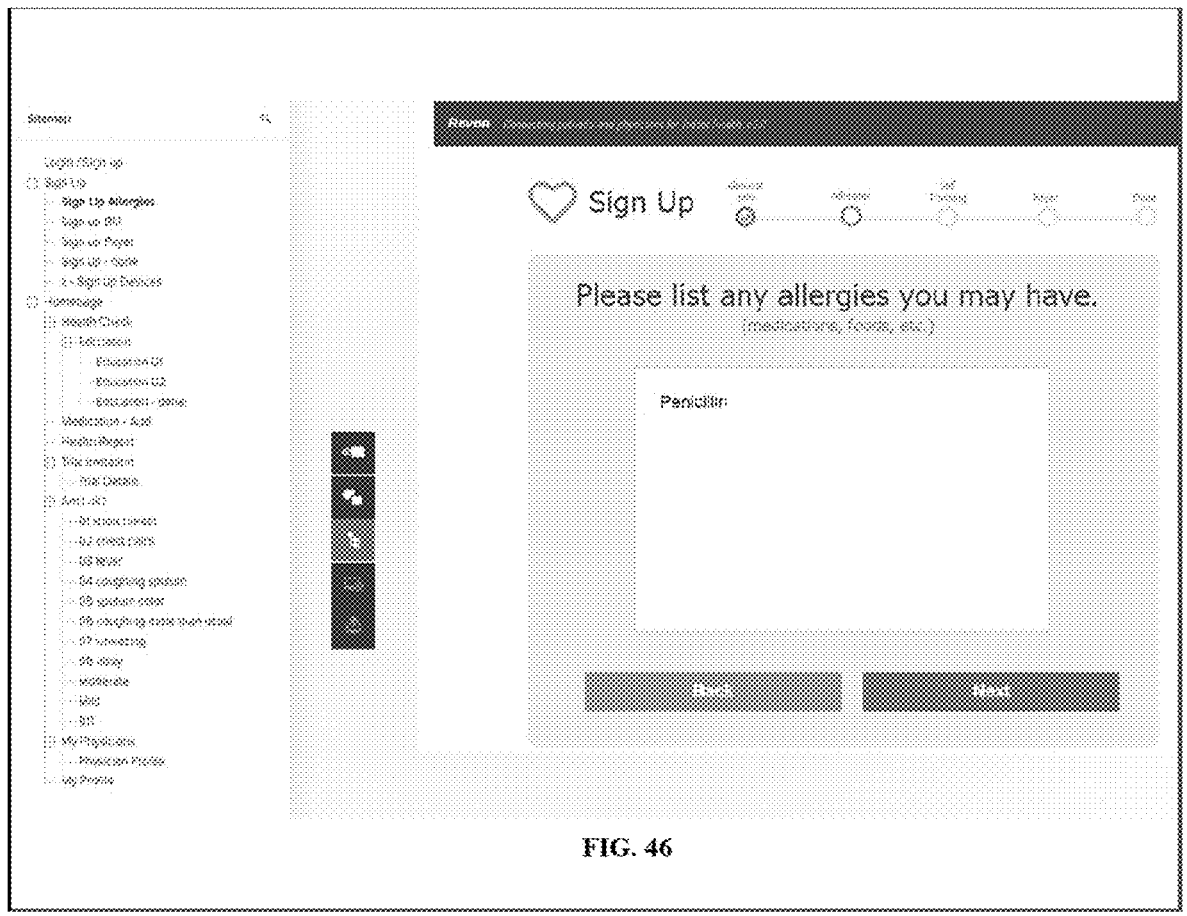
Figure 47:
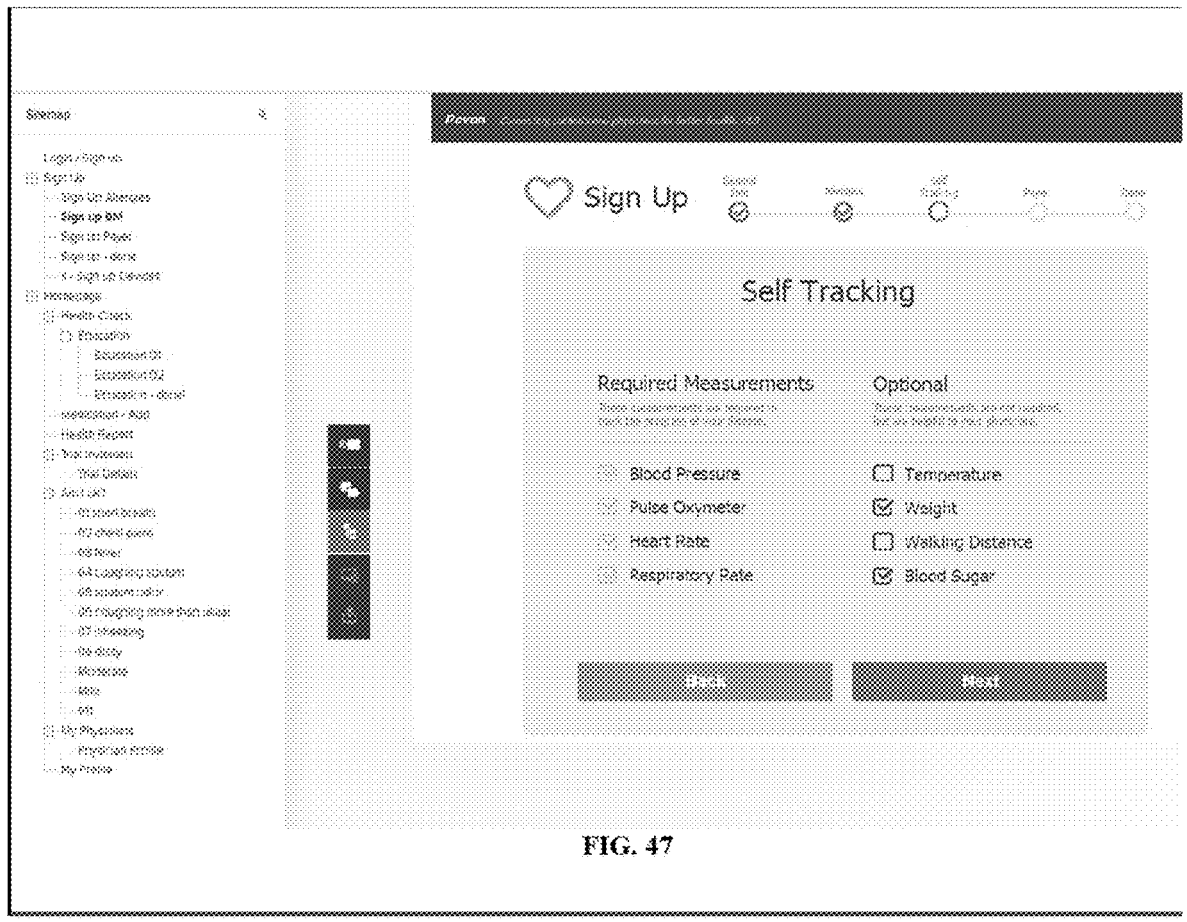
Figure 48:
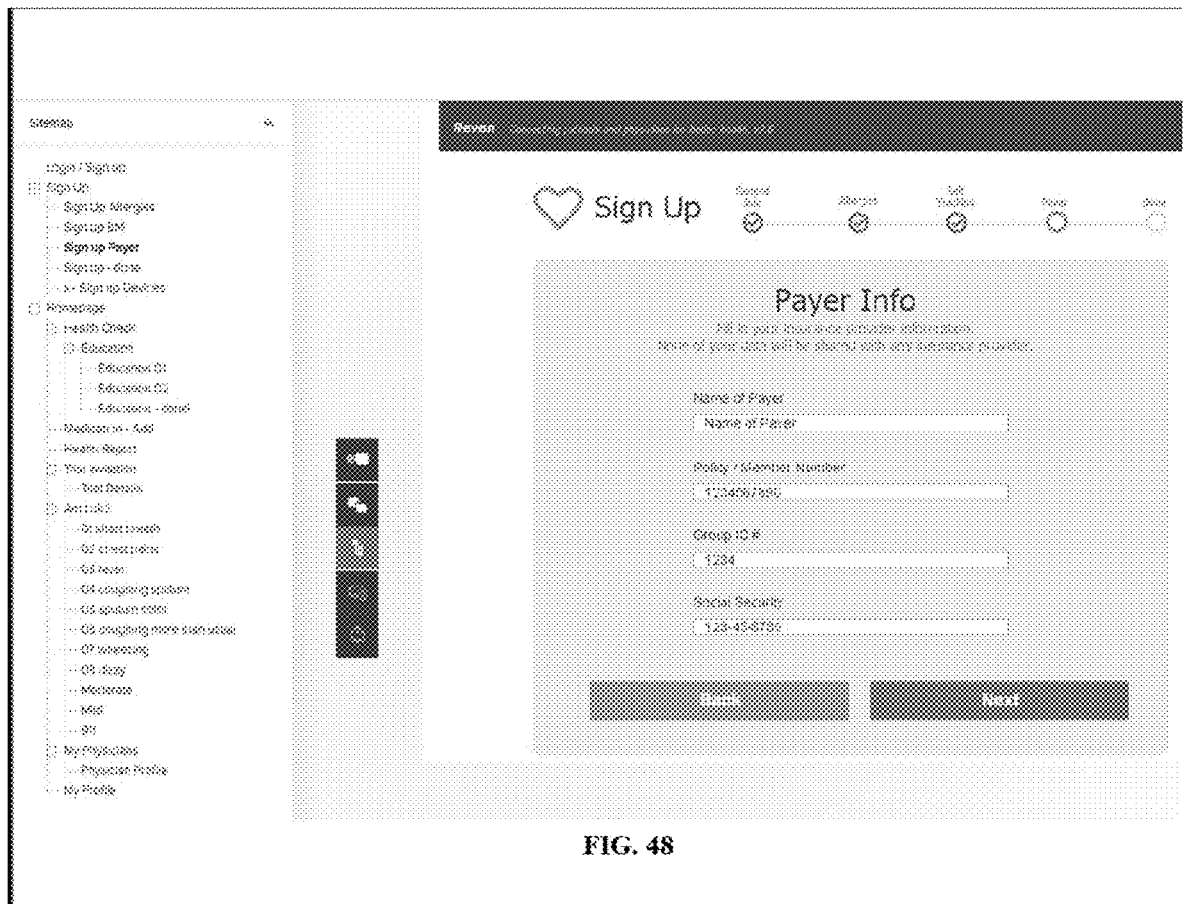
Figure 49:
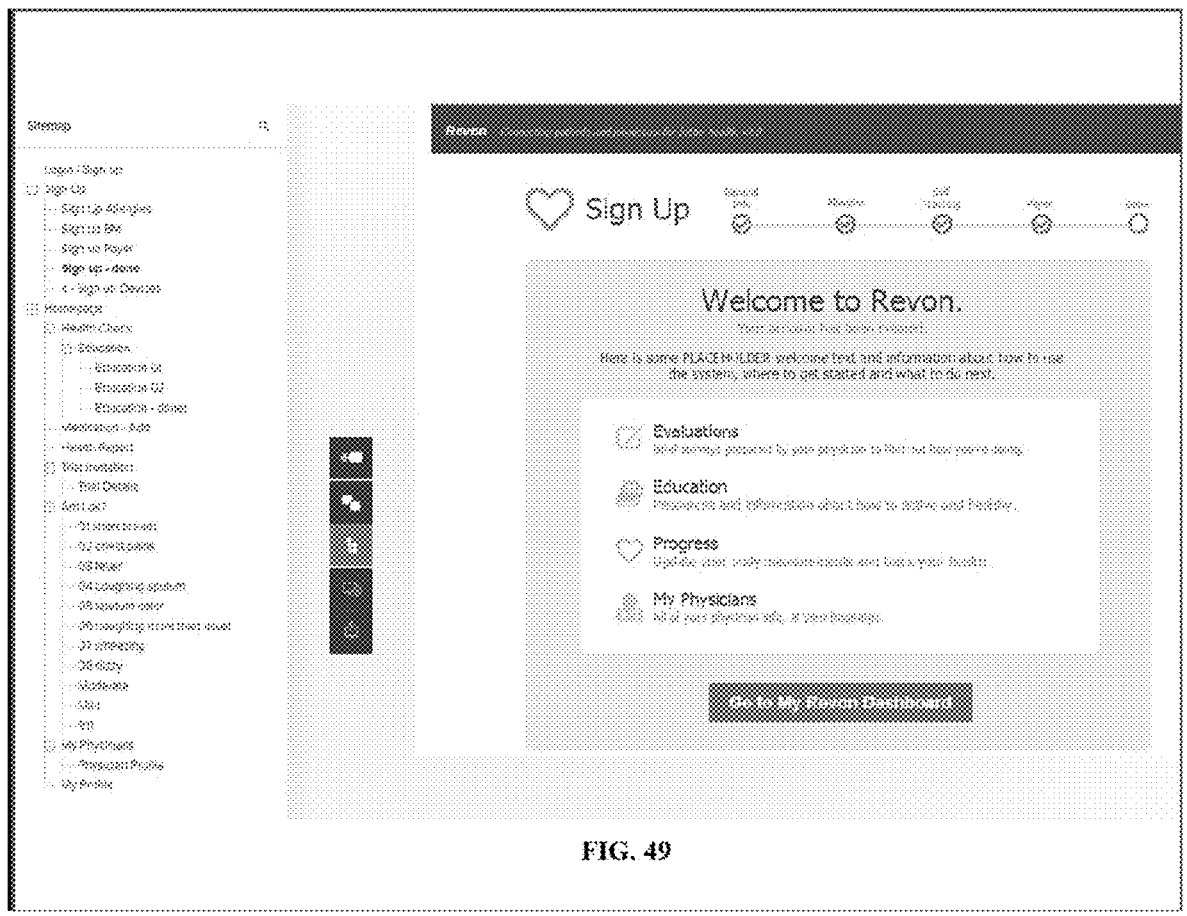
Figure 50:
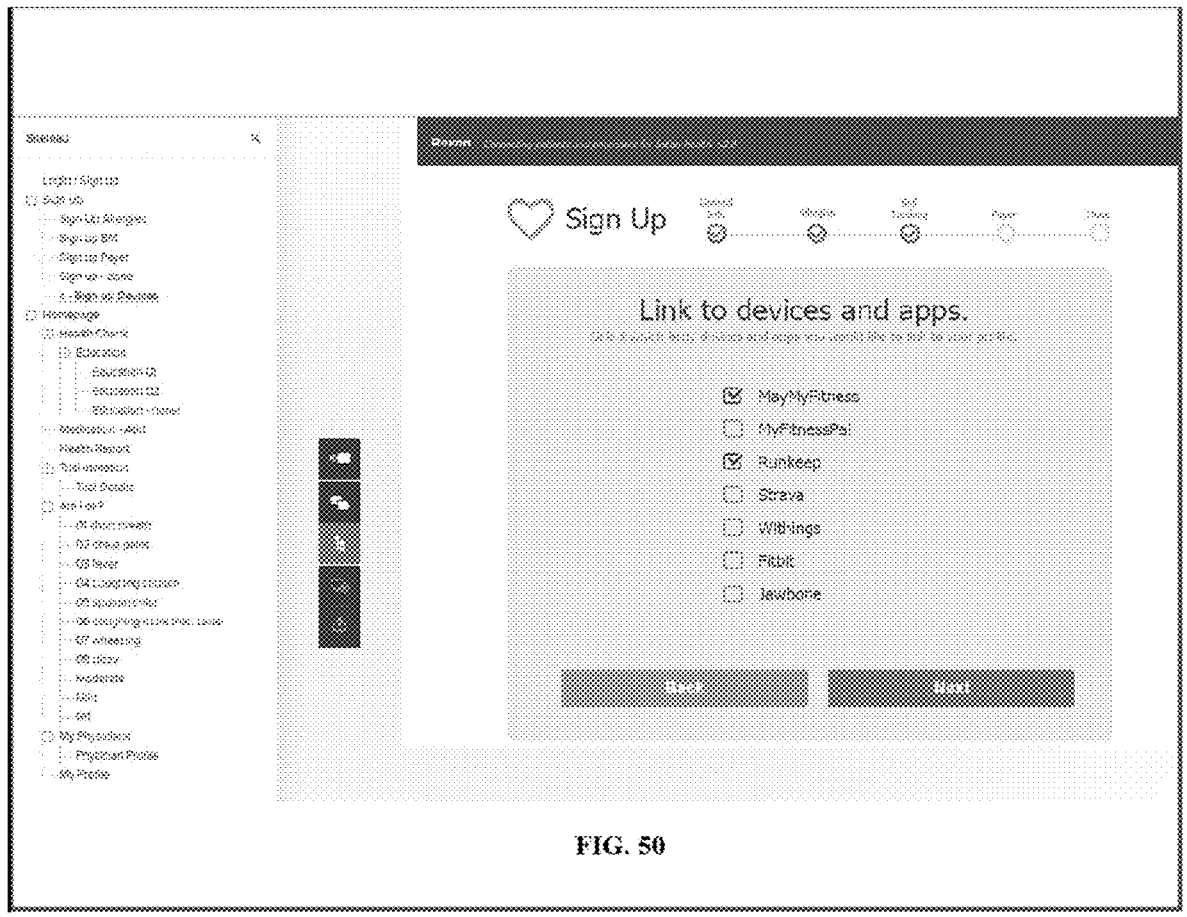
Figure 51:
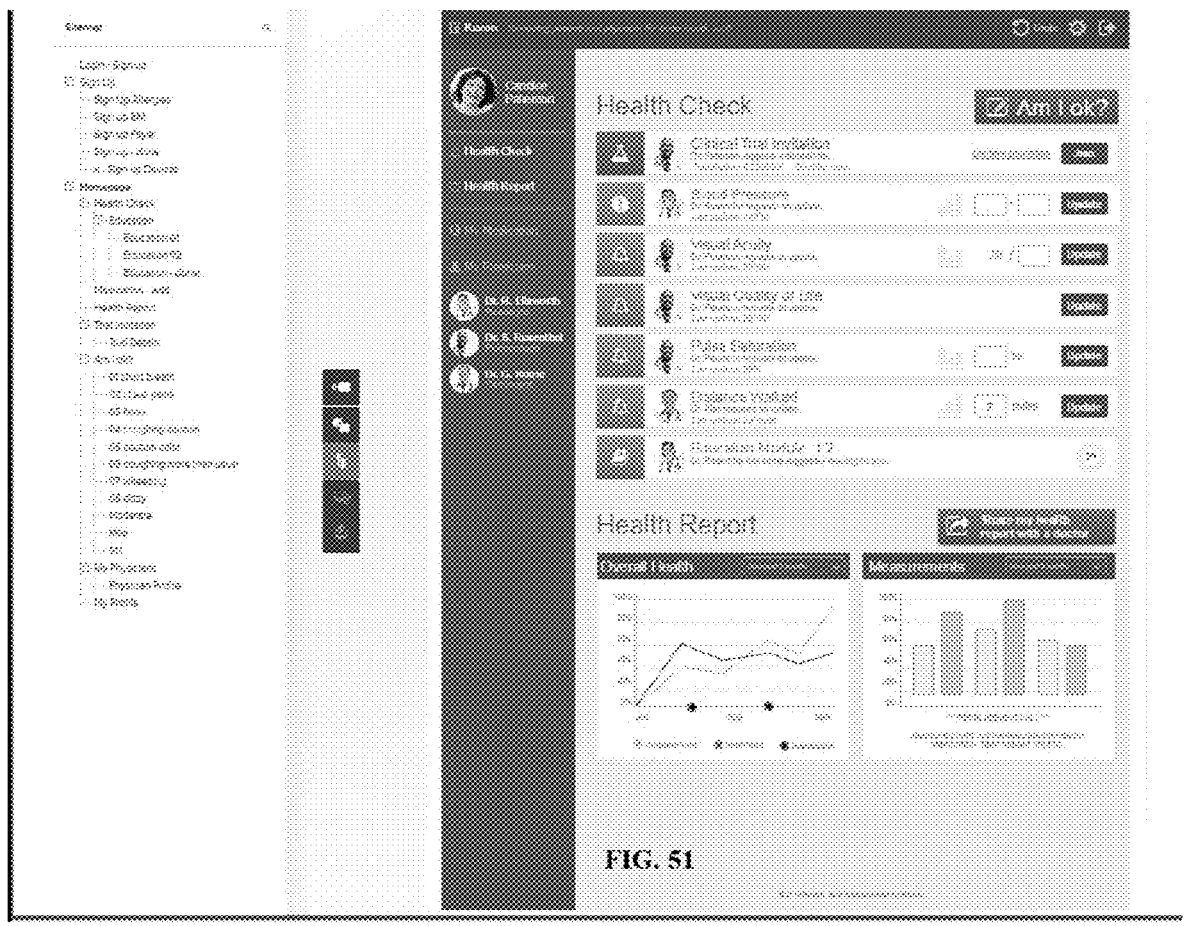
Figure 52:
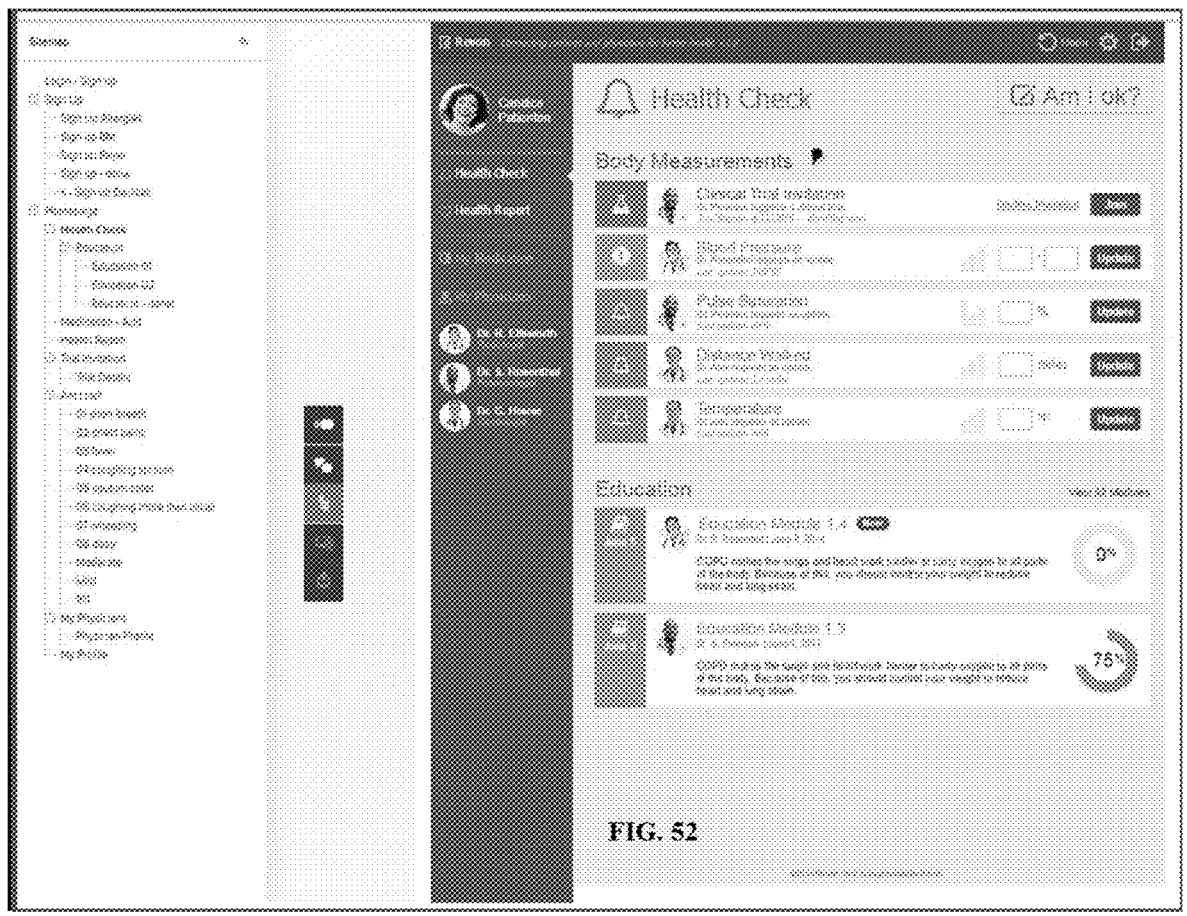
Figure 53:
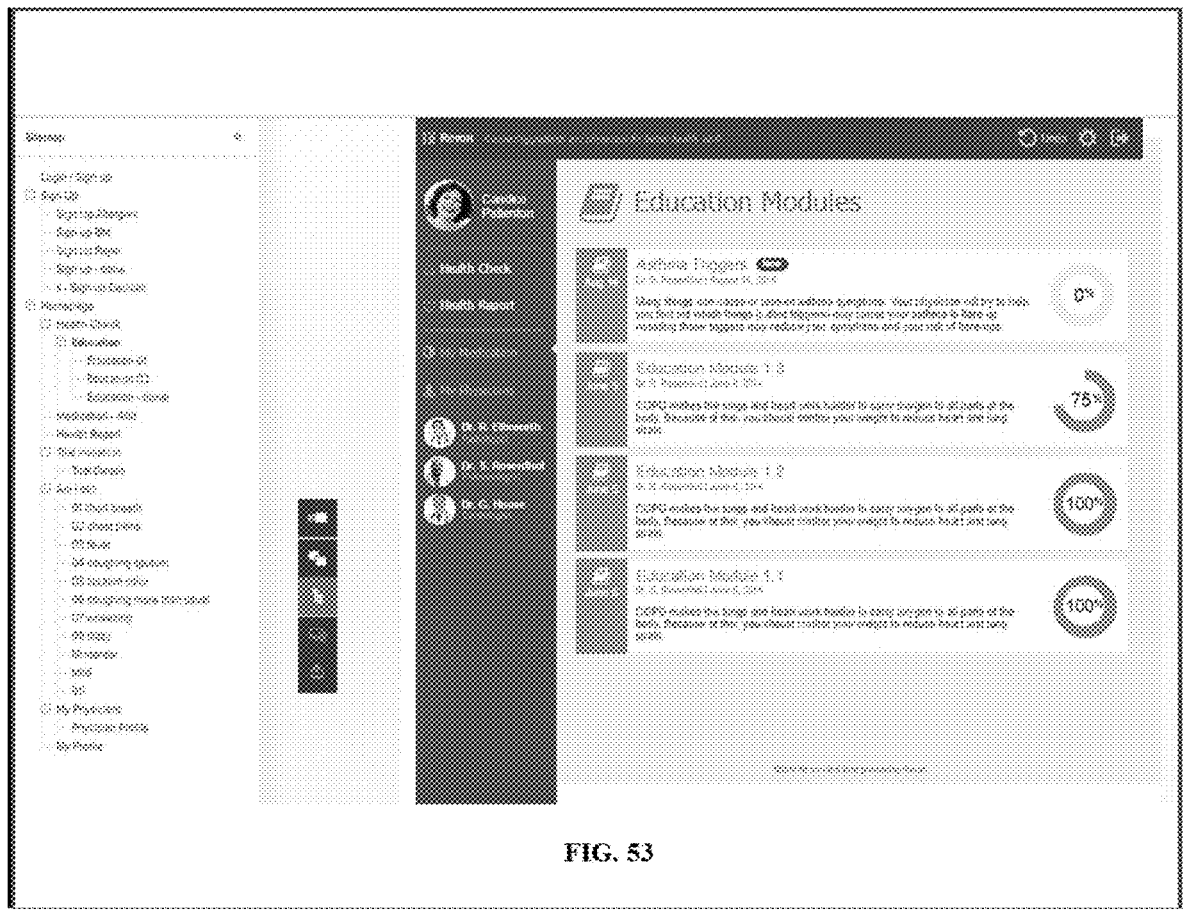
Figure 54:
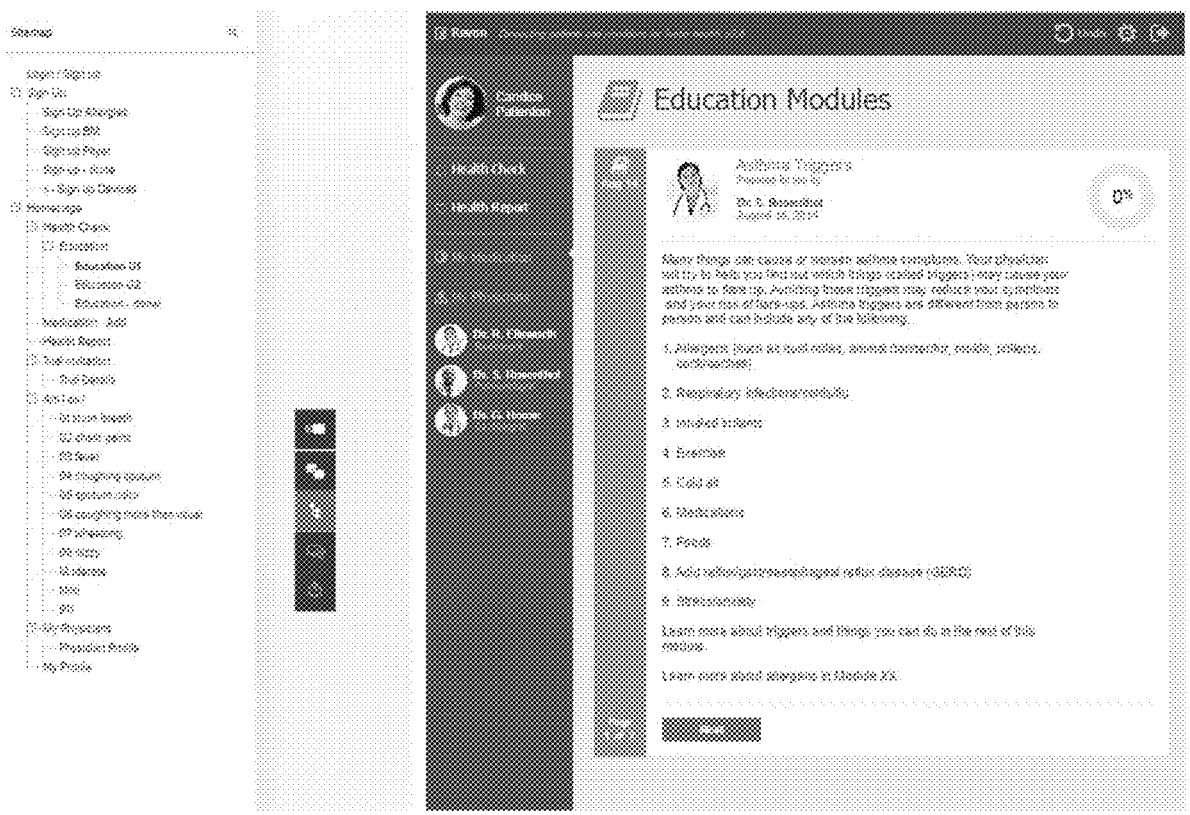
Figure 55:
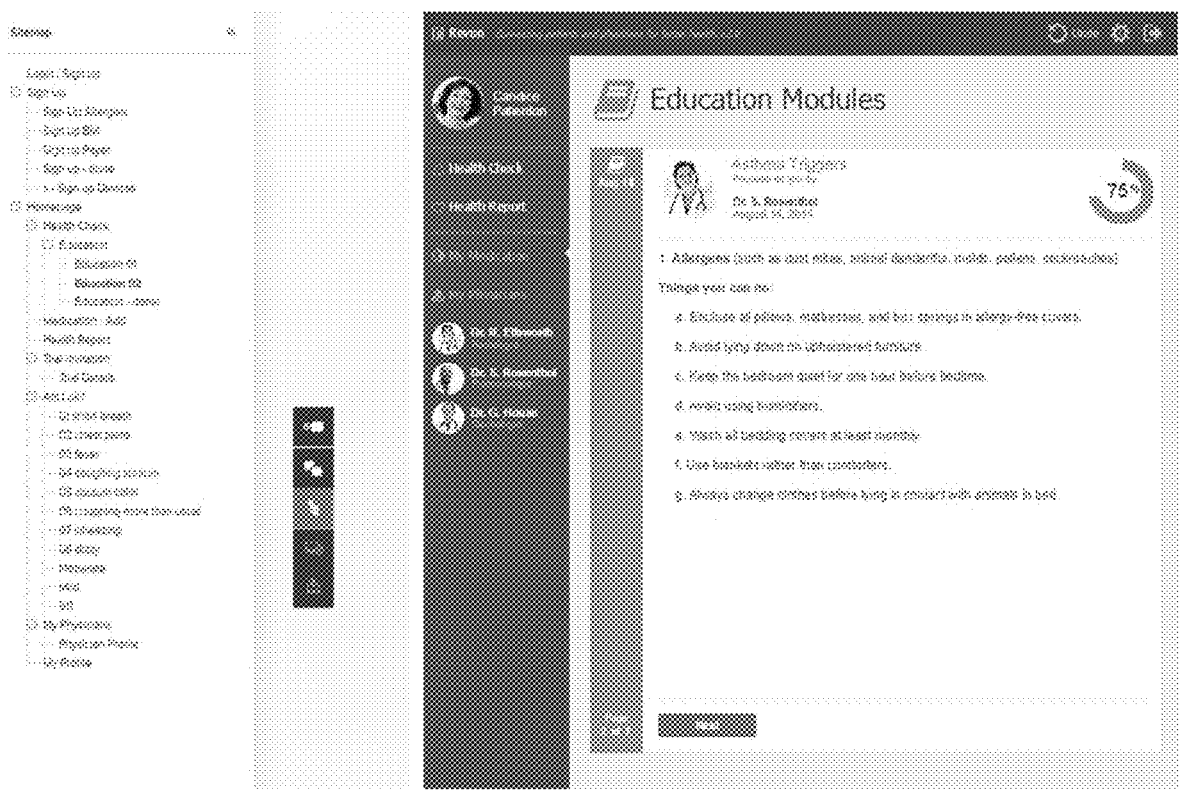
Figure 56:
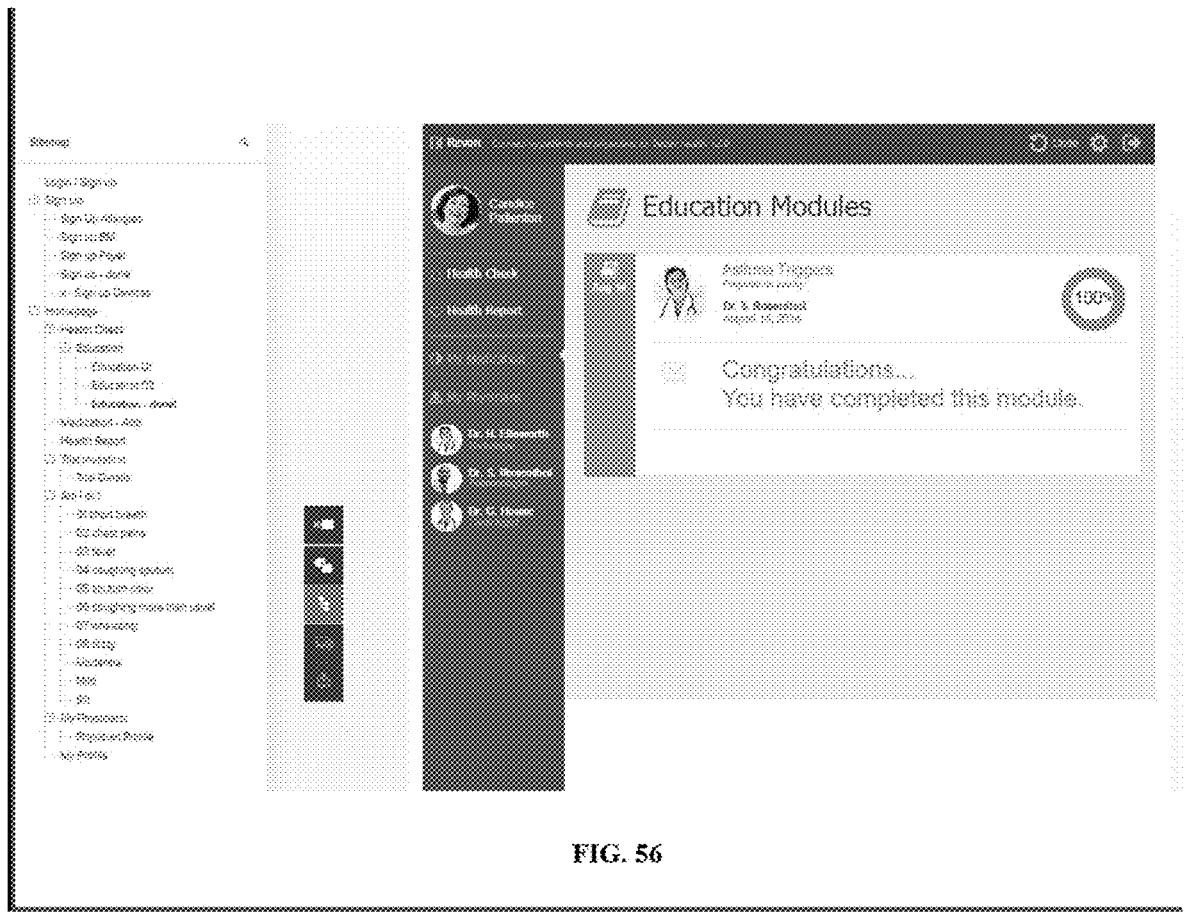
Figure 57:
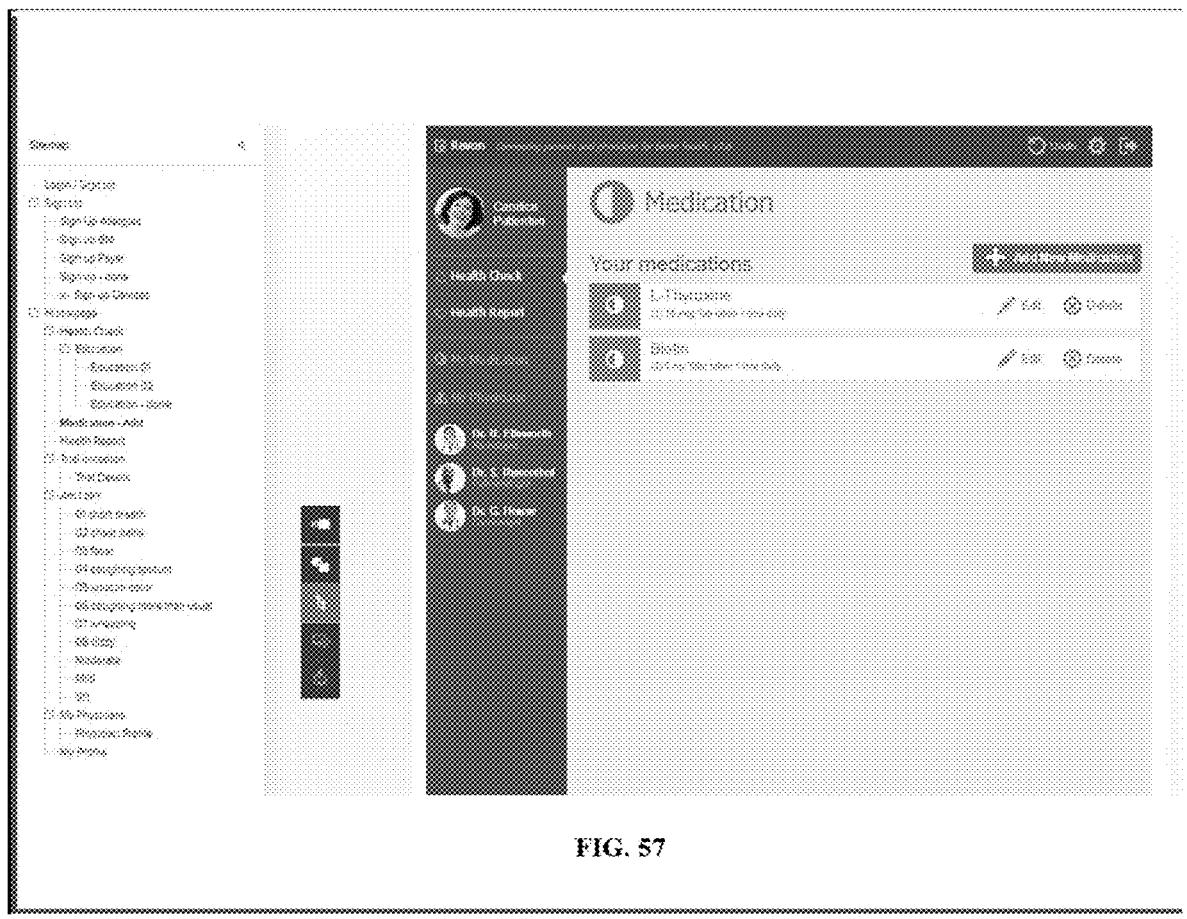
Figure 58:
Figure 59:
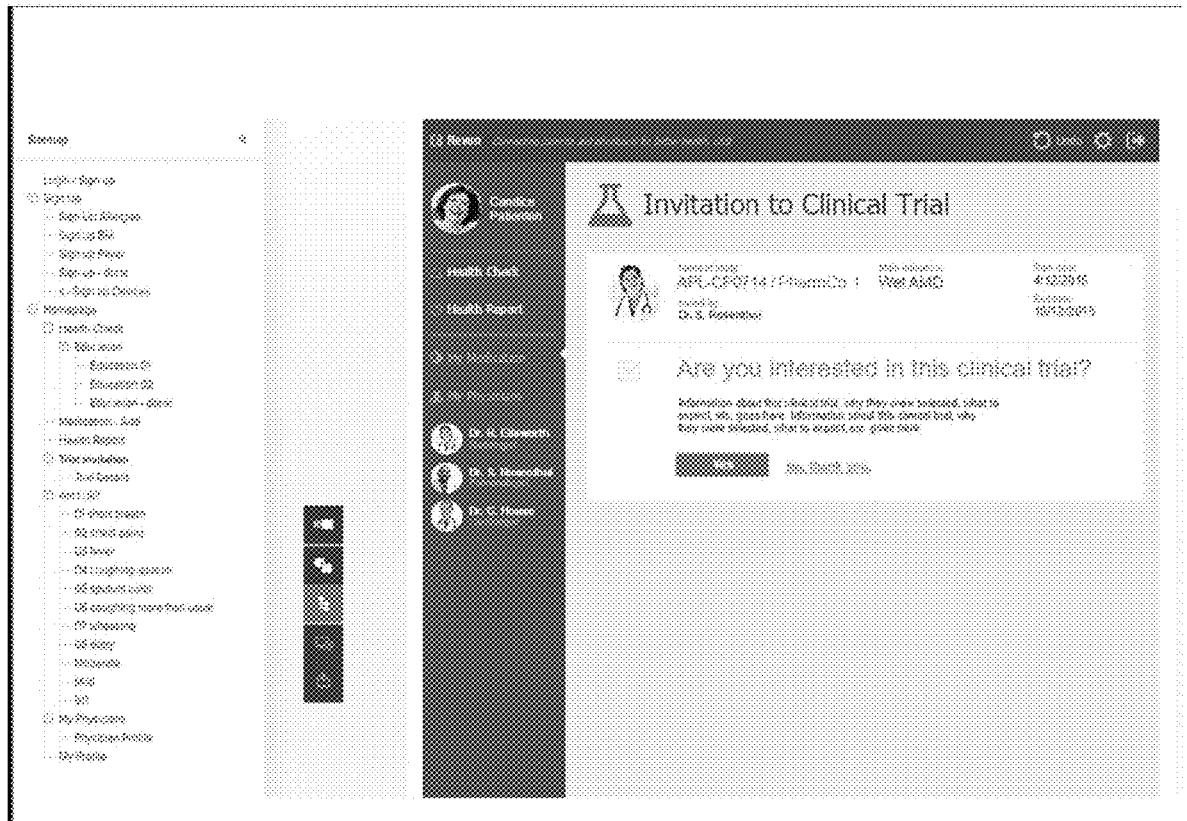
Figure 60:
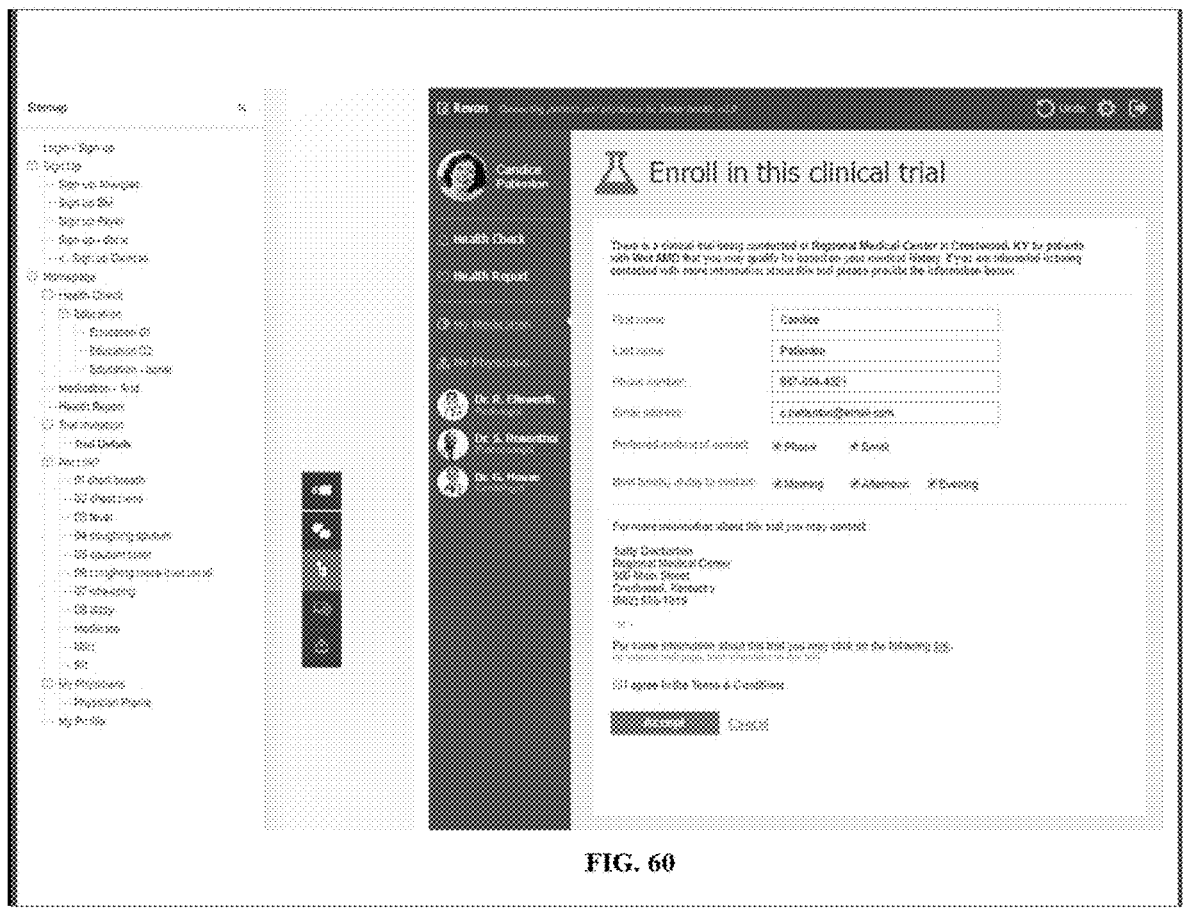
Figure 61:
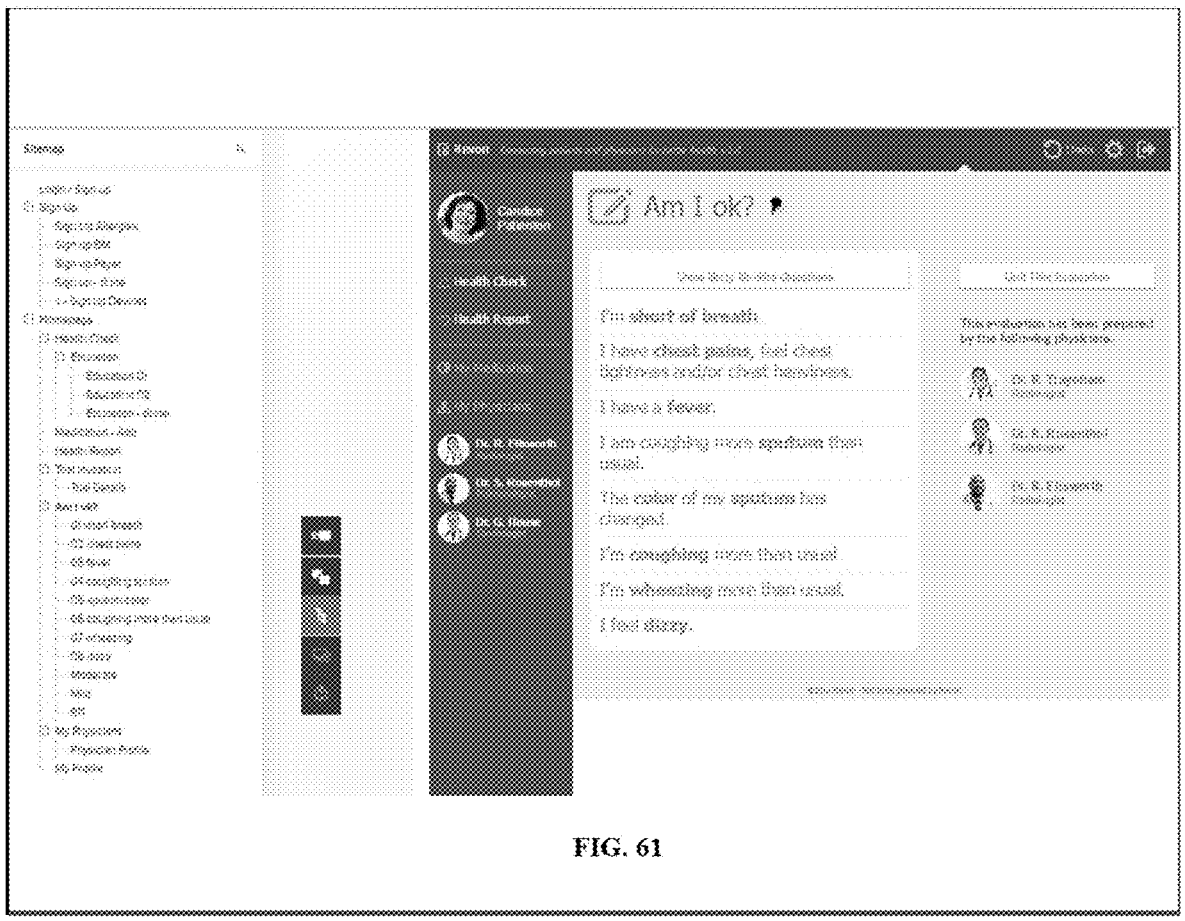
Figure 62:
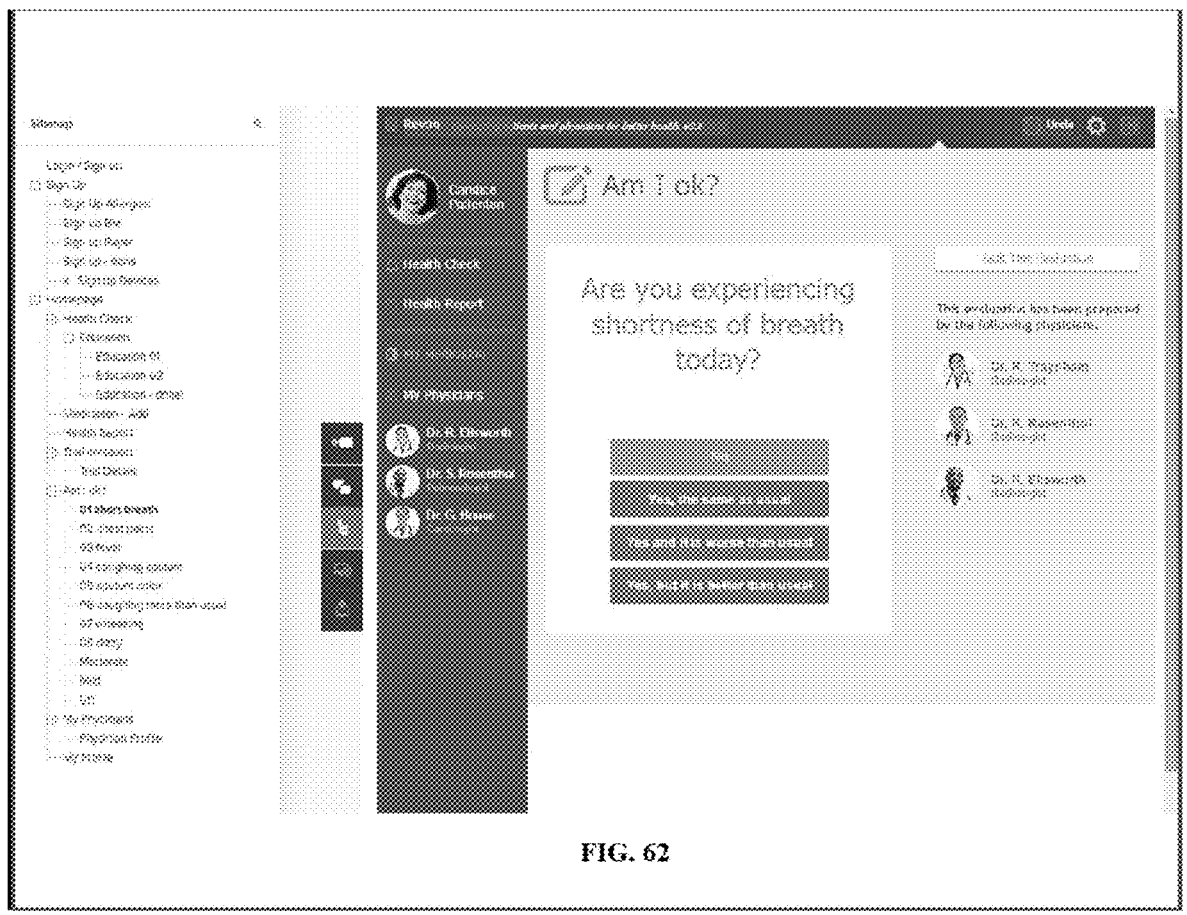
Figure 63:
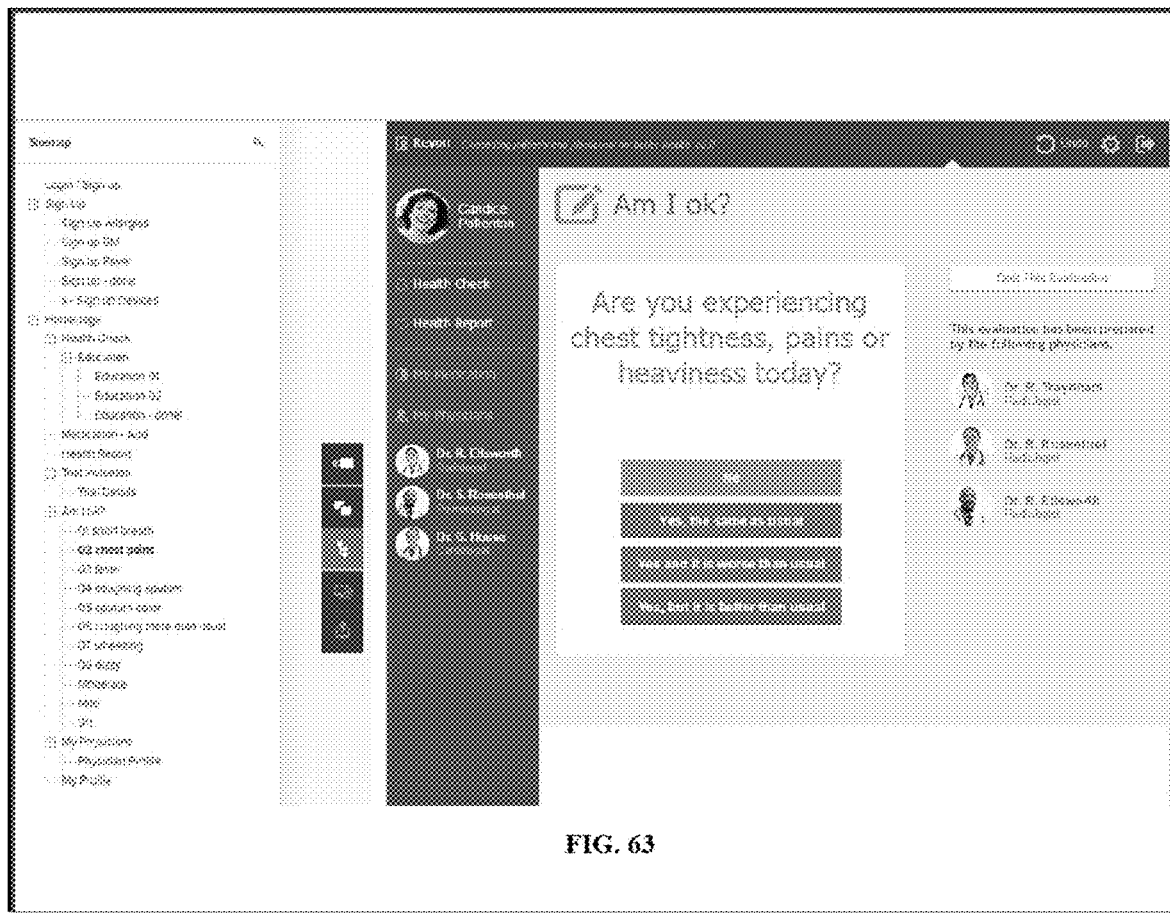
Figure 64:
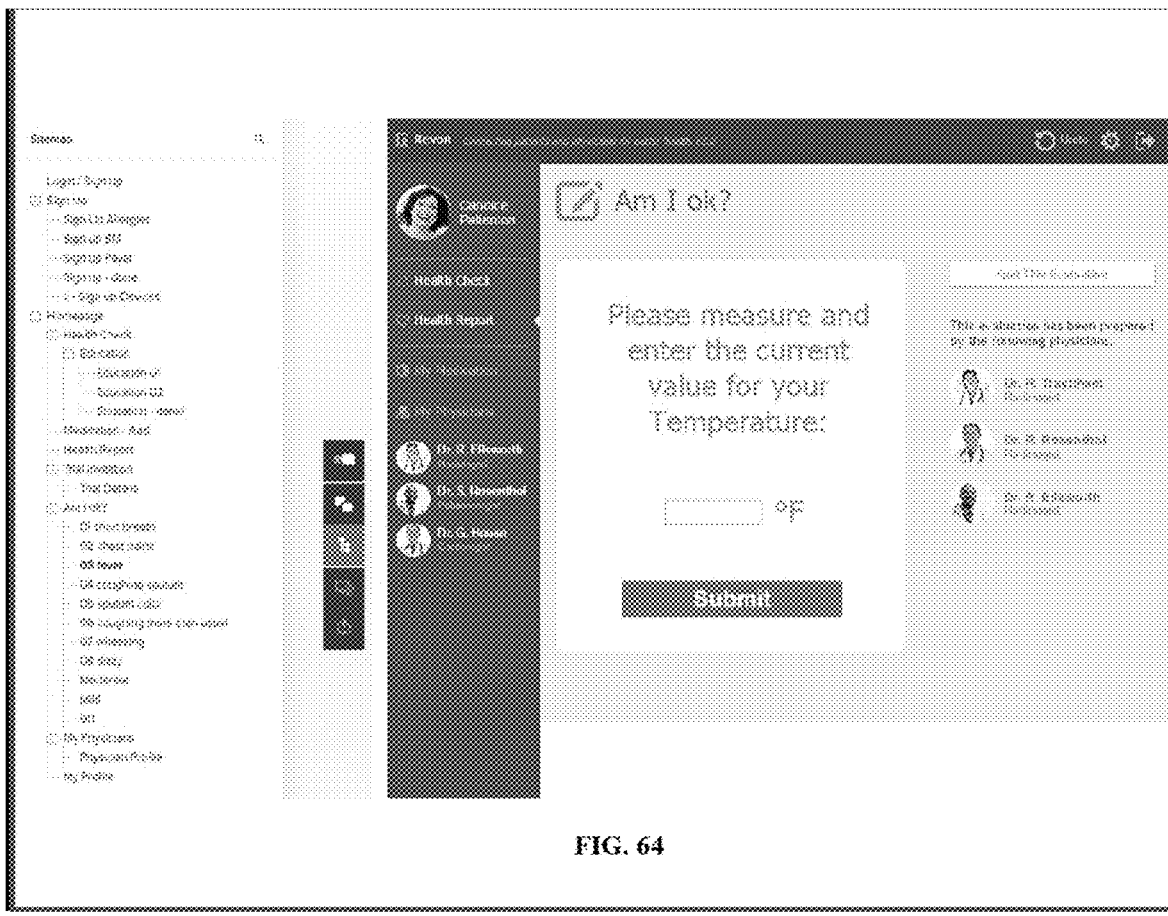
Figure 65:
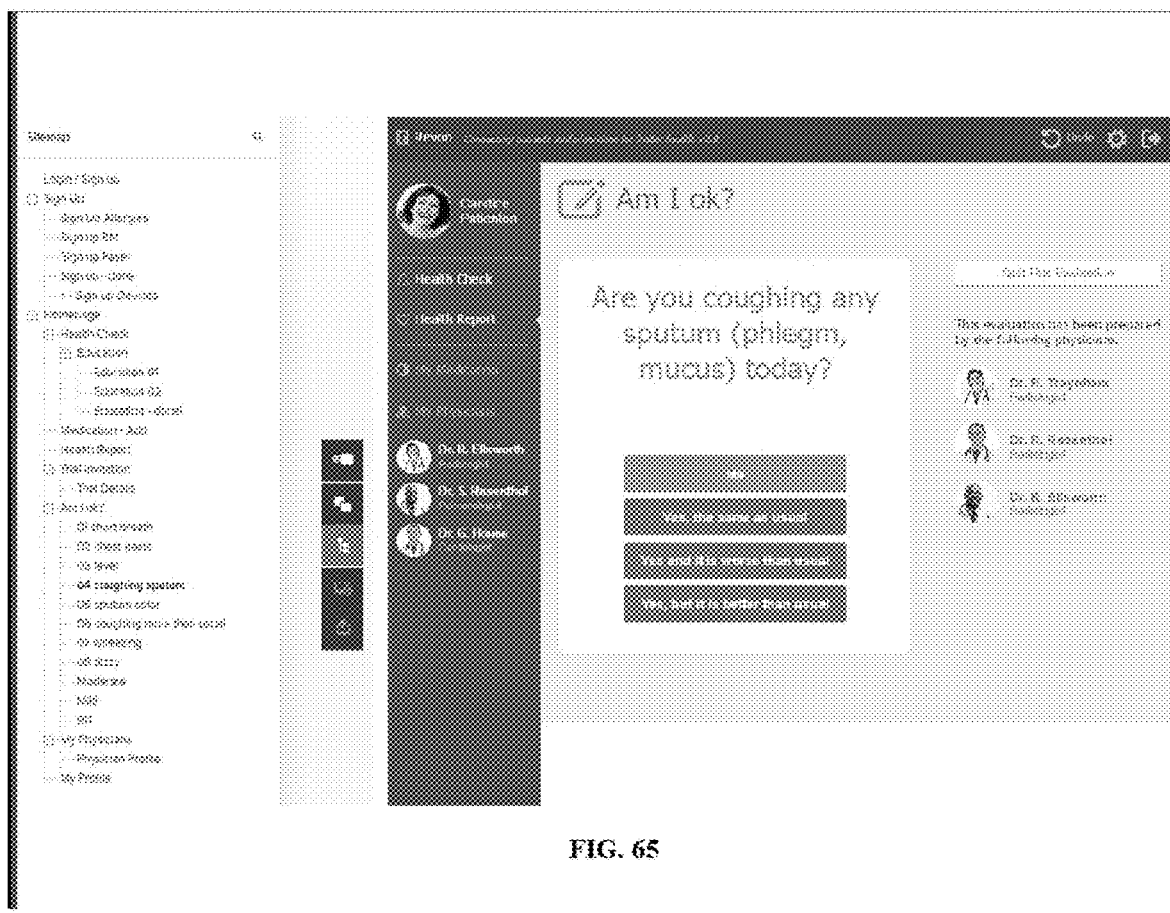
Figure 66:
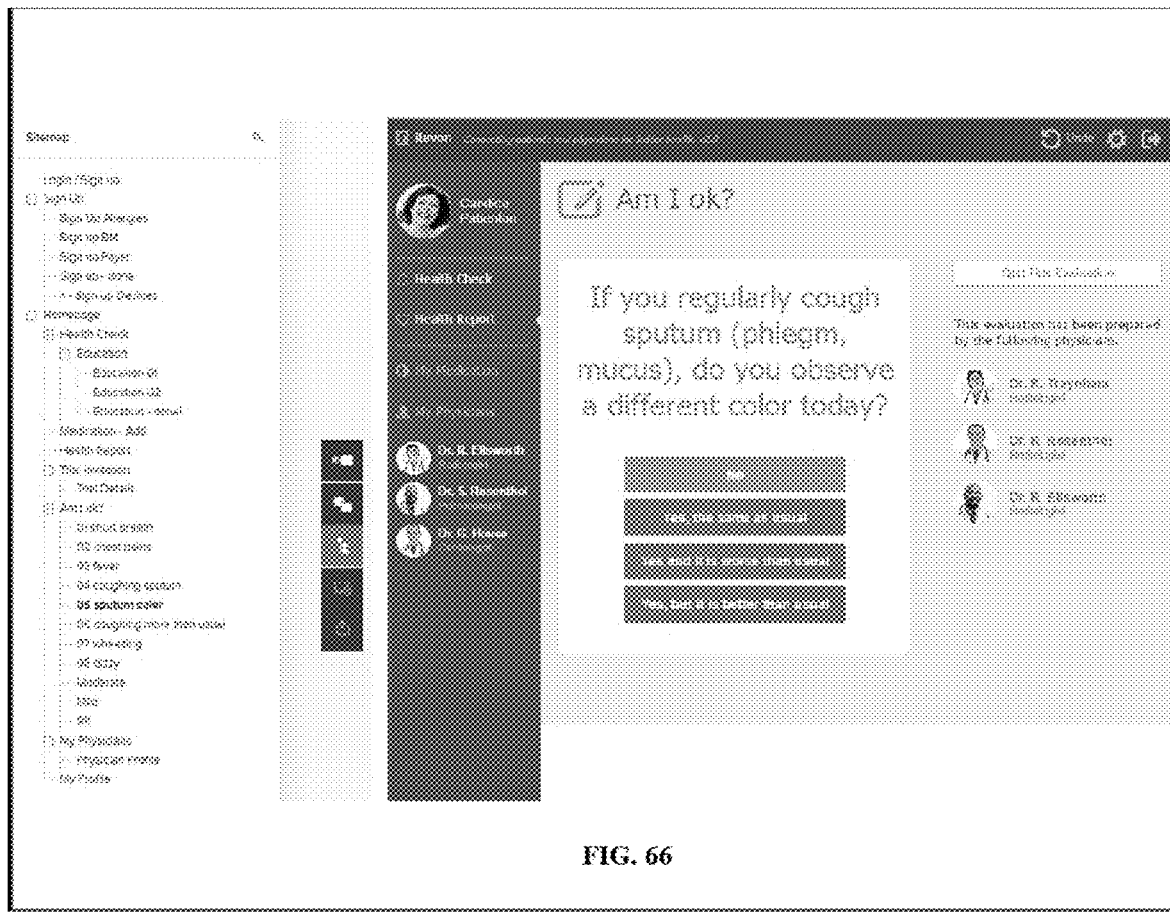
Figure 67:
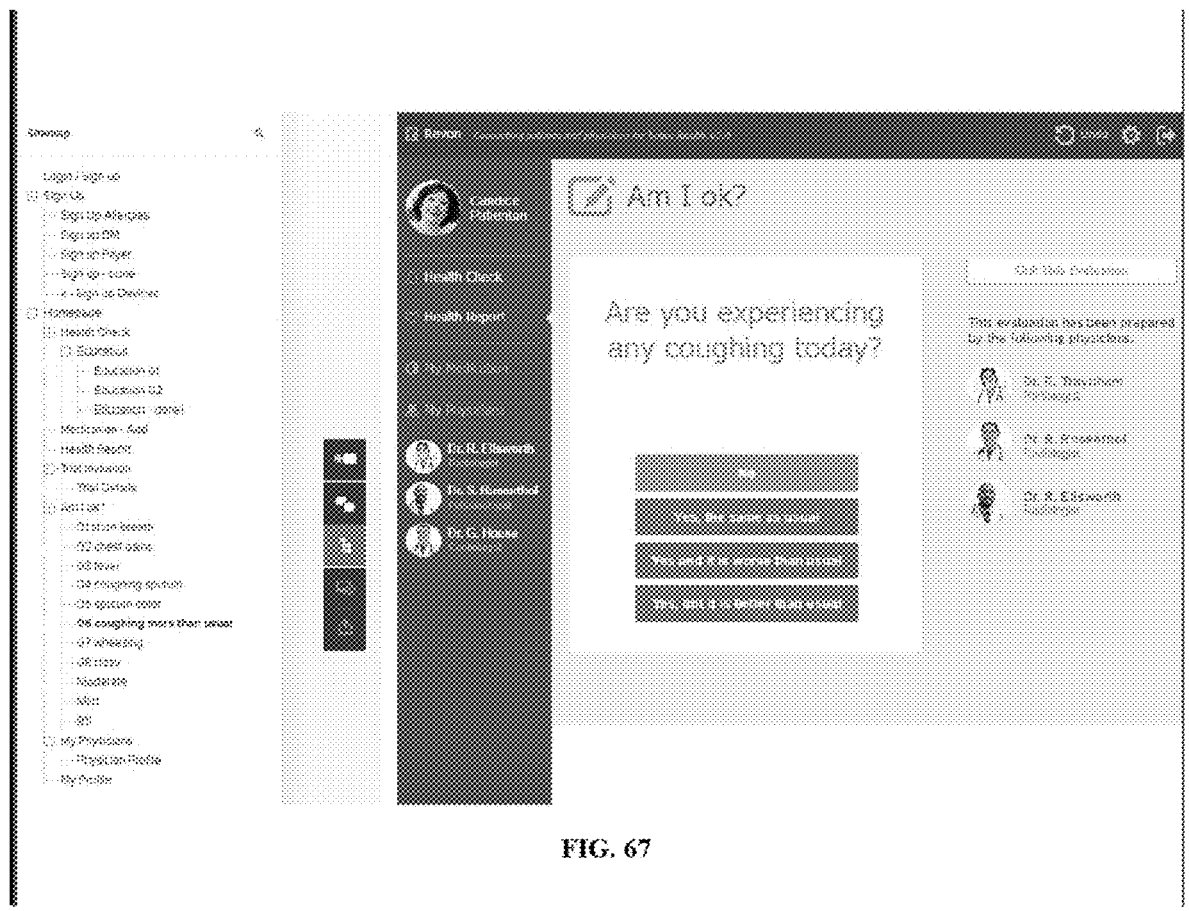
Figure 68:
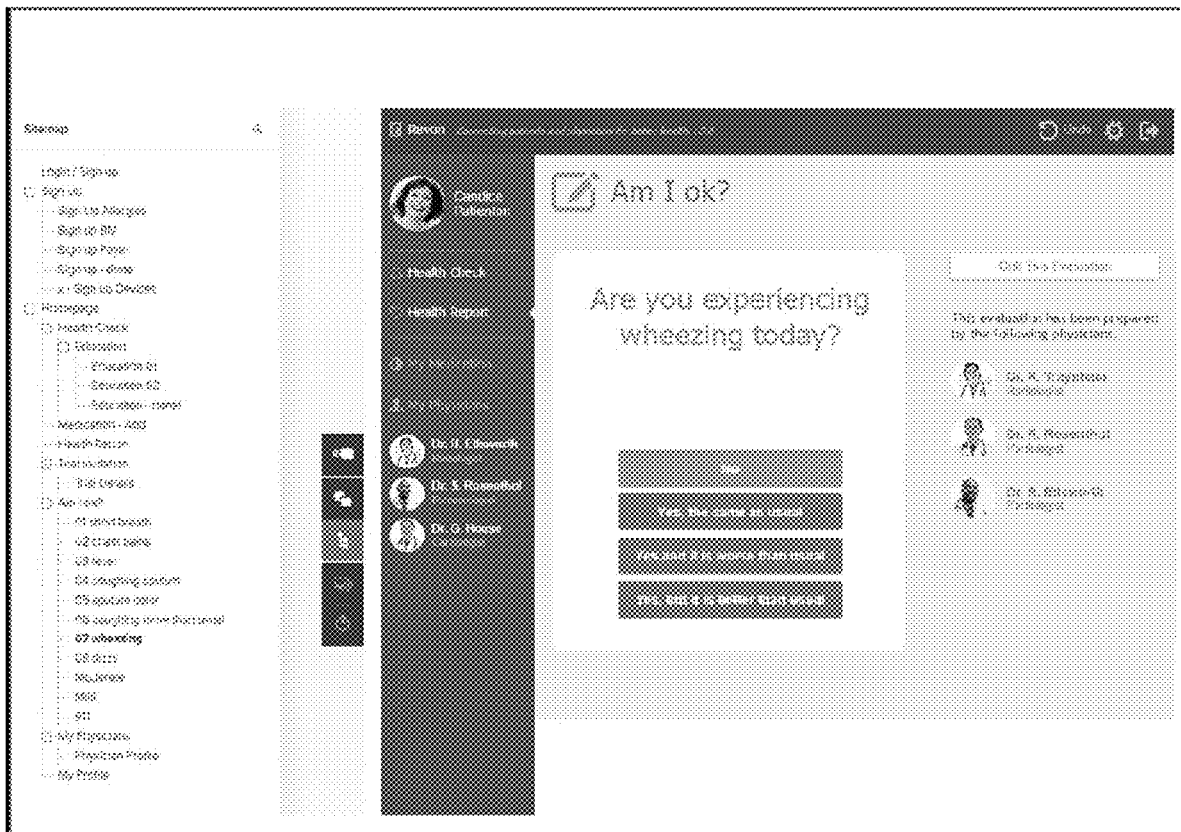
Figure 69:
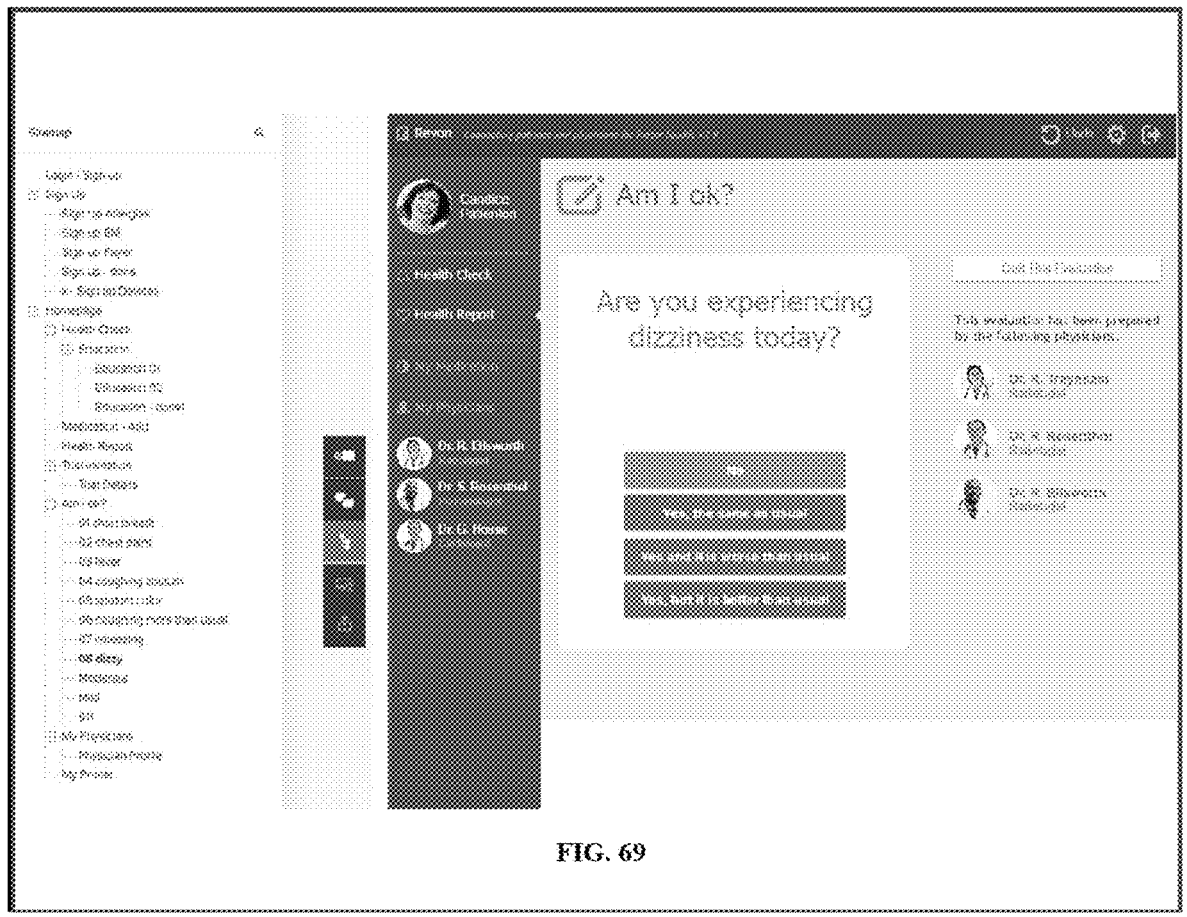
Figure 70:
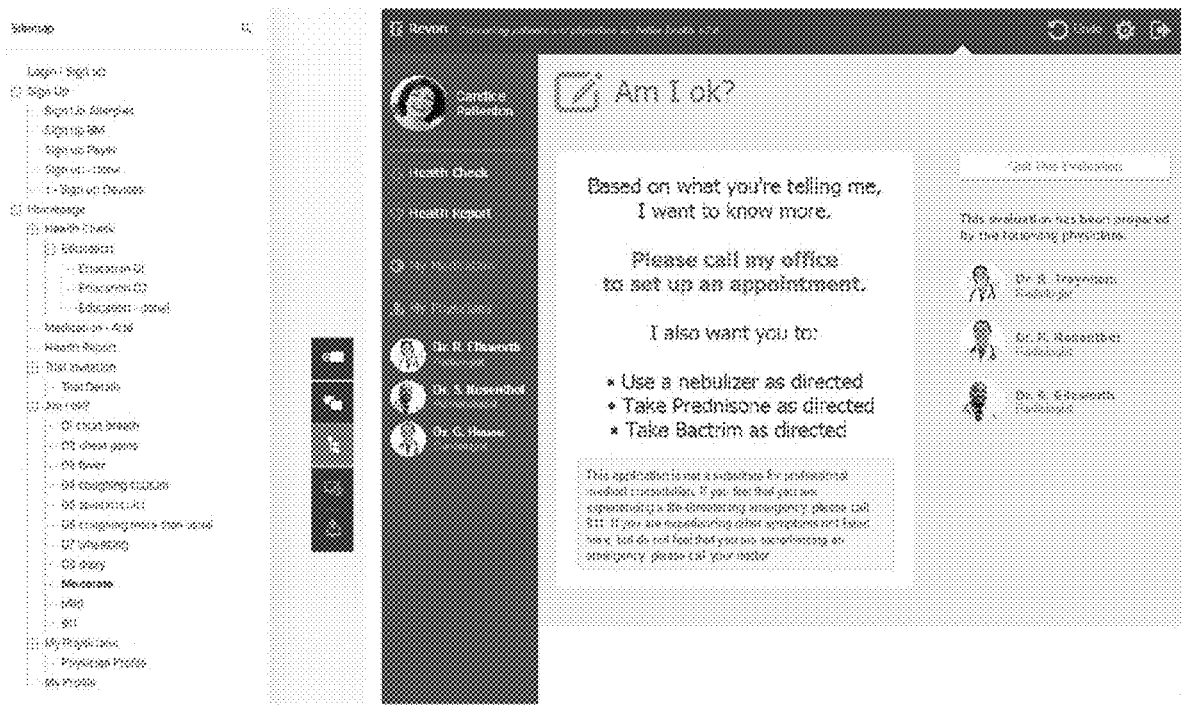
Figure 71:
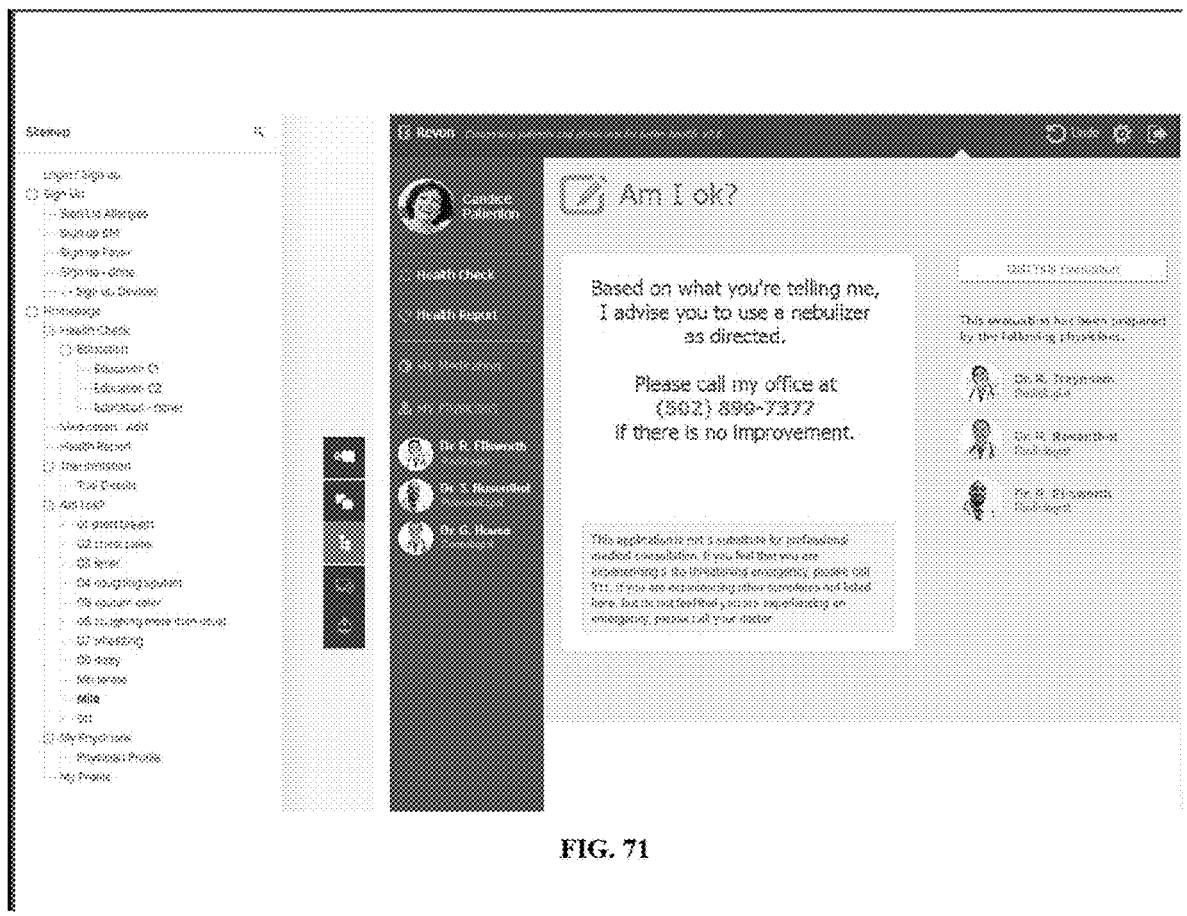
Figure 72:
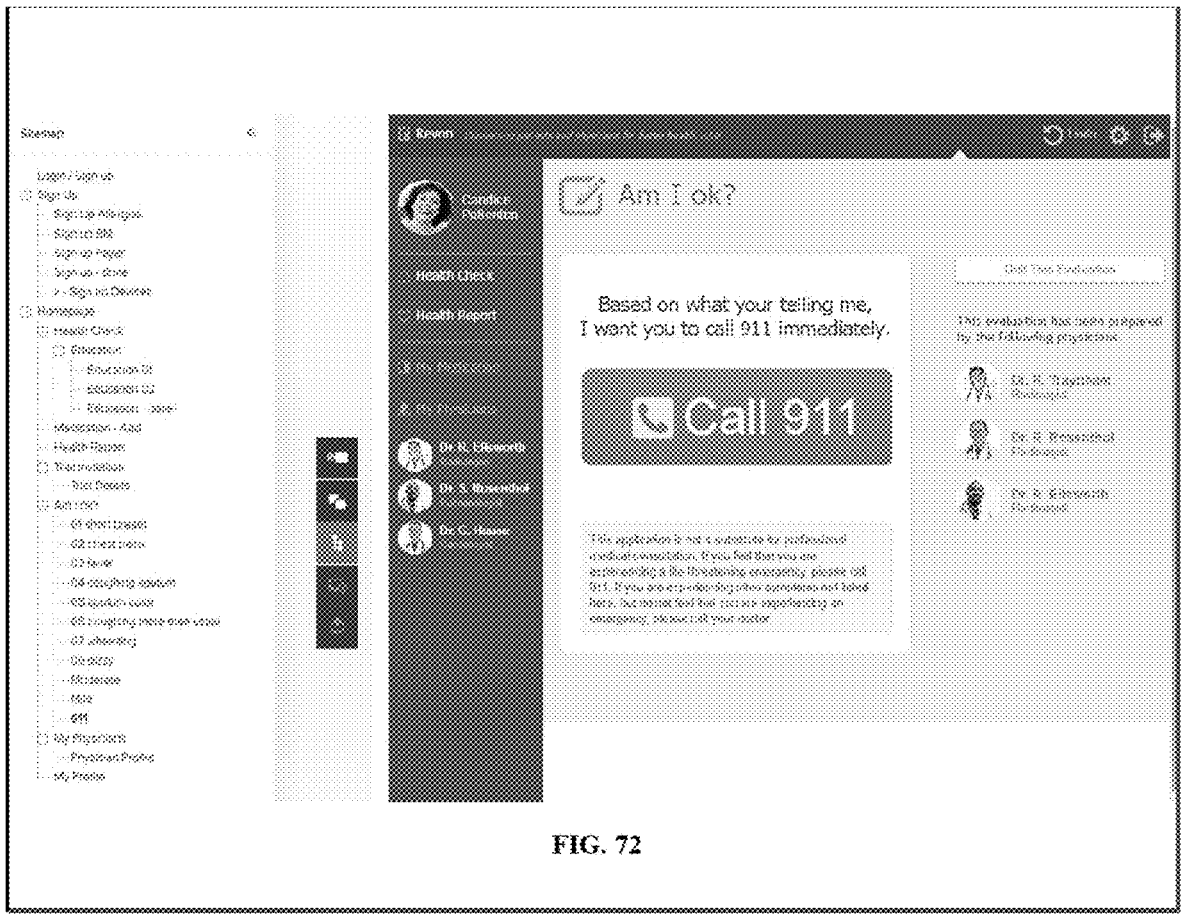
Figure 73:
Figure 74:
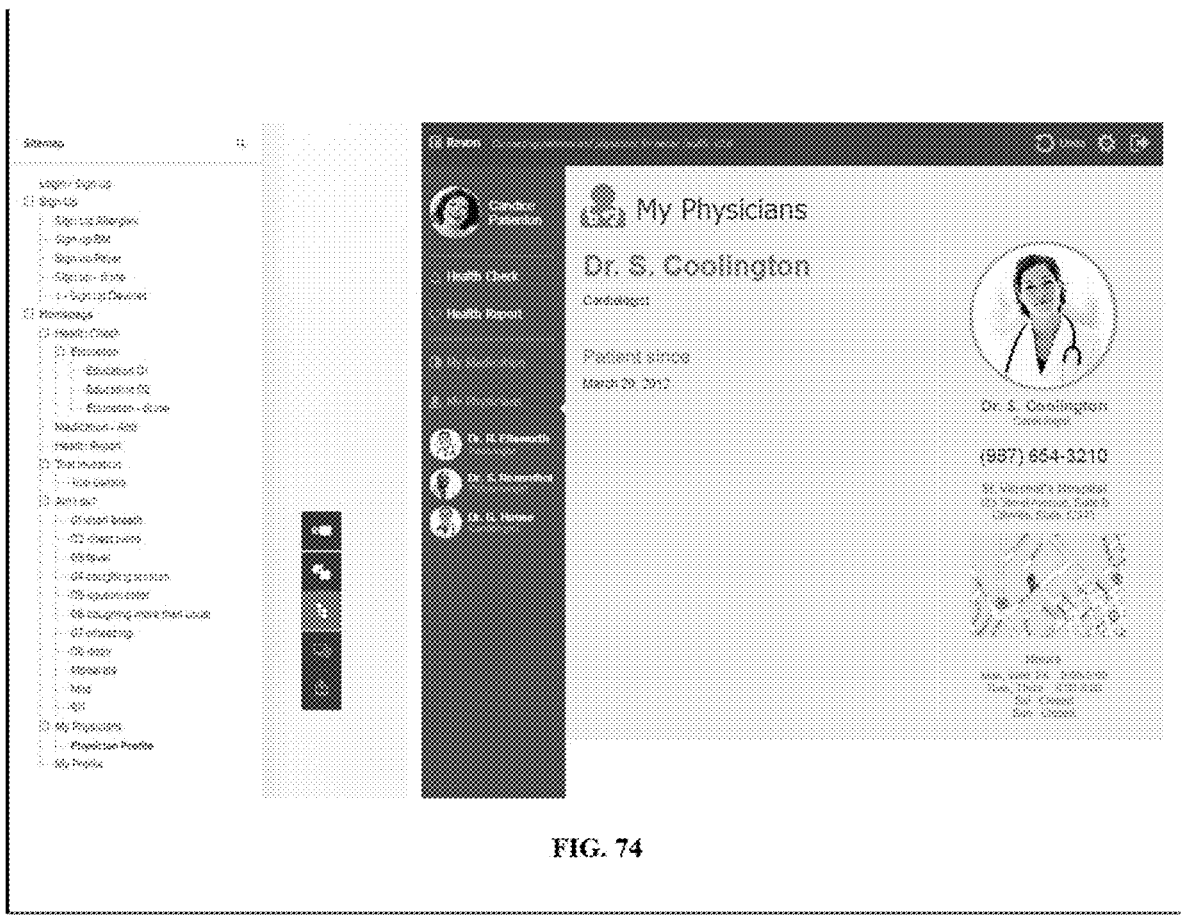
Figure 75:
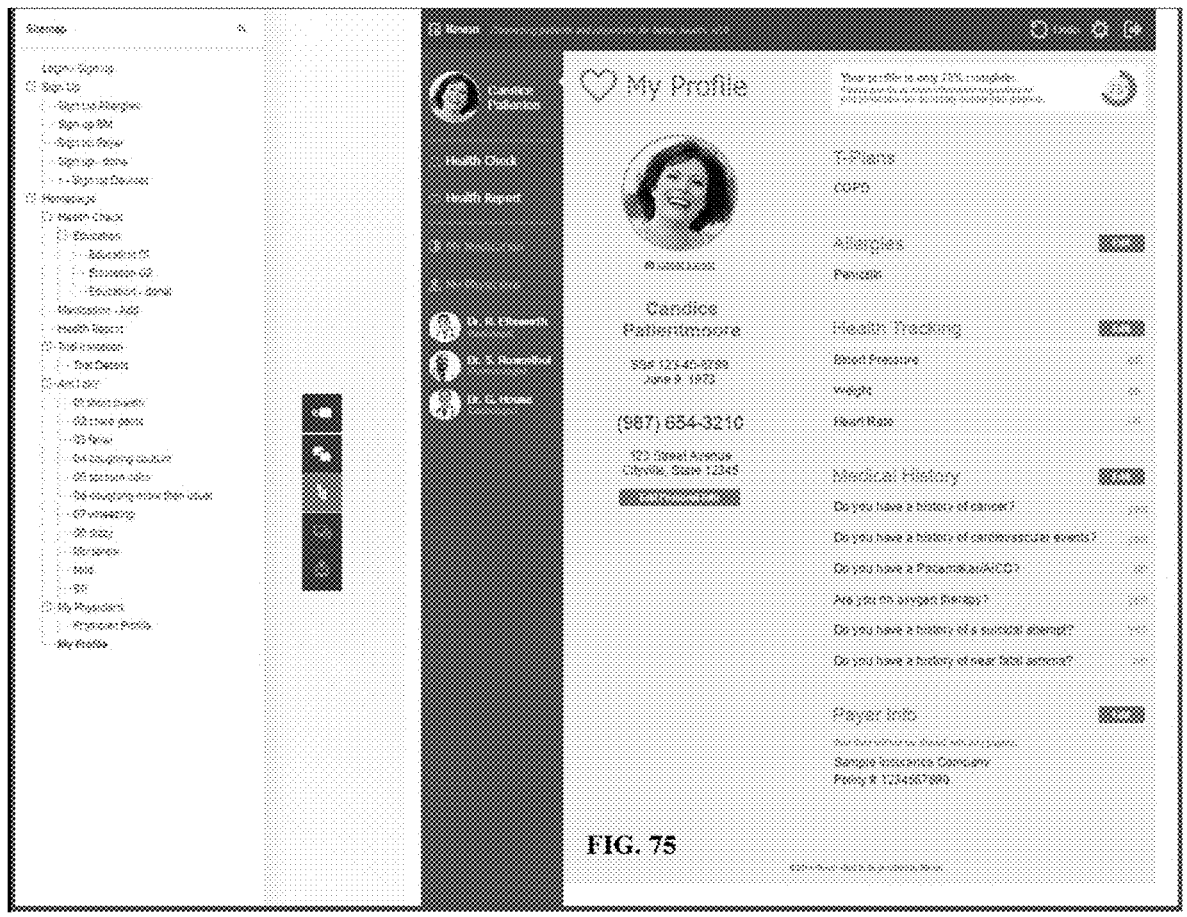
Figure 76:
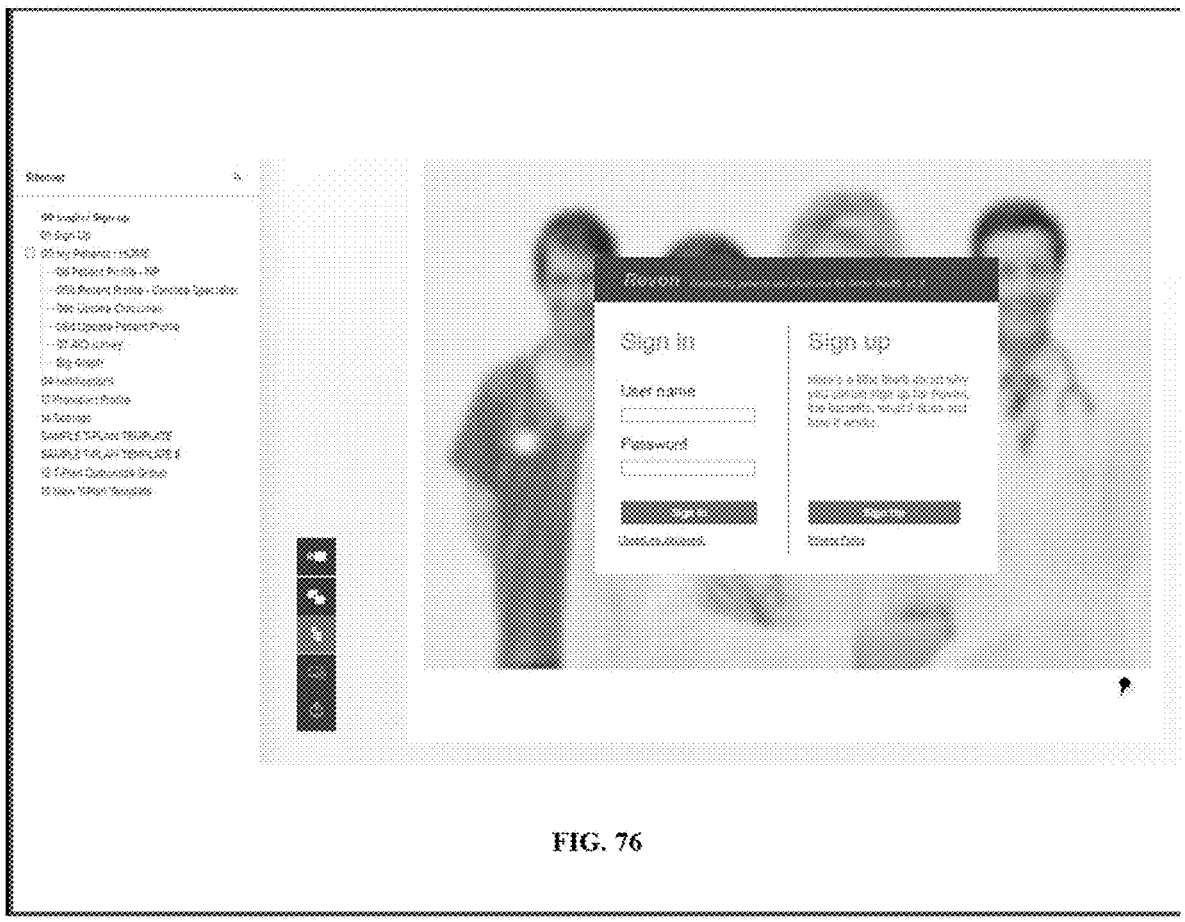
FIGS. 76-91 illustrate interfaces which could be presented by a web based physician portal, along with a site map in the leftmost portion of the illustrations illustrating how the various interfaces relate to each other.
Figure 77:
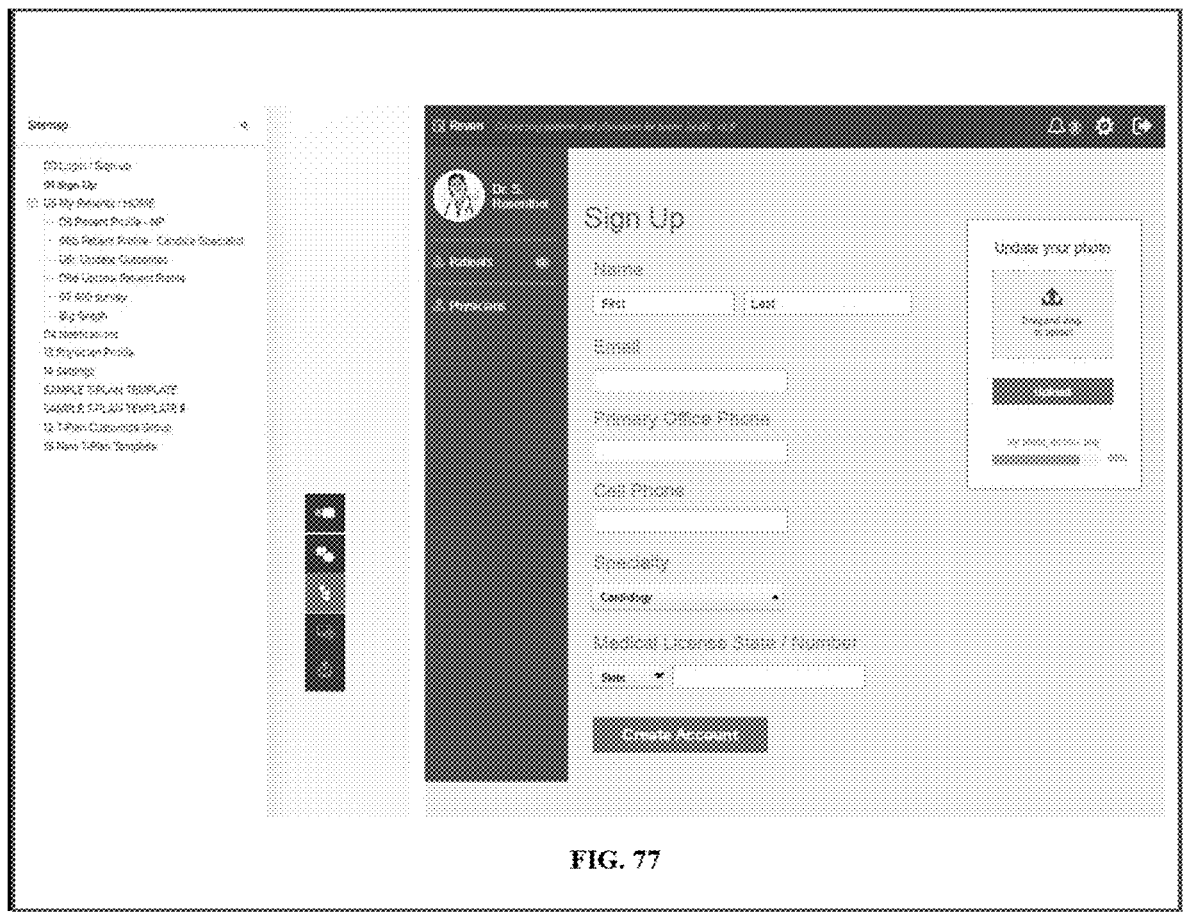
Figure 78:
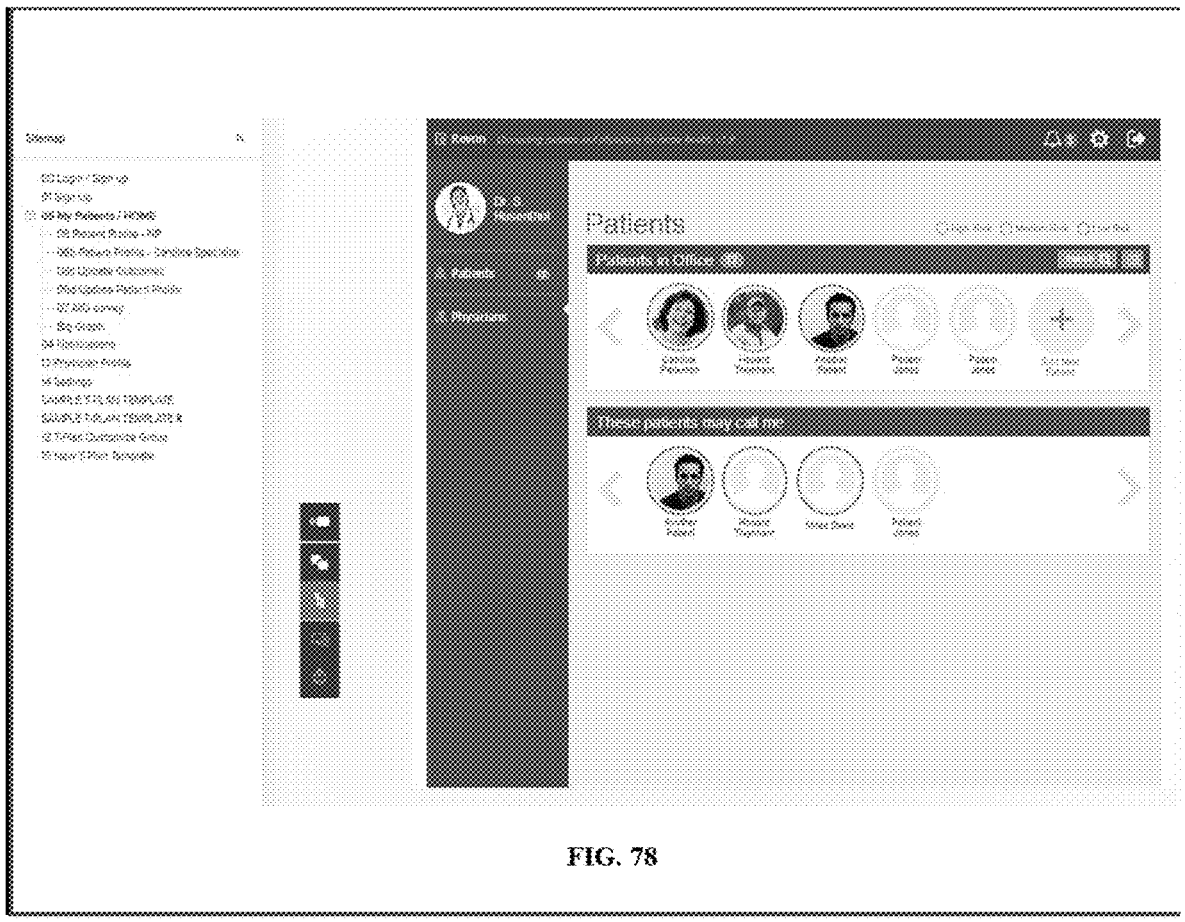
Figure 79:
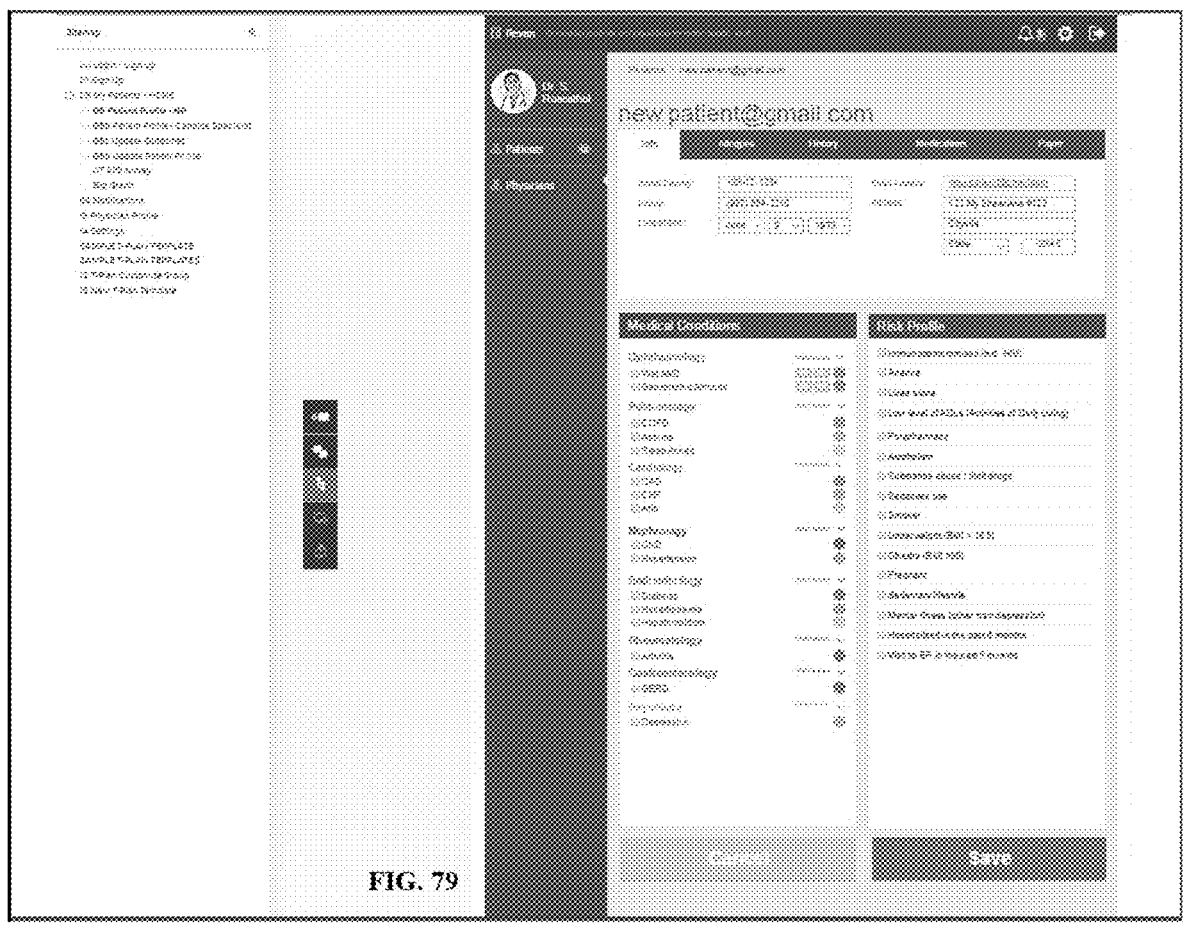
Figure 80:
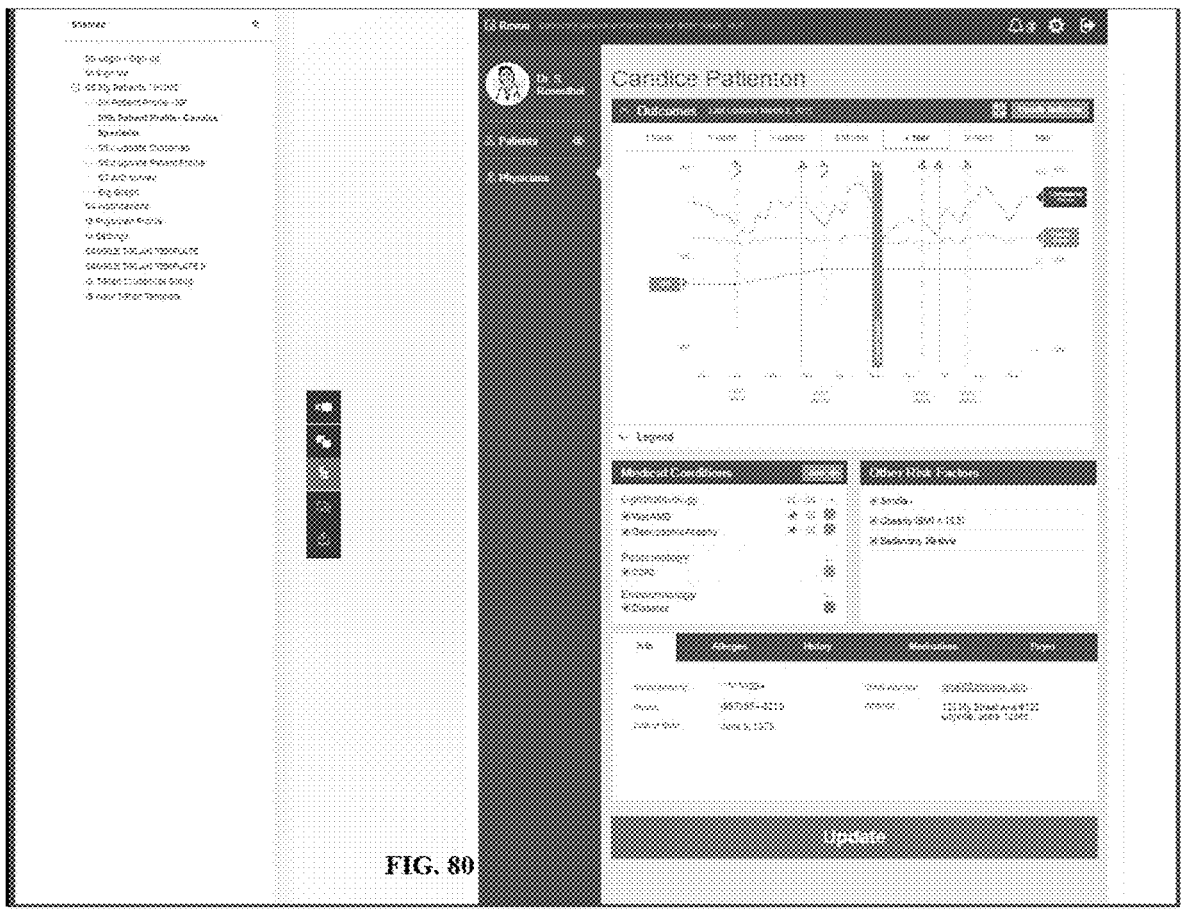
Figure 81:
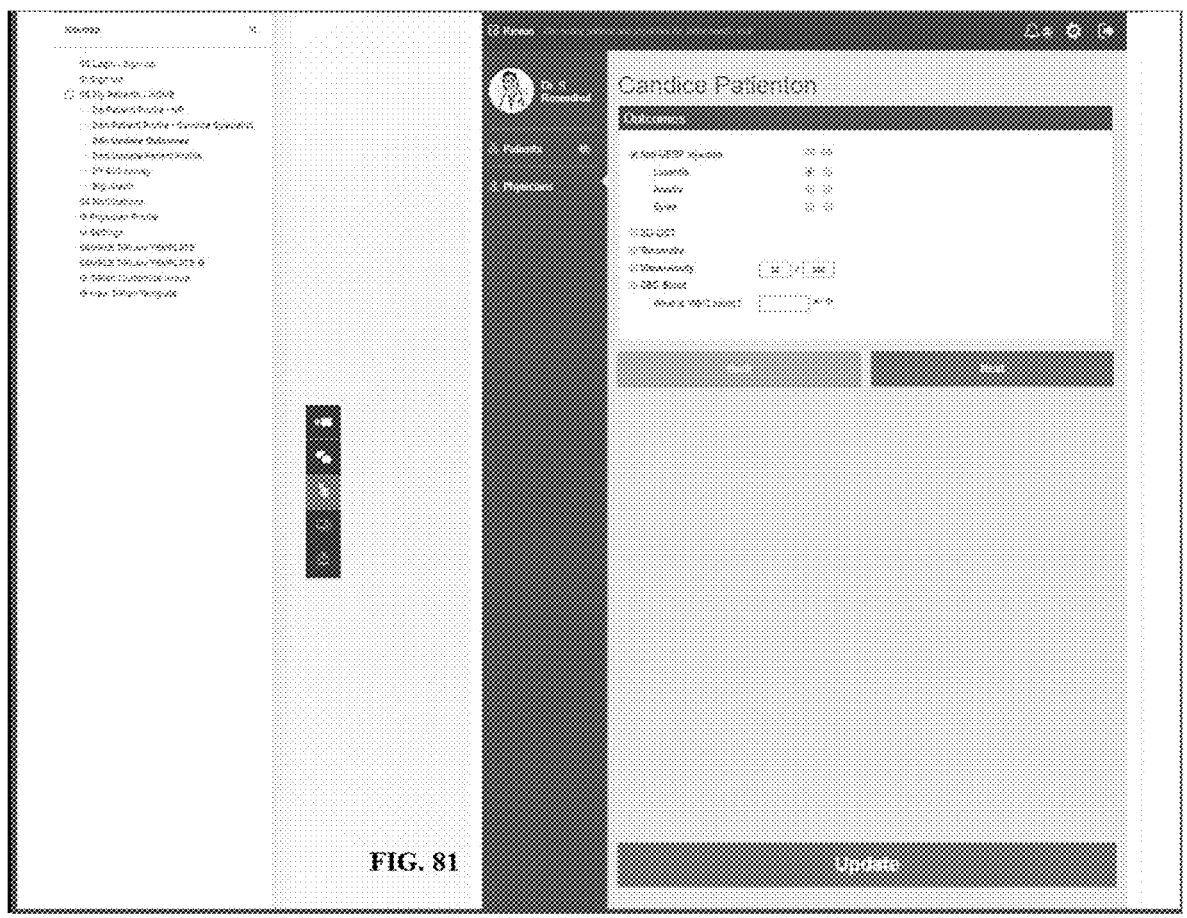
Figure 82:
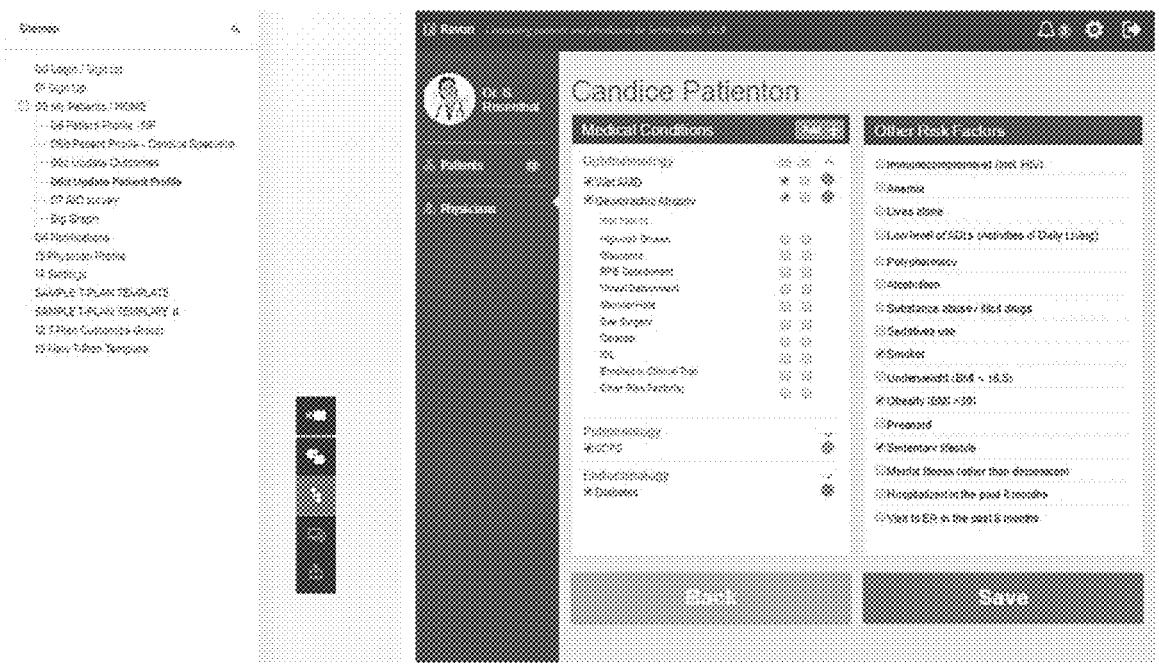
Figure 83:
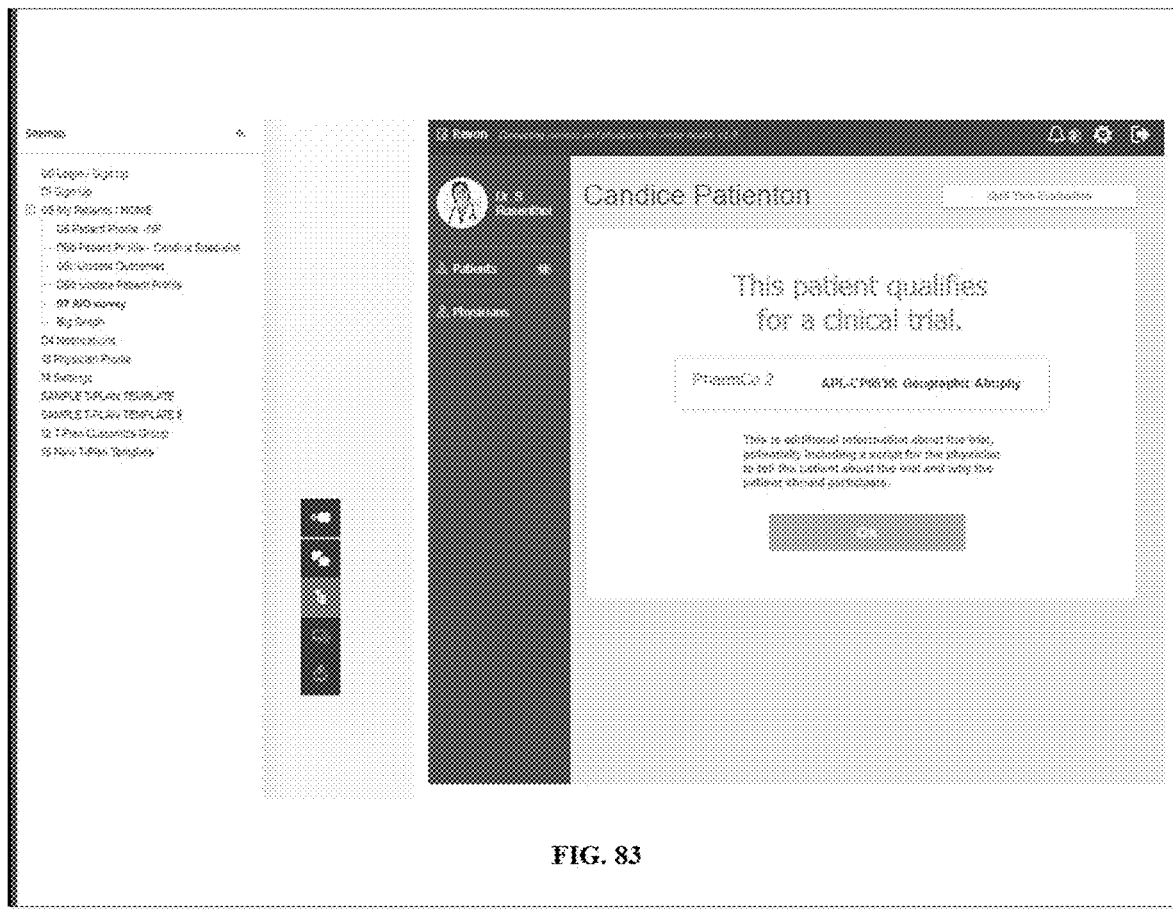
Figure 84:
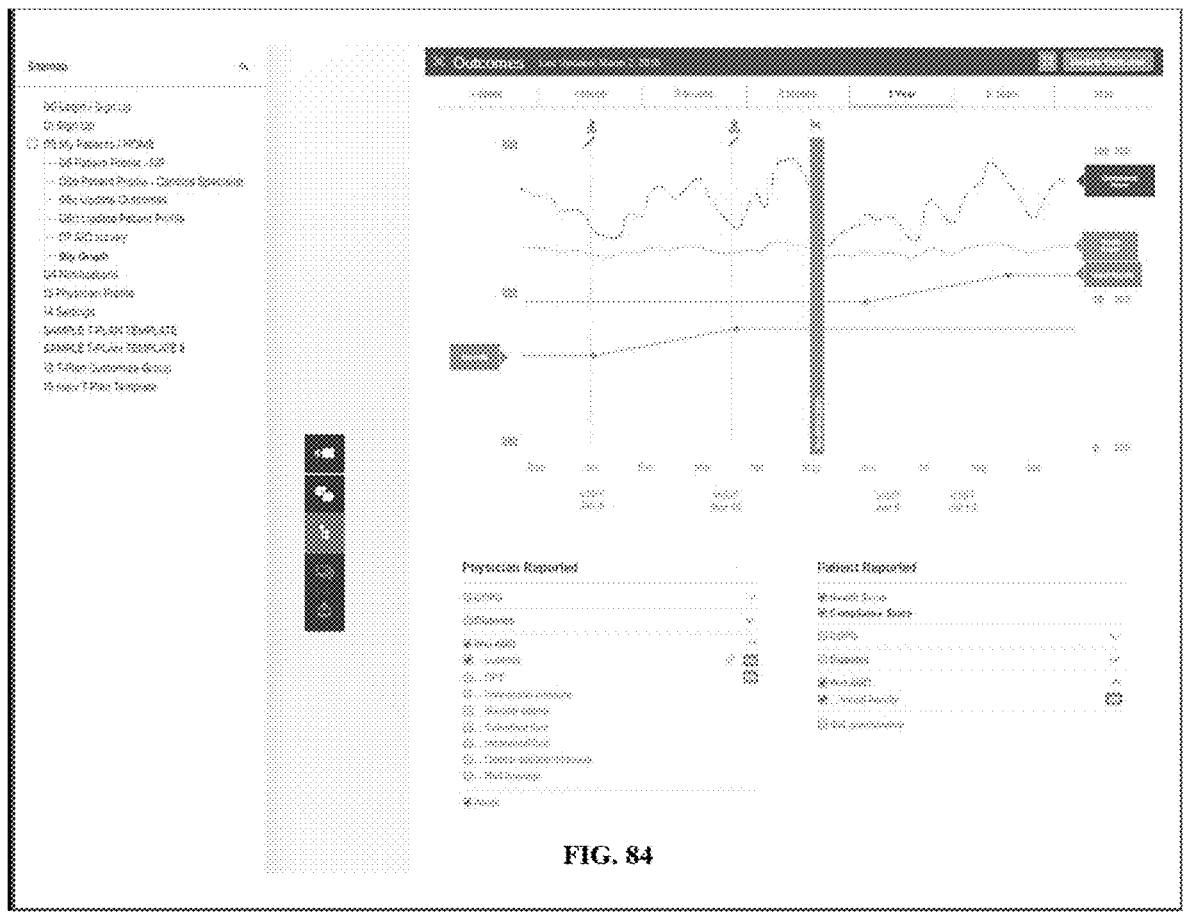
Figure 85:
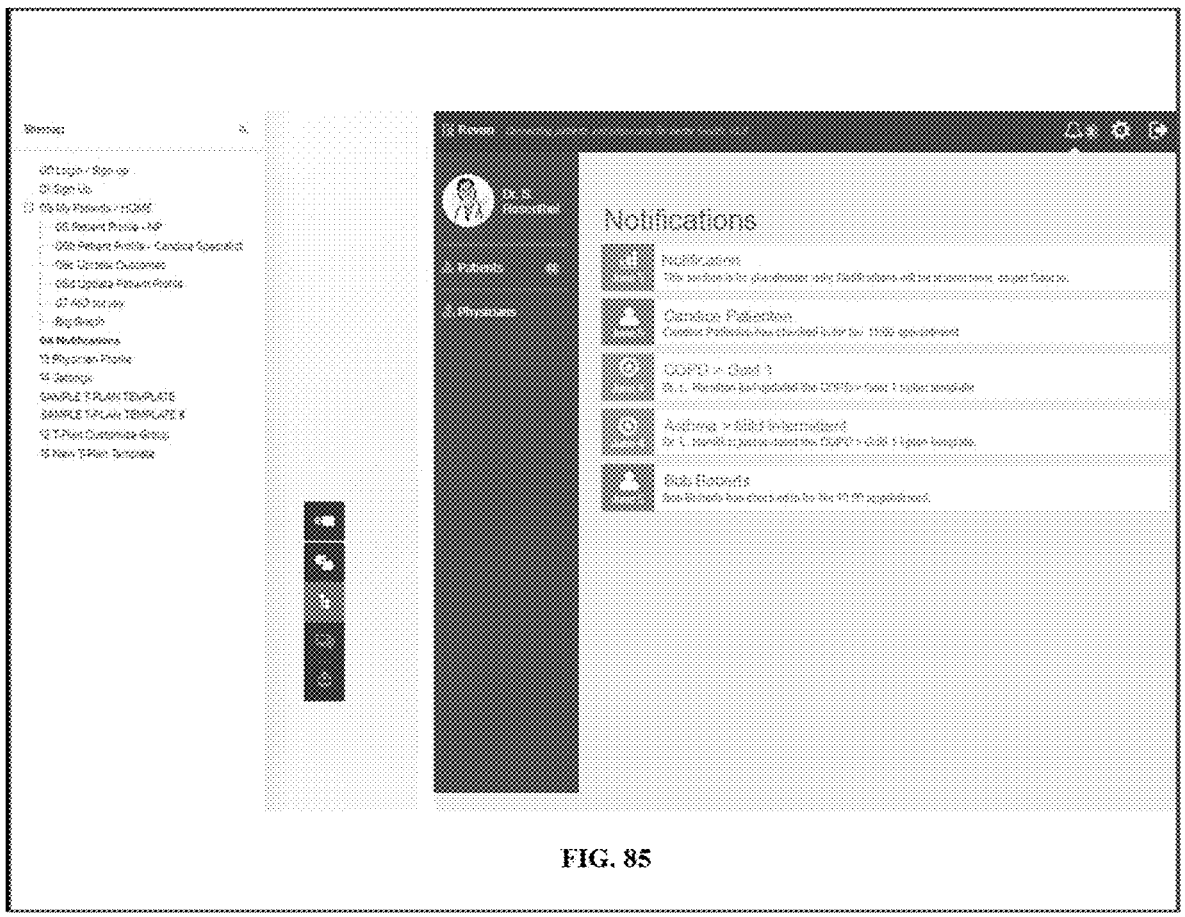
Figure 86:
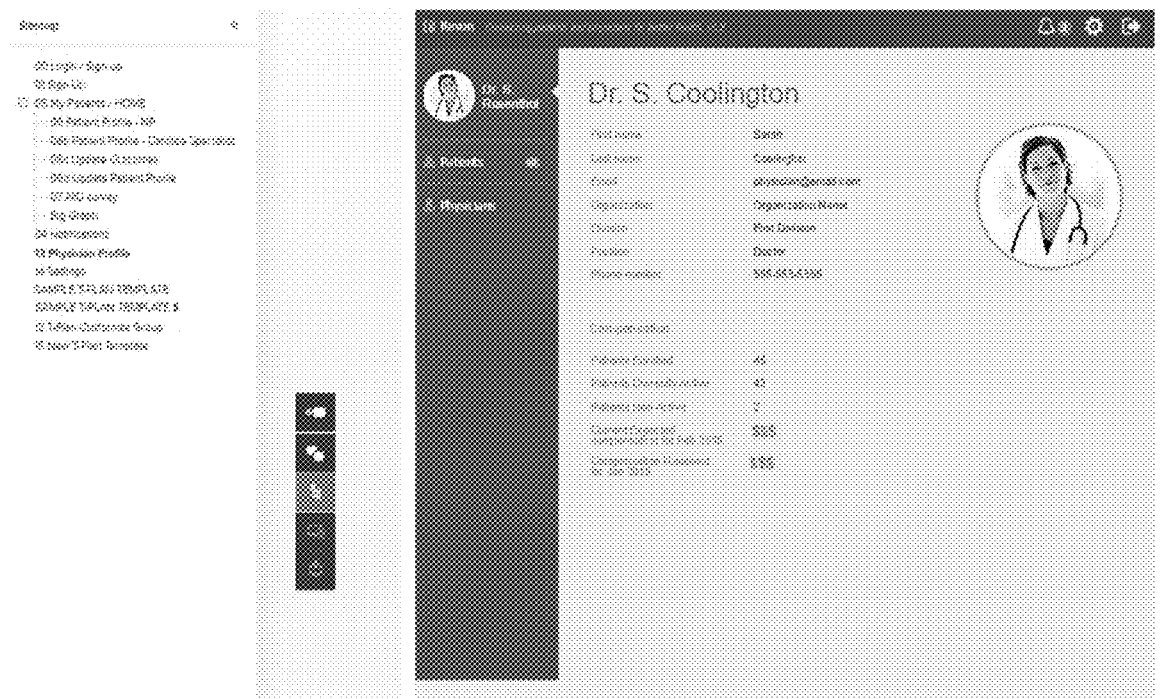
Figure 87:
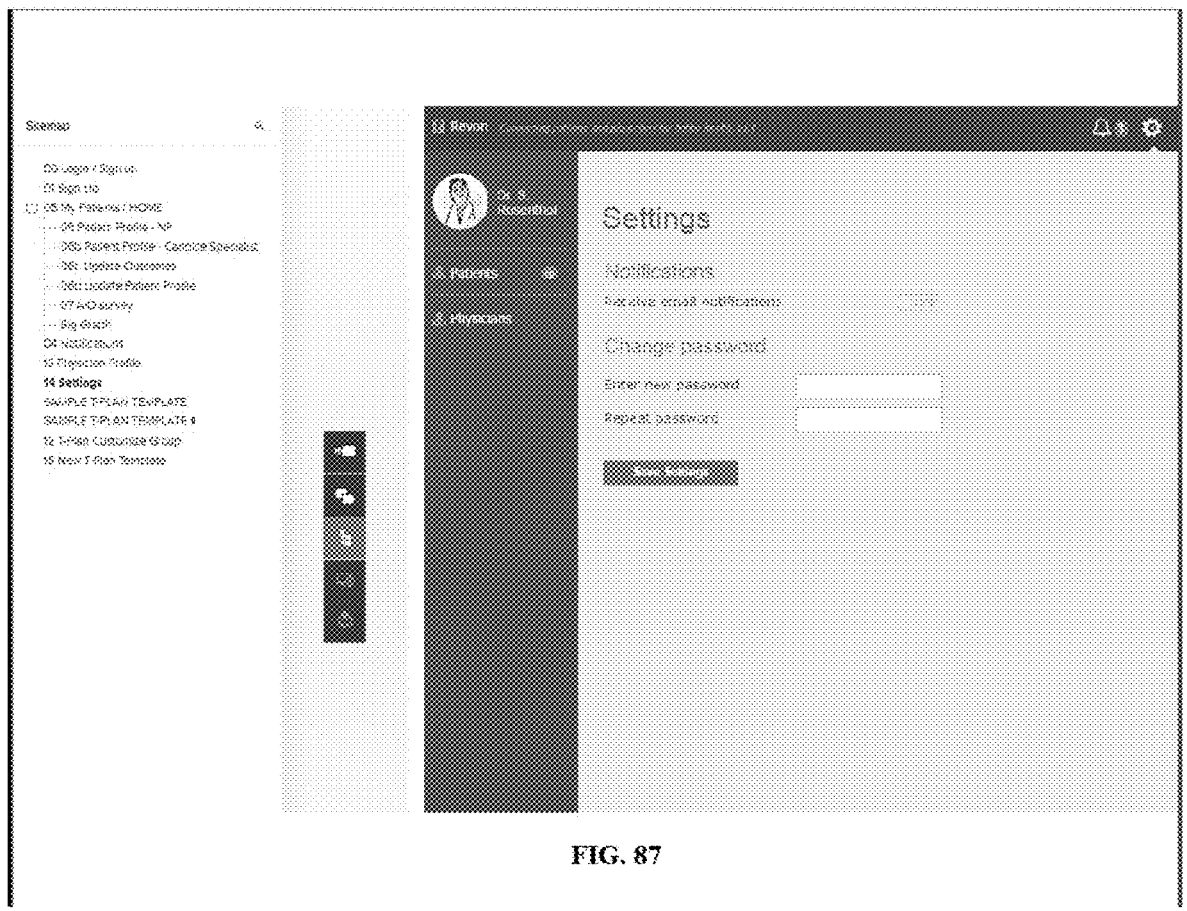
Figure 88:
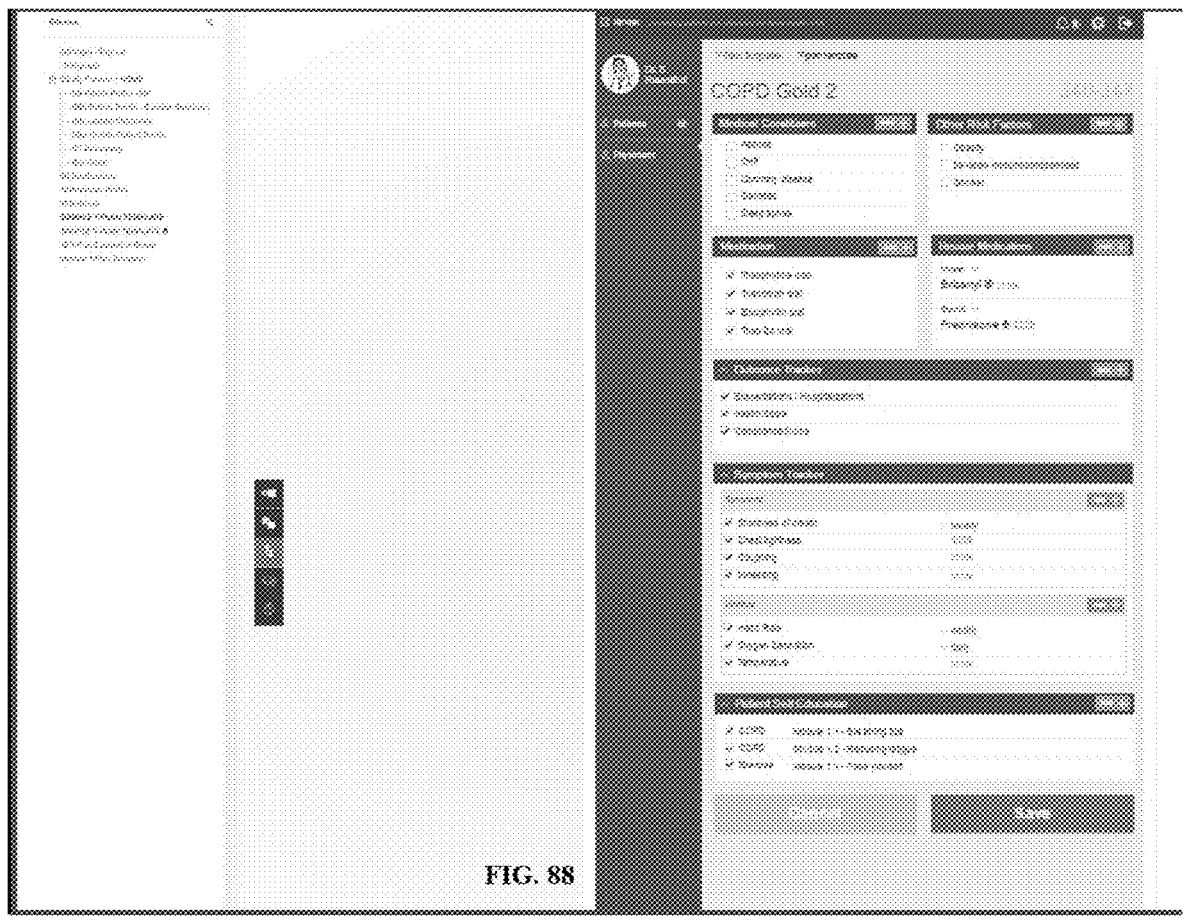
Figure 89:
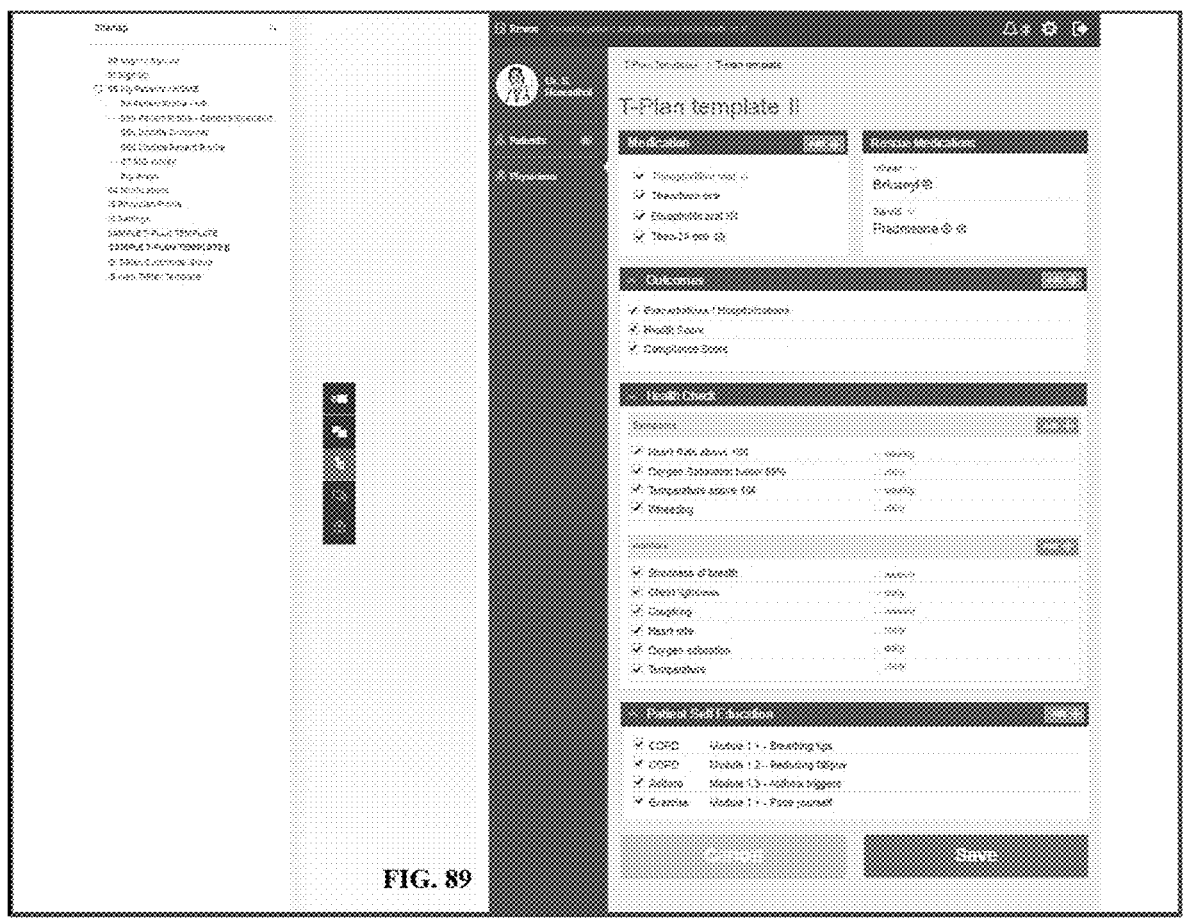
Figure 90:
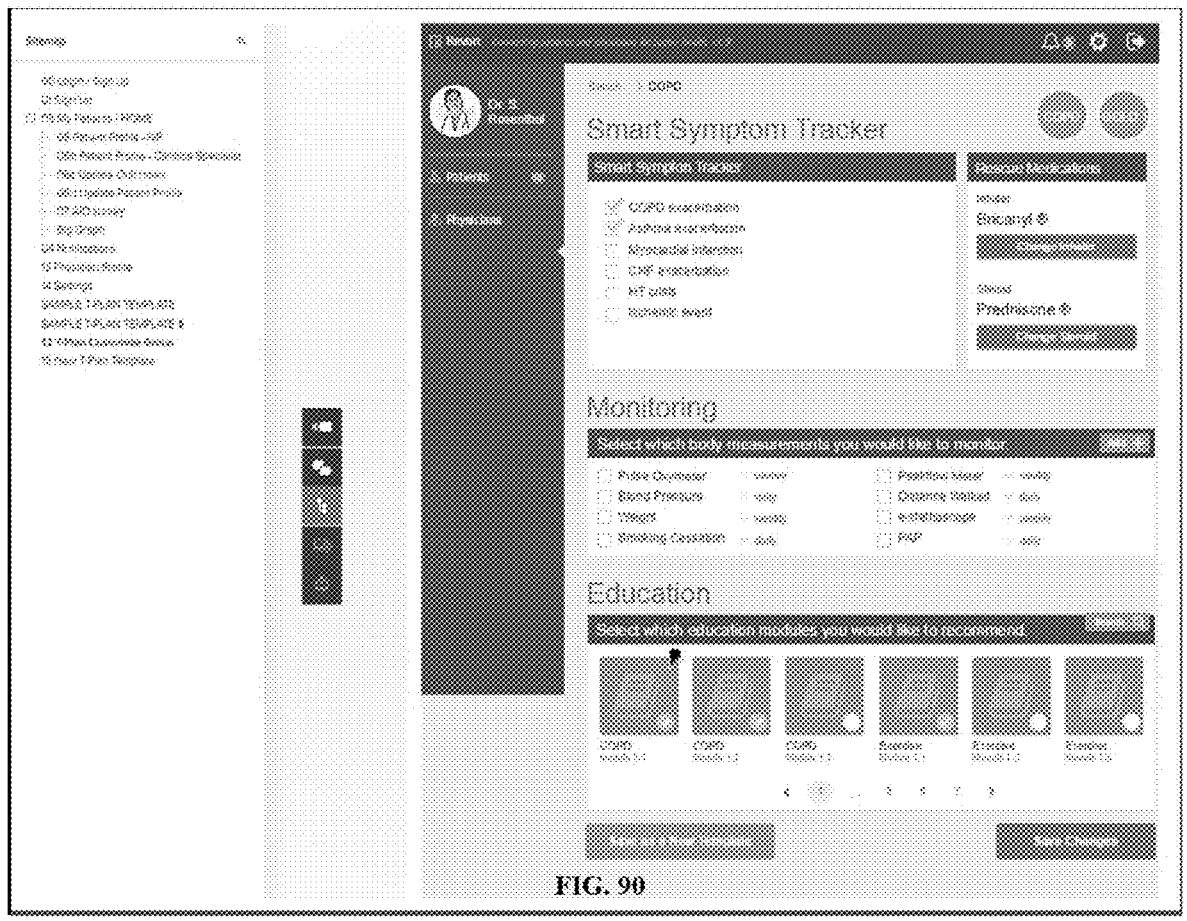
Figure 91:
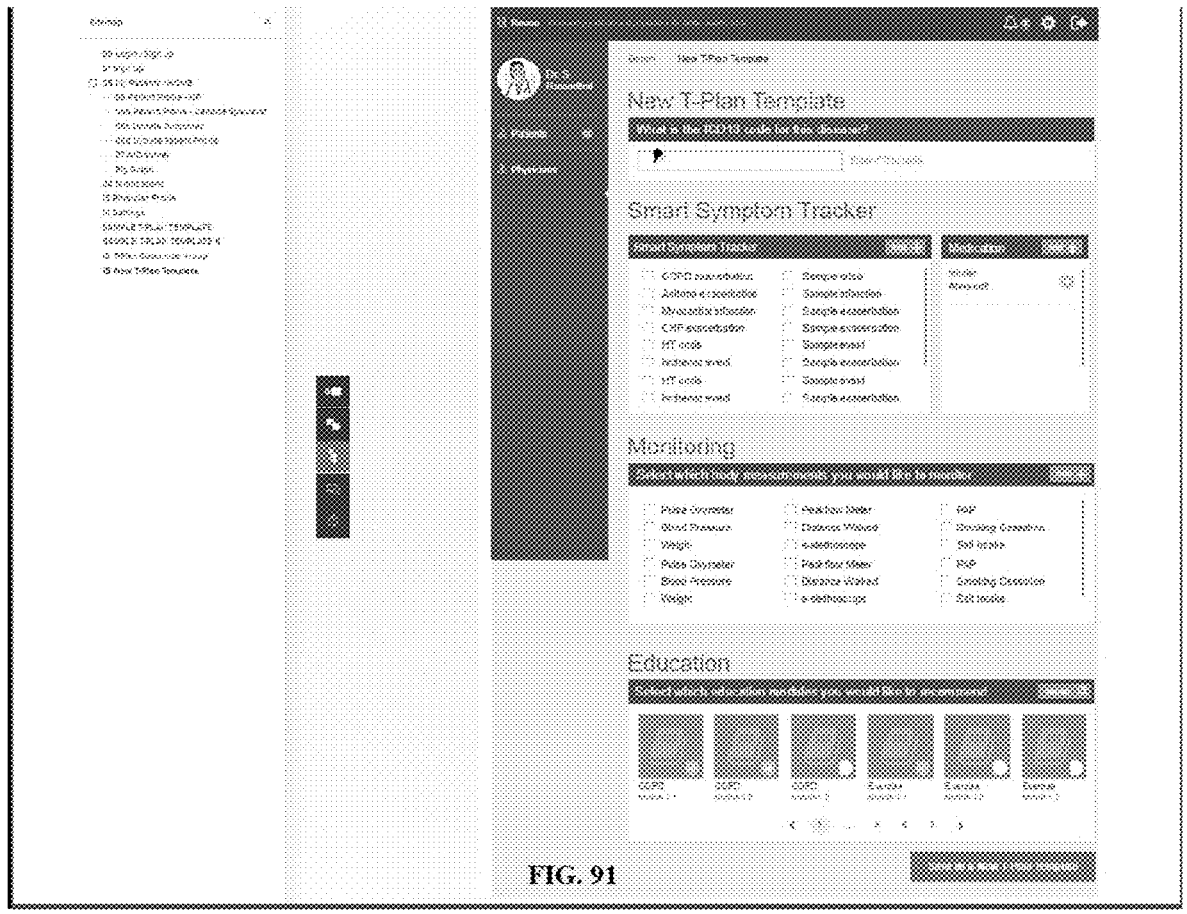
Figure 92:
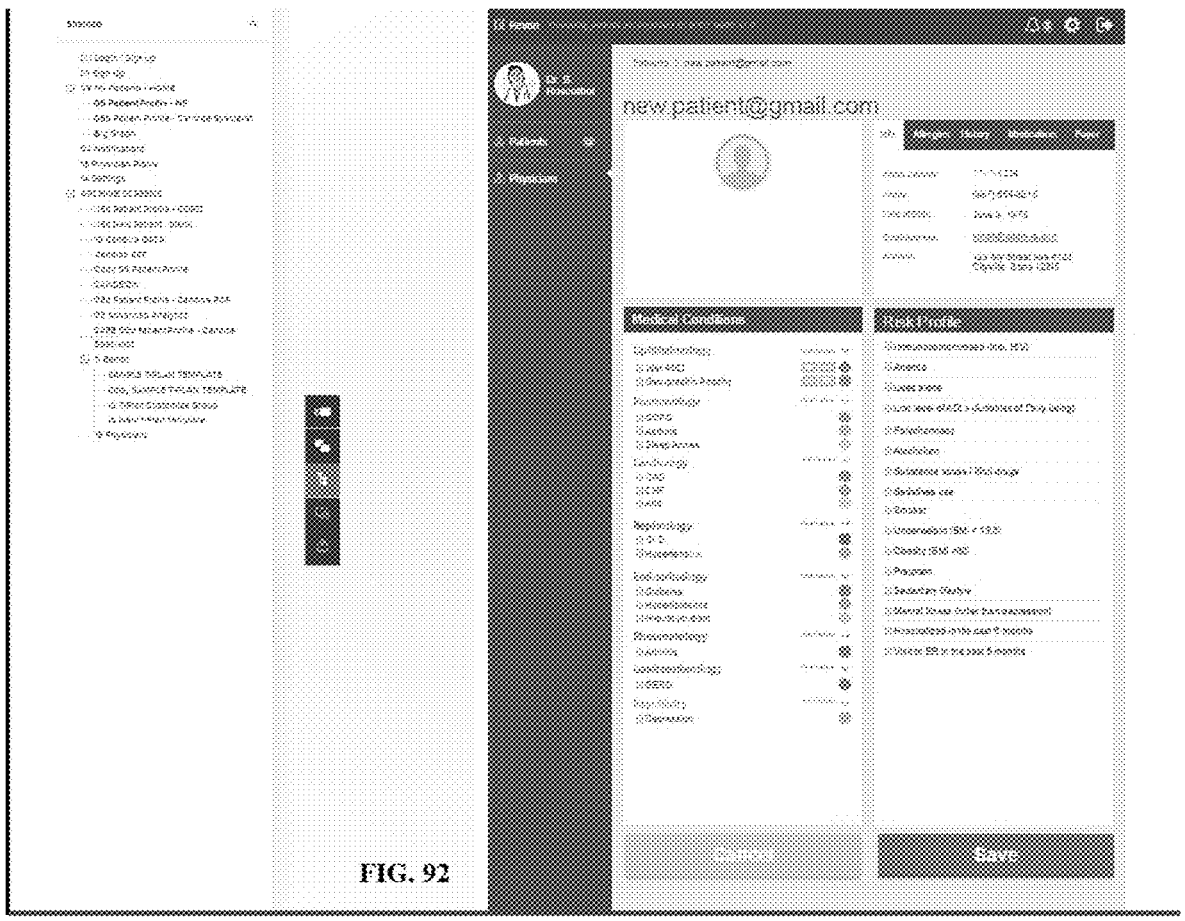
FIGS. 92-114 illustrate interfaces which could be presented by a web based physician portal, along with a site map in the leftmost portion of the illustrations illustrating how the various interfaces relate to each other.
Figure 93:
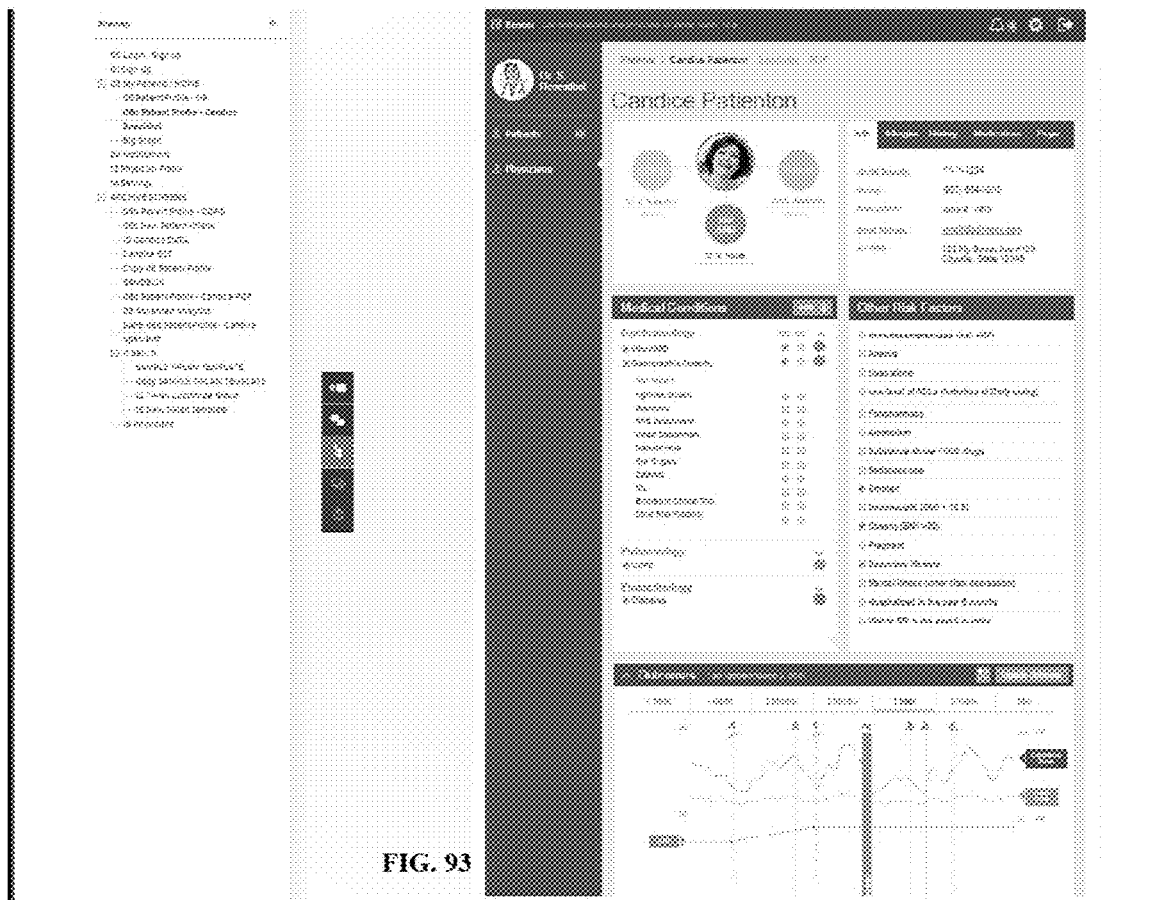
Figure 94:
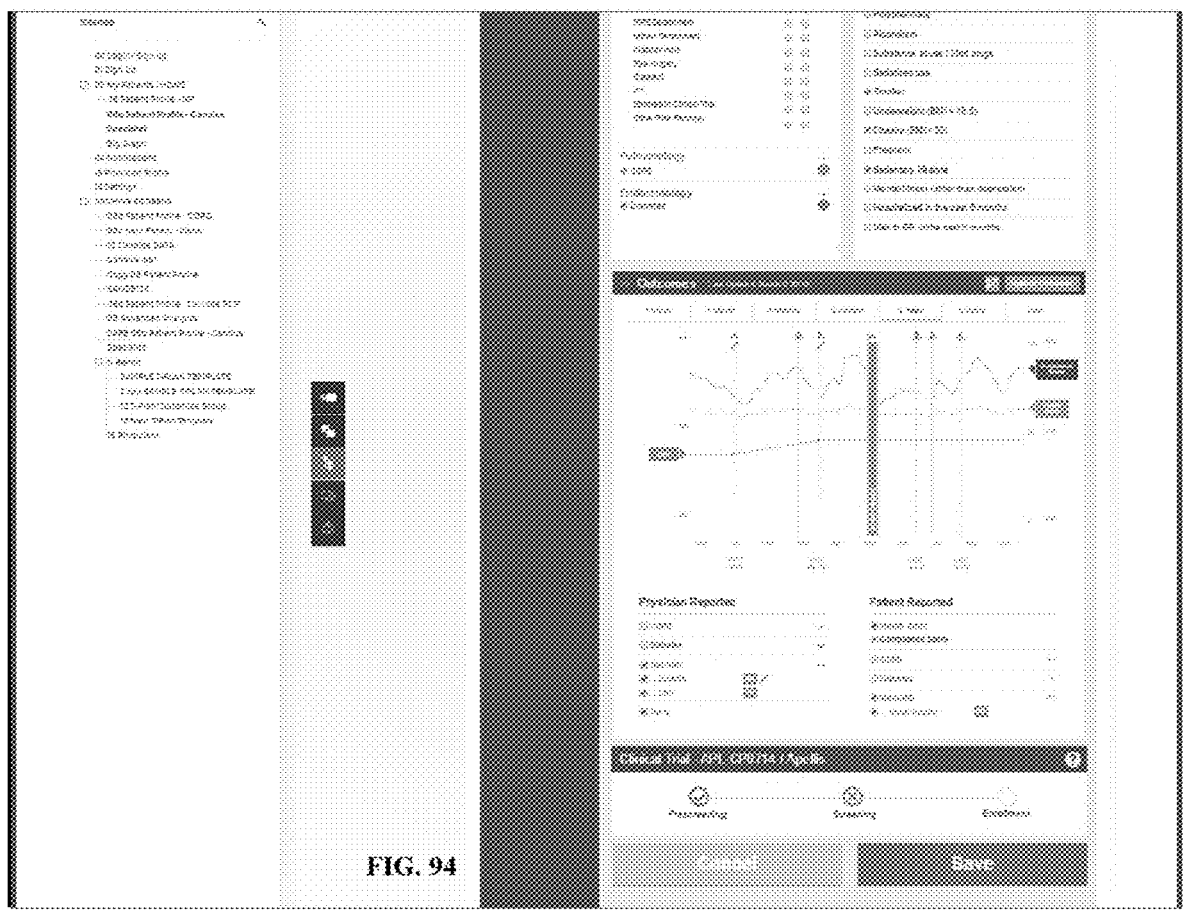
Figure 95:
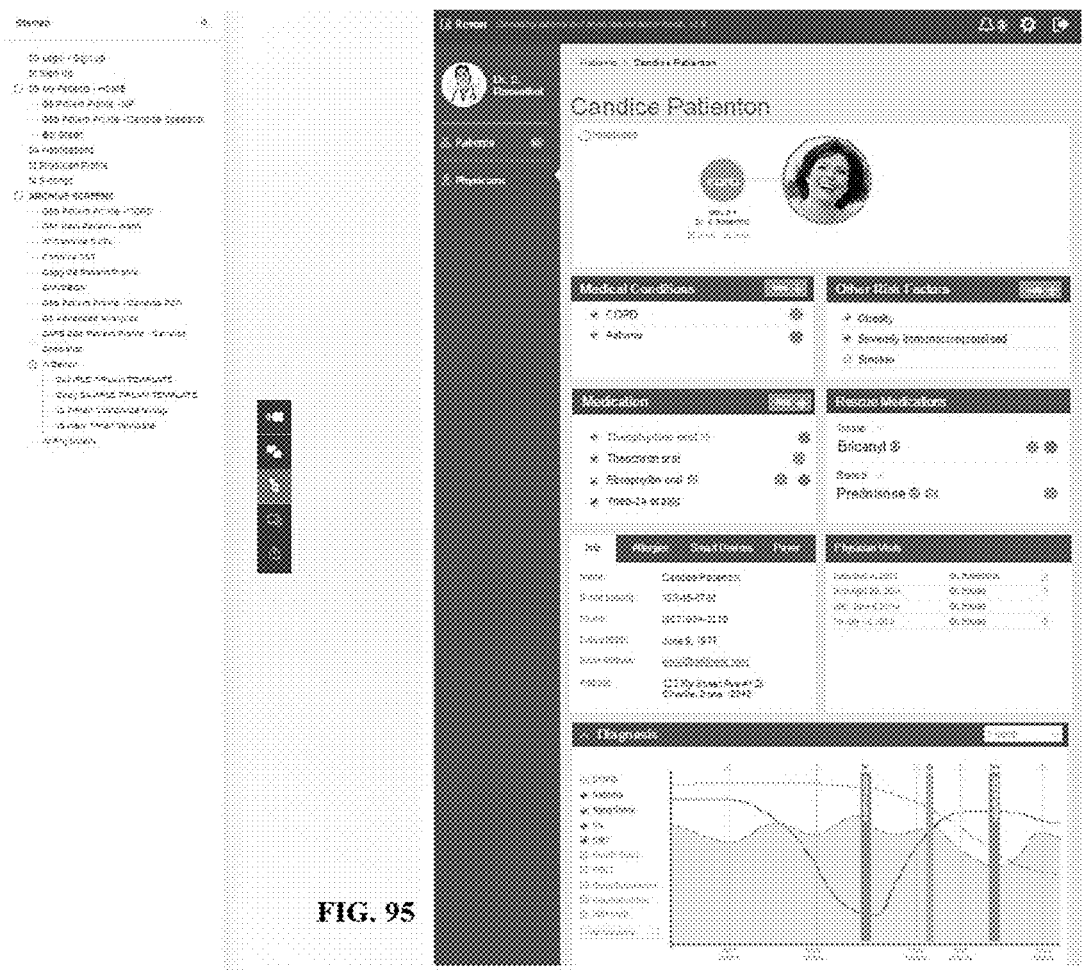
Figure 96:
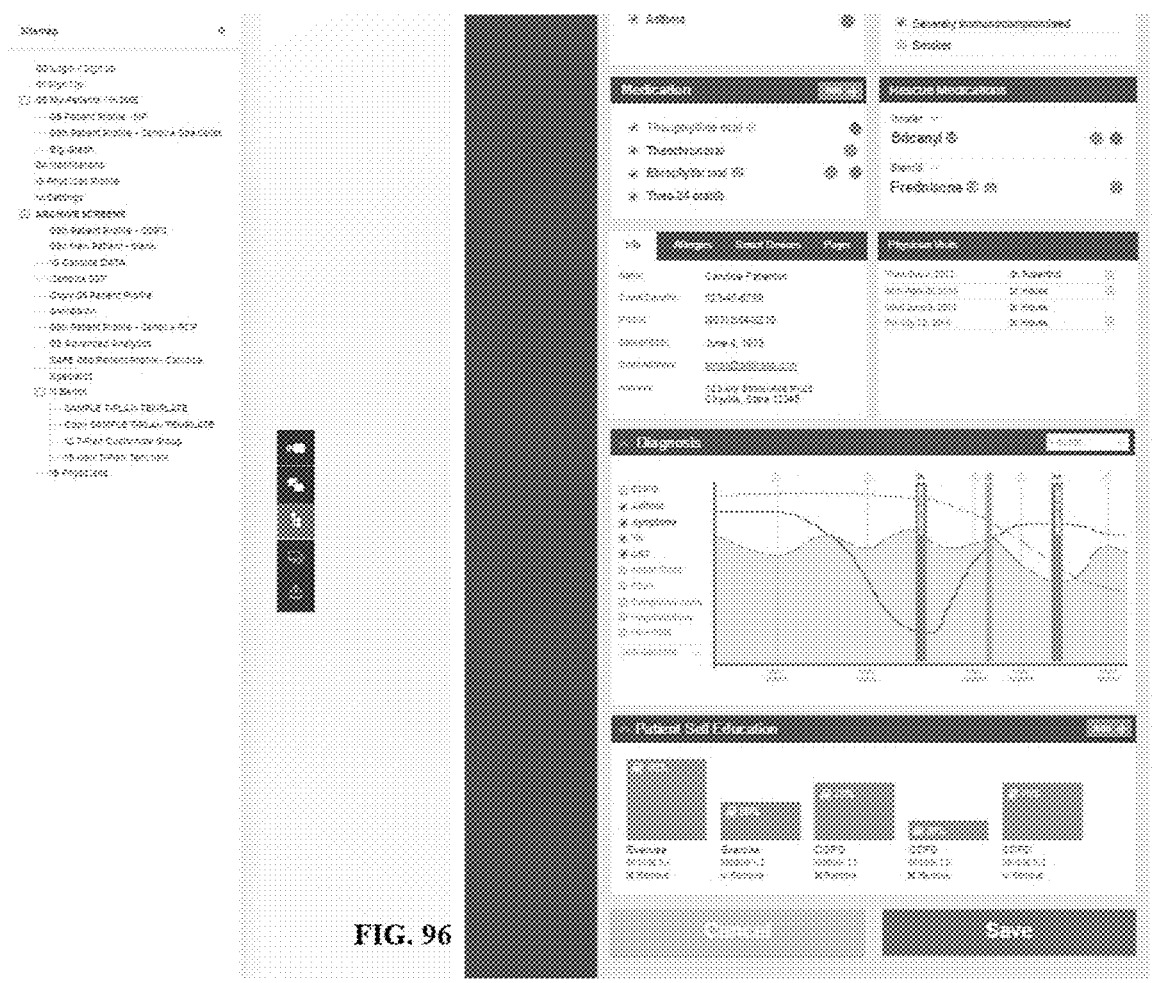
Figure 97:
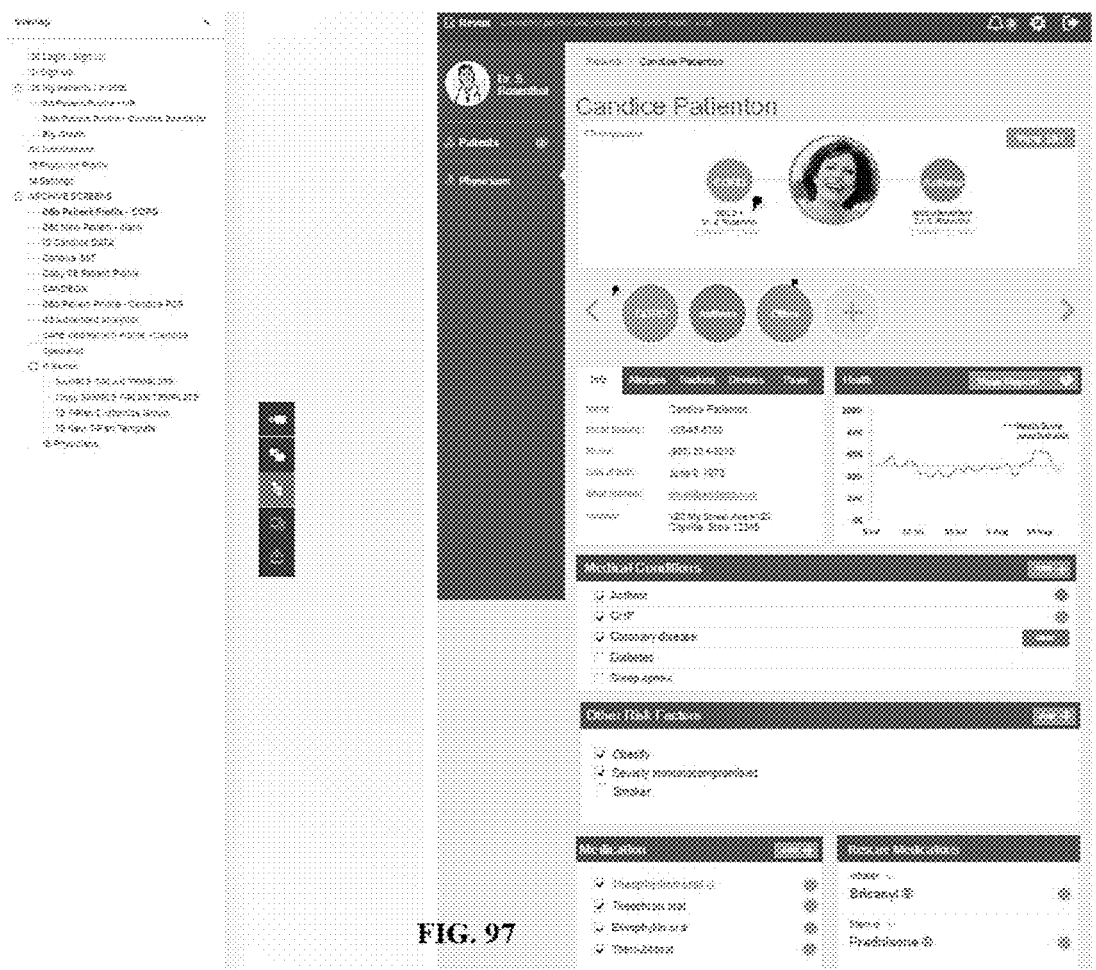
Figure 98:
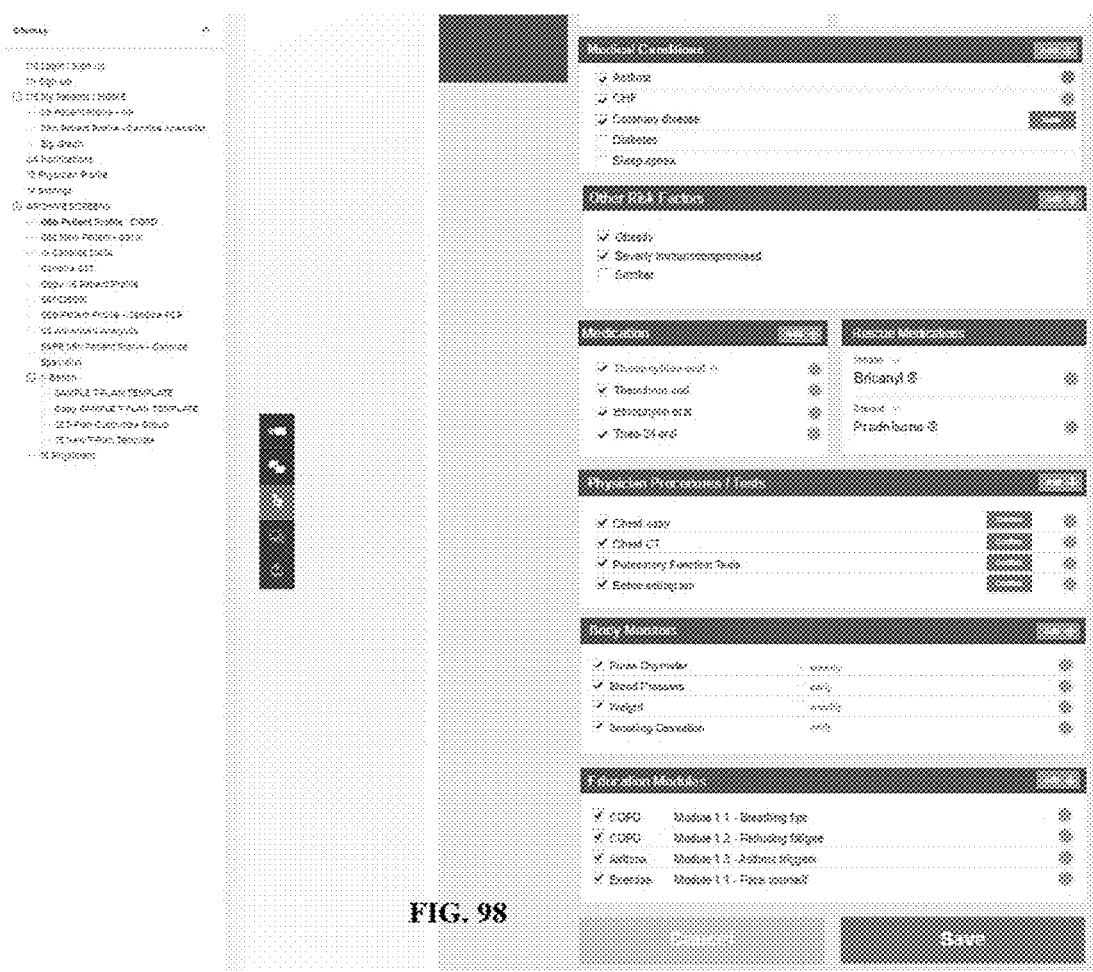
Figure 99:
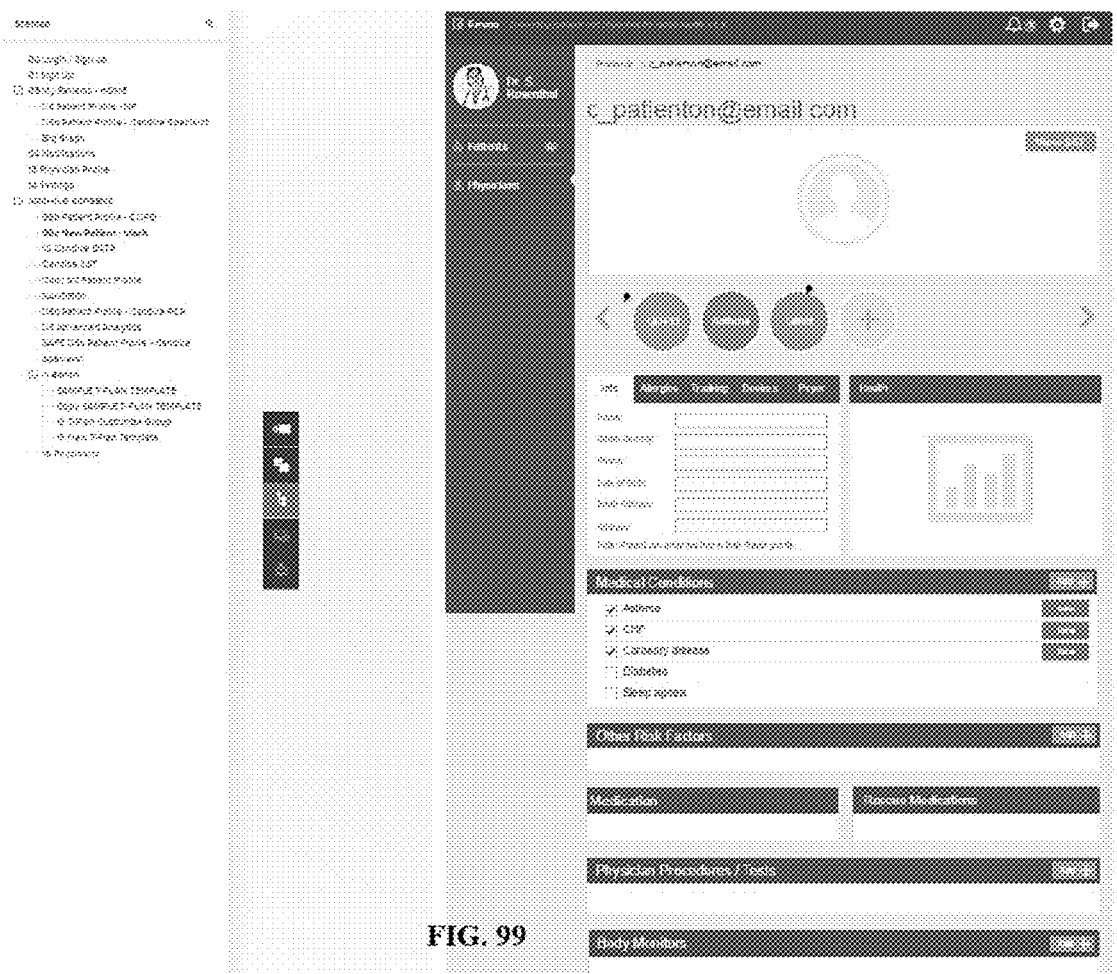
Figure 100:
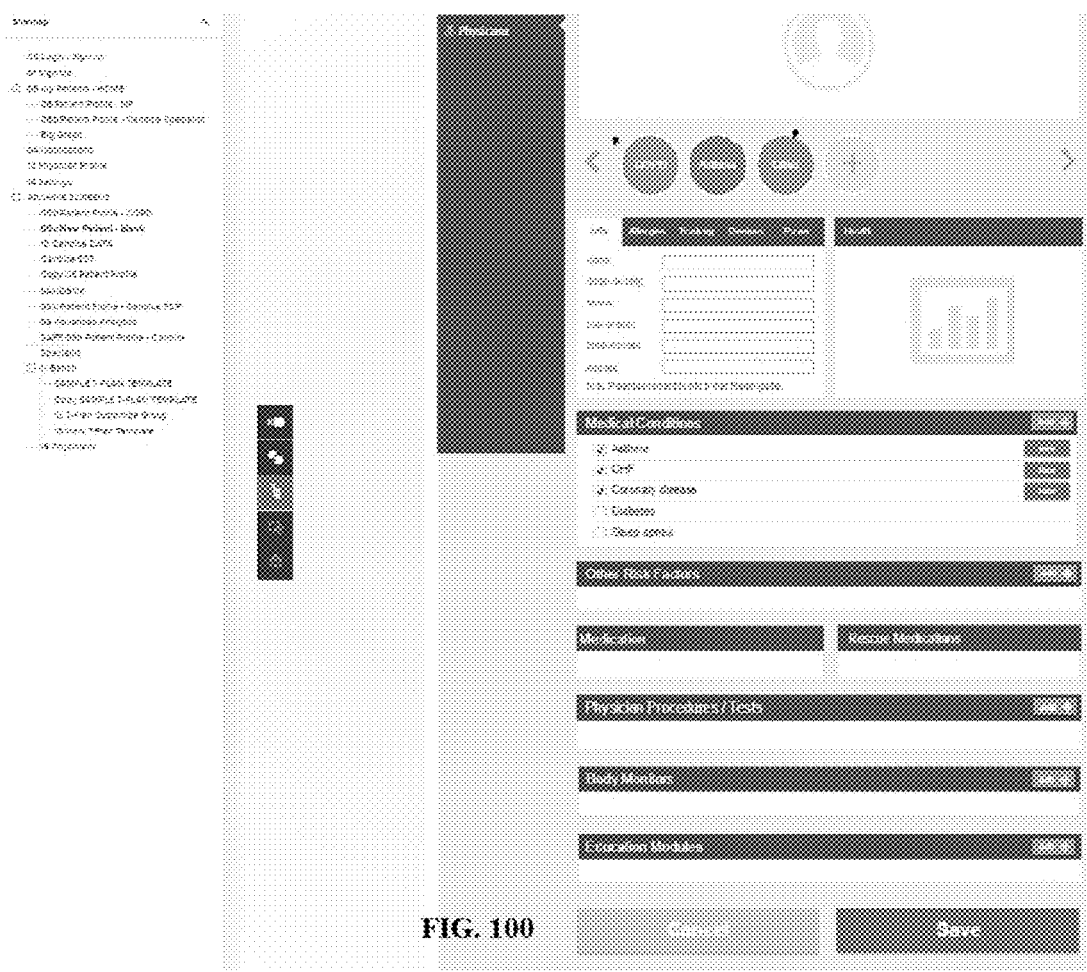
Figure 101:
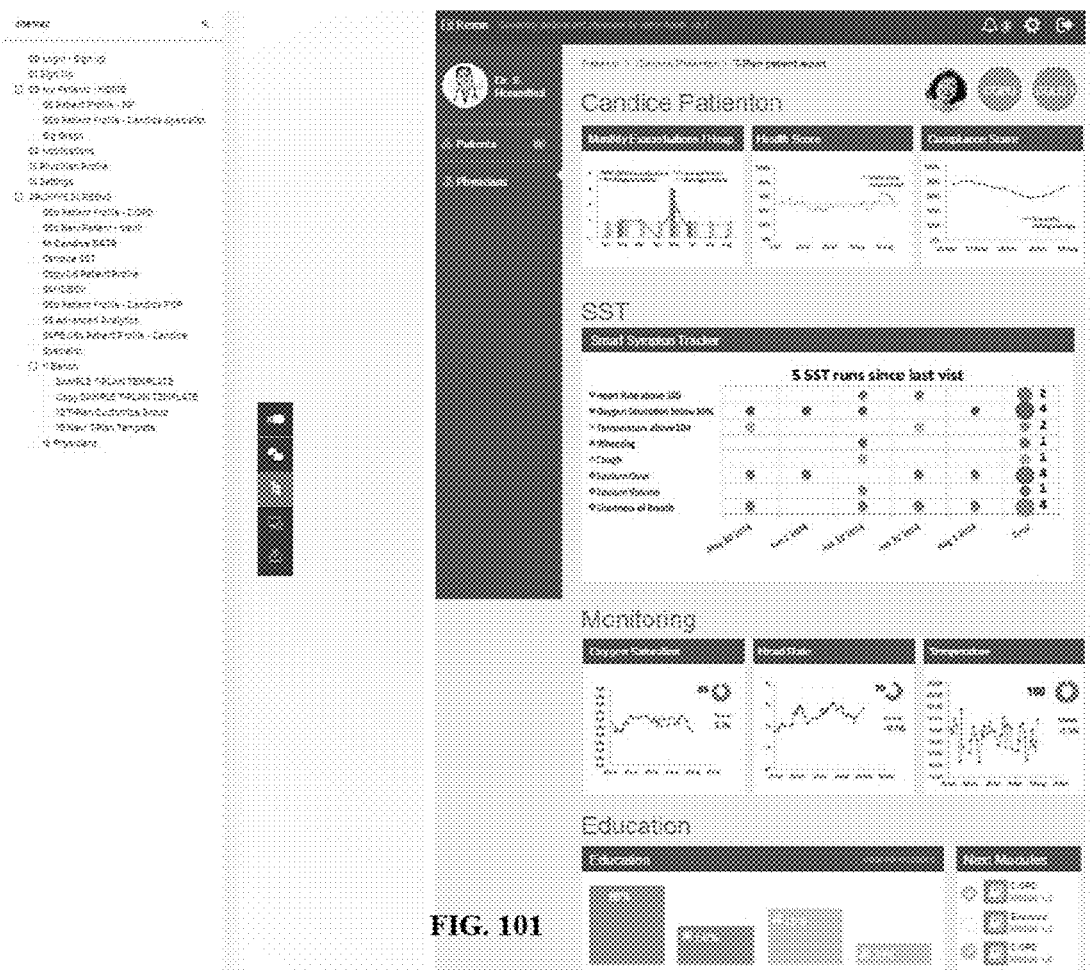
Figure 102:
Figure 103:
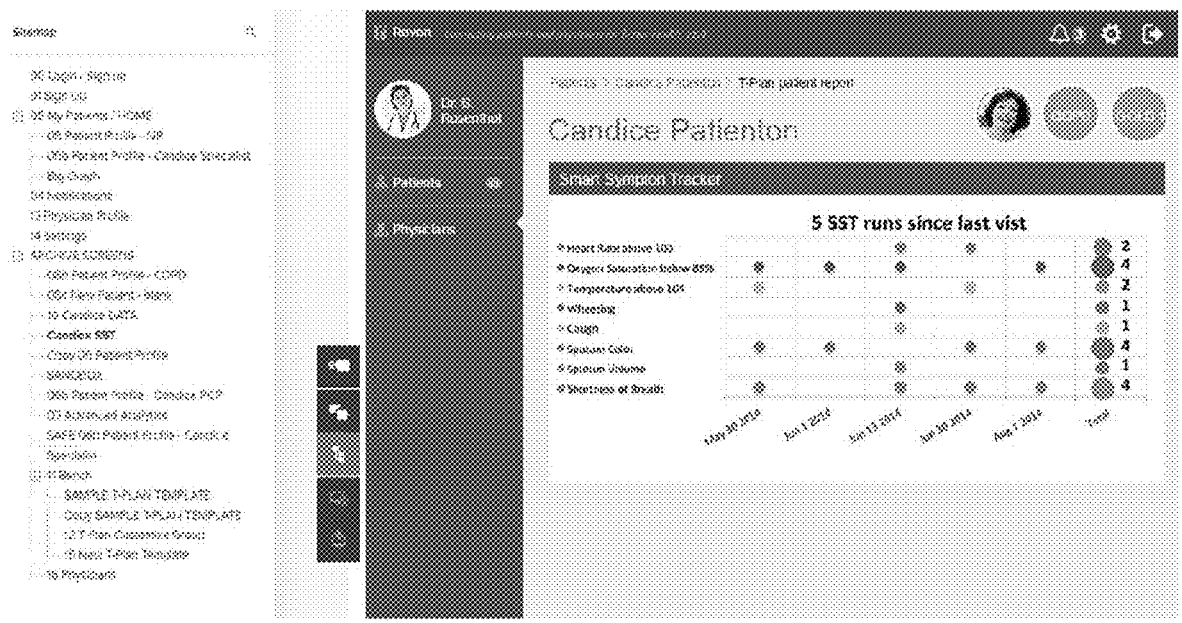
Figure 104:
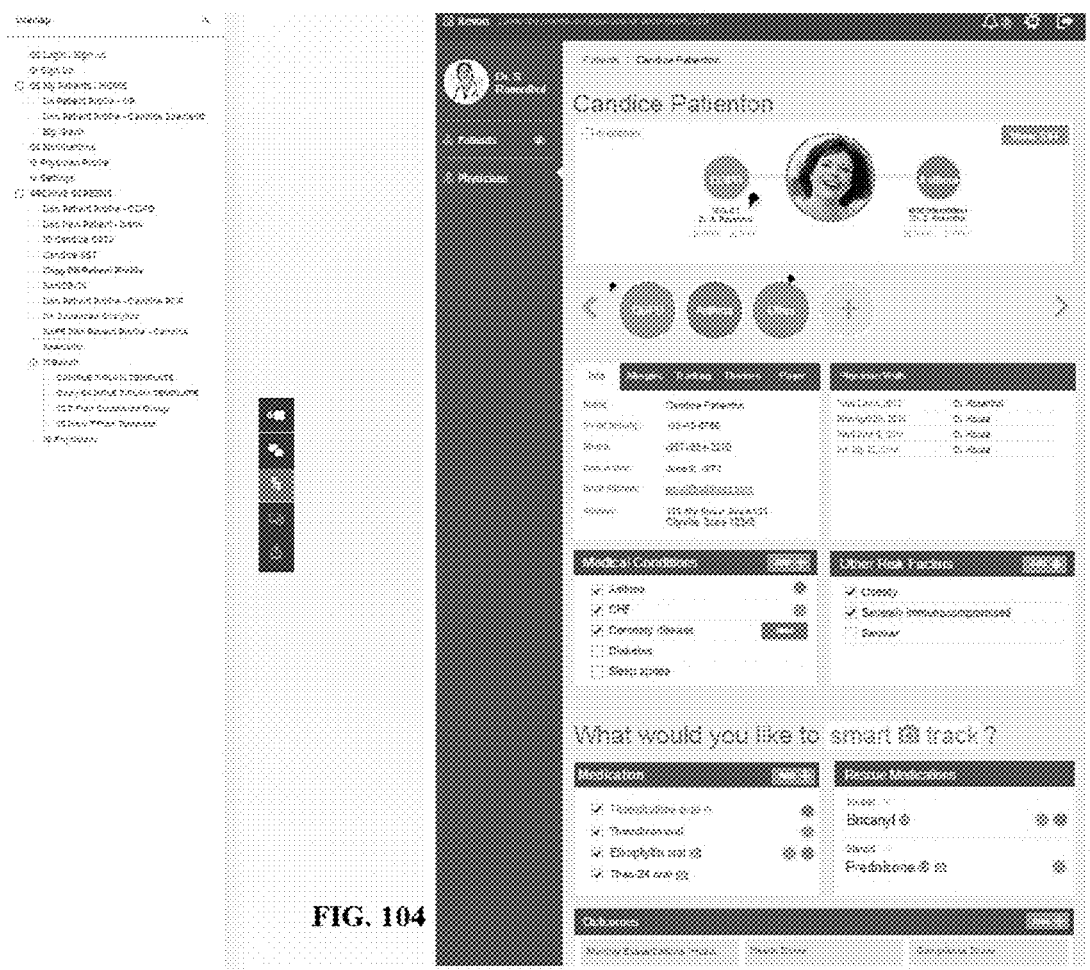
Figure 105:
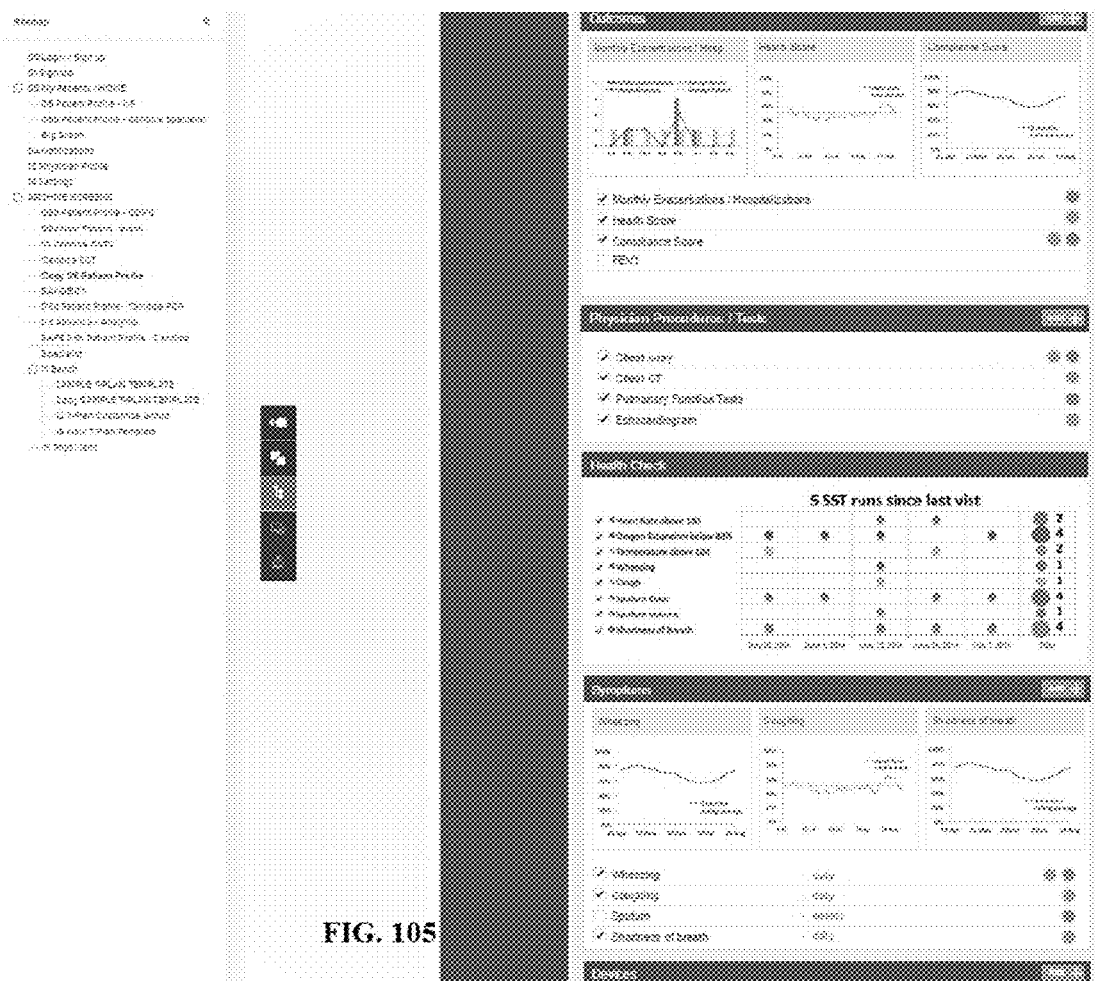
Figure 106:
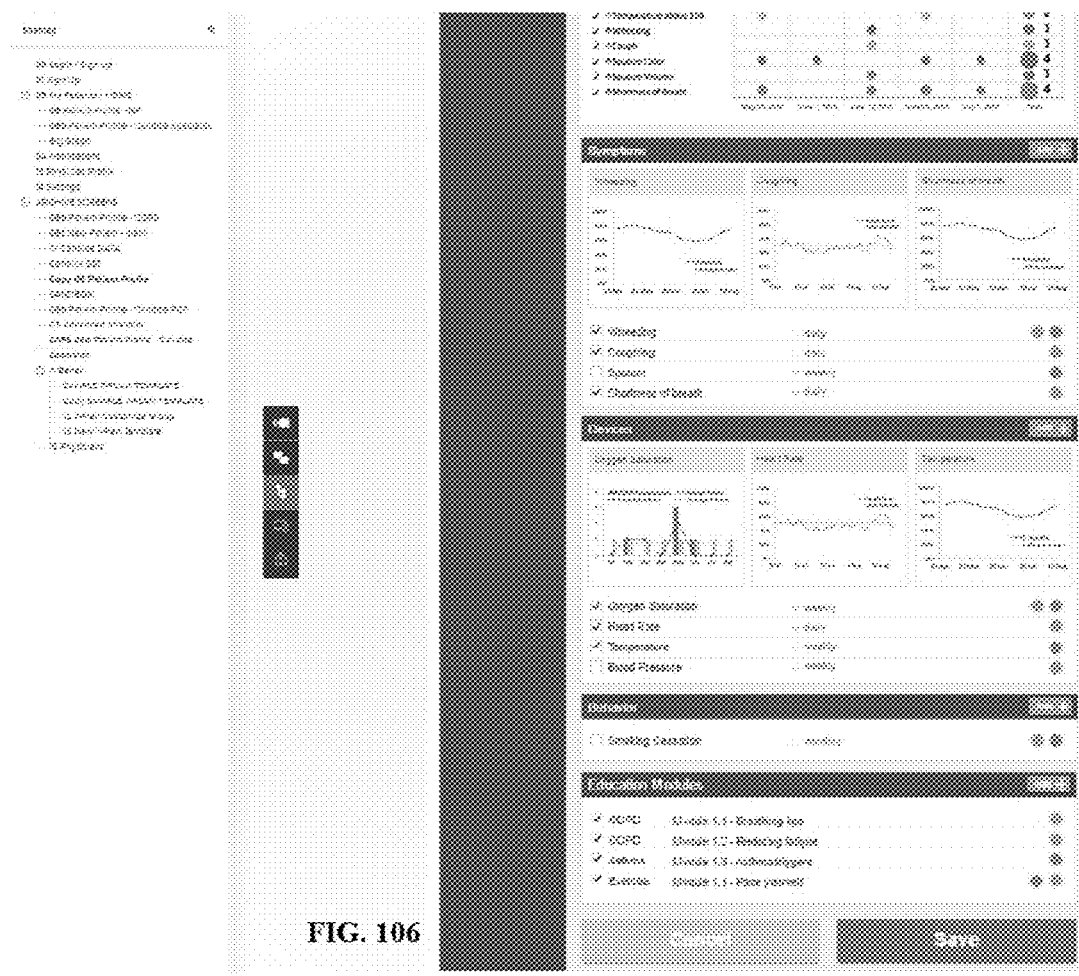
Figure 107:
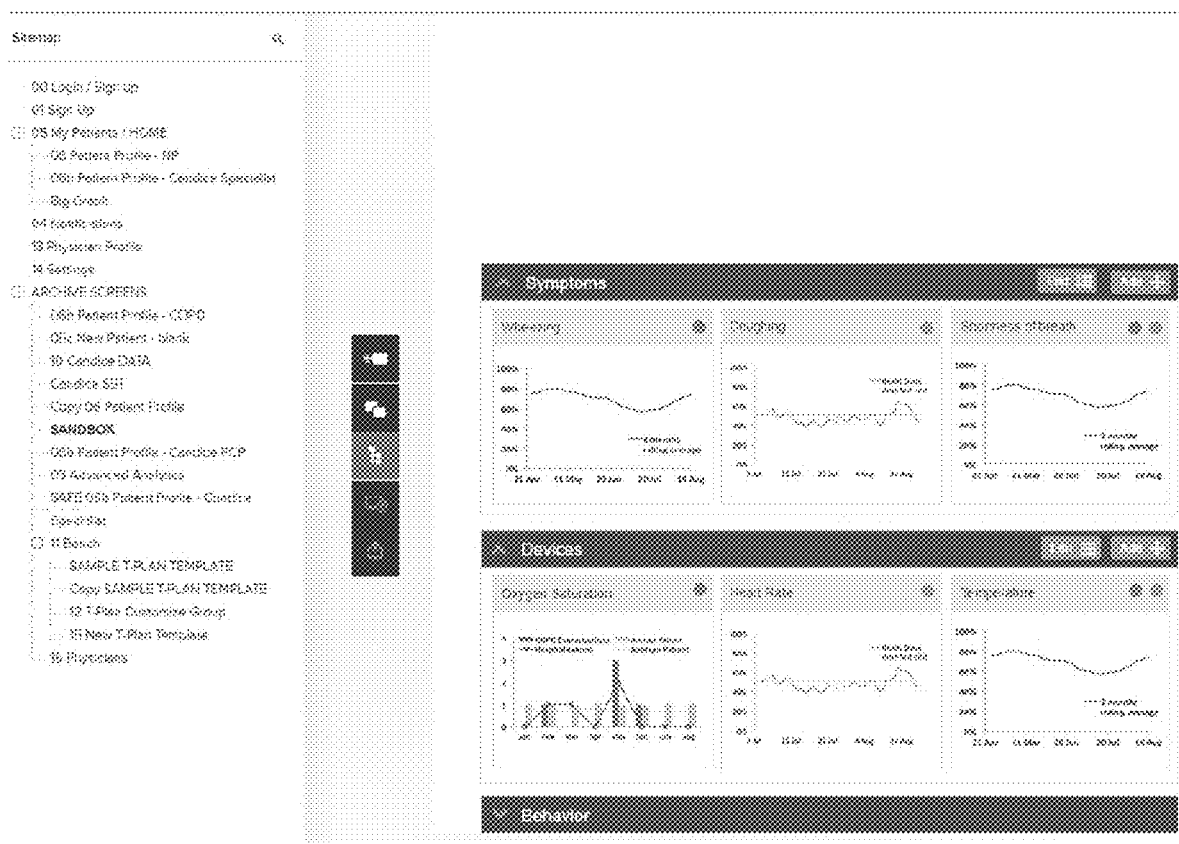
Figure 108:
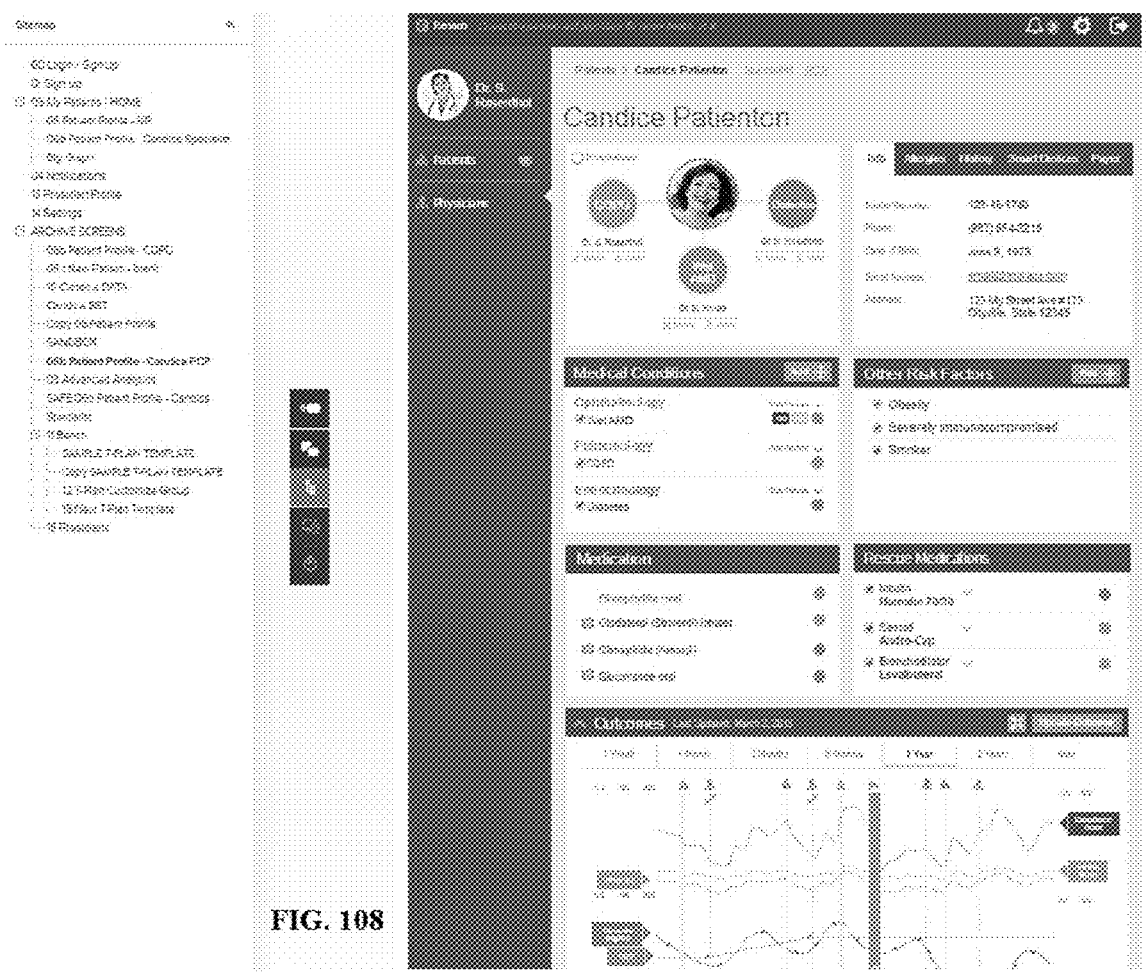
Figure 109:
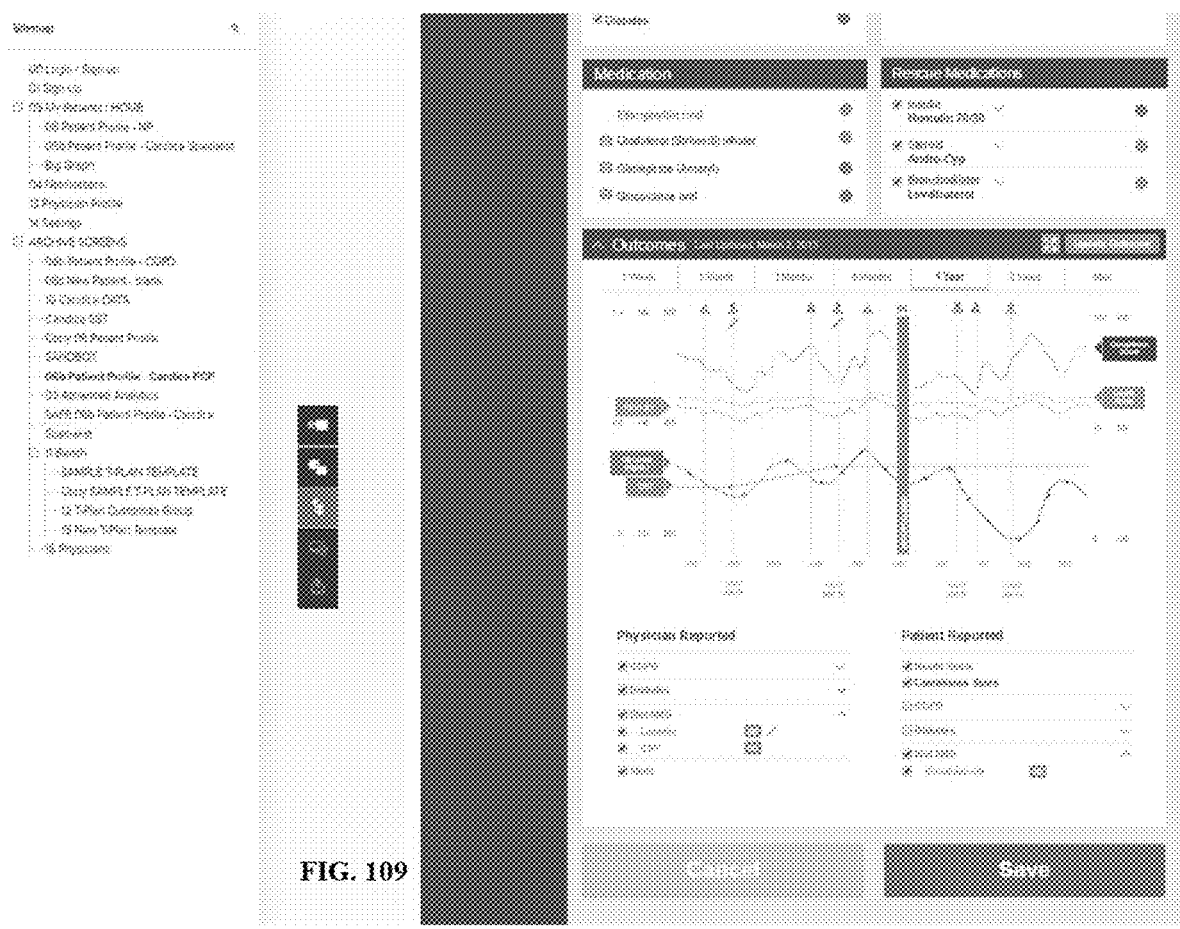
Figure 110:
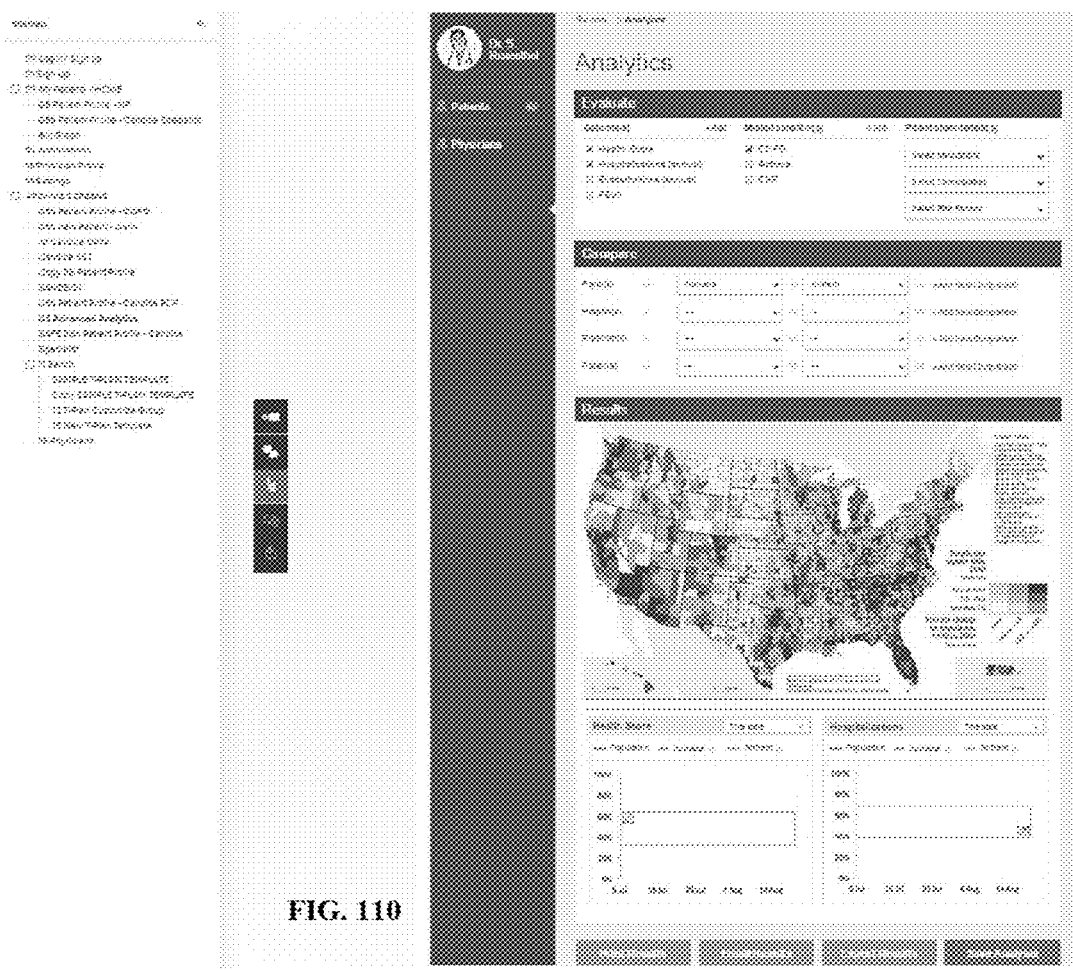
Figure 111:
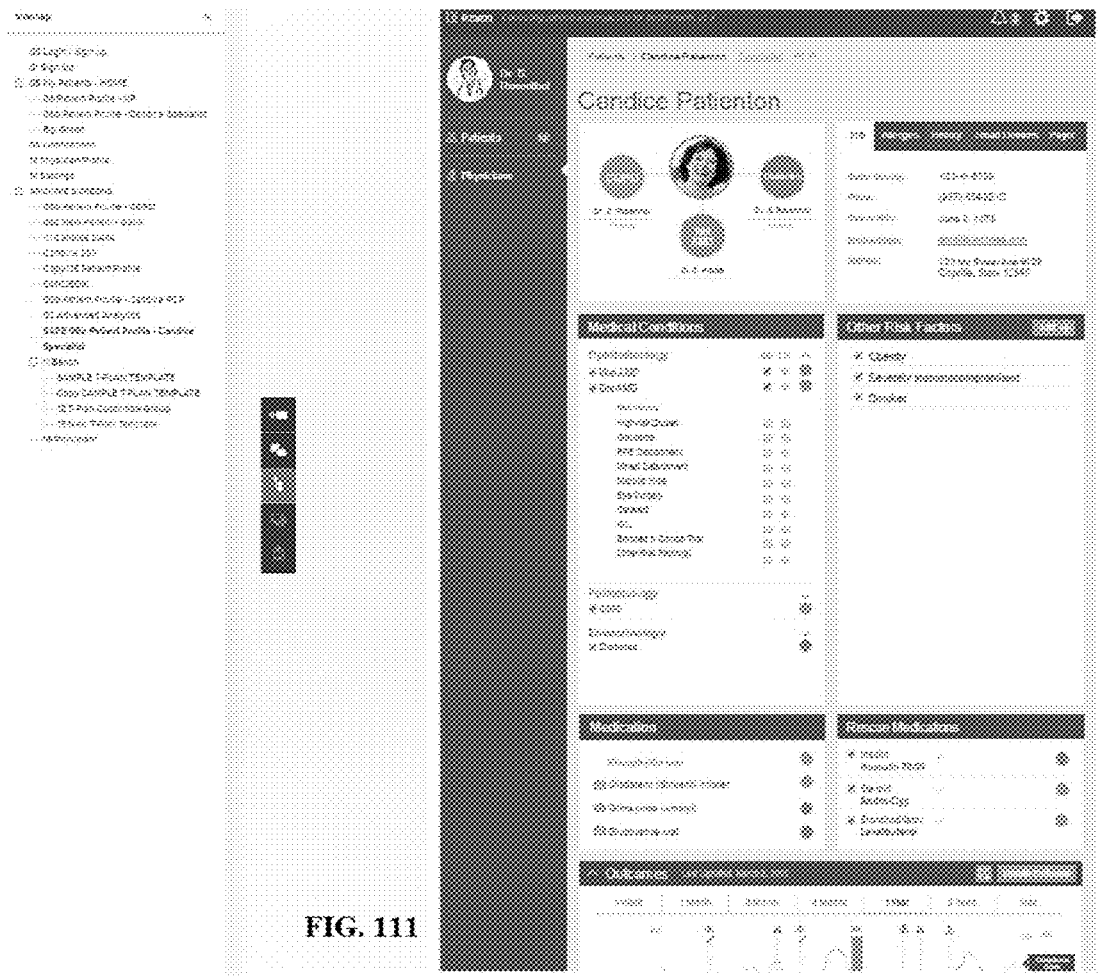
Figure 112:
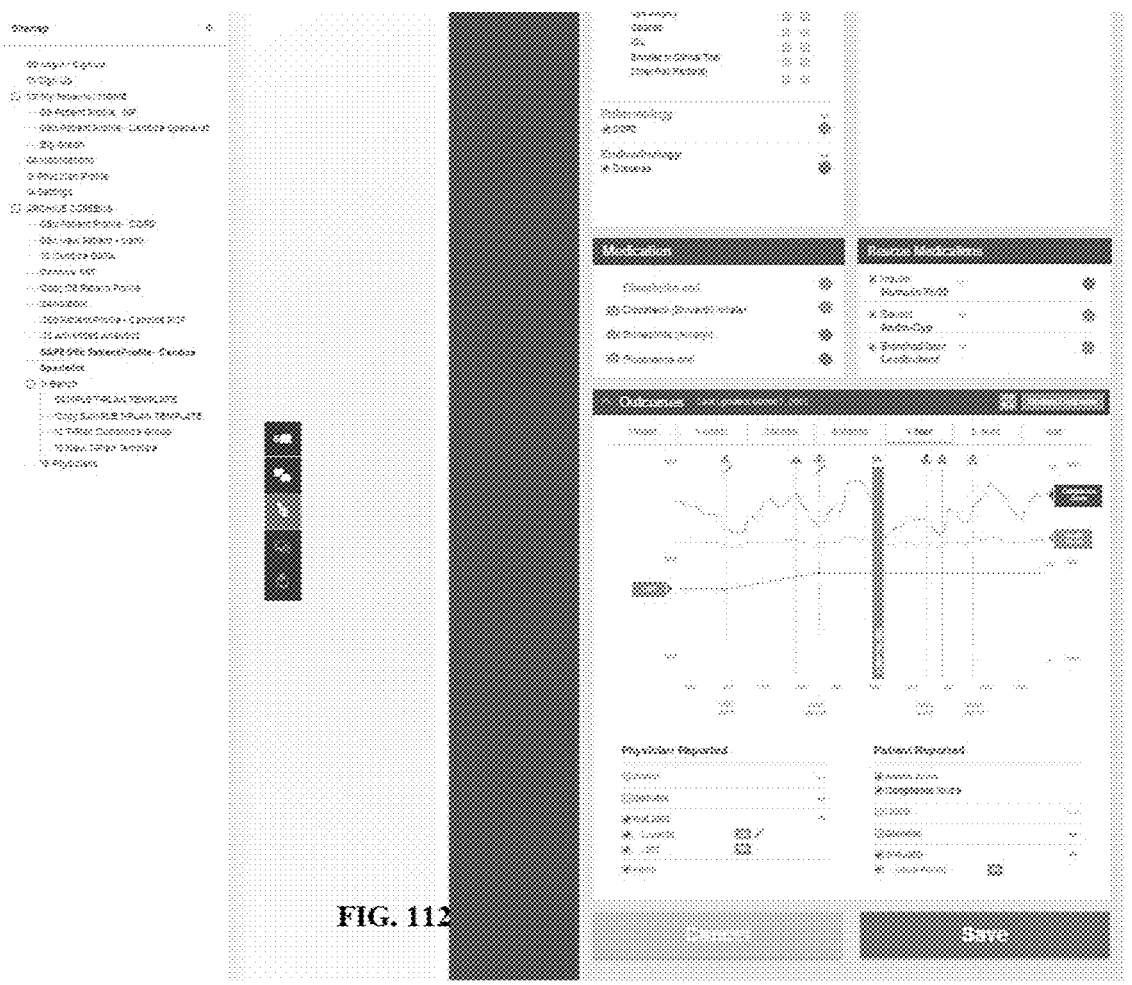
Figure 113:
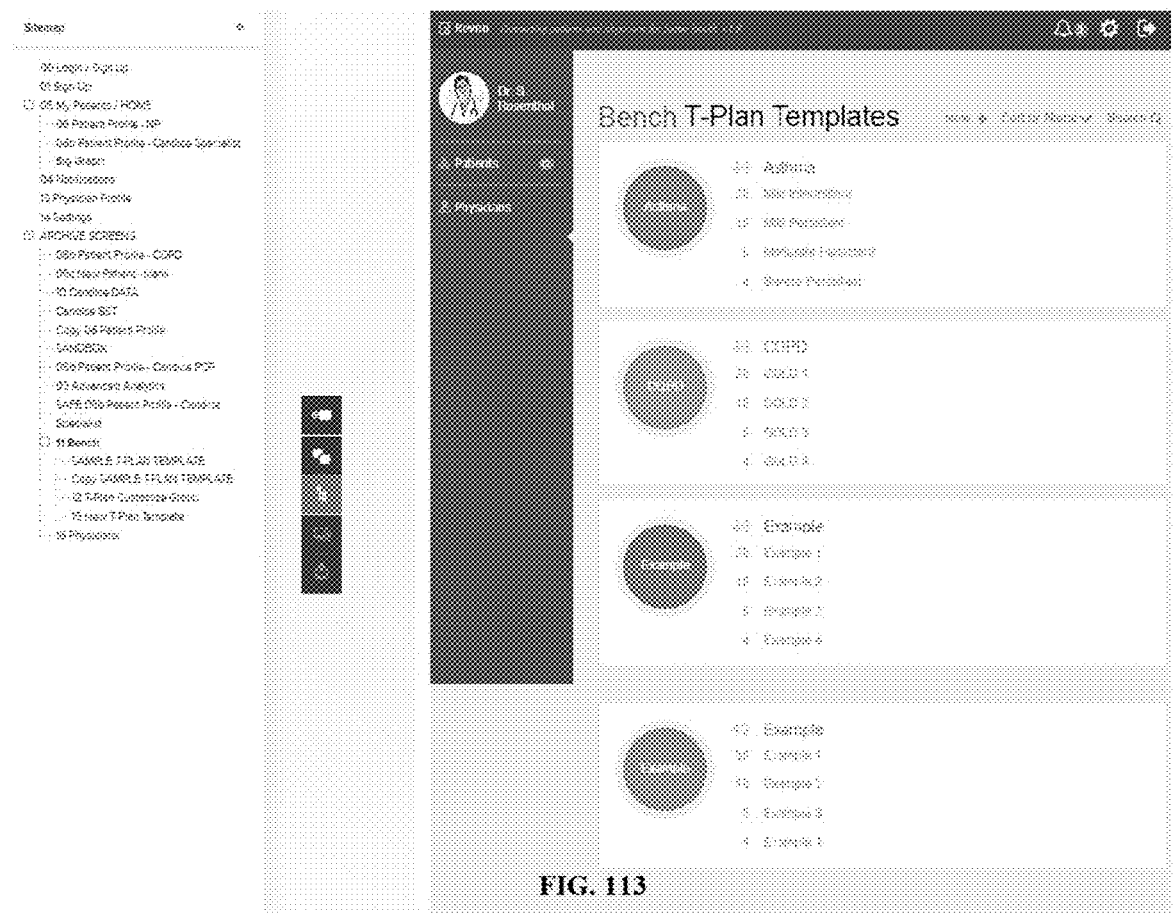
Figure 114:
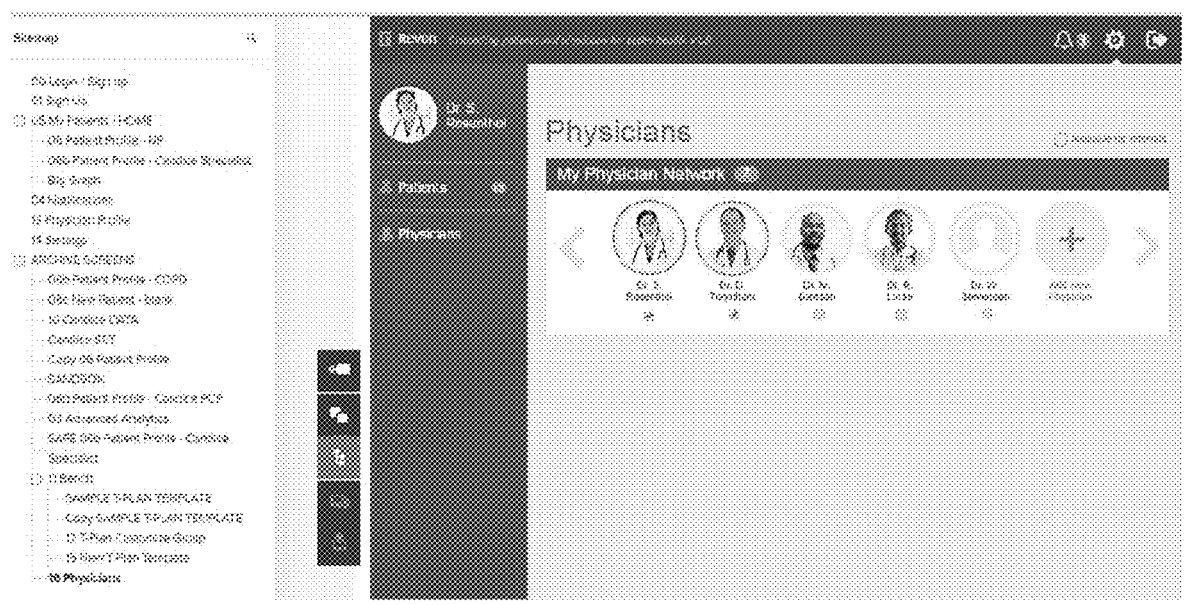

An illustration of these types of global instruction data structures and their interactions with the components of FIG. 5 in an implementation using the virtual SST (VSST) concept is provided in FIG. 14. In this context, an ACE 503 can operate by running the triage nodes first, looking at the PSO. SSTscore field and activating the appropriate instruction (or instructions, if multiple instructions are on at once). Next a VSST session node runs. If the VSST flag is off, then the node does nothing. If VSST is on (i.e., a VSST session is being run), and if there are questions left to be asked (in the AllQuestions[ ] array), then this node sends the next question to the ICE 507, to be asked. If there are no questions left to be asked, then this node does nothing (in some embodiments, there may be logic to short-circuit evaluation, by stopping a VSST session 'early.'). The AllQuestions[ ] array keeps track of which questions will be asked, and which questions were already asked (in this VSST session). Next a PSO node runs. In some embodiments, this node may be empty. Finally an instruction node runs. This node checks if a VSST is running. If not (the flag is off) and there are instructions in the global instructions list(s), this node combines those instructions into one string message and sends to the ICE 507 for immediate release to the patient. This node resolves conflicts also, though the nature of this conflict resolution may vary from case to case, and in some embodiment may only be that the highest priority triage instruction is the only one sent. An illustration of this sequence of events as various nodes are executed by the ACE 503 is provided in FIG. 15.

To further illustrate potential applications of the disclosed technology, consider how the technology disclosed in this application could be used to support various front end interfaces for providing a unitary view of a patient's health to both the patient and his or her physician(s). As shown in FIG. 5, such interfaces could be provided to a patient or physician through an application running on a mobile device controlled by the relevant patient or physician. However, as will be immediately apparent to those of ordinary skill in the art in light of this disclosure, an architecture such as shown in FIG. 5 could easily be adapted to interact via website based interfaces, either as an alternative to, or in addition to interfaces provided by a mobile application. For example, a patient portal (i.e., interface or connected set of interfaces) through which a patient could input his or her health information and/or receive instructions and information about his or her health could be supported equally well by components such as a PSO 501, SCE 502 and ACE 503 regardless of whether was presented via a mobile application such as the portal illustrated in FIGS. 16-43, or via a website in the manner of the portal illustrated in FIGS. 44-75. Similarly, website based physician portals such as shown in FIGS. 76-91 and 92-114 could easily be adapted to be provided via a physician mobile application rather than via a website.

Just as the architecture of FIG. 5 included various engines and data structures which performed specialized tasks to provide a unified view of patient information in a flexible and adaptable manner, portals such as the physician and patient portals referred to above could similarly be structured according to specialized modules which work together to provide a seamless experience for their respective users. As an example of this, consider a patient profile module, which could function as the primary mode of interaction of physicians with a web or application based portal. Such a patient profile could perform tasks such as allowing physicians to review details of a patient, make updates to patient data, and see outcomes reported by the patient and/or his or her other physicians. An example of such a patient profile is provided by FIGS. 118A and 118B, in which those figures each depict a partial profile which can be reconstructed by placing the bottom edge of FIG. 118A adjacent to the top edge of FIG. 118B.

In general, in embodiments where it is present, a patient profile will allow a physician to specify which medical condition(s) a patient has and will identify those medical conditions that a physician has already indicated that the patient has. The information can be presented in any of a variety of ways. An example of this is the flower schematic 11801 at the top left of FIG. 118A comprising a picture of the patient surrounded by circles (which, in practice, would generally be colored). Such a flower schematic 11801 will be populated with medical condition petals as the physician checks on medical conditions in the box below. Each medical condition petal would preferably be associated with a D-plan, which the physician could assign to a patient by clicking the conditions on/off in the Medical Conditions section 11802 of the patient profile. When a condition is checked the associated D-plan will be assigned to the patient and the flower will populate with the medical condition petal. When a condition is unchecked, the physician could be asked why he or she is switching it off, and a menu of explanatory options (e.g., passed-away, disease controlled, patient transferred, other) could be provided. Once a condition has been switched off (which, in some embodiments, might only happen after a physician confirms that switching it off is correct), the petal representing that condition could disappear. Other results, such as a patient being notified that a D-plan has been switched off next time he or she accesses his or her corresponding portal could also take place in some embodiments, though it may be possible for a patient whose D-plan has been turned off to indicate that he or she still wishes to continue receiving reminders regarding the condition and to engage in self-tracking despite the D-plan being removed. In addition to petals corresponding to conditions, a flower schematic 11801 could also provide information on a patient's state, as determined by a back end system (e.g., a system implemented according to the architecture of FIG. 5). Such information could be provided, for example, by circling the picture of the patient in a color corresponding to his or her condition (e.g., red=poor condition, or currently hospitalized, which information could also appear on an outcomes chart 11803).

A patient profile could also (or alternatively) potentially present information on a patient by means of a patient bio. Such a bio could comprise information provided by the patient and the physician, and will typically be viewable to the physician and patient at all times, except for the social security number which will likely be at least partly hidden for privacy reasons. The patient will provide basic demographic and contact information and, in some embodiments, a list of allergies, brief medical history, the list of medications he or she is using, smart devices they have, and/or payer information. In some embodiments, most of this information will be collected as part of the sign up process. To facilitate the provision (or updating) of this information, in some embodiments there may be a patient survey system via which Revon would send questions to the patients related to their health, answers to which would be added to the patient profiles. This approach may be used for any patient information, though will preferably be used to capture at least most of the information regarding allergies and the patient's health history. The basic patient information will typically include name, social security number, date of birth, phone number, email address, and mailing address. The email address, mailing address, phone number, or any combination thereof may be used for contacting the patient about clinical trial eligibility. In some embodiments, there may be a smart devices section which will display the cloud-connected devices the patient is using to measure their outcomes which the patient has connected to Revon. Payer information will typically consist of information about the insurance provider that the patient uses. The physician will provide a list of comorbidities (secondary medical conditions), a list of factors that leads to a higher risk of complications/exacerbations. Additionally, in some embodiments, the physician will provide the list of rescue medications the patient may need (at least for those conditions for which the physician has assigned a D-Plan to the patient). The patient will provide a list of regular medications he or she is using themselves. Elements of the patient bio provided by the patient can be edited at any time by the patient. Elements added by the physician can be edited by the physician. Whenever the patient makes changes to their history, they will typically need to confirm that the changes were intentional. The backend will preferably maintain an audit log of any changes.

Figure 118A:
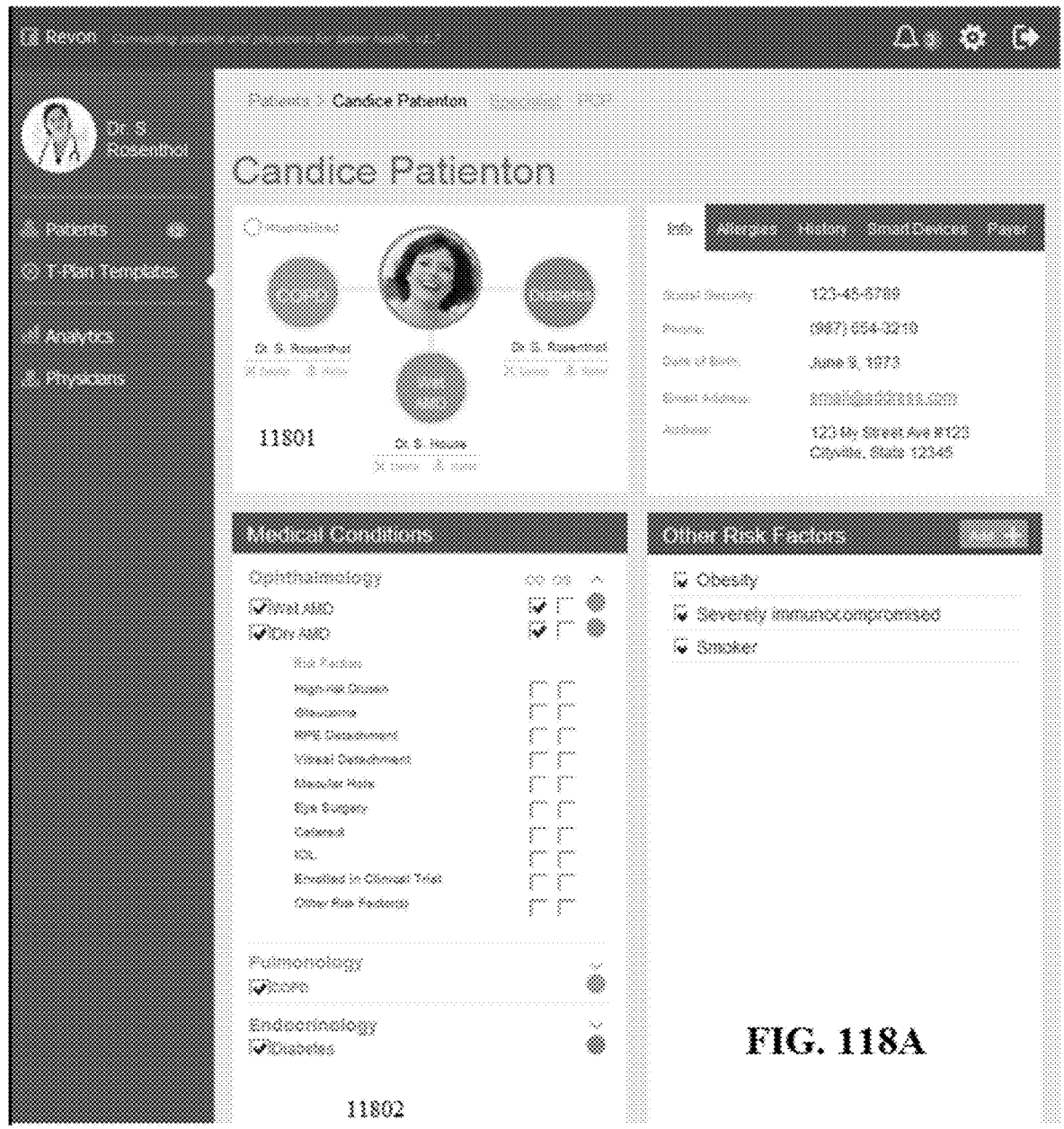
FIGS. 118A-118B illustrate an example of a patient profile.
Figure 118B:
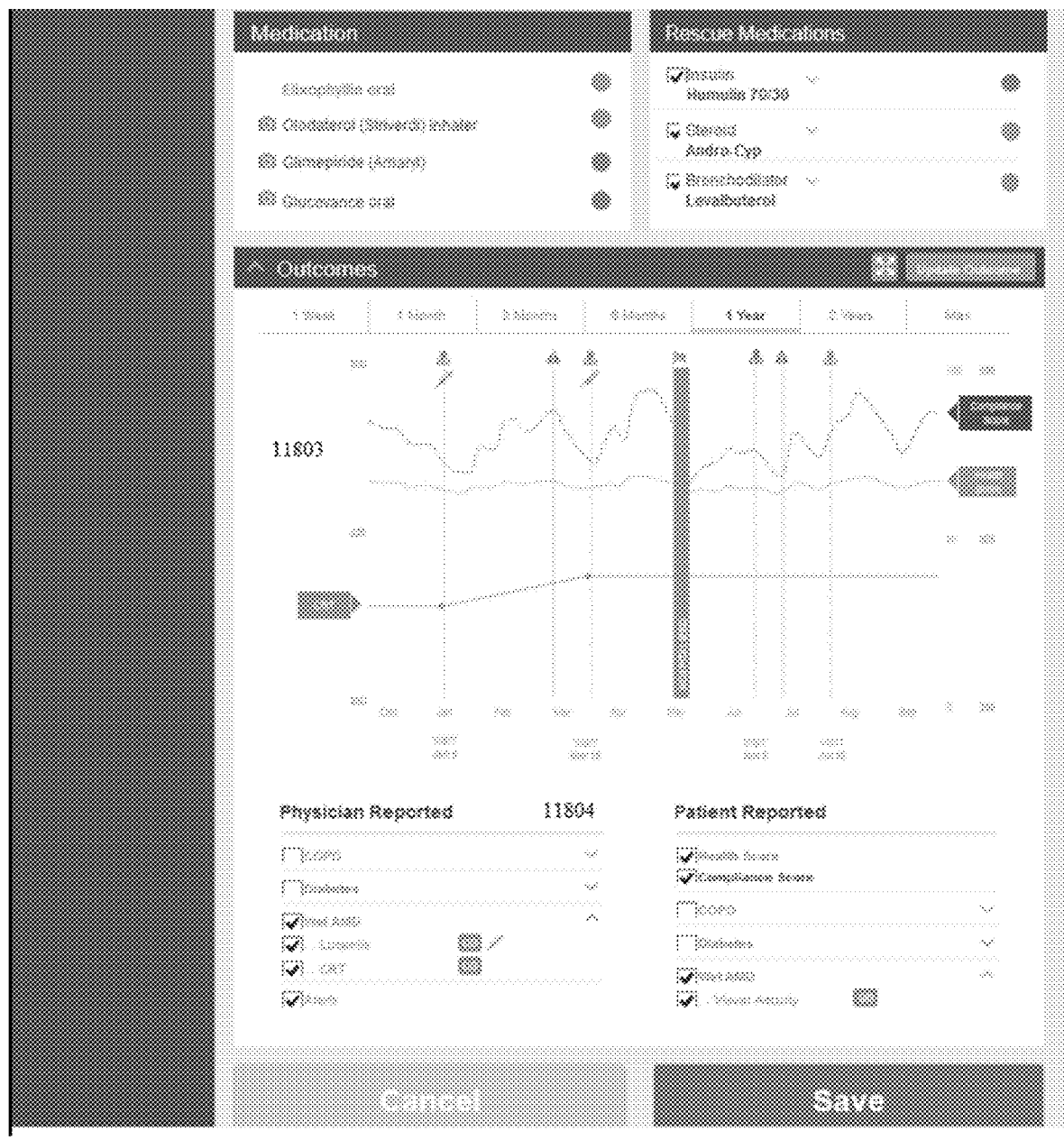
Figure 119:
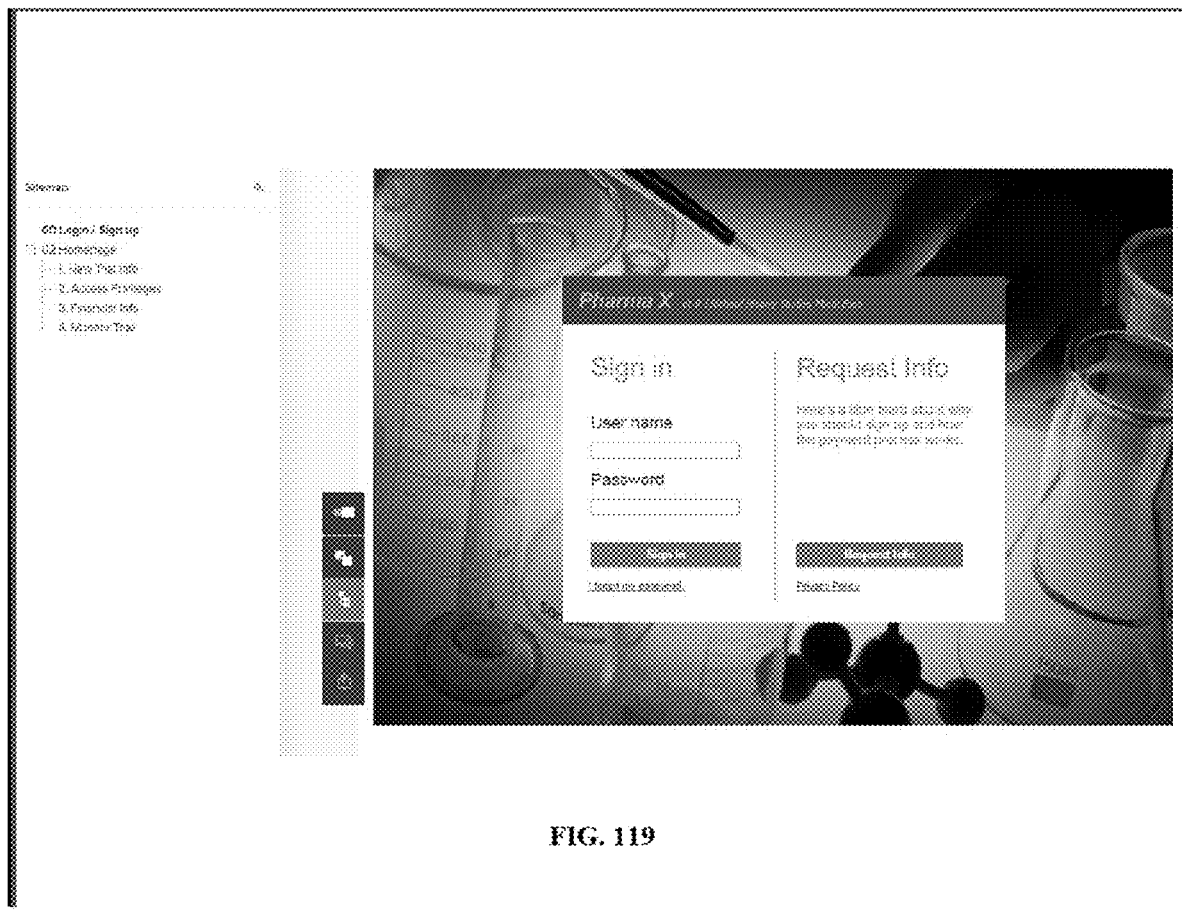
FIGS. 119-124 illustrate interfaces which could be presented in a pharma portal, with a map in the leftmost portion of the illustrations illustrating how the various interfaces relate to each other.
Figure 120:
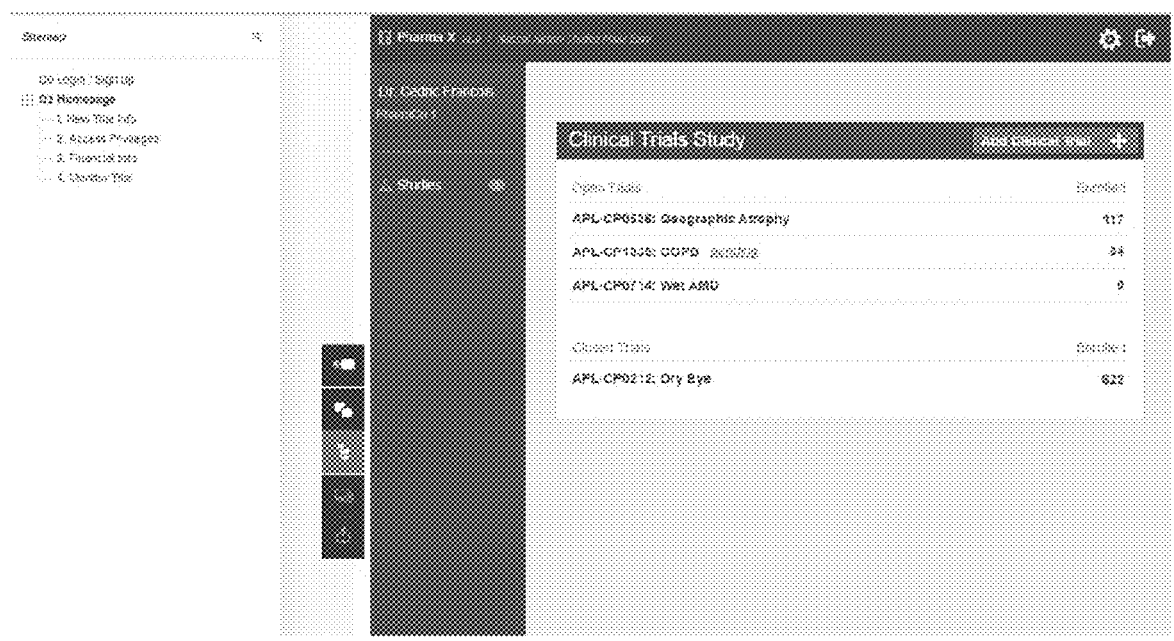
Figure 121:
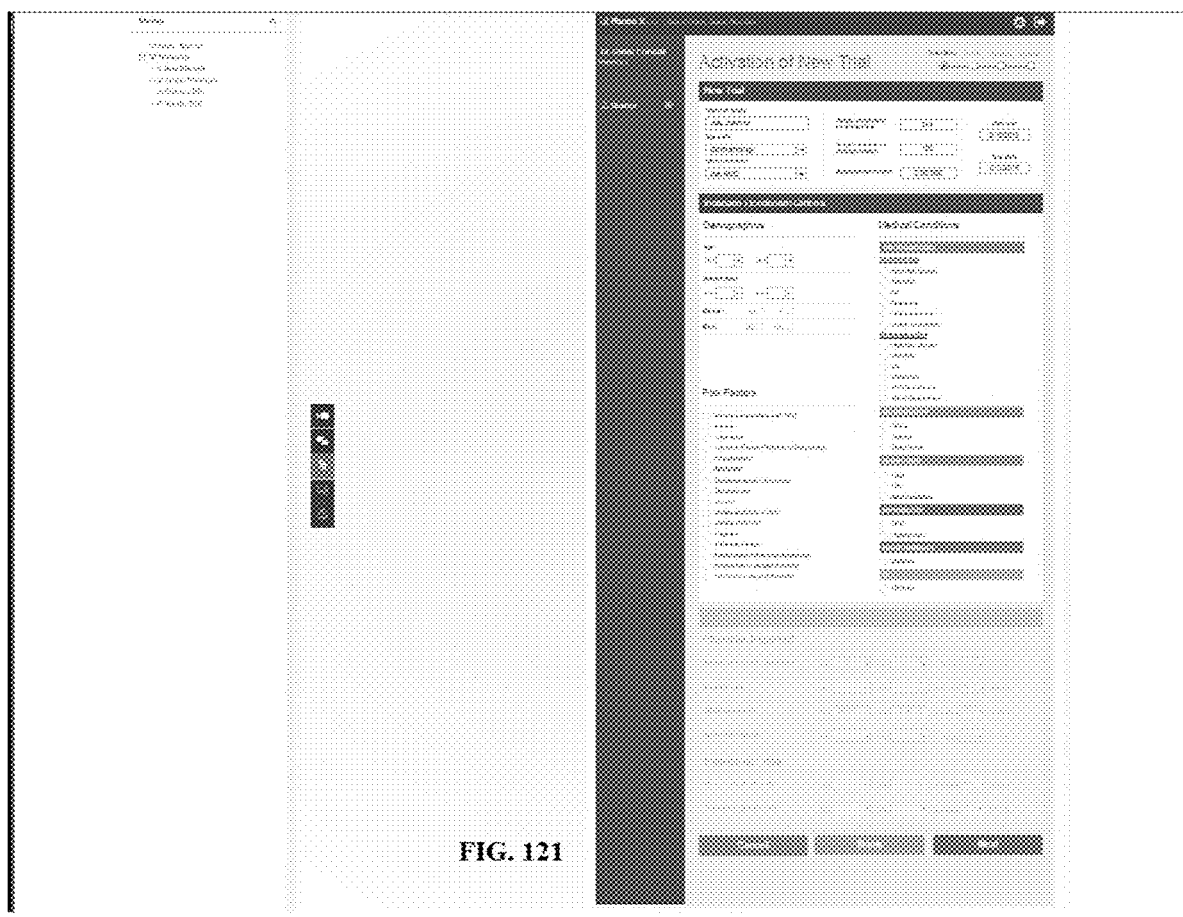
Figure 122:
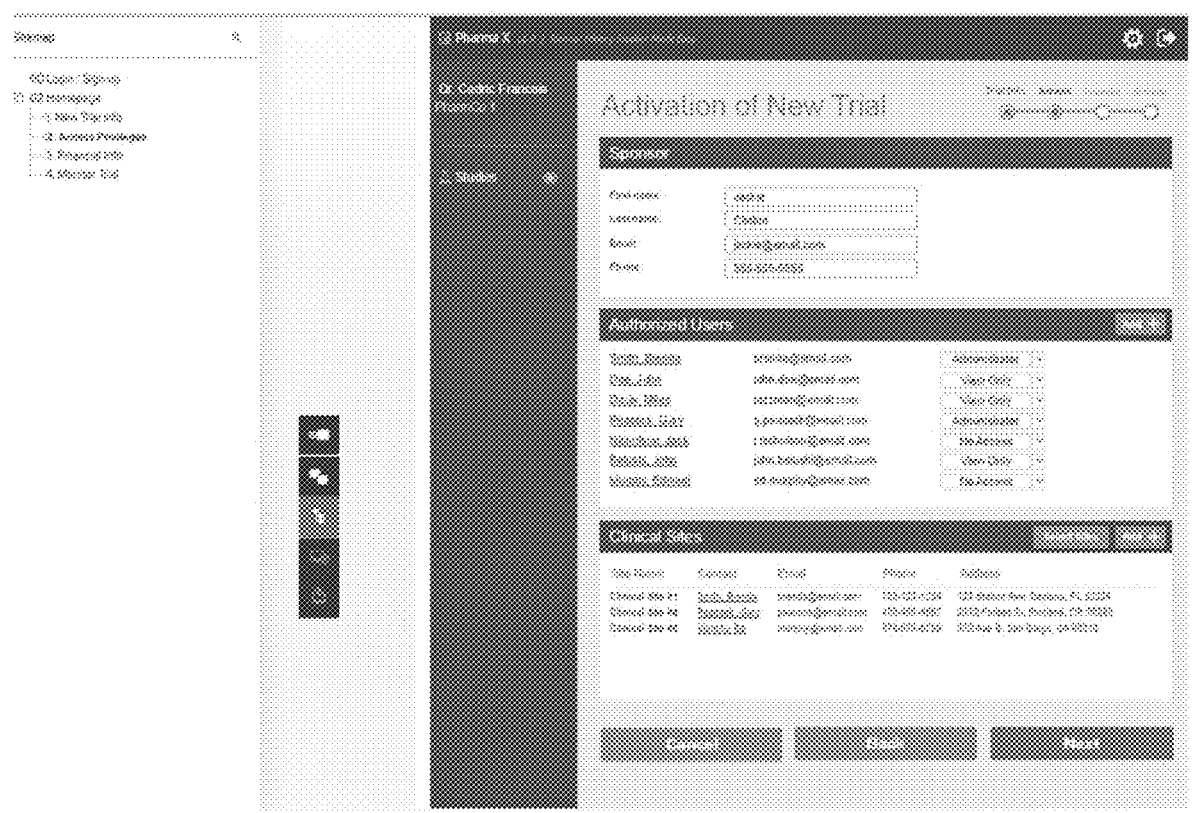
Figure 123:
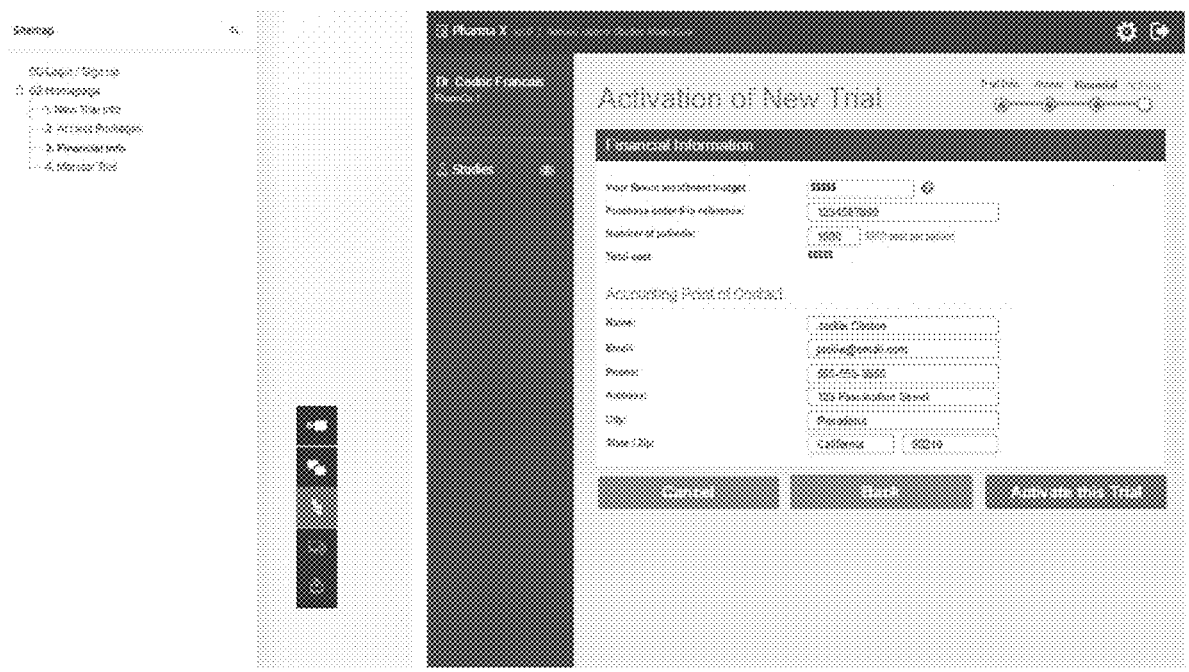
Figure 124:
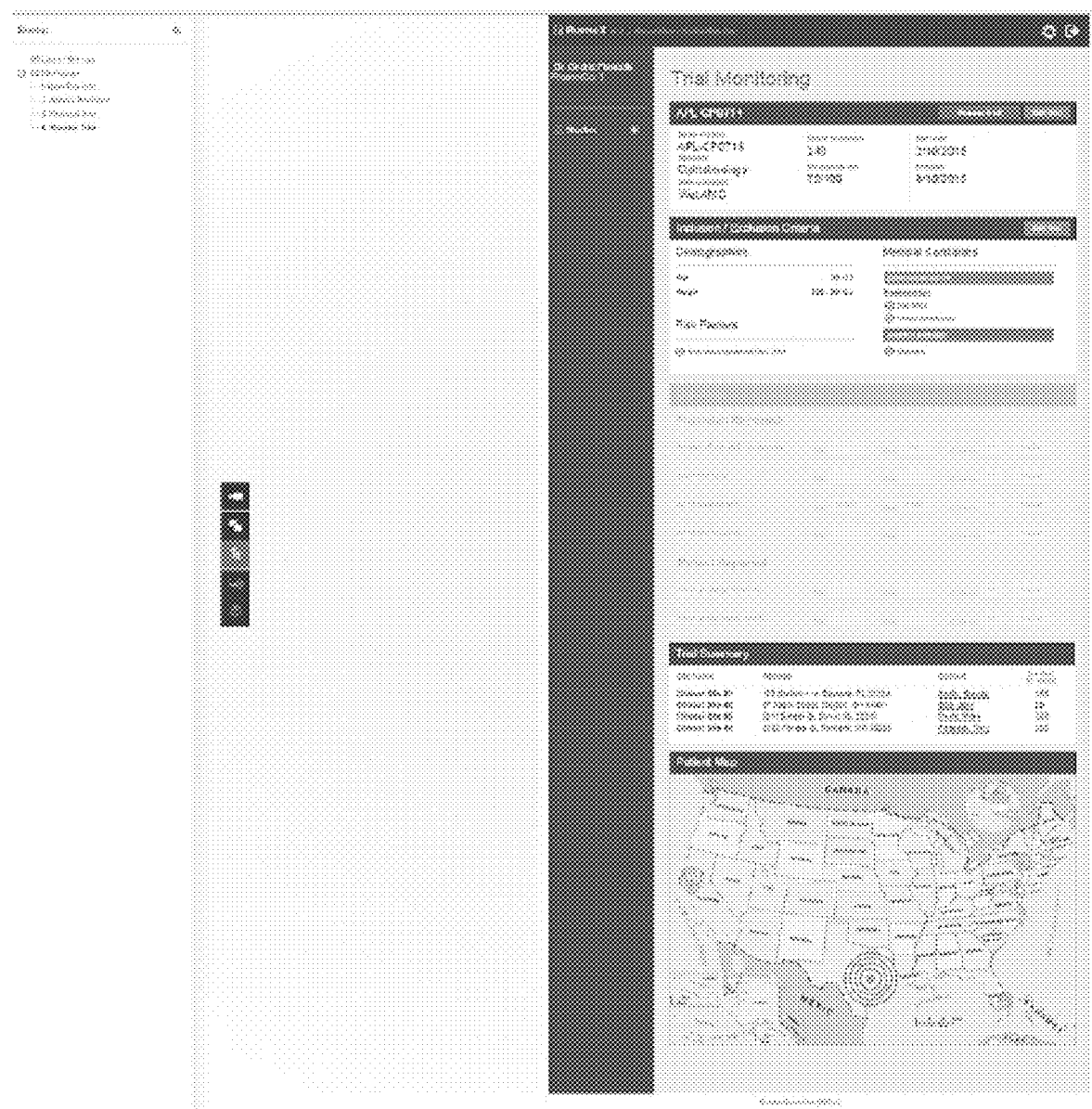
Figure 125:
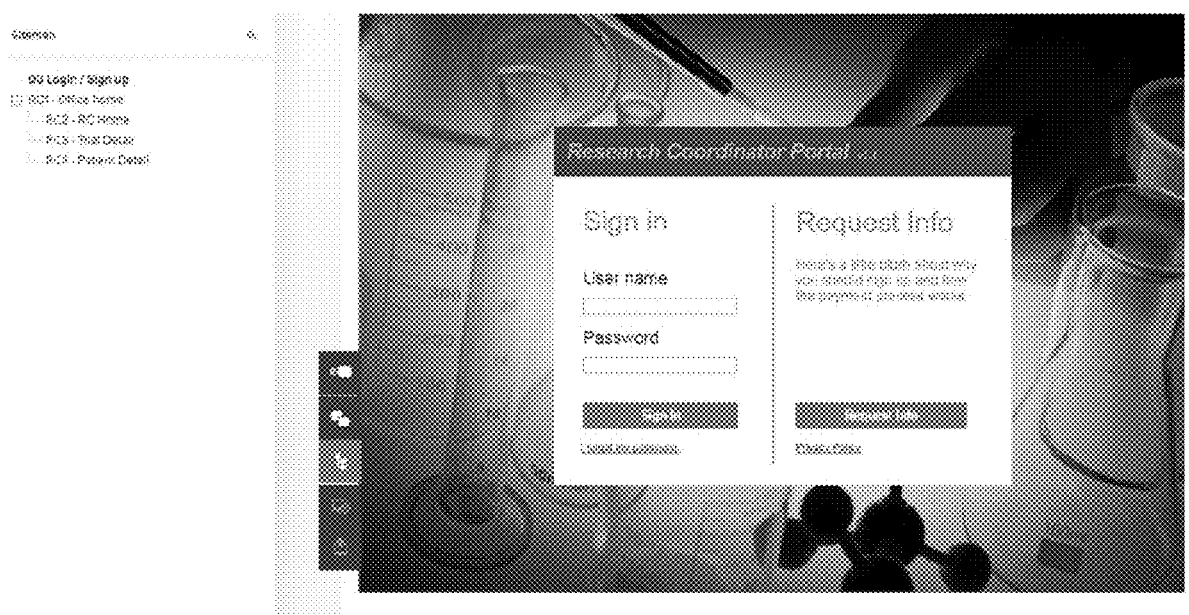
FIGS. 125-130 illustrate interfaces which could be presented in a research coordinator portal, with a map in the leftmost portion of the illustrations illustrating how the various interfaces relate to each other.

Another tool which can be used to provide information about a patient is an outcomes chart 11803 such as illustrated in the patient profile of FIGS. 118A and 118B. An outcomes chart may display one or more outcomes and, in some embodiments, may display one or more actions. Actions displayed on an outcomes chart 11803 will preferably include at least the following types of events—hospitalization (i.e., when a patient is admitted to a hospital, as recorded by the patient or indicated by some other data source), SST execution (i.e., when a patient is recorded as having run an SST module, or engaged in a virtual SST session), and physician intervention (i.e., when the patient meets a physician), and the chart will preferably be updated when either a patient or physician provides new outcomes data so that it will always reflect the latest data regarding the patient. When being displayed in an outcomes chart 11803, data will preferably be displayed in chronological order, and a back end system supporting the display of such an outcomes chart 11803 will preferably record data with timestamps to facilitate this. An interface presenting an outcomes chart 11803 may use REST api calls to fetch the data for populating the chart. However, it is also possible that the disclosed technology could be implemented to use a call which is refined to return data optimized for graphing in a browser client (e.g., preprocess data points server-side to smooth lines instead of implementing necessary data processing in javascript in the browser).

Features that an outcomes chart 11803 may provide in various embodiments may include one or more of the features described in this paragraph. One feature that an outcomes chart 11803 may provide is timescale options, which could be provided at the top of the chart under the title bar. Using such a feature, a user can select one of the options and based on which option is selected, the chart will zoom-in or zoom-out. If '1 Month' is selected, one month of data will be displayed on the chart. If the '6 Month' is selected, six months of data will be displayed on the chart. If 'Max' is selected, all data available for the patient will be displayed on the chart. If time period selected is longer than period for which data is available, autoset to max (which will display all data available for patient, with corresponding x-axis time lines, which will be less than manually selected time period). Conditions may be color coded, and outcomes and events associated with a particular condition may be displayed in the color associated with that condition. Additionally, events may be displayed with icons on vertical lines representing individual event types. Icons which may be displayed in some embodiments include physician outlines (indicates a physician intervention), exclamation in triangle (indicates an SST activation), bed (indicates a hospitalization) and syringe (indicates an intervention by a physician involving administration of some procedure/test/drug).

An outcomes chart 11803 may provide multiple ways of displaying outcomes. For example, outcomes could be displayed in the form of smooth line graphs (this approach will generally be treated as appropriate for most patient reported outcomes), straight lines (this can be applied to outcomes that are reported infrequently, which will generally be the case for physician reported outcomes), vertical lines with icons (this will generally be associated with events, such as hospitalizations, physician interventions, and SST activations), and horizontal lines with binary dots indicating the placement of an outcome on a predetermined scale (which may be used for outcomes with yes/no responses or graded responses such as yes/no/moderate/severe). Additionally, an outcomes chart 11803 may provide a user with a zoom in tool which, when activated, will cause the outcomes chart 11803 to be displayed in a new window rather than as part of the existing window of the patient profile.

An outcomes chart 11803 may also provide an easy way for a user to obtain more detail on information provided by the outcomes chart 11803 itself. For example, when outcomes are displayed as dots on an outcomes chart 11803, the interface in which they are displayed may be configured such that, when a user mouses over or otherwise selects a particular dot, additional information about the associated outcome will be provided. Similarly, when a user hovers his or her mouse over a line in an outcomes chart 11803 at a location within a specified radius of an outcome, the coordinates of the nearest datapoint on that line may be displayed. Otherwise, if no datapoints on the line are within the max radius, no line datapoints would be displayed. Additionally, in embodiments which display icons such as described previously in association with events, selecting those icons could result in further relevant data being provided. For example, when a user clicks on an SST icon, a popup may display and show data from the SST (e.g., questions asked, answers given and final recommendation). Similarly, when a user clicks on a physician icon a popup may display showing physician name, date of meeting and any actions by physician (outcomes entered by physician). When a user clicks on a hospitalization icon, a popup may be displayed showing which hospital, at what date, patient was admitted to. In some embodiments, additional information relevant to the hospitalization, e.g., admission diagnosis, discharge diagnosis, discharge date, discharge summary (or links to any of the foregoing), may be provided. It should be understood that similar information regarding patient admission to other health care facilities such as a skilled nursing facility or rehabilitation facility, etc., could be provided. Such events may have their own distinct icon associated with them for display on an outcomes chart. Similarly, a user may be enabled to add additional outcomes via a legend 11804 (discussed in more detail infra). When an additional outcome is selected, a new line displays on the chart. Additionally, an additional axis should display on the chart, related to the newly added outcome. Axes related to physician reported outcomes may all be displayed on the same side of the chart, while axes related to patient reported outcomes may be displayed on the other side of the chart. For example, in some embodiments, for all physician reported outcomes, axes will display on the left, and for all patient reported outcomes, axes will display on right. In general, multiple axes will be displayed on each side, as multiple outcomes can be displayed in parallel. To help distinguish them, each condition may have a color associated with it, so each outcome of that condition also has a color linked to it. The line on the graph, and its axis will also have the same color. Different outcomes under same condition may use different shades of the same color as the condition.

Just as an outcomes chart 11803 may provide an easy way for a user to obtain more data, in some implementations an outcomes chart 11803 may display less than all available data for a particular patient. As an example, some implementations could include a tool such as the legend 11804 illustrated in FIG. 118B which organizes various measures by the condition to which they correspond and then by whether they are patient reported or physician reported. With a legend 11804 such as shown in FIG. 118B, the user can select which of these measures to display on the screen and which ones not, by clicking the checkboxes next to each, on or off. The user can also select the checkboxes next to individual conditions. When such a checkbox is turned on, all 'default' outcomes related to that condition will be displayed. Each condition will have some default outcomes associated with it. So if a condition has 4 possible outcomes that can be displayed, 2 of those may be default outcomes. For another condition with 5 possible outcomes, there may be only 1 default outcome. Additionally, the user may be able to hide/reveal outcomes available under a condition by clicking a chevron icon displayed in the interface. Similarly, user may also be able to switch on and off a health and compliance score by clicking on a checkbox for such a score in a legend in the same manner described previously for conditions and measurements. Finally, if a physician selects a certain group of outcomes to display for a patient, and then closes that patient file, the next time the physician loads that patient's outcomes chart, he or she should be presented with the same set of outcomes that he or she selected previously. This can be supported by a back end system which keeps a record of the last selected outcomes for a given physician-patient pair.

Limits on the data displayed on an outcomes chart 11803 may also be determined automatically, or by default, rather than being set by a user. For example, in some embodiments, only two physician reported outcomes and three patient reported outcomes (including health score and compliance score) will be displayed on an outcomes chart 11803 by default, with the specific outcomes displayed determined by their importance rankings (discussed in more detail infra). Additionally, in some embodiments, there may be a maximum number of outcomes which may be displayed on a chart. For example, the disclosed technology could be implemented to only allow display of a maximum of {5} physician reported outcomes and {5} patient reported outcomes on the chart at a time. In such a case, when the maximum is reached, all other possible selections will preferably be disabled (e.g., greyed out). If the physician wants to see more, he or she will have to switch one off before switching another on.

As mentioned previously, in addition to providing information about a patient (e.g., via an outcomes chart 11803), a patient profile might also allow the entry of additional information about a patient. An example of a tool which could be used for this purpose in the exemplary patient profile illustrated in FIGS. 118A and 118B is the medical conditions section 11802. Using the medical conditions section 11802, a physician can indicate which conditions (and therefore associated D-Plans) should be associated with the patient, and preferably will also be able to provide additional information related to a condition's D-plan. For instance, in case of Ophthalmology, a physician will preferably be able to specify which eye (OS/OD) a condition relates to. Similar deep specifications may be possible for any or all other diseases tracked by the system. To support this, the back end will preferably allow for up to 2 levels of specification such that each top level medical condition can have 2 additional associated terms which conceptually narrow the scope of the condition. For example, for COPD preferably it will be possible to additionally specify GOLD stage and can also add MMRC scale. Additionally, in some embodiments, there may be features focused on condition specific risk factors. For example, a physician may be able to add condition specific risk factors by clicking a "Risk Factors" dropdown menu and making selections there. Access to condition specific risk factors is typically controlled by ownership. The physician who has ownership of a given D-plan can edit the condition specific risk factors for that medical condition. This means, the physician who adds a medical condition (D-plan) can also edit the risk factors for that condition.

For an empty (e.g., newly created) patient profile, a medical conditions section 11802 may show all available conditions in the system. For an existing patient, it will only show ones which have been checked on by prior physician. If physician wants to add more, he or she can click the Add+ button available in the existing patient view. In some embodiments, in addition to, or as an alternative to, a condition specific risk factor feature as described above, for each specialty, there may be a list of associated Risk Factors. Such a list, rather than being linked to a disease, may be linked to a specialty. A physician profile may be configured to display a List of Risk Factors by default for the specialty of the using physician. For example, if an Ophthalmologist is logged in, the ophtha risk factors should show by default. If Pulmonologist is logged in, then pulmo risk factors should show by default. Risk factors for other specialties (outside the current physician's area) will preferably not be shown. However, if the user is a primary care provider, he or she preferably will be able to see risk factors for any specialty. As another alternative (or additional feature), there may also be a list of universal risk factors that are common across all patients. Where such a list is present, any physician will preferably be able to edit these risk factors for a patient in their care. Data from here could be used to determine current patient state in the PSO 501 and/or SST engines. For new patient (empty profile), this section will preferably show all available risk factors. For existing patients, it will only show switched-on risk factors. The physician can add additional risk factors for existing patients by clicking the Add+ button.

In addition to, or as an alternative to, condition and risk factor information such as described above, in some embodiments, a patient profile might also allow a user to provide information on medications. For example, in some embodiments, a physician may be provided with a tool to enable him or her to manually enter a rescue medication list which will be associated with an SST for a condition. Rescue meds will preferably have a two level specification: Category/type and specific brand. However, some implementations may only present the type of rescue med (e.g., steroid, bronchodilator, etc) without specifying a specific brand. In some embodiments where it is present, this feature may be implemented to allow specification at both levels—physicians can first select the medication TYPE (steroid, Insulin etc.) and then within the category they can select a specific BRAND. Both the list of rescue medication TYPEs and BRANDs will be provided from the seed data file. Preferably, such embodiments will allow for physicians to select and edit from this list. It should be noted that, in some implementations, rescue medication information entered by a physician may also be made available to a patient, though when being accessed by a patient this information may be presented in a read only form, and may not be editable.

Just as a patient profile could allow entry of information, a patient profile will preferably provide some validation of that information as well. For example, if a physician adds an impossible combination of conditions and/or risk factors, such as male and pregnant, or underweight and BMI>30, a popup message could be provided saying that the combination of elements is impossible and requesting that an appropriate change be made. Other validation and error correction features, including error correction such as described subsequently in the context of outcomes capture, could also be incorporated into a patient profile in addition to basic incompatibility detection as described above.

To provide a concrete illustration of the role a patient profile may play in practice, consider the following description of how a physician could use enroll a new patient, and thereby create a new profile for his or her. In this process, first, the physician could click on a +Add New Patient button or similar control. This would result in him or her being provided with a text box into which the physician could enter the patient's email address and click an "Add" button or similar control when the information is provided. After the profile is provided, the physician could select the patient's Medical Conditions from a displayed list to add D-Plans in the backend. This will make new 'petals' appear in the flower section. Additionally, the physician can select any medical condition specification like OD/OS. The physician can also click on the disease specific Risk Factor upside down caret icon next to medical conditions, select the patient's disease specific Risk Factors by checking the check boxes, and select the relevant elements for the patient from an 'Other risk factors' section. Rescue medication information can also be added by selecting it from a list and/or checking or unchecking certain rescue medication categories. The physician can conclude by reviewing default physician and patient captured outcomes available for capture for the given condition and click a save button (or similar control) to indicate that data entry is complete. This will cause the list of medical conditions, risk factors and rescue medication to be updated in the appropriate back end systems, such as in a patient state object 501 if the back end system is implemented using an architecture as illustrated in FIG. 5. Alternatively, it is possible that the physician will close or navigate away from the portal without clicking save, in which case any data entered will be cached on the physician's local machine and reloaded when the physician returns, but will not be propagated to the back end without the physician taking some affirmative action (e.g., hitting a "Save" button).

As a further concrete illustration of the role a patient profile may play, consider the use of such a profile for an existing patient. In this case, a physician could access the profile by clicking a patient profile picture on a home page. When the profile was open, the physician could review and/or update the previously selected Medical Conditions, disease specific Risk Factors, and Risk Profile elements if necessary. The physician may also add a physician reported outcome, such as by clicking an update outcome button (or similar control) provided with the patient profile. For example, if the physician has seen the patient and run some measurements/tests/procedures on the patient, this information can be provided via an interface (which could include a list of potential tests/outcomes) which would become available when the "Update Outcomes" button is clicked. The physician could also view the outcomes chart 11803, at the bottom of the profile page and optionally may modify the outcomes visible on the chart by selecting or deselecting from legend 11804. Finally, after the physician had obtained whatever information he or she felt was necessary and updated the data for the patient as appropriate, he or she could click a save button (or activate a similar control) and the information provided would be used to update the appropriate back end systems (e.g., the patient state object 501 in an embodiment following the architecture of FIG. 5). Of course, in some embodiments, a physician could also "use" the profile of an existing patient by deleting it (e.g., by deleting all conditions associated with his or her practice), though this will preferably not impact the data for that patient, which should be retained by the appropriate back end systems, and which may even remain accessible to other physicians via their own patient profile interfaces.

Other course, while it is possible that a patient profile could provide for data entry, some embodiments of the disclosed technology may include other data entry features, either as an alternative to, or in addition to, the data entry described for a patient profile. As an example of this, consider a medication module, which could allow a patient to enter medications currently being taken. Using such a module, an app (which, in this document unless the surrounding context clearly indicates otherwise, should be understood as also referring to website based implementation of portals similar to what could be provided via an app) could store medication name (generic or brand), type, dosage and frequency. An app may also, in some embodiments, set a medication schedule or provide reminders, though this functionality may be omitted in some embodiments. However, even in embodiments where it does not set a medication schedule or provide reminders, an app which includes a medication module as described will preferably provide a way to collect all the medications being taken by a patient for inclusion into the patient profile and D-plans. Medication data gathered through a medication module will preferably be accessible through a patient profile (which, as described previously, could also allow a patient or physician to add, delete or modify medications). Additionally, in some embodiments this data may also be visible to the physician and others (e.g., research coordinators) in their data views of this patient.

Embodiments of the disclosed technology which include a medication module may provide user interfaces to a patient which would include one or more views. For example, some embodiments may provide a page in web and/or mobile access channels called "My Medications." This page may initially be empty but will eventually contain a list. The list will typically comprise or consist of the following:
a) Drug name, form, dosage, frequency as in "Lipitor, pill, 10 mg, 1/day".
b) A minus sign icon next to each name to remove drug
c) A pencil icon next to each name to edit drug details
d) An add button at, for example, the top or bottom of the list for adding a new medication As another example, in some embodiments, clicking on an "add" button or otherwise indicating that a drug should be added may take a user to a new view which may include one, all, or a combination (e.g., items a, b, d, e and f) of the following items
a) Drug Name (search bar, with autofill) at top
b) Drug Form drop-down (e.g. pill, liquid, spray)
c) Total quantity drop-down (e.g. 30, 60, 100 mL)
d) Dosage drop-down (e.g. 1 Tablet, 2 drops, 15 mL)
e) Frequency with number drop-down, time drop down (daily, weekly, etc.) and "as needed" checkbox.
f) Save and Cancel buttons In some embodiments, clicking on Drug Name (search bar) will bring up a new window with a list of all drugs stored in the database and a search bar for typing in a name. The list may be dynamically filtered to display only entries that match the text entered in the search bar. A drug matches the text entered if any substring of the drug name matches the text entered. The search is preferably case-insensitive and ignores whitespace and punctuation. Once the name is selected by clicking a matching element in the list this search window disappears and the user returns to the "add drug" window. Fields in the "add drug" window will now be populated with backend database information matching the selected drug name.

In some embodiments, a medication module may also provide certain other functionality to facilitate the gathering of medication information. For example, in some cases, selecting a "Form" option will auto-populate based on database information for drug name (e.g., acetaminophen may be liquid or tablet or capsule). Similarly, selection a "Dosage" option may auto-populate based on drug name and form (acetaminophin liquid as 5 mL, 10 mL or tablet as 50 mg, 100 mg, etc). In such cases, a backend database (e.g., a database maintained by an entity operating a system implemented according to the architecture of FIG. 5, or a database accessed through an API such as Medispan http://www.medispan.com/drug-database, RxNorm http://mor.nlm.nih.gov/download/rxnav/RxNormAPIs.html, or Cerner Multim VantageRX http://www.multum.com/vantagerxsdk.html) may provide discrete values for dosage (50 mg, 100 mg, 150 mg) or possibly indications such as (1 ml/10 kg) where dosage is based on patient's weight, for example. If no discrete list of dosages is available, drop-down box provides a reasonable range of values (10 mL, 11 mL, 12 mL, 13 mL . . . ). As an additional feature, in some embodiments, a medication module will include logic causing frequency options to be inactive if "as needed" is selected and re-activated if "as needed" is deselected. There may also be a dosage control which will auto select the correct unit of measure based on medication and form. (e.g., mL for liquids/sprays, mg for tablets/pills etc.). In some embodiments, the patient may be able to add or delete a medication by taking a photo of it, e.g., using a mobile device running an app. The medication will be automatically identified based on the photo and added to the patient's medication list. In some embodiments the medication module may collect at least some information regarding the patient's medications automatically, e.g., from electronic prescriptions or EMRs. In some embodiments, a patient may be asked to indicate whether a prescription has been filled. If the patient confirms, the medication may be automatically included in the patient's medication list.

Figure 115:
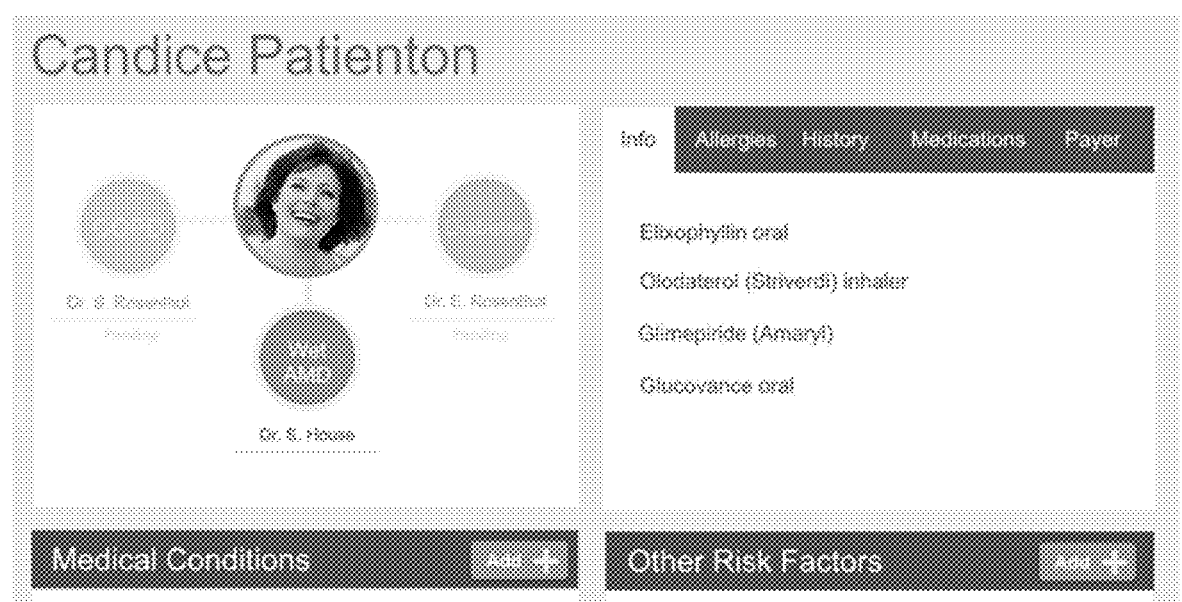
FIG. 115 illustrates an example of medication information which could potentially be provided through a portal.

A medication module may also or alternatively provide a medication detail view which would allow a user to view details of a single medication. In some embodiments, this could be accessed from a list view by clicking on a medication in the list. Such a detail view would preferably show all details of a medication (e.g., Name, Form, Dosage, Frequency). The user would preferably be able to click an edit button here to go to the edit view to modify the details of the medicine. In some embodiments, further details may also be added to this interface, like a photograph of the med, compliance history, reminder settings etc. Of course, a patient's current medication data could also be made available other than through a medication module to a patient. For example, in some embodiments a physician and/or others (e.g., a research coordinator) could view medication data through a patient profile provided by their own portals. An example, of medication information which could potentially be provided through such a portal is provided in FIG. 115, though information other than or in addition to what is shown in FIG. 115 (e.g., dosage and frequency for the various medications, in addition to their names) could also be provided.

To illustrate how a medication module could operate in practice, consider the following exemplary flows which could, in some embodiments, be used to structure user interactions with a medication module. To add a medication:
1. User navigates to My Medications
2. Clicks on "add" icon in medications window
3. A new view pops up with search bar at top of window and list of matching drugs below. There is also a "back" button.
4. User types in partial name of drug and selects from menu
   a. If there is no match to the text string currently entered, then the filtered list of drug names will be empty. User will be unable to select a match and must edit text or click "back".
   b. If the user types in a partial name and clicks on a match in the list, then the drug name fills in the search bar and the drug is selected.

c. If the user types in a full name and a unique match is found, user must still select the matching entry from the list before the drug is selected
d. If user clicks on "back" at any point then the search view closes and My Profile is displayed again.
e. Note: depending on the API there may never be an empty list, but always a list of "best matches."
5. Fills in rest of information and clicks on "save"
6. Search view closes and patient info window lists new drug at top of list (list shows most recent drugs first)

To remove a medication:
1. User navigates to My Medications
2. Finds medication in list
3. Clicks on delete icon
4. Confirmation window appears
5. User confirms and drug is removed from list To edit a medication:
1. User navigates to My Medications
2. Finds medication in list
3. Clicks on edit icon
4. The same view appears as when adding a medication, pre-populated
5. User may not edit drug name (help text can explain that to edit the name, user must delete entry first)
6. All other fields are editable
7. Save and cancel buttons at bottom of screen. User clicks on "save" to save the changes To view medications:
1. User navigates to My Medications
2. Views list of medications
3. Preferably, all medications and all relevant data will be presented here and no "expanding" fields will be needed.

In addition to, or as an alternative to, a medication module such as described above, some embodiments of the disclosed technology may include an outcomes capture module. Preferably, an outcomes capture module will be able to capture both physician reported outcomes and patient reported outcomes. Patient reported outcomes will preferably be run through at least one level of validations (e.g., standard validations, like verifying that an entered outcome is within a plausible range, such as might also be applied to body monitors), and may have other levels of validation applied to them as well. Such validation can be performed using rules (e.g., encoded in an SCE 502). Physician reported outcomes may also be subjected to some validations: complete, well-formed, within plausible range, syntactically incomplete (e.g., when a box is checked signifying that a procedure is done, any required outcome values for that procedure should also be present). An outcomes capture module may be implemented to identify when data fails a validation check as soon as it is entered (e.g., rather than waiting until a separate "submit" command is provided), and to prevent submission of outcomes data until all data in that form passes its applicable validations.

Patient reported outcomes may have an associated fixed frequency at which the patient is expected to update, and a patient will preferably be reminded via a notification when a measurement update is late. All outcomes will preferably come with default frequencies set by Revon. However, the patient and/or patient's HCP may be allowed to modify the frequency (e.g., using a slide-scale UI element made available in a "Settings" section of a portal provided by an application or website). The frequency of update will determine how often patients are sent notifications to update their measurements. In some embodiments the system could automatically modify the frequency of update based, e.g., on events or patient data. For example, if a patient has recently been discharged from hospital or experienced a health issue, patient reported outcomes (e.g., one or more patient reported outcomes relevant to the health issue) may be requested more frequently than previously. The system could have rules for modifying frequency of update. Physician reported outcomes may not have a default frequency, but instead may be accepted as they are received from the physician.

What outcomes to track may be determined and controlled by a D-Plan. In some embodiments, Revon will hardcode the total list of all possible patient reported and physician reported outcomes to capture in the D-Plans. Based on which medical conditions are selected for a patient, the D-Plans will determine which outcomes need to be tracked. In some embodiments, the patient may not be able to change the list of outcomes to track. However, even in such embodiments, the physician will preferably be enabled to change the outcomes he or she wants tracked. In some embodiments a physician may be able to change both the list of patient reported outcomes and physician reported outcomes. In some embodiments, physicians may receive compensation for entering certain outcomes. In some embodiments, if a physician decides to stop tracking an outcome for which they get compensation, this will be permitted, but the physician will be notified that some outcomes are compensated and switching them off may lead to less compensation. Preferably, however, the physician will not be notified which specific outcomes are compensated for. In some embodiments, physician compensation is not linked to entry of particular outcomes.

Such outcomes could be captured via the relevant portals presented to physicians and patients, though it is possible that an outcomes capture module could also capture information from other sources, and in some embodiments actual entry of outcome data by physicians may not be necessary. For example, some embodiments might capture outcomes data from EMRs, medical instruments or devices which capture such data for physicians, and treat such data as physician outcome data. Additionally, in some embodiments, certain outcomes (e.g., Blood Pressure) can be both a physician reported outcome and patient reported outcome. If same measure is both a physician reported outcome and patient reported outcome, then they will preferably be stored as two separate time series. They may also be displayed on an outcomes chart as two separate time series, which could be used for purposes such as comparing the same measure as reported by physician versus as reported by patient, which comparison may reveal systematic bias or trends.

When a portal with an outcomes capture module is supported by an architecture such as that illustrated in FIG. 5, an outcome will preferably be a data point which will not itself trigger any action in the regular course of operation. Instead, outcomes would be evaluated by an SCE 502 to determine if they are in a range of concern. If an outcome is such that it triggers a smart symptom tracker (SST), the outcome becomes a "Sign." Once an outcome becomes a sign, and a sign triggers an SST, the SST asks the patient various questions which are related to symptoms. In some embodiments, there may not be a mechanism for linking signs to particular conditions. However, even in embodiments where there is no mechanism for linking signs and conditions, the occurrence of signs will preferably be recorded as events. Signs will typically be dynamically determined, and such determination will preferably be based on dynamic processing rather than hardcoded linear rules, such that rules encoded in an SCE 502 will leverage a PSO 501 to dynamically determine if an outcome qualifies as a sign. Through leveraging a back end architecture such as shown in FIG. 5, such rules may look into multiple aspects of a patient's health data and determine if a given outcome reading qualifies as a sign. Of course, it is possible that, in some embodiments, not all outcomes will be processed in order to determine if they qualify as signs. For example, some embodiments may be implemented to prevent physician reported outcomes from triggering SSTs, in which case it might simply be impossible for a physician reported outcome to be treated as a "Sign." It is also possible that, in some embodiments, signs could be used for purposes other than triggering SSTs, such as serving as data markers for studies and analytics. For example, signs linked to particular potential causative factors may be used for data analysis (e.g., to find relations and causations).

Just as it is possible for some outcomes captured using an outcomes capture module might be designated as signs for various processing purposes (e.g., analytics, triggering SSTs, etc), it is also possible that, in some embodiments, different outcomes might be treated as having different importance for the purpose of display. For example, in some embodiments, outcomes might be rank ordered (either based on a hard coded ordering or dynamically determined ordering using rules), with only higher ranking outcomes being displayed by default on an outcomes chart. An exemplary list of outcomes which could be used for eye disorders such as age related macular degeneration, including metadata such as ordering which could be used by or encoded into a system implemented using the disclosed technology is provided below in table 6.

TABLE 6

Exemplary outcomes for eye disorders, including metadata

| No. | Type | Rank | Name | OD/OS | Mnemonic | Disease | UOM | Validation | 'Sign' Range relative to: |
|---|---|---|---|---|---|---|---|---|---|
| 1 | Patient Reported | 1 | Visual Acuity (OD, OS) | Yes | OUTP_EYE_VAC | AMD, GA | N/A | Lower Limit = 12 Upper Limit = 2000 | Range of normal vision 20/12.5-20/25 |
| 2 | Patient Reported | 2 | Visual Quality of Life | No | OUTP_EYE_VQOL | AMD, GA | N/A | Lower Limit = 0 Upper Limit = 30 | Normal vision = 2.99, Vision-impaired = 9.99 |
| 3 | Physician Reported | 1 | Visual Acuity | Yes | OUT_EYE_VAC | AMD, GA | N/a | Lower Limit = 12 Upper Limit = 2000 | N/A |
| 4 | Physician Reported | 5 | IOP | Yes | OUT_EYE_IOP | AMD, GA | mmHg | Lower Limit = 10, Upper Limit = 30 | N/A |
| 5 | Physician Reported | 1 | Anti-VEGF Treatment (OD, OS) | Yes | OUT_EYE_AVEGF | AMD | N/a | | N/A |
| 6 | Physician Reported | 1 | Macular Edema (cystic changes) (OD, OS) | Yes | OUT_EYE_MECC | AMD | N/a | | N/A |
| 7 | Physician Reported | 1 | Subretinal Fluid (OD, OS) | Yes | OUT_EYE_SRF | AMD, GA | N/a | | N/A |
| 8 | Physician Reported | 1 | Intraretinal Fluid (OD, OS) | Yes | OUT_EYE_IRF | AMD, GA | N/a | | N/A |
| 9 | Physician Reported | 1 | Central subfield thickness (OD, OS) | Yes | OUT_EYE_CST | AMD | um | Lower Limit = 100, Upper Limit = 1,000 | N/A |
| 10 | Physician Reported | 1 | GA (OD, OS) | Yes | OUT_EYE_GA | GA | N/a | | N/A |
| 11 | Physician Reported | 1 | Foveal encroachment (OD, OS) | Yes | OUT_EYE_FE | GA | N/a | | N/A |
| 12 | Physician Reported | 3 | Dark Adaptation (OD, OS) | Yes | OUT_EYE_DA | AMD, GA | mins | Lower Limit = 0, Upper Limit = 30 | Normal = average 5.5 but 6.5 or less is normal, Early AMD = 13.9, Intermediate AMD = 16.4, Advanced |

TABLE 6-continued

Exemplary outcomes for eye disorders, including metadata

| No. | Type | Rank | Name | OD/OS | Mnemonic | Disease | UOM | Validation | 'Sign' Range relative to: |
|---|---|---|---|---|---|---|---|---|---|
| 13 | Physician Reported | 3 | Macular sensitivity (OD, OS) | Yes | OUT_EYE_MS | GA | N/a | AMD = over 20 mins N/A | N/A |

Figure 116:
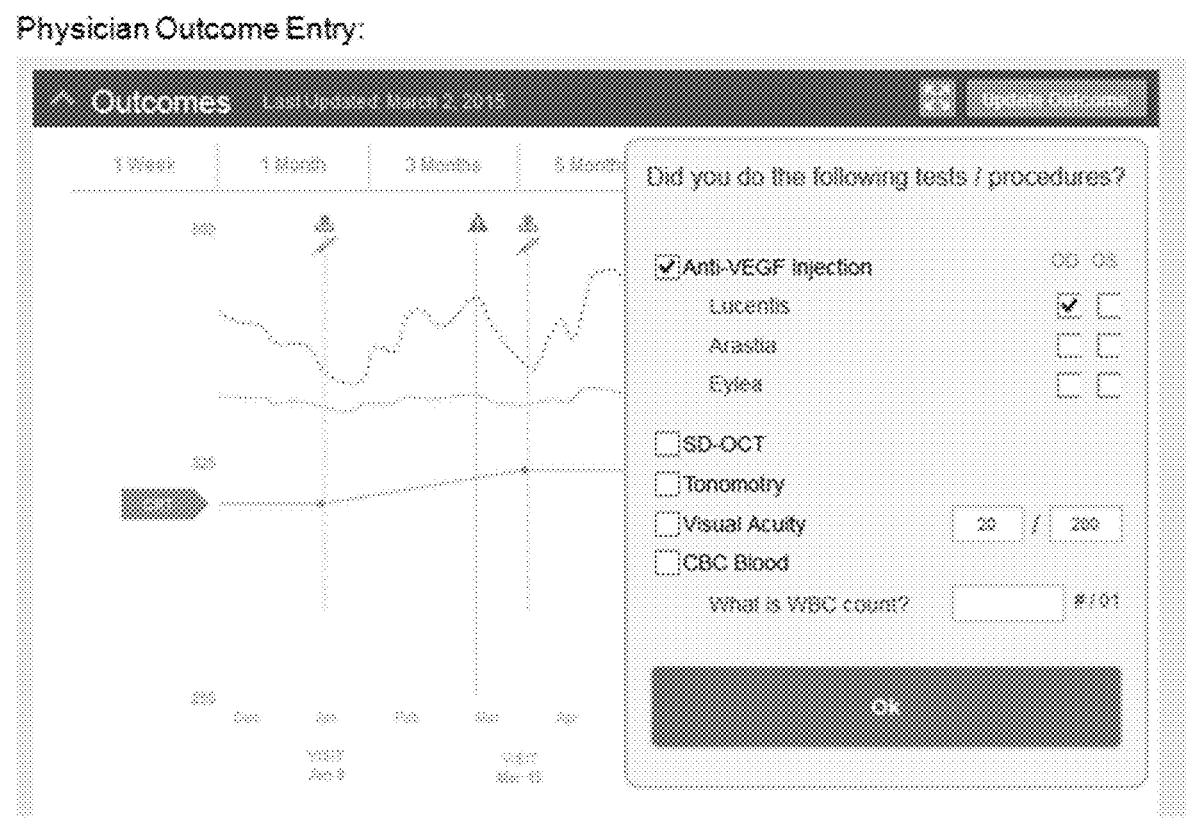
Figure 117:
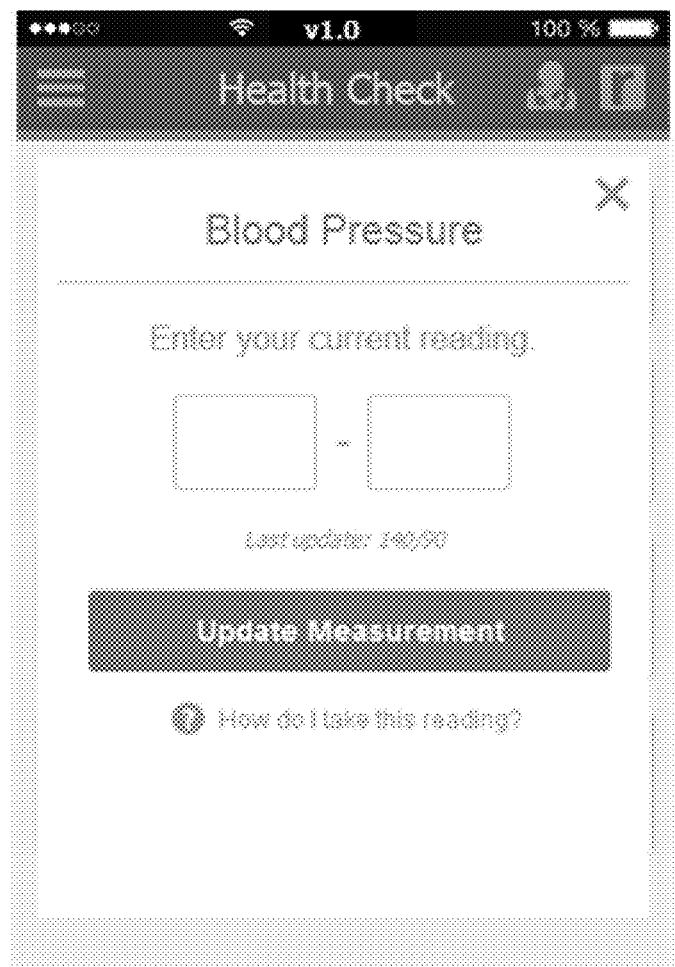
FIG. 117 illustrates an interface which could be used for patient outcome entry.

Outcomes capture modules could support various methods of outcome collection, depending on the relevant embodiment. For physician reported outcomes, in some embodiments, a physician will enter outcomes into a portal (e.g., provided by a web application). The entry will consist of, e.g., entering numerical values using a keyboard or answering of Boolean questions or making a selection from among multiple options using a keyboard or other input device. In some embodiments, entry of outcomes in other forms, such as free form text or audio, video, photograph or other non-text media may also be permitted. In some embodiments, entry of physician reported outcomes may occur directly from an EMR system or directly from a medical instrument or device (e.g., imaging equipment) used to collect the outcome data. Such direct entry may be automatic or under control of the physician. For patient reported outcomes, a patient will typically enter outcomes data using mainly a smartphone app, but also possibly using a web app, both of which may present essentially the same application. Patient reported outcomes data will typically also consist of numerical values and Boolean answers (or making a selection from among multiple options) entered using a keyboard or mouse or other input device. In some embodiments, entry of outcomes in other forms, such as verbally, may be permitted. In some embodiments, patient reported outcome data may be captured from smart devices. It should be understood that, for both physician reported outcomes and patient reported outcomes, a combination of different outcome entry methods may be used in various embodiments. Examples of interfaces which could be used, respectively, for physician and patient outcome entry are provided in FIGS. 116 and 117.

To trigger entry of patient reported outcomes, a request for outcome data will preferably be presented to a patient as a health action (in which requests sent to a patient for the same measure across OS/OD may be sent together, such as if the patient is asked for visual acuity, the patient could get two health actions, OUTP_EYE_VAC_OS and OUTP_EYE_VAC_OD so that they patient could update them simultaneously) in a health check feed from a patient portal. The patient will then click a button on (or otherwise select) this action, which will trigger the start of a questionnaire which will ask the patient a series of questions related to Vision Quality of Life (VQOL). Once patient completes the questionnaire, the VQOL score will be auto-calculated and recorded. In some embodiments, this may include a patient using an external mechanism to calculate their visual acuity. This could be a smartphone app or paper methods like Snellen Charts. Once the patient has tested their visual acuity they will enter the end result into an interface presented by the patient portal (e.g., on a Revon app). A visual acuity Health Action data request will show in the Health Check feed. The patient will enter the measurement in the textboxes provided and submit, and the submitted data will be recorded in an appropriate data store. In some embodiments a mechanism for checking visual acuity may be provided as part of the same application or website providing the patient portal, or even as part of the patient portal itself. In such a case, the app or underlying website software may automatically determine visual acuity based on patient input. In this use case, visual acuity (VA) is reported as a composite number of the form 20/x. When patients use an external mechanism to calculate their VA they will generally get results in the form A/B (e.g.: 20/40). But the first number is always 20. So when the user enters this, they will preferably only enter the second number. So a Health Action box for enabling this number to be entered will preferably have the form 20/{ }, where the user fills in only the { } textbox. Similarly, when graphing the VA values, the 20/x measurement will preferably be automatically converted to a decimal value and the decimal values will be graphed as a line graph in which as x increases the line will drop and as x increases the line rises.

Other features which may be provided by an outcomes capture module include supporting deletion and addressing fraud/repeated entry and conflicts. For deletion, preferably a portal including an outcomes capture module will also implement an UNDO feature which will be globally accessible, both in the outcomes capture module and otherwise. Such a feature could be used by an individual entering outcome data (e.g., patient or physician) to delete the last entered value and replace it with a new value. For addressing fraud/repeated data entry, if a physician repeatedly enters the same outcome data, either an application through which the data is entered or software supporting a website through which the data is entered will preferably allow for the repeated data to be entered, but have a monitoring mechanism in place to detect it. Such issues can then be handled on case by case basis as they arise. Other possible fraud modes such as entering false data without seeing patients may also be detected and handled offline on case by case basis. This can potentially be supported by deploying outcomes data monitoring systems in the backend to run through application wide outcomes data and find potential abuses. For addressing conflicts, when the same outcome is entered by multiple physicians, preferably, the disclosed technology will be implemented to allow this but will store each outcome data point separately per patient and physician. To facilitate this, physician reported outcomes could be stored and displayed with patientID and physicianID labels. Similarly, in some implementations, while it is possible that a physician could choose to merge various external data sources, outcomes could be presented in outcome graphs which are unique to particular physicians, so a physician would not see outcomes measured by other physicians, even for the same measure. As an alternative approach to addressing conflicts, when two data points for a particular outcome are submitted (e.g., by different physicians, or by a physician and a patient) within a given time window (e.g., 20 minutes), an outcomes capture module could determine which of the two to accept (e.g., using rules giving primacy based on whether a point was entered by a patient or physician, on which point was entered more recently, and/or on other factors), could request the user specify which to accept via a UI element, or could give the user an option to either accept both points, accept only the later point, or to accept only the previous point.

The flows set forth in the following paragraphs are provided to further illustrate the potential operation of an outcomes capture module and potential impacts of data captured from such a module.

A flow for outcome entry by a physician could begin with the physician opening a patient D-plan view in a portal, scrolling to outcomes, and clicking (or otherwise selecting) "update outcomes" in the portal. This could result in a pop-up window appearing to allow the entry of outcomes, ranked by order. The physician could then fill in numerical, boolean or multiple choice responses as appropriate, and may leave any or all fields blank where no response is required. Additionally, the outcomes capture module could provide a follow up message if provided information requires certain additional data. For example, if a physician indicated that he or she did procedure X, a follow up message may be provided indicating that a value for that procedure is needed. Conversely, if a physician does not indicate that he or she did procedure X, then the tools for entering a value for that procedure may be deactivated. Once the physician enters numerical data, this data could be compared with valid ranges, and out of range values could be flagged immediately so they can be edited without unnecessary delay. Additionally, where an outcome has a dependency where only one option may be selected (e.g., did you do A or B or C), the physician could be prevented from selecting more than one option, rather than allowing selection of multiple options and identifying the error after the fact as part of validation. After the physician has entered the necessary data, and the data has been validated, he or she could click an "update" or other submission tool, and the submitted outcomes would be saved on the backend with a timestamp of "now" and an outcomes graph would be updated. A final validation may also be performed at this time, though ideally all validations would have been performed in real time as data was entered. Alternatively, if the physician desired he or she would preferably be able to activate a "Cancel" button or other appropriate control to exit the outcome entry interface without having to complete the entry of outcome data.

In some embodiments, a flow for outcome entry by a patient could be either prompted or unprompted. In this context, prompted means the entry is in response to a push notification requesting a specific outcome, while unprompted means the patients activates the patient app and selects an outcome to enter. In embodiments where they are supported, unprompted outcome entries could allow patients to enter any outcome they want, at any time. Whether prompted or unprompted, once a particular outcome is selected by the patient (e.g., from a Health Check screen), the patient is presented with a question/answer screen, describing the outcome requested and presenting either numerical, boolean or multiple-choice entry. There is also help text available to explain how to take the measurements required for the outcome (via a link or pop-up). The time and value of the most recent outcome of this type is also displayed in the window. The patient will then enter the appropriate value(s) on the question and answer screen and click (or otherwise activate) "update" or other appropriate data submission tool. As described above, the values entered by the patient would preferably be validated in real time as they are entered. Additionally, in patient outcome entry, entry of one outcome may lead to prompting for another. For example, if an outcome is single entry (like temperature), then after the entry an "Am I Ok" (AIO) survey session may be initiated if the outcome is in the "sign" range. Similarly if outcome is multiple questions then after the patient clicks on update, s/he may be presented with the next question in the series, and this may repeat until all questions in series are complete. To enable some editing of answers, single and multiple-question outcomes will preferably support a 1-step immediate UNDO feature that erases the most recent outcome entry from the patient's history and (if necessary) restores the PSO 501 to the previous state. UNDO may cancel any AIO sessions initiated by outcome entries, but will not cancel an AIO session already in progress. In-progress AIO sessions will return to the previous question. UNDO will always return to a prior screen and allow patient to re-enter the data being undone. The UNDO feature may have a timeout value (e.g., 10 minutes, 2 minutes, etc). After this time, the UNDO option will be unavailable and the user interface element will deactivate or disappear.

As set forth in the preceding paragraph, flows for actions triggered by outcomes data may include triggering an AIO session if an entered value is within the "sign" range. Additionally, in an implementation following the architecture of FIG. 5, entered outcome data will modify a PSO 501 using rules defined in an SCE 502 and ACE 503. It can also trigger updates to various related data, such as a patient's health score and compliance score. Additionally, patient outcome data, when entered, will reset timers associated with data frequency and will move the entered outcome to the bottom of the list of outcomes on a patient's health check screen. The most recently entered outcome data, whether physician reported data or patient reported data, will also be used to update an outcome graph for the patient.

In addition to updating data reporting interfaces or triggering actions such as requests for more data, information provided via a Revon app could also be used for other purposes. For example, information from a Revon app, either on its own or when combined with other information could be used by the entity deploying the technology to identify whether patients whose data is accessible via the deployed implementation of the disclosed technology are potential candidates for participating in a pharmaceutical research study. This could be done by comparing the information about a user's health with information indicating requirements for participating in a research trial provided to a Revon system by a research sponsor via a Pharma Portal such as shown in FIGS. 119-124. In this comparison, both the values of the accessible health data (e.g., outcome values, such as could be displayed in an outcomes chart such as described previously) and the number of those values (e.g., the number of outcomes gathered for a particular patient) could potentially be used to determine eligibility.

In some embodiments, Revon may determine whether a patient is a potential match for a trial (i.e., meets at least one of the requirements for participation in the trial) while a physician is in the process of entering outcomes for the patient or updating the patient profile of the patient. For example, an outcome or patient profile item entered by the physician may indicate that the patient meets an inclusion criterion for a trial (e.g., that the patient has a particular disorder or condition for which an experimental therapy will be tested in the trial). In some embodiments, if an initial match for a trial's requirements occurs while a physician is in the process of entering outcomes for the patient or updating the patient profile (e.g., if an outcome or patient profile element entered by the physician is an inclusion criterion for the trial and the patient otherwise matches the trial requirements based on the user's other health information), Revon automatically conducts an interview with a physician (e.g., using dialog boxes and/or other standard user interface elements) regarding the patient for whom the physician is currently entering outcomes or updating the patient profile. This interview may ask the physician one or more questions related to inclusion/exclusion criteria for the trial, answers to which could further qualify or disqualify the patient for a trial (possibly across multiple trials simultaneously). The health information so obtained may be used to further determine whether the patient qualifies for the trial. In some embodiments, the interview may end if an answer entered by the physician disqualifies the patient for the trial(s) for which he or she initially matched.

In some embodiments, Revon may conduct patient interviews through the patient application (which, as indicated herein, could, in some embodiments, be accessed by the patient via software downloaded to a mobile or other computing device, or through a web based portal). Such interviews may be designed to collect specific health information from the patient. Revon may conduct an interview with a patient according to a predetermined schedule or upon occurrence of a trigger such as, for example, a health event, and/or entry of particular outcomes data or patient profile data by the patient's physician. The content of the interview may be predetermined or may vary depending in part on the patient's responses. In some embodiments, an interview may comprise a set of questions that may be used as an outcome measure. The relevant outcome(s) may be, e.g., quality of life, functional status, disease severity, and/or disease control. In some embodiments, a patient interview may collect health information that may help determine whether a patient is potentially eligible or is not eligible for a trial.

After the comparison had taken place, if the user's health information showed that he or she was eligible to participate in the trial, an invitation for the trial might automatically be sent to him or her (e.g., through the Patient Portal, or through some external channel, such as email). If the user responds to the invitation by indicating that he or she is interested in participating in the trial, then a research coordinator (RC) responsible for the trial (e.g., an RC responsible for coordinating/managing the trial at a particular site, e.g., a site located within a specified distance from the user's address) can be notified. For example, the research coordinator could be notified that the user had been pre-screened but not enrolled through a RC Portal such as shown in FIGS. 125-130, so that he or she could complete the user's enrollment in the trial. Additionally, in some embodiments, functionality beyond simply notifying an RC of potential trial participants could also be provided via an RC portal. For example, a RC may oversee multiple trials for multiple sponsoring pharmaceutical companies, and so a RC portal may be configured to allow the RC to access information about any of the trials the RC is overseeing. An RC portal may also include interfaces which provide overview information about trials in progress, and patients who have already enrolled in a trial, rather than only providing information about patients who may enroll but have not yet done so.

Figure 126:
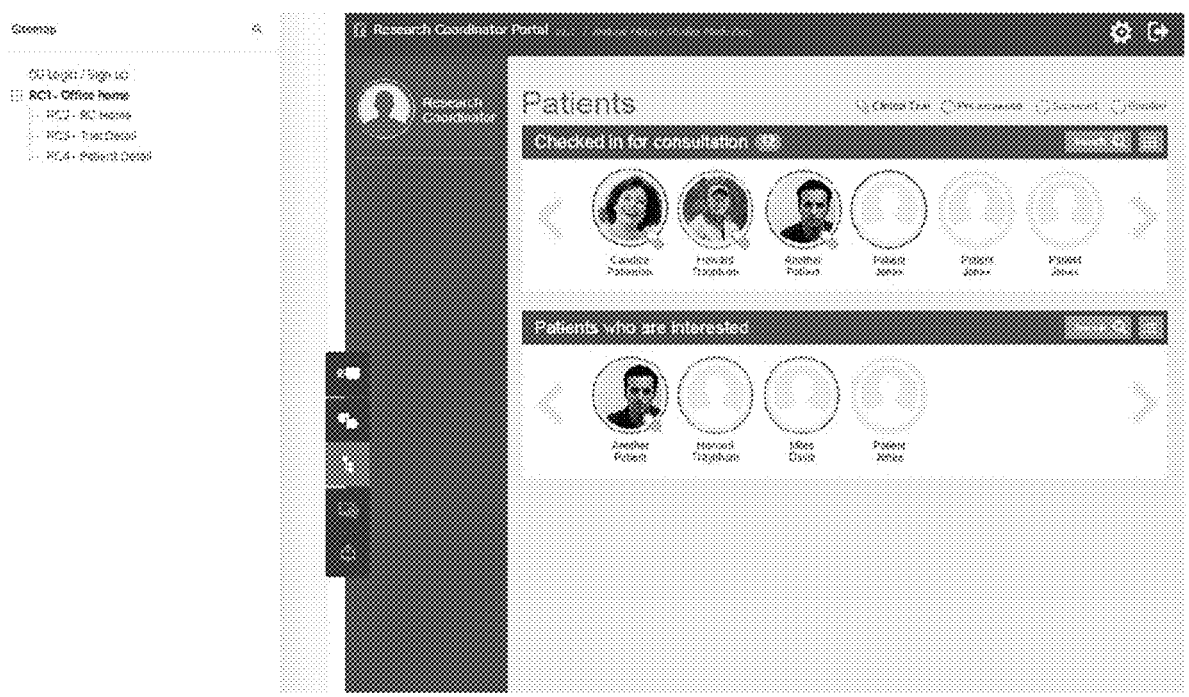
Figure 127:
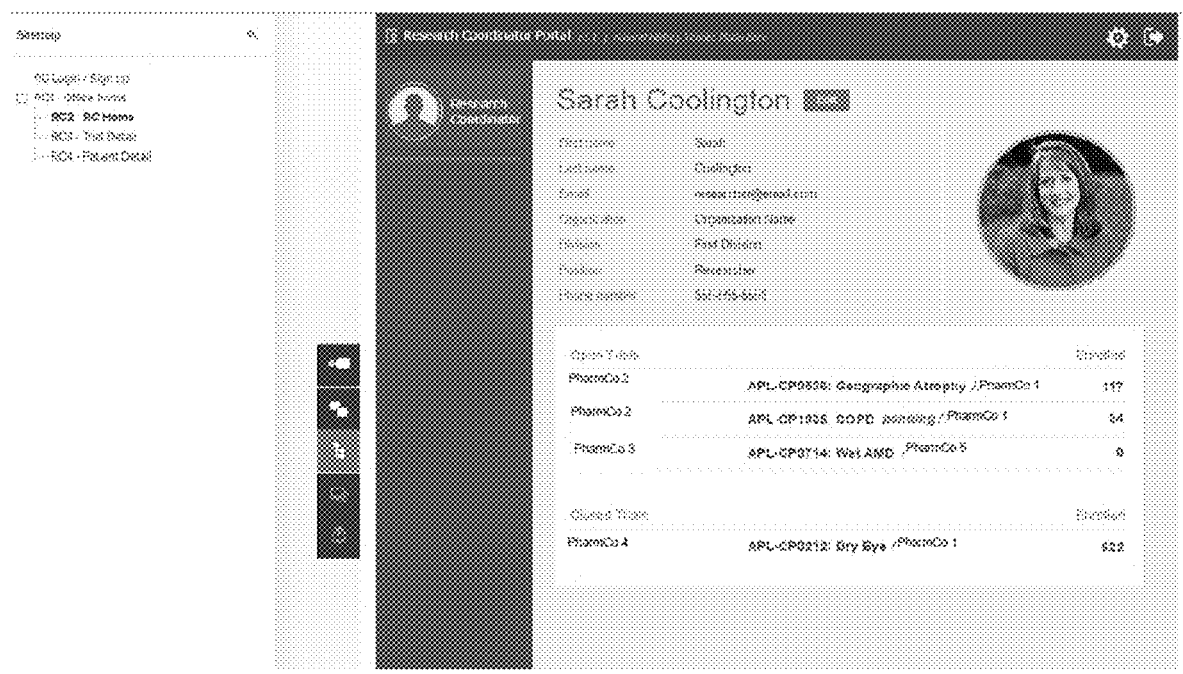
Figure 128:
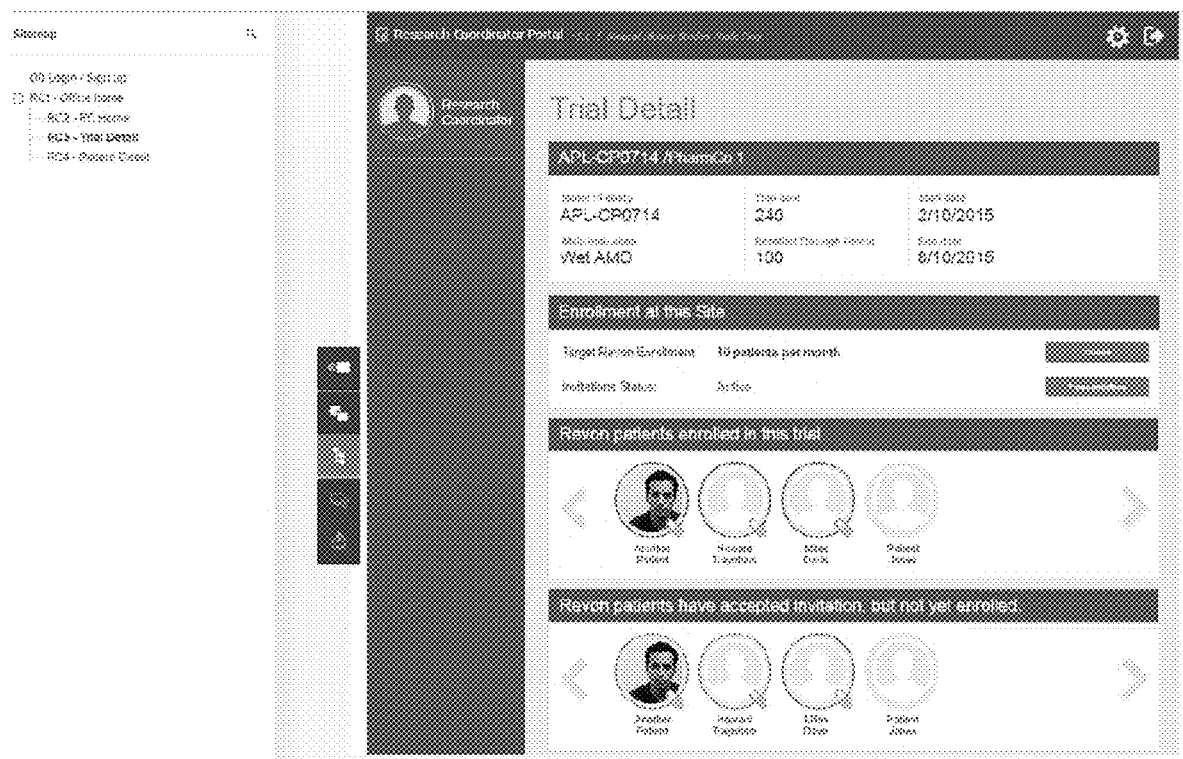
Figure 129:
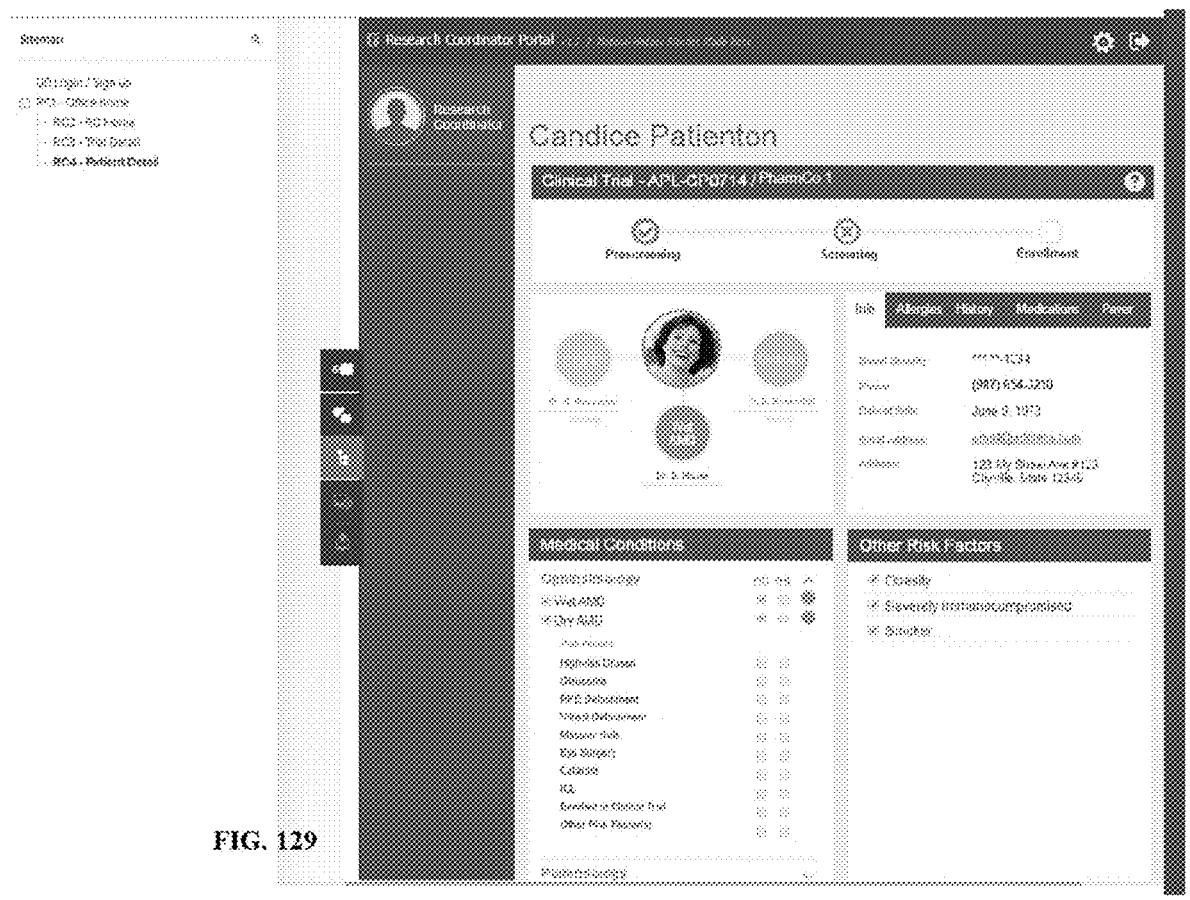
Figure 130:
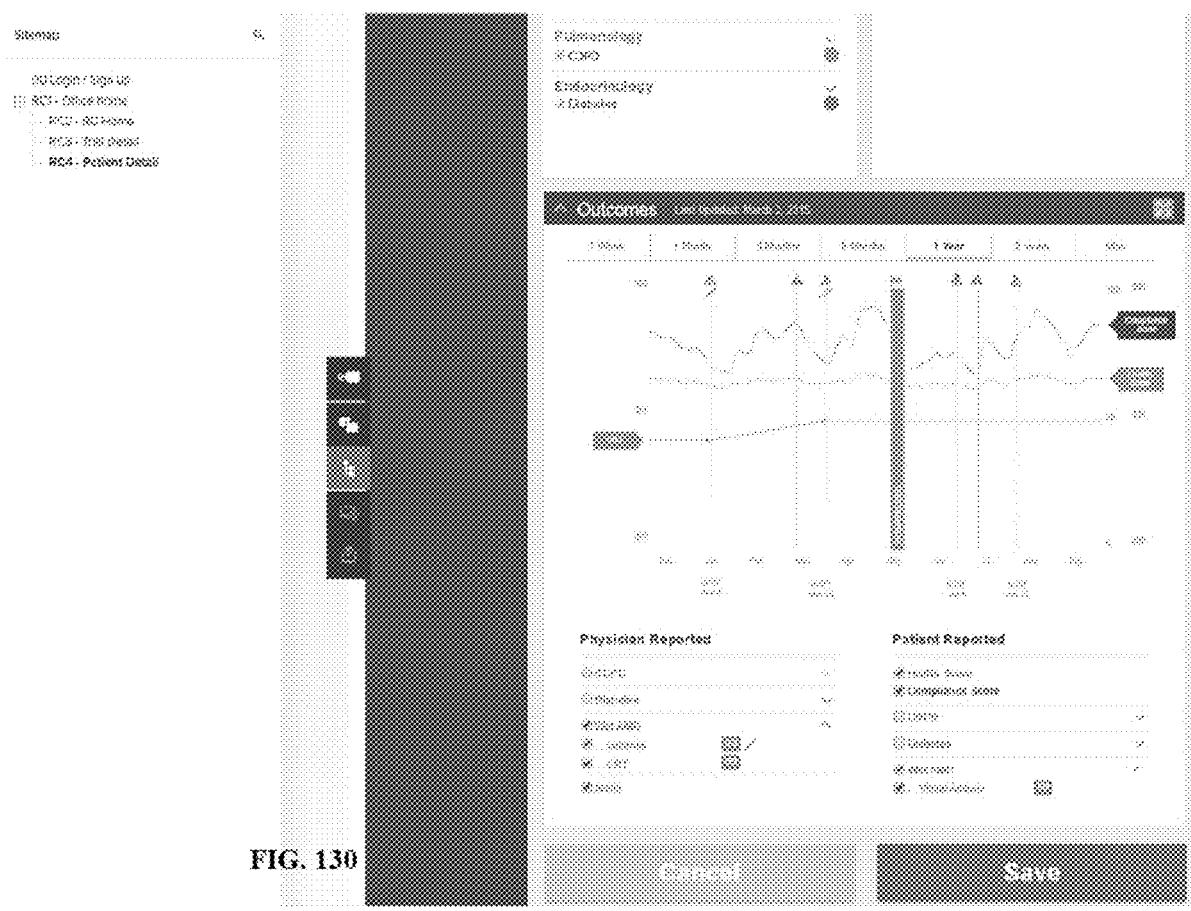

As shown in FIGS. 125-130, a RC portal could include a variety of pages which could potentially be used by an RC. For example, as illustrated in FIG. 126, an RC portal could include an office home page which could help an RC quickly find a patient who has been sent to them, get details for that patient (e.g., by clicking on his or her picture), and updating that patient's status. Such an office home page could include sections identifying patients checked in for consultation and/or patients who may call because they have responded to a trial invite (e.g., patients who responded affirmatively when Revon invited them to visit this RC, but who have not yet visited this RC). An office home page could also include search and list features, such as a search box where an RC can enter patient name or email to find them, or a list view showing patient names, checked-in/will-call status, and the name of the trial for which they are in the office. There might also be a home page for the RC, such as shown in FIG. 127. This could provide personal and professional information about the RC, an overview of the trials assigned to the RC (potentially including information such as trial name, sponsor, end date, number of participants enrolled by Revon and/or in total, and/or start and end dates in Revon's involvement with the enrollment process), and/or the ability to edit personal information.

Beyond the home pages, an RC portal could also include details on particular trials, which details could preferably be accessed by clicking on a trial name from the RC home page. In some embodiments, an interface providing trial details could allow the RC to define his or her desired patient load (i.e., appointments) per period (week/month). This information could be used by the entity operating the back end system (i.e., Revon) to calculate the number of invites to send per period given a particular estimated response rate (alternatively, if an RC does not provide desired load per period, invites could be sent based on assigning a percentage of overall trial patients to the RC's site). In addition to, or as an alternative to, allowing an RC to indirectly control invitations through defining his or her desired load per period, a trial detail interface could also allow an RC to pause invitations for a particular trial. In a case where this feature is provided, preferably the entity operating the disclosed technology would send some type of reminder (e.g., via email) to RCs who have paused invitations for more than a threshold period (e.g., more than a week). Of course, a trial detail interface could include functionality not related to controlling invitations as well. For example, it could display patients who are "in process" in a trial, such as in table format. Preferably, such a display will include anyone who has made an appointment, visited the RC and is currently active for that RC. In some embodiments, color may be used to define a patient's status (e.g., enrolled=green, screened=yellow, pre-screened=blue).

An RC portal could also provide patient details which, as described previously, would preferably be accessible through the office home page and would likely also be accessible via clicking on a patient name in a trial detail pages as well. An example of a patient detail page is provided in FIGS. 129 and 130, and, as shown in those figures, the patient detail page of an RC portal could potentially be extremely similar to the interfaces provided in a physician portal for presenting information about a patient (though preferably the research coordinator, unlike a physician user, will not be provided with the ability to edit information about a patient other than as it relates to enrollment status in a particular trial). However, a patient detail page from an RC portal could potentially also include additional information. For example, it could include a clinical trial status portion, which would indicate the patient's status in a trial relative to various key points, each of which could have various statuses. The statuses may be the same for all keypoints (e.g., all keypoints of true, false, and null), or there could be different status for different points. For example, a pre-screening keypoint could have statuses of {accepted, rejected_not_eligible, scheduling_conflict, trial_suspended, other (in which case a text string explanation entered by the RC would be stored), null}. A screening keypoint could have statuses of {passed, failed, null}, and an enrollment keypoint could have statuses of {enrolled, patient_did_not_consent, scheduling_conflicts, trial_suspended, other, null}.

In such a trial status portion, the initial state for a patient will preferably have all keypoints set to null, and a false or null keypoint would only be followed by null keypoints, while a true keypoint could potentially be followed by any type of keypoint. Preferably, the RC could use this portion to track the recruitment status of a patient relative to a trial, and could change keypoint statuses by clicking on or otherwise selecting them. Additionally, in some embodiments an RC could provide more information than simply that a keypoint status had changed. For example, it is possible that, in some embodiments, when a change is made to a keypoint status (e.g., it is changed to false) the RC could be provided with a tool for entering additional information about the status change (e.g., a text box where the RC could indicate why a keypoint is being set to false), and in some cases if the RC does not provide this additional information, changes to a keypoint may not save until the RC has provided some explanation for the change.

The following scenarios further illustrate the potential uses and operation of the disclosed technology in the context of a pharmaceutical trial. When a new patient accepts an invitation, he or she can call the RC to schedule an appointment, or, in some embodiments, the RC might be enabled to access the patient's information through Revon (preferably, when a patient accepts an invitation, he or she would provide consent to the RC accessing his or her contact and medical information) and contact him or her directly. If a patient never calls to make an appointment (or never shows up), then they may stay in the system. However, an interface presented to an RC will preferably sort patients by most recent, so patients who are unresponsive or unavailable will either be easily avoidable or may disappear entirely (e.g., if a list of patients extends off of the applicable interface). When a new patient responds to an invitation, makes an appointment, shows up and checks in for a visit, the RC will see the patient appear in the office home page when he or she checks in, or could locate the patient using a search tool. Once the patient has been found, the RC can navigate to a detail page for him or her, consult with the patient, and update the patient's status accordingly. If a new patient responds to an invitation, shows up but does not check in, then the patient can be found through a search tool, then can be handled in the same manner described above for if the patient checked in. Similarly, if an existing patient checks in or drops out, the RC can access his or her record through the RC portal and update his or her status as appropriate. Once the trial is underway, the physician(s) conducting the trial could use the physician portal to record and access information about the patient's health, and the research sponsor could be billed for the Revon patients who enroll in the trial (or who reach some other milestone, such as trial completion or expressing an interest in participating after pre-screening).

In some embodiments a Revon patient may be automatically checked in to an appointment (e.g., with a HCP or RC) through use of the location feature of the patient's mobile device or the patient may check himself or herself in for the appointment using the Revon app on their mobile device. In some embodiments, a list of patients who may call the HCP or RC or who are presently checked in for an appointment may be presented on the HCP's or RC's screen. In some embodiments, a list of patients who may call the HCP may comprise or consist of those patients who have recently (e.g., within a specified time period such as the previous 12, 24, or 48 hours), run an SST that has provided output suggesting that the patient call the HCP. In some embodiments, a list of patients who may call an RC may comprise or consist of those patients that the Revon system has determined are potentially eligible for a clinical trial for which that RC serves as a research coordinator.

In some embodiments, a patient application may include a feature that provides a user with the ability to share his or her health information with a physician, e.g., a physician who the patient is visiting for the first time, or an existing physician of the patient. The user's health information may be shared by providing the physician with whom the health information is to be shared with access to the Revon physician portal, for purposes of allowing the physician to view the patient's health information, or a portion thereof, that is available to the physicians who already use Revon in caring for the patient. One or more screens of the patient application may display an icon saying "Share My Health Record" or the like. The "Share My Health Record" feature could function in any of a variety of ways. In some embodiments, if the patient selects the "Share My Health Record" icon, the patient is provided with a code (e.g., a random sequence of numerals, letters, non alpha-numeric symbols, or combinations thereof) that he or she can share with a physician. For example, if the patient is visiting the physician at that time, the patient would simply tell the code to the physician or show the code to the physician on the patient's mobile device. The physician can enter the code into the Revon physician application, which the physician could access using a web browser. The Revon physician application could provide a suitable interface allowing the physician to enter the code. For example, the physician application could permit the physician to sign on as a "Guest" by entering the code. The physician would then be provided with access to the patient's health information that is stored in the Revon system. The Revon system could then record that the patient's health information was accessed by an individual using the specific code provided by the patient (potentially, in an embodiment in which the code is sent to the physician at an email address supplied by the patient by the Revon system, in combination with maintaining data indicating the email address to which that code had been sent), thereby allowing for tracking of the individuals who accessed the patient's records, even if not all of those individuals had accounts which would generally allow them to access the Revon system.

In some embodiments, if the patient selects the "Share My Health Record" icon, the patient can then enter a physician's email address into a dialog box. Revon then sends the physician an email that contains a code that the physician can enter into the physician application and/or a link that the physician can click on or enter into a web browser to obtain access to the patient's health information. In some embodiments, access may be provided to the physician for a limited period of time, e.g., up to 24 hours (though of course the time period could be longer). Typically, the physician to whom temporary access is provided is permitted to view the patient's health information but not to modify or download it. In some embodiments, the code and/or link "expires" (i.e., is no longer functional) after a predetermined period of time, e.g., between 5 minutes and 60 minutes. In some embodiments, if an individual attempts to use the code or link after it has expired, a message appears indicating that the code or link has expired and the individual is not permitted to log on to Revon as a guest or to view the patient's health information.

While use of a physician portal could potentially offer a convenient way for physicians to easily access relevant health information for Revon patients under their care, in some instances as an additional inducement for those physicians to use a Revon system to manage information regarding their patients, it is possible that those physicians might be provided with some kind of consideration beyond simply the convenience and other benefits provided by the physician portal and/or the underlying Revon system. To support this, there could be a physician compensation module to allow physicians to track upcoming payments and to compute payments on the back end correctly. Such payments may be based on enrollment of patients into the Revon system, on updates to patient information (e.g., updates to D-plans associated with patients), or both. For example, when a physician initially enrolls a patient, he or she may be paid a fixed sum of money, once a month for 12 months, for each patient enrolled. Subsequently, every time the physician updates the patient's D-Plan, the term of the payments could extended for an additional 12 months from the update. Alternatively, a physician might be paid for enrolling a patient, but not for providing updates.

In cases where a physician is compensated for initial enrollment of a Revon patient, that initial compensation event would begin with the physician inviting the new Revon patient and assigning him or her a D-plan. That patient would then be sent an email request to create a Revon account. If the patient (a) creates said account and (b) agrees to the Revon Terms of Service (TOS), then the patient enrollment is complete and it would be marked as an enrollment event. Therefore, the physician will, in some embodiments, now receive a fixed monthly payment (represented herein as: $A/month) for a specified time period (e.g., 12 months), which may be disbursed at the end of each month, beginning the first month after the patient signs up. For purposes of description it is assumed herein that the specified time period is 12 months (1 year), but it could be different, e.g., 9 months, 15 months, etc. A payment termination date is initialized for this physician-patient pair, set with a date equal to last calendar day of the month, 12 months from first month of payment. Payments continue until the termination date. Therefore, if a patient is enrolled on Jan. 15, 2015, physician will receive $X for that patient on Feb. 28, 2015 and end of every month until and including Jan. 31, 2016. Payment termination date will thus be Jan. 31, 2016. It should be understood that the afore-mentioned details are exemplary only. Other systems of calculating payment start and termination dates resulting in a series of payments spread out over a specified time period can be used.

Figure 131:
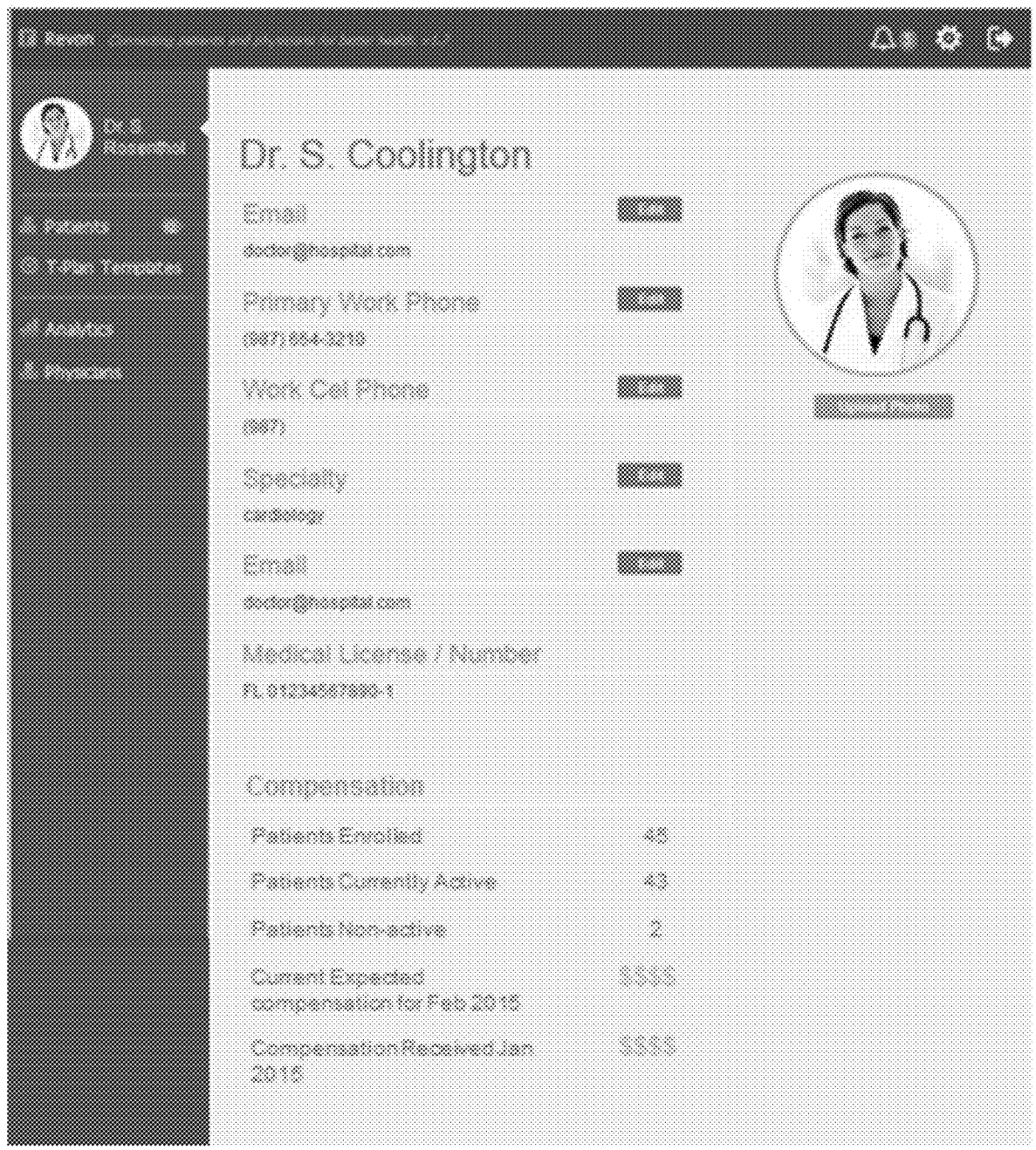
FIG. 131 provides an example of a physician information screen with compensation information.
Figure 132:
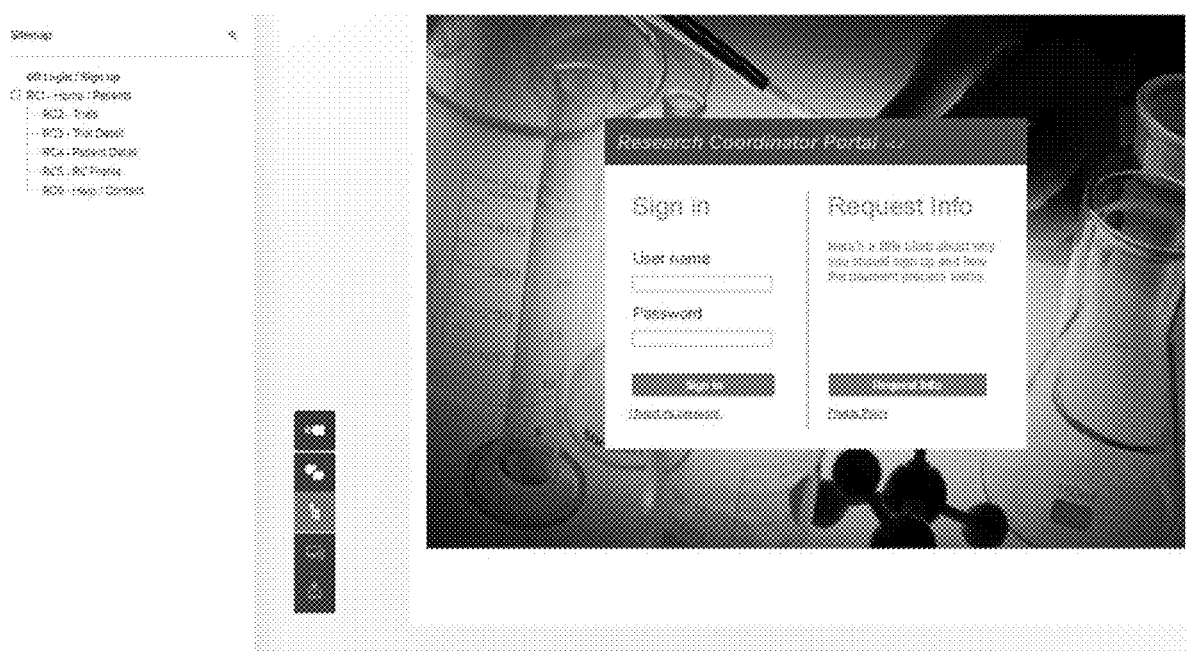
FIGS. 132-138 illustrate interfaces which could be presented in a research coordinator portal, with a map in the leftmost portion of the illustrations illustrating how the various interfaces relate to each other.

In cases where physicians are compensated for updates after initial enrollment, those updates could take place when a Revon physician opens, modifies, and saves a Revon patient's file (D-Plan). This would cause the physician's patient termination date to be reset to the most recent modification date, plus one calendar year. Accordingly, if a physician who enrolled the patient on Jan. 15, 2015, now updates the patient D-Plan on Jun. 5, 2015, then the last-paymentdate will be reset from Jan. 31, 2015 to Jun. 30, 2016. To support this, a backend system (e.g., one implemented according to the architecture of FIG. 5) would preferably track not only edits to a patient's file but who performed those edits and when. Additionally, it may also record the following information:

a. Which physician enrolled which patient on which date;
b. Physician payment start date, related to a given patient-physician pair;
c. Physician initial payment end date, related to a given patient-physician pair;
d. Every D-Plan update event (preferably with the exception of deletion of a D-plan): patient-physician pair, timestamp, what edit was made (audit trail from D-plan module);
e. Current and history of last payment dates (history is every last payment date that was set before a new edit was made which created a new last payment date); and
f. Dollar payment due per payment patient per month: In general, a fixed monthly payment of $X is paid to any physician for any 'active' patient. The amount due to a physician for any end of month payment cycle is equal to total number of 'active' patients multiplied by a fixed monthly payment per patient ($X). Additionally, in some embodiments, if the fee per patient is changed from $X to $X+Y, the physician gets $Y extra per patient for every 'active' patient they have. An 'active' patient here is defined as a patient enrolled by the physician, and whose last payment date is not already passed In addition to keeping records of information such as described above, embodiments of the disclosed technology which provide additional consideration to physicians may also include an administrative module that supports the export of physician payment accounting data to third party applications, such as Quickbooks, or may be exported into some human readable format for subsequent manual entry (e.g., by an accountant) into other systems as necessary. This could allow a Revon Admin to select a physician or physicians, and click a button, to export all physician compensation data. Physician compensation data file may be a simple csv or pipe-delimited file with the following 3 columns of data:

a. Physician Name
b. Physician ID (EIN)
c. Amount physician needs to be paid for current month Such a file may also include other information, such as a header to identify the date and time of creation. Additionally, some embodiments of the techniques described herein may be supported by software having the ability to export all compensation data in a simple format, for audit purposes. The datafile generated by such an export will preferably contain the following data columns: Physician ID, Physician Email, Physician Name, Patient ID, Compensation Event (enrollment OR file update), Date. This will output the log of all compensation events within a given date range. In some embodiments, a Revon admin will trigger this from the admin portal, by selecting a date range and then clicking a button. Compensation information (e.g., year to date balance and outstanding payment balance) will also preferably be accessible via a display in the physician portal. An example of a physician information screen with compensation information is provided in FIG. 131.

It should be noted that, while the above discussion focused primarily on additional consideration to a physician who originally enrolls a patient, in embodiments where such additional consideration is provided, it need not be limited to a physician who initially enrolls a Revon patient. For example, in some embodiments, any time a doctor makes a compensable update to a Revon patient's file, that doctor will receive payment, even if he or she did not enroll the patient. Accordingly, if two physicians make compensable edits to a Revon patient's file, then both will receive compensation for 12 months from the time of their respective edits. Similarly, if a patient joins Revon before being invited by a doctor, and a doctor starts treating that patient, then the payment (if any) would preferably start immediately for that doctor. On the other hand, if a patient is invited to join Revon by multiple physicians, then only the physician whose invitation is accepted (e.g., if invitations are sent by email, the physician whose email was first used to access the Revon system) would be treated as enrolling the patient. Additionally, if a Revon patient de-registers, then payments associated with that patient will preferably proceed as scheduled prior to the d-registration, even after the patient is de-registered.

Figure 133:
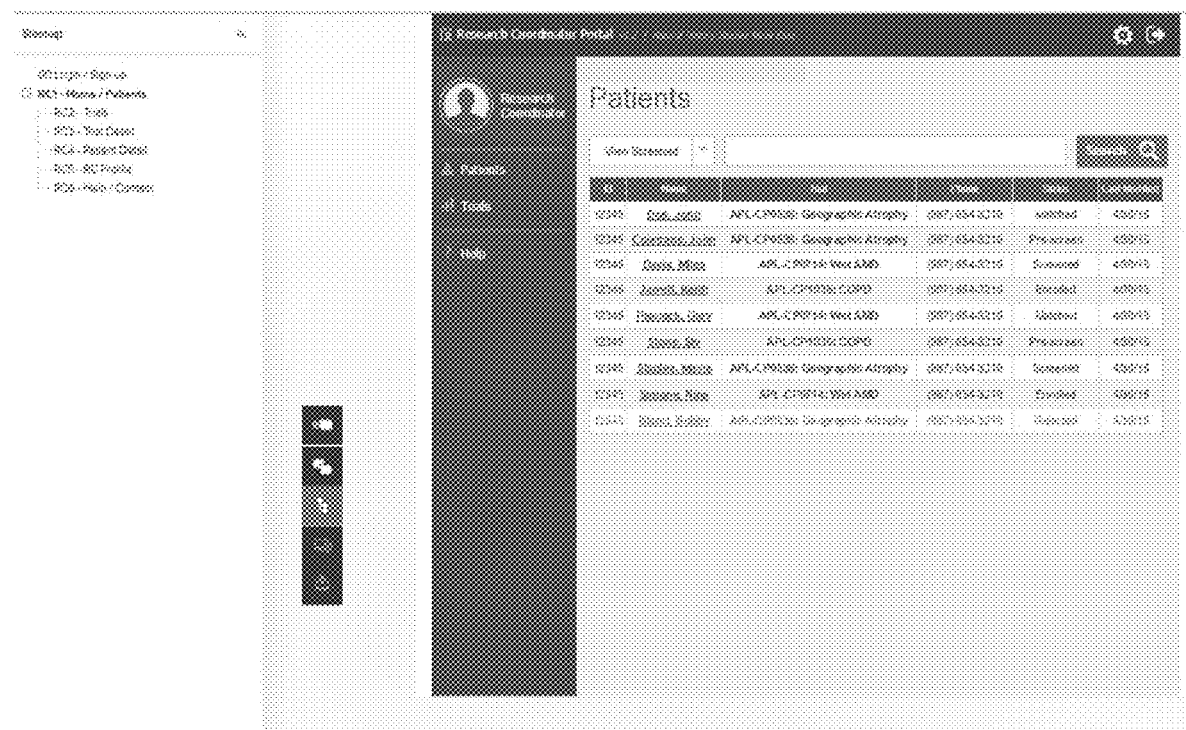
Figure 134:
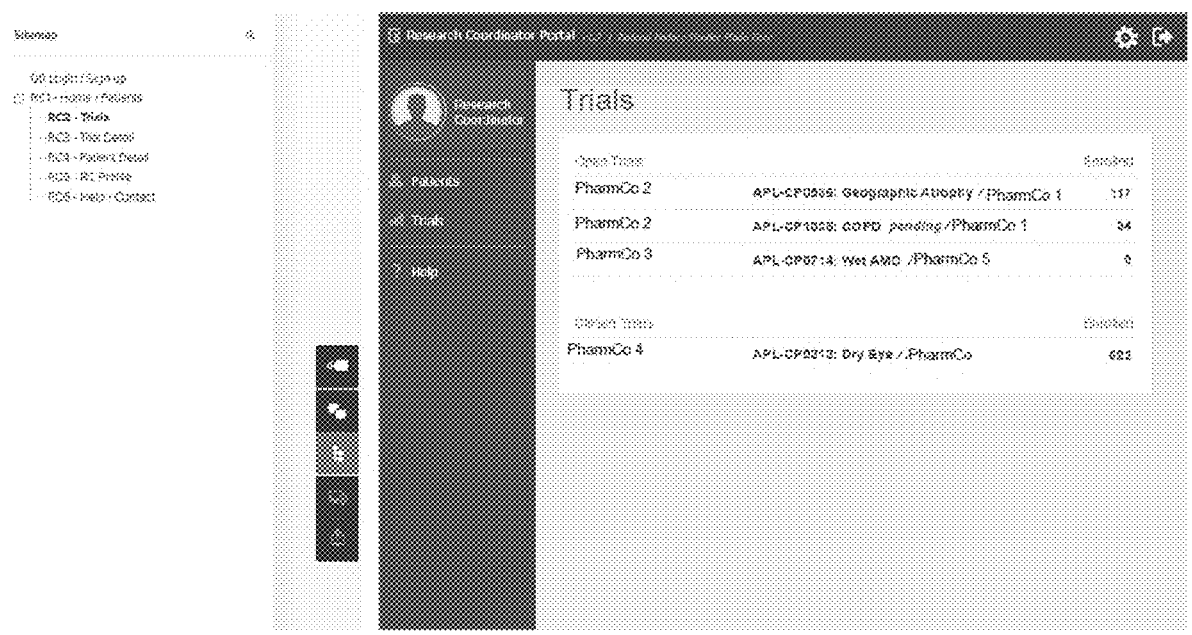
Figure 135:
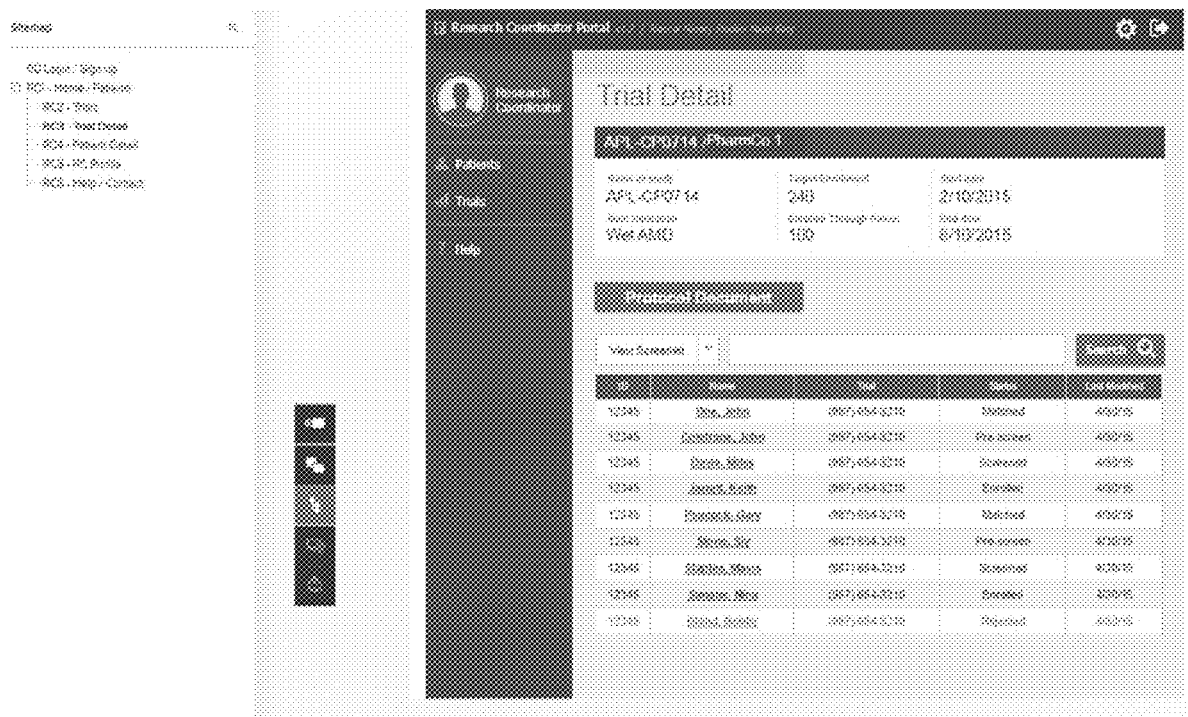
Figure 136:
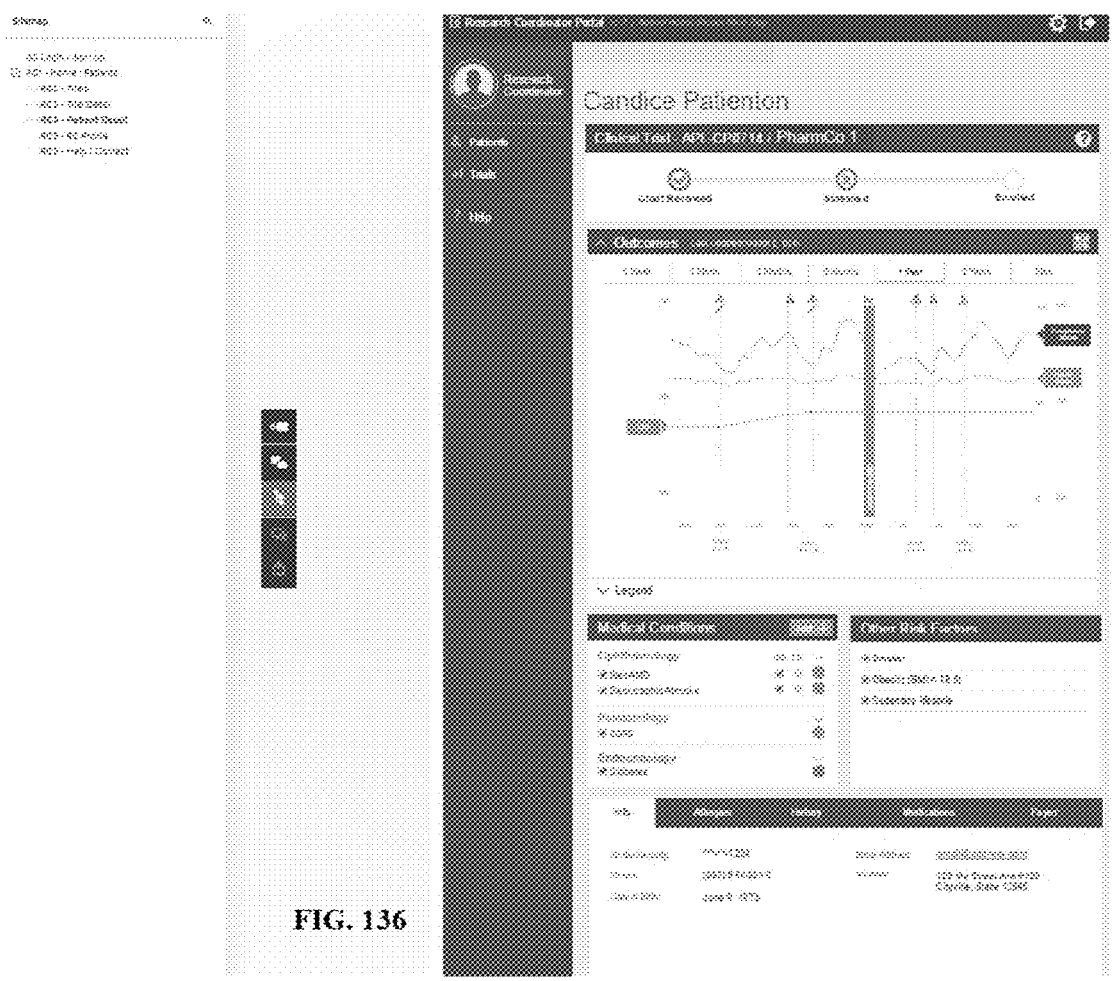
Figure 137:
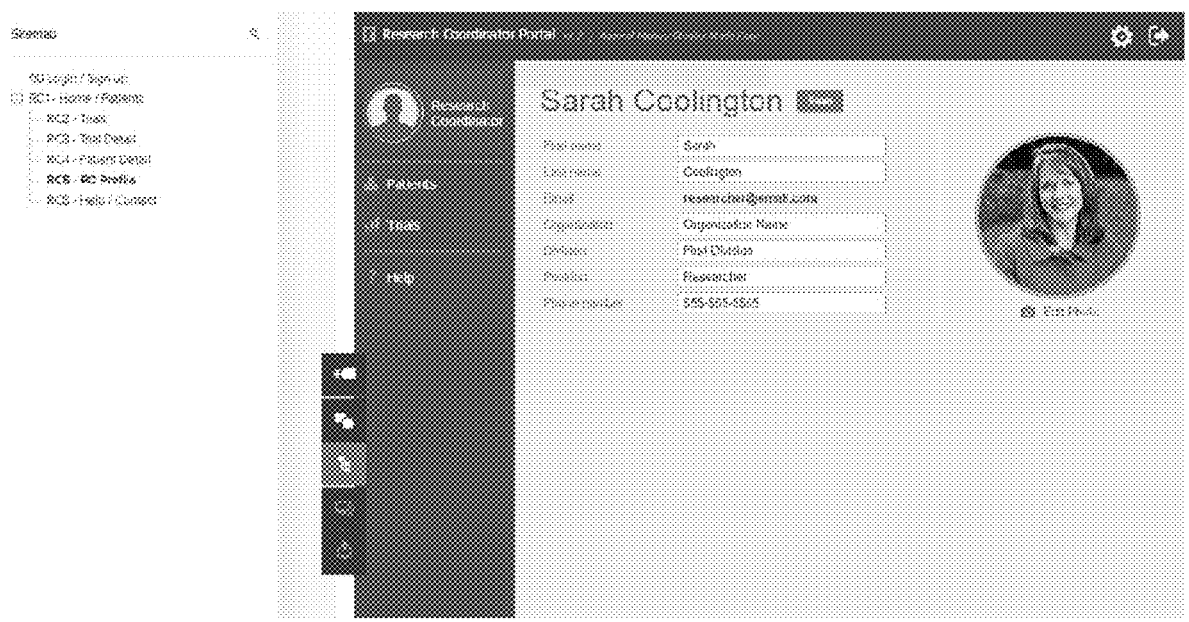
Figure 138:
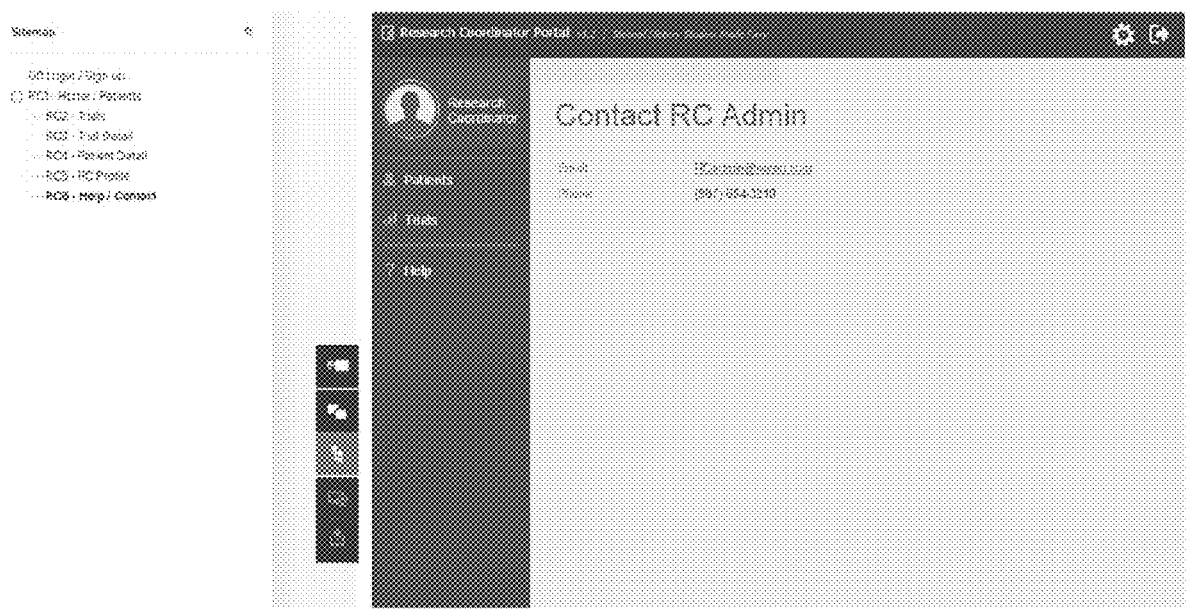

Of course, variations on the above description are possible, and, based on this disclosure, could be implemented without undue experimentation by those of ordinary skill in the art. For example, while a Revon system could be implemented and used in a context in which the entity operating that system would invite patients to participate in clinical trials, it is possible that this process flow could be modified, such as by relying on a physician to inform patients about trials that they might be interested in. Additionally, beyond just modifying the invitation process flow, it is possible that some embodiments might use different implementations of the relevant interfaces, such as the alternate RC portal depicted in FIGS. 132-138. As shown in FIG. 133, such an RC portal could have a combined home/patients page with a table listing patients found by Revon for some or all of the relevant RC's open trials. Such a table could include the information illustrated in FIG. 133, as well as other information such as match date and/or information which may be included in other fields as appropriate for a particular implementation. That information could potentially be used to filter the patients displayed in the table. For example, there may be pre-defined filters such as a status filter which could be used to ensure that only patients having status of Matched, Pre-screened, Screened and Enrolled would be listed. Of course other statuses are also possible, and various embodiments could handle determining patients to display in ways other than the use of pre-defined filters. For example, in some embodiments, there could be patients with a status of "Rejected," and patients with such status could become invisible after {15} days and not be available in the tables. Similarly, it is possible that RC's may be allowed to do their own filtering, but not be limited to pre-defined filters such as described (e.g., they could be allowed to define their own parameters to use in determining what patients should be included/excluded from the list). Additionally (or, in some embodiments, alternatively), a table such as that shown in FIG. 133 might be sortable according to the identified attributes and/or searchable (e.g., based on matching patient names).

A variety of other functionality could also be provided by an RC portal instead of (or in addition to) that discussed previously. For example, in some embodiments, there could be a navigation tool (e.g., a navigation bar included in a margin of the portal interface) which would include links to common destinations such as the home/patients page and/or a trial detail page. Similarly, while an alternative RC portal such as illustrated in FIGS. 132-138 could duplicate much of the functionality of the RC portal of FIGS. 125-130, it is possible that such an alternative RC portal could enhance that functionality. For example, in the trial detail portion of an RC portal, it is possible that that functionality could be added in the form of links to the study protocol documents for each trial and/or links to other trials that patients may be qualified for or enrolled or interested in. Additionally, it is possible that further integration and/or interaction between RCs and back end systems or personnel may also be provided for. For example, instead of allowing an RC to directly edit his or her own profile information, in some embodiments an RC would make changes, and those changes would then be emailed to an administrator who would make those changes in the back end. There may also be tools (e.g., a help link in a navigation bar) for easily contacting such an admin so as to ensure close collaboration between RC users and the back end staff which would support them.

Similarly, in some embodiments, a back end system could be configured to track how long a patient remains in a particular status, and to trigger various actions based on that information to ensure that patients continue to move through the enrollment process. For example, in some embodiments, a backend system may flag patients that should be highlighted (e.g., in tables on the patient home and trial details pages) by front end. Patients to highlight may include patients who are matched but have not been they have not been moved to Pre-screened status or rejected in {e.g., 2} weeks. Patients to highlight may also include patients who are pre-screened but not screened or rejected for {2} weeks, and/or patients who are screened but not enrolled or rejected for {e.g., 2} weeks, will also be highlighted. Preferably, in implementations where there are multiple reasons why a patient may be highlighted, the highlighting will be in different colors to reflect the reasons which apply to particular patients.

Modifications to the roles of the various entities in enrolling patients in clinical trials are also possible. For example, in some cases, the RC may be provided with health information about the user that the RC could review in order to help the RC determine whether to contact the user. For example, it is possible that the Revon system may determine that the user meets certain of the requirements for participating in a research trial but may not determine whether the user meets certain other requirements for participating in the trial. The RC may be notified and provided with access to view the user's patient profile and/or outcomes chart used by the user's Revon physicians (or non-Revon physicians, i.e., those who had not set up an account with Revon, such as in the case where the patient has provided his or her physician a code which he or she could use with a Revon physician application to access the patient's records through a "Share my Health Record" feature such as described above) in providing care to the user and could use the health information therein to determine whether the user meets at least some of the other trial requirements. Upon reviewing the user's health information and comparing it with the trial requirements, the RC may update the user's status on the RC Portal as appropriate. If the RC contacts the user, the RC may provide the user with information regarding the trial, invite the user to be screened for the trial, and/or make an appointment for the user to be screened for the trial.

Figure 139:
FIG. 139 illustrates a view of a patient profile with an outcomes chart depicted at the top of the interface and the interface's legend hidden.
Figure 140:
FIG. 140 illustrates how a patient profile with a hidden legend could be displayed after the legend has been unhidden.

Modifications in portals provided to various users of the Revon technology are also possible even when not accompanied by such process modifications. For example, a patient profile such as illustrated in FIGS. 118A-118B could be modified by removing various features, such as the flower schematic 11801 and/or the navigation breadcrumbs in the profile's top portion. Similarly, the outcomes chart 11803 could be moved to the top portion of the profile interface, and/or the legend 11804 for that chart could be hidden with a user activated hide/unhide feature. Unchecked medical conditions and risk factors could potentially also be hidden from view, as opposed to being shown below the outcomes chart 11803. As an illustration, FIG. 139 depicts a modified view of a patient profile with the outcomes chart 11803 depicted on the top of the interface and the legend hidden. FIG. 140 illustrates how such a patient profile interface could be displayed after a user has unhidden the legend 11804 (e.g., by clicking on it).

Figure 141:
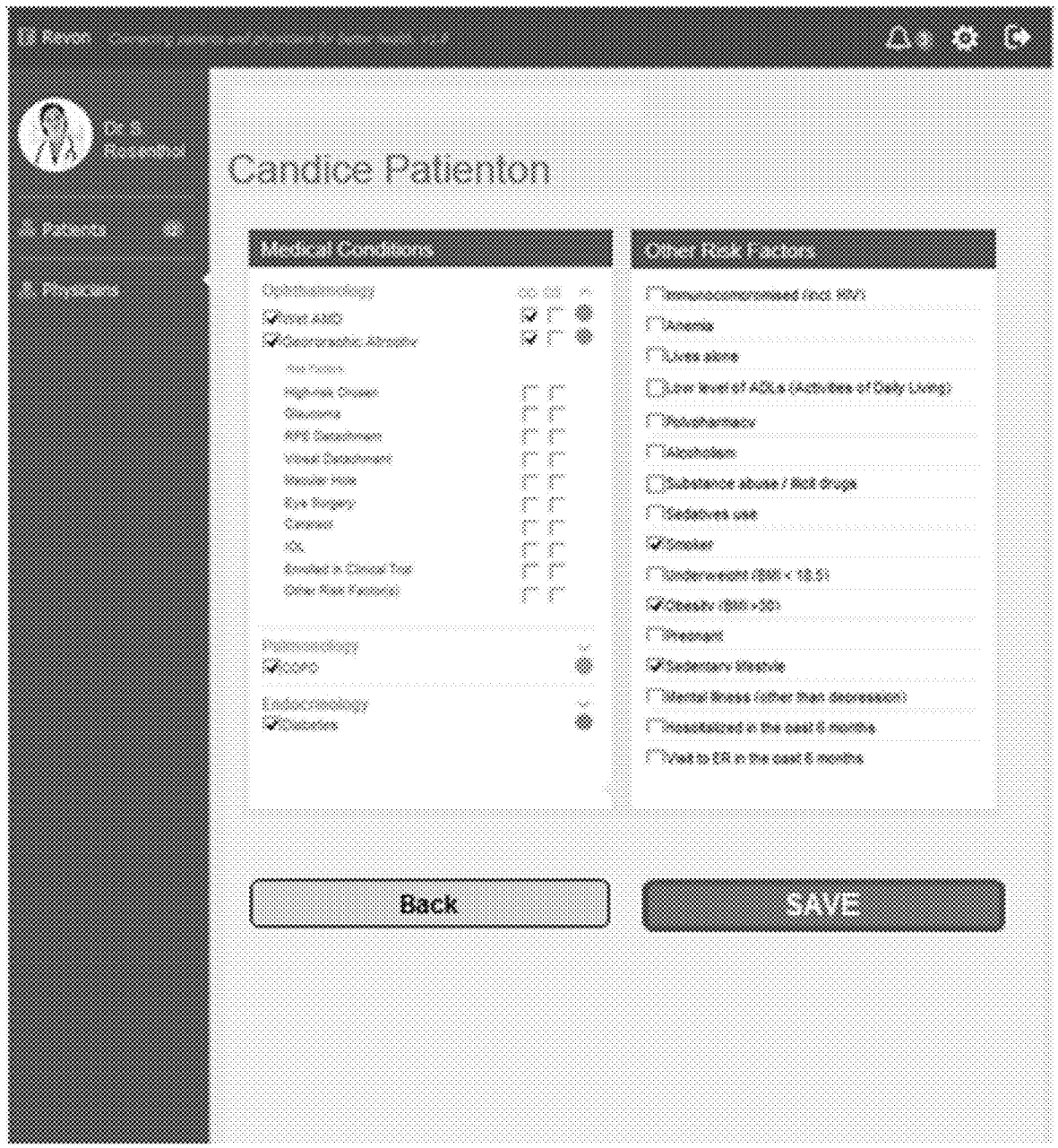
FIG. 141 illustrates an interface displaying medical conditions and risk factors with check boxes which could be actuated by a physician.
Figure 142:
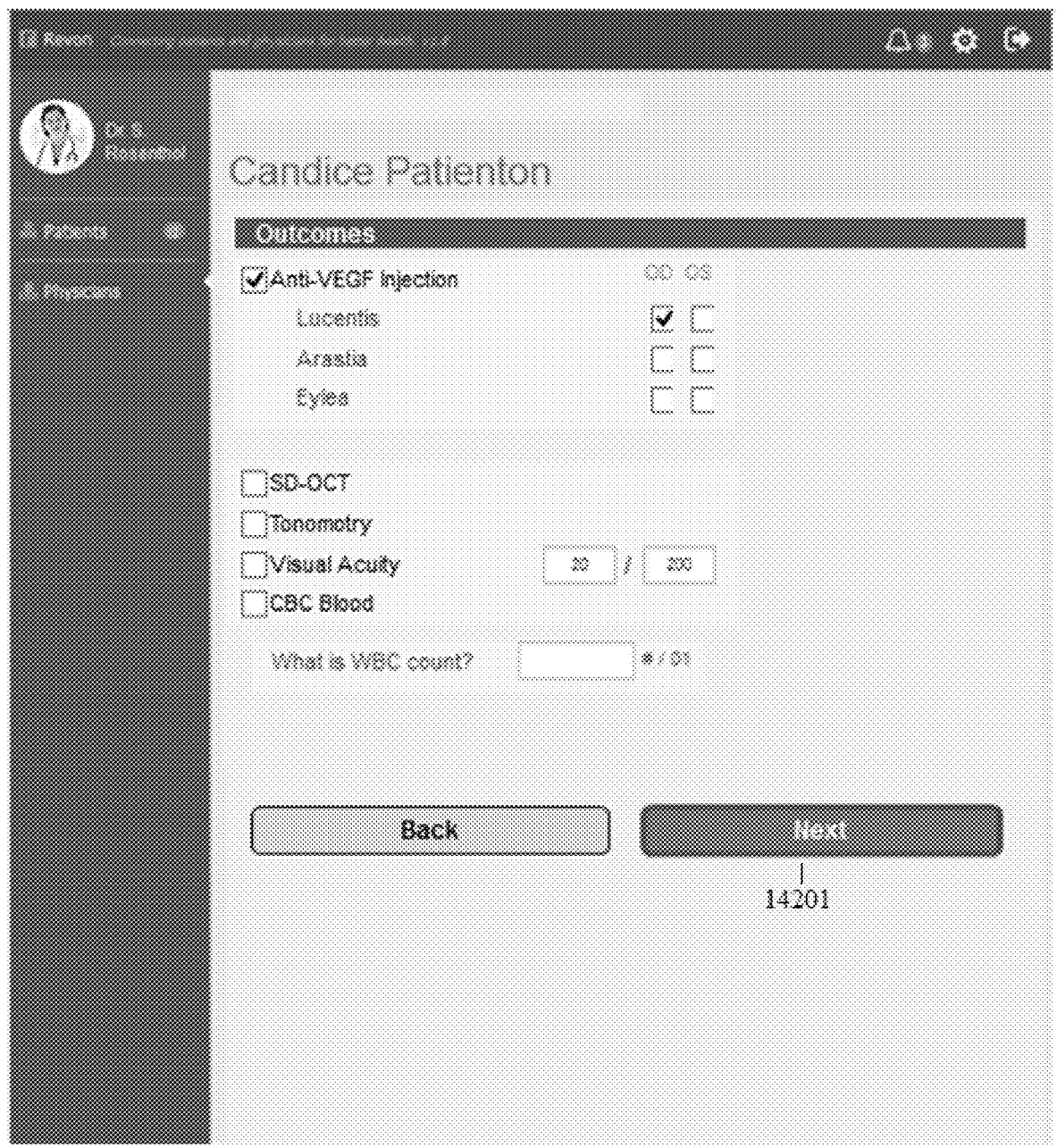
FIG. 142 illustrates a tool which could be used to update condition information for a patient.

Further functionality could also be provided. For example, when a physician makes changes using a patient profile such as shown in FIGS. 118A-118B, 139 or 140, the changed information could automatically be compared with requirements for a pharmaceutical research trial and, if there was a match, a session could be started with the physician to ask additional questions about the patient and obtain information for determining whether the patient should be invited to participate in the trial. Similarly, when a physician activates an update button 13901 such as shown in FIGS. 139 and 140, he or she could be presented with an update tool in a new interface, an example of which is provided in FIG. 142. Yet another new interface displaying all medical conditions and risk factors and checkboxes which could be actuated by the physician, an example of which is provided in FIG. 141, could then be provided when the physician actuates a further control, such as the next button 14201 illustrated in FIG. 142.

Further variations are also possible. For example, there could be changes in terminology (e.g., the status of "Pre-Screened" in an RC Portal could be referred to in another manner, such as "Chart Review"), there could be changes in allocation of functions (e.g., functionality described as being provided through a web interface could be provided by an app, and vice versa), among other types of changes. Similarly, it should be understood that patient centric data structures could be used in systems implemented to use the disclosed technology with components and/or architectures which do not follow the architecture of FIG. 5 (e.g., a virtual representation of a patient could be included in a system in which logic for determining how to update a patient's representation is included in SSTs, either in addition to, or as an alternative to, including it in rules for a state controller engine 502).

Accordingly, in light of the potential for variations and modifications to the material described explicitly herein, the disclosure of this document should not be treated as implying limits on the protection provided by this document or any related document. Instead, the protection provided by a document which claims the benefit of or is otherwise related to this document should be understood as being defined by its claims, when the terms in those claims which are explicitly defined under the "Explicit Definitions" heading are given their explicit definitions, and when all other terms are given their broadest reasonable interpretation as shown by a general purpose dictionary. To the extent that the interpretation which would be given to the claims based on the above disclosure is in any way narrower than the interpretation which would be given based on the explicit definitions under the "Explicit Definitions" heading and the broadest reasonable interpretation as provided by a general purpose dictionary, the interpretation provided by the explicit definitions under the "Explicit Definitions" heading and broadest reasonable interpretation as provided by a general purpose dictionary shall control, and the inconsistent usage of terms in the specification shall have no effect, unless and to the extent that any particular claim or claims is amended to incorporate a narrower interpretation or limitation or a narrower interpretation or limitation is clearly and unambiguously adopted by Applicants during the course of prosecution of a particular claim or claims. It should also be understood that where the above disclosure refers to a species of a term that is defined generically in the Explicit Definitions or is otherwise encompassed by a definition in the Explicit Definitions, such reference in the above disclosure would support use of the full scope of the corresponding definition in the Explicit Definitions, including the species thereof. Thus, the use of a specific term in a particular context in the above disclosure would support use of the corresponding generic term as defined in the Explicit Definitions (as well as species thereof). By way of example, references to a "smartphone" in various contexts in the above disclosure would support use of the term "mobile computing device" and species thereof in such contexts.

EXPLICIT DEFINITIONS

When used in the claims, "activity tracking device" refers to a type of "monitoring device" (defined infra) for monitoring and tracking fitness-related physiological parameters such as movement (e.g., distance walked or run, steps climbed), calories used, heart rate, sleep-related physiological parameters such as sleep duration, sleep depth, and any of a variety of others. An activity tracking device may use a three-dimensional accelerometer to sense user movement and measure steps taken, which it may use, sometimes together with user data, to calculate metrics such as distance walked, calories burned, floors climbed, and activity duration and intensity. Often an activity tracking device is a wearable electronic device that is or can be synchronized, in many cases wirelessly, to a computer or mobile device such as a smartphone. An activity tracking device may in some embodiments monitor activity in a room or within a home by means of heat-sensing (e.g., infrared), light-sensing, or other devices that detect movement or heat without necessarily being worn by or connected to the patient. Such devices may, for example, determine whether a patient has deviated from his or her normal level of activity within a home, failed to get out of bed, etc.

When used in the claims, "based on" should be understood to mean that something is determined at least in part by the thing that it is indicated as being "based on." When a claim is written to require something to be completely determined by a thing, it will be described as being "based EXCLUSIVELY on" the thing. Where the above disclosure refers to something being based on a thing or things, it should be understood that that "something" may, in certain embodiments, be based exclusively on that thing or things, or on any particular proper subset of such things.

When used in the claims, "behavioral data" should be understood to refer to any data pertaining to the way an individual acts, particularly those ways that may affect or reflect the individual's health, examples of "behavioral data" include, but are not limited to, data pertaining to: the individual's diet, physical activity, sleep, smoking, use of drugs with addictive potential, the way an individual interacts with a system implemented with the disclosed technology and components thereof (e.g., time spent accessing or otherwise engaging with educational materials), and/or compliance with a treatment plan.

When used in the claims a "body monitor" should be understood to refer to a general health measure which may not be specifically linked to a given disease. An example of a body monitor is a patient's temperature. A "dangerous" body monitor or outcome value is referred to as a "sign," which is simply a marker for an adverse value measurement and will typically be recorded as an event.

When used in the claims, a "computer" should be understood to refer to a device or group of devices (e.g., a device comprising a processor and a memory) capable of storing and executing instructions for performing one or more logical and/or physical operations on data to produce a result. A "computer" may include, for example, a single-core or multi-core microcontroller or microcomputer, a desktop, laptop or tablet computer, a smartphone, a server, or groups of the foregoing devices (e.g., a cluster of servers which are used in combination to perform operations on data for purposes such as redundancy and availability).

When used in the claims, "computer readable medium" should be understood to refer to any object, substance, or combination of objects or substances, capable of storing data or instructions in a form in which they can be retrieved and/or processed by a device. A computer readable medium should not be considered limited to any particular type or organization, and should be understood to include distributed and decentralized systems however they are physically or logically disposed, as well as storage objects of systems which are located in a defined and/or circumscribed physical and/or logical space.

When used in the claims, "condition" should be understood to refer to a circumstance of set of circumstances which can be used to characterize the state of an individual's health. Thus, a "condition" would include a health problem or abnormality or any state of abnormal or normal health or function for which an individual seeks or obtains care from a health care provider (e.g., any disease, disorder, or other diagnostic entity known to medical practitioners of ordinary skill). A "condition" would also include the state of good health which an individual might wish to maintain, but for which he or she would not necessarily seek or obtain care from a health care provider.

When used in the claims, in the context of health data "condition-centric" should be understood to mean that the relationship of the health data to a condition is the guiding principle used to determine which health data to obtain, analyze, store, and/or present to a user, and/or to determine how the health data are presented to a user.

When used in the claims, "data element" should be understood to refer to an individual unit of data, which may be indivisible or may consist of one or more data items. A data element may, for example, be something as simple as an individual measurement of a physiological variable such as body weight, a level of an analyte in a body fluid, or a patient's response to a yes/no question about the presence or severity of a symptom, or may be more complex, such as a medical image (e.g., an X-ray image), a pathology report, or the like.

When used in the claims, a "data element type" should be understood as being synonymous with a "type of data element," and should be understood to refer to a particular kind or category of data element. A data element type may have a specific name, e.g., "body weight", "cough severity change", "6 minute walk distance", or "chest X-ray" and a definition.

When used in the claims, to "determine" something should be understood to mean to produce or generate, compute, establish, or specify that thing. For example, something may be "determined" by selecting it from a group of alternatives or options, by analyzing data (e.g., by applying an algorithm to the data) to generate a result.

When used in the claims, "environmental data" refers to data concerning a patient's indoor or outdoor environment. In this context, "indoor environment" refers to inside the patient's home and/or workplace or such other place as the patient spends a significant amount of time (e.g., at least 10 hours per week), while "outdoor environment" refers to the environment outside of buildings, and can be measured with data such as outdoor temperature, and levels of pollen or pollutants or others substances in the air.

When used in the claims, "genotypic data" should be understood to refer to any data pertaining to the genetic makeup of a cell, population of cells, or an individual, usually (though not necessarily) with reference to a specific characteristic under consideration, specific gene or genes of interest, or specific nucleotide position(s) in a gene or genes of interest.

When used in the claims, "geographic data" should be understood to refer to data about a geographic region, which may include data about environmental conditions in a region or people in the region. It should be understood that "geographic data" may overlap with "population-based data" (defined infra) and that both "geographic data" and "population-based data" may include epidemiologic data, such as data about the prevalence of particular infectious diseases in the geographic region where a patient lives.

When used in the claims, "health care institution" should be understood as being synonymous with "health care facility" and should be understood to refer to an institution that provides health care to multiple persons on a systematic basis, such as a hospital, health clinic, health center, surgery center, skilled nursing facility, or physicians' practice.

When used in the claims, "health data" should be understood to refer to any data or information about or relating to an individual or group of individuals that is descriptive of, informative about, affects, or potentially affects the health of the individual or group of individuals in more than merely a tangential or insignificant way. Health data can include, for example, physiological data, symptom data, results of medical tests (e.g., clinical chemistry or other types of laboratory tests, imaging, pathology tests, or any other type of test that might be performed on a patient by or at the direction of a health care provider), genotypic data, behavioral data, environmental data, demographic data, demographic data, geographic data, population-based data.

When used in the claims, a "mobile computing device" (sometimes referred to simply as a "mobile device" herein) should be understood to refer to a computer adapted to be moved by a user and to be operable during such movement, such as by including a local power supply (e.g., a battery). Examples of "mobile computing devices" include, but are not limited to portable digital assistants (PDAs), "smartphones" (defined infra) tablet computers, and laptop computers. Often, a "mobile computing device" will weigh under about 1-2 pounds, e.g., between about 2-3 ounces and about 1.5 pounds. For example, a "smartphone" or PDA may weigh between about 3 ounces and about 6 ounces and have height and width dimensions in the range of less than about 7×5 inches and depth less than about 0.5-1.0 inch, though smaller or larger weight and/or dimensioned devices may also fall within the scope of "mobile computing device."

When used in the claims, "monitoring device" should be understood to refer to a device that can be used for detecting or measuring one or more physiological variables, environmental variables, or behavioral variables relevant to a patient. It should be understood that a "personal monitoring device" (defined infra) is included within the definition of "monitoring device" unless otherwise indicated. Examples of "monitoring devices" include body weight scales, pulse oximeters, blood pressure monitors, thermometers, activity tracking devices, heart rate monitors, blood glucose measuring devices (glucometers), stethoscopes, medication dispensers that in some way monitor medication usage, and any other devices capable of obtaining physiological data, environmental data, or behavioral data relating to a patient. Monitoring devices may be referred to as "body monitors", it being understood that such devices may collect data that pertains to a patient's environment or behaviors and are not limited to devices that collect data from or about a patient's body per se.

When used in the claims, an "outcome" should be understood to refer to health measurements or actions which may be, but are not necessarily, the ultimate results of a particular course of treatment or intervention or may serve as indicators of whether, or to what extent, a course of treatment or intervention is controlling or ameliorating a condition or symptom). Examples of outcomes include oxygen saturation for COPD, and hemoglobin A1C for diabetes mellitus. An outcome may be a result of a procedure or laboratory test or the fact that a procedure was performed on the patient (e.g., administration of a medication). In general, a given condition can have one or more outcomes associated with it. Some conditions may be associated with a single outcome, whereas other conditions may be associated with multiple outcomes. In general, a given outcome can be associated with one or more conditions. Some outcomes may be associated with a single condition, whereas other outcomes may be associated with multiple conditions.

When used in the claims, a "patient" should be understood to be an individual who seeks or receives health care from a health care provider.

When used in the claims, "personal monitoring device" should be understood to refer to a monitoring device that can be used by a patient in his or her daily life (i.e., while he or she is not under care in a health care facility).

When used in the claims, "physiological data" should be understood to refer to any qualitative or quantitative measurement of any indicator of a biological state, function, structure, process, response, or condition in a patient.

When used in the claims, "population-based data" should be understood to refer to data about groups of individuals, e.g., groups of patients having a particular condition or living in a particular geographic region. In this context, a geographic region may be a city, county, zip code area, state, or any other region as defined or used in an implementation of the disclosed technology. It should be understood that "population-based data" may overlap with "geographic data," and that both "population-based data" and "geographic data" may include epidemiologic data, such as data about the prevalence of particular conditions, e.g., infectious diseases, in the geographic region where a patient lives.

When used in the claims, a "set" should be understood to refer to a collection of zero or more things, which may be referred to as "elements" of the set. A "subset" of a set A is a set which does not include any elements that are not also in A. A subset of a set may include all the elements of the set.

When used in the claims, a "smartphone" should be understood as any mobile electronic device that combines the functions of a wireless phone and a computer within a single handheld unit and is capable of web browsing and running software applications. A "smartphone" can be understood in contrast with a "basic mobile phone" (i.e., a mobile phone that allows a user to make and receive calls but lacks the capability of executing software applications), or a "fixed phone" (i.e., a hard-wired or cordless phone that makes use of a fixed phone line).

When used in the claims, a "set" should be understood to refer to a collection of zero or more things, which may be referred to as "elements" of the set. A "subset" of a set A is a set which does not include any elements that are not also in A. A subset of a set may include all the elements of the set.

When used in the claims, a "symptom" should be understood to include things like headache, impaired ability to walk, shortness of breath and other items related to subjective aspects of patient health about which data can be collected.

When used in the claims, "means for responding to a patient event" should be understood as a means+function limitation as provided for in 35 U.S.C. § 112(f), in which the function is "responding to a patient event" and the corresponding structure is an interface controller engine ("ICE") as described herein.

When used in the claims, "means for creating, updating, and maintaining a patient interface data set" should be understood as a means+function limitation as provided for in 35 U.S.C. § 112(f), in which the function is "creating, updating, and maintaining a patient interface data set" and the corresponding structure is an interface design engine ("IDE") as described herein.

When used in the claims, "means for controlling data" should be understood as a means+function limitation as provided for in 35 U.S.C. § 112(f), in which the function is "controlling data" and the corresponding structure is a data controller engine ("DCE") as described herein.

When used in the claims, "means for maintaining a patient state data set" should be understood as a means+function limitation as provided for in 35 U.S.C. § 112(f), in which the function is "maintaining a patient state data set" and the corresponding structure is a state controller engine ("SCE") as described herein.

When used in the claims, "means for consolidating a set of relevant rules" should be understood as a means+function limitation as provided for in 35 U.S.C. § 112(f), in which the function is "consolidating a set of relevant rules" and the corresponding structure is a action controller engine ("ACE") as described herein.

When used in the claims, "means for delivering messages to patients" should be understood as a means+function limitation as provided for in 35 U.S.C. § 112(f), in which the function is "delivering messages to patients" and the corresponding structure is an engagement engine ("EE") as described herein.

When used in the claims, "means for gathering health information for, and providing trial and health information to, a patient" should be understood as a means+function limitation as provided for in 35 U.S.C. § 112(f), in which the function is "gathering health information for, and providing trial and health information to, a patient" and the corresponding structure is a computer configured to provide a patient portal as illustrated in FIGS. 16-43 and 44-75 and the accompanying disclosure, including the discussion of the Medication Module.

When used in the claims, "means for providing patient information to, allowing patient information to be updated by, and plan creation and assignment by, a physician" should be understood as a means+function limitation as provided for in 35 U.S.C. § 112(f), in which the function is "providing patient information to, allowing patient information to be updated by, and plan creation and assignment by, a physician" and the corresponding structure is a computer configured to provide a physician portal as illustrated in FIGS. 76-91 and 92-114 and the accompanying disclosure, including the discussion of the outcomes capture module, the outcomes chart module, and the patient profile and modifications thereto.

When used in the claims, "means for enabling enrollment of patients in trials and providing details on trial and trial volunteer status" should be understood as a means+function limitation as provided for in 35 U.S.C. § 112(f), in which the function is "enabling enrollment of patients in trials and providing details on trial and trial volunteer status" and the corresponding structure is a computer configured to provide a RC portal as illustrated in FIGS. 125-130 and 132-38 and the accompanying disclosure.

When used in the claims, "means for automatically identifying patients as potential participants in trials" should be understood as a means+function limitation as provided for in 35 U.S.C. § 112(f), in which the function is "automatically identifying patients as potential participants in trials" and the corresponding structure is a computer configured to process patient health information received from one or more of a "means for gathering health information for, and providing trial and health information to, a patient" and/or a "means for providing patient information to, allowing patient information to be updated by, and plan creation and assignment by, a physician" by matching it against requirements for a clinical trial.

What is claimed is:

1. A system for assembling, analyzing, facilitating access to, and performing actions based on health information, the system comprising a plurality of patient state objects, wherein each patient state object:
   a) corresponds to, and provides a holistic and continuously updateable view of, a different patient from a plurality of patients registered with the system;
   b) is a data structure adapted to store, for the patient to whom it corresponds, data comprising:
      i) physiological data regarding that patient;
      ii) behavioral data regarding that patient; and
      iii) demographic data regarding that patient;
   c) stores all health data used by the system for performing actions for the patient to which it corresponds;
wherein:
   A) the system comprises a non-transitory computer readable medium storing instructions encoding an action controller engine (ACE) having a plurality of rules for determining actions to perform based on data from patient state objects;
   B) for each patient state object from the plurality of patient state objects, the system is adapted to cause the ACE to evaluate rules for taking action based on data from patient state objects based on one or more of:
      i) receipt of a message indicating an update to that patient state object; and
      ii) a time based trigger for running rules in a batch process
   C) the plurality of rules for the ACE are organized into a plurality of nodes;
   D) the plurality of nodes into which the rules for the ACE are organized comprise a plurality of macro nodes, wherein each macro node:
      I) dedicated to a specific rule type; and
      II) comprises a set of micro nodes, wherein each micro node:
         a) comprises one or more rules which, when that micro node is run for a patient, are evaluated with data from the patient state object corresponding to the patient for which that micro node is run;
         b) has a single output instruction it could potentially issue upon being run; and
         c) has a local priority establishing an order in which it is run in the macro node it is comprised by;
   E) the ACE is configured to perform a smart symptom tracker ("SST") session for a patient by performing a set of acts comprising:
      I) running each macro node from the plurality of macro nodes in a predetermined sequence, wherein, for each macro node, running that macro node comprises running the micro nodes comprised by that macro node for the patient for which the SST session is being performed in descending order of the local priorities of those micro nodes;
      II) adding all output instructions issued by the micro nodes comprised by the macro nodes while running the macro nodes in the SST session for the patient to a stack; and
      III) holding the output instructions issued by the micro nodes comprised by the macro nodes while running the macro nodes in the SST session for the patient in the stack until the SST session for the patient is concluded;
   F) the system is adapted to, after the SST session for the patient is concluded, provide the patient for whom the SST session was performed with information specified by the output instructions added to the stack during the SST session for the patient via an interface on a computing device associated with the patient for whom the SST session was performed;
wherein the plurality of macro nodes comprises:
   i) a macro node dedicated to triage instruction rules, wherein the macro node dedicated to triage instruction rules is first in the predetermined sequence and comprises:
      a) a micro node comprising one or more rules which, when evaluated, could potentially issue an instruction to call 911, wherein the local priority of this micro node is greater than the local priority of all other micro nodes within the macro node dedicated to triage instructions;
      b) a micro node comprising one or more rules which, when evaluated, could potentially issue an instruction to call a physician, wherein the local priority of this micro node is greater than the local priority of all other micro nodes within the macro node dedicated to triage instructions, with the exception of the micro node comprising one or more rules which, when evaluated, could potentially issue an instruction to call 911;
      c) a micro node comprising one or more rules which, when evaluated, could potentially issue an instruction to take action if there is no improvement after 24 hours, wherein the local priority of this micro node is less than the priority of the micro node comprising one or more rules which, when evaluated, could potentially issue an instruction to call a physician but greater than the local priority of all other micro nodes within the macro node dedicated to triage instructions; and
      d) a micro node comprising one or more rules which, when evaluated, could potentially issue an instruction that no triage action should be taken, wherein the local priority of this micro node is less than the priority of all other micro nodes within the macro node dedicated to triage instructions;

ii) a macro node dedicated to medication instruction rules, wherein the macro node dedicated to medication instruction rules is second in the predetermined sequence and comprises:
  a) a micro node comprising one or more rules which, when evaluated, could potentially issue an instruction to use a medical device, wherein the local priority of this micro node is greater than the local priority of all other micro nodes within the macro node dedicated to medication instructions; and
  b) a micro node comprising one or more rules which, when evaluated, could potentially issue an instruction to take a medication, wherein the local priority of this micro node is greater than the local priority of all other micro nodes within the macro node dedicated to medication instructions, with the exception of the micro node comprising one or more rules which, when evaluated, could potentially issue an instruction to use a medical device;
and
iii) a macro node dedicated to future instruction rules, wherein at least one micro node comprised by the macro node dedicated to future instruction rules comprises one or more rules which, when evaluated, could potentially trigger a future SST session after conclusion of the SST session being performed for the patient.

2. The system of claim 1, wherein each patient state object is a multidimensional vector accessible using an identifier for the corresponding patient as an argument to patient state object retrieval function.

3. The system of claim 1, wherein:
a) the demographic data each patient state object is adapted to store for its corresponding patient comprises:
  i) age of the corresponding patient;
  ii) gender of the corresponding patient;
  iii) income level of the corresponding patient;
  iv) education level of the corresponding patient;
  v) environment of the corresponding patient; and
  vi) location of the corresponding patient;
b) the behavioral data each patient state object is adapted to store for its corresponding patient comprises:
  i) compliance by the corresponding patient with requests for survey data;
  ii) compliance by the corresponding patient with using medications as directed;
  iii) a compliance level score for the corresponding patient;
  iv) a recent compliance level score for the corresponding patient;
  v) a compliance score trend for the corresponding patient;
  vi) a compliance score volatility for the corresponding patient; and
  vii) for each of a plurality of body monitors, a compliance score for providing measurements from that body monitor;
c) the physiological data each patient state object is adapted to store for its corresponding patient comprises:
  i) an overall health score for the corresponding patient;
  ii) a heath score trend for the corresponding patient;
  iii) a health score volatility for the corresponding patient;
  iv) a general hospitalization risk for the corresponding patient;
  v) for each of a plurality of conditions:
    A) a risk level for the corresponding patient for that condition; and
    B) a condition exacerbation risk for the corresponding patient for that condition;
  vi) for each of a plurality of body monitors:
    A) an urgency score for the corresponding patient for that body monitor; and
    B) a risk level for the corresponding patient for that body monitor;
  vii) an overall exacerbation risk for the corresponding patient;
  viii) allergies of the corresponding patient; and
  ix) medications taken by the corresponding patient.

4. The system of claim 1, wherein:
a) the system comprises a state controller engine ("SCE") having a plurality of rules for updating patient state objects;
b) for each patient state object from the plurality of patient state objects, the system is adapted to cause the SCE to evaluate rules for updating patient state objects based on one or more of:
  i) receipt of new data regarding the patient corresponding to that patient state object; and
  ii) a periodically scheduled trigger for determining updates to that patient state object based on historical data regarding that patient state object.

5. The system of claim 4, wherein the system has only a single SCE, and all updates to all patient state objects from the plurality of patient state objects are performed using that SCE.

6. The system of claim 4 wherein the system is configured to use the SCE to continuously update the plurality of patient state objects as new data becomes available.

7. The system of claim 1, wherein the ACE has rules adapted to, based on evaluation of rules with data from a patient state object corresponding to a specific patient, cause the system to perform actions comprising:
a) communicating with the specific patient by sending a message to a computer of the specific patient;
b) communicating with a healthcare provider of the specific patient by sending a message to a computer of the healthcare provider of the specific patient;
c) communicating with a caregiver of the specific patient by sending a message to a computer of the caregiver of the specific patient;
d) requesting health data from the specific patient;
e) requesting an update to a body monitor measurement for the specific patient;
f) recommending the specific patient seek medical attention by performing an action selected from a group consisting of:
  i) calling 911; and
  ii) calling a physician;
g) recommending that the specific patient take a medication;
h) sending a reminder message to the specific patient; and
i) adjusting a timing or frequency for collecting data from the specific patient.

8. The system of claim 1 wherein the SST session is a virtual SST session wherein:
a) the ACE is adapted to evaluate, at initiation of the virtual SST session, a rule for modifying the patient state object corresponding to the patient for whom the virtual SST session is performed to indicate that the virtual SST session is in progress for that patient;

b) the system is configured to, during performance of the virtual SST session for the patient, implement any modifications to the patient state object corresponding to the patient for which the virtual SST sessions is performed triggered by evaluation of rules during the virtual SST session; and c) the ACE is adapted to conclude the virtual SST session for the patient by evaluating a rule for modifying the patient state object corresponding to the patient for whom the virtual SST session is performed to indicate that no virtual SST session is in progress for that patient.

9. The system of claim 8 wherein;

a) the system comprises an output instructions data structure comprising all output instructions which could potentially be issued by the micro nodes comprised by the macro nodes while running the macro nodes in the SST session for the patient;

b) adding all output instructions issued by the micro nodes comprised by the macro nodes while running the macro nodes in the SST session for the patient to the stack comprises, for each issued output instruction, modifying information in the output instructions data structure for that output instruction to indicate that that instruction should be issued to the patient for whom the virtual SST session is performed;

c) providing the patient form whom the virtual SST session was performed with information specified by the output instructions added to the stack during the SST session for the patient comprises:

i) analyzing the output instructions which information in the output instructions data structure indicates should be issued to the patient for whom the virtual SST session was performed for conflicts;

ii) modifying information in the output instructions data structure for any conflicting output instructions to indicate that the conflicting instructions should not be issued to the patient for whom the virtual SST session was performed; and iii) providing the patient for whom the virtual SST session was performed with information specified by the output instructions which information in the output instructions data structure indicates should be issued to the patient for whom the virtual SST session was performed.

10. The system of claim 9 wherein the output instructions data structure is an array.

11. The system of claim 1, wherein:

a) the medical device is a nebulizer; and b) the medication is a steroid.

12. The system of claim 1, wherein the system is adapted to, during the SST session for the patient, provide one or more prompts requesting information to the patient form whom the SST session is performed.

13. The system of claim 1, wherein the system is configured to use the ACE to flexibly react to patient data in a real time manner.

* * * * *